(12) United States Patent
Pierce et al.

(10) Patent No.: US 8,623,611 B2
(45) Date of Patent: Jan. 7, 2014

(54) GLYCOPROTEIN CANCER BIOMARKER

(75) Inventors: James Michael Pierce, Athens, GA (US); Karen L. Abbott, Statham, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 378 days.

(21) Appl. No.: 12/814,184

(22) Filed: Jun. 11, 2010

(65) Prior Publication Data

US 2011/0033875 A1    Feb. 10, 2011

Related U.S. Application Data

(63) Continuation-in-part of application No. PCT/US2008/013658, filed on Dec. 12, 2008.

(60) Provisional application No. 61/007,442, filed on Dec. 12, 2007.

(51) Int. Cl.
    *G01N 33/574*    (2006.01)

(52) U.S. Cl.
    USPC .......................... 435/7.23; 435/7.1; 530/350

(58) Field of Classification Search
    None
    See application file for complete search history.

(56) References Cited

U.S. PATENT DOCUMENTS

| | | | |
|---|---|---|---|
| 7,087,727 B2 | 8/2006 | Chen et al. | |
| 2006/0228763 A1* | 10/2006 | Chen et al. | 435/7.92 |
| 2009/0041836 A1 | 2/2009 | Boons et al. | |

FOREIGN PATENT DOCUMENTS

| | | |
|---|---|---|
| WO | WO 2006/121892 A2 | 11/2006 |
| WO | WO 2006/121892 A3 | 2/2007 |
| WO | WO 2007/079448 A2 | 7/2007 |
| WO | WO 2007/079448 A3 | 1/2008 |
| WO | WO 2009/075883 A2 | 6/2009 |
| WO | WO 2009/075883 A3 | 8/2009 |
| WO | WO 2010/002478 A2 | 1/2010 |
| WO | WO 2010/002478 A3 | 7/2010 |

OTHER PUBLICATIONS

Lindsley et al, Dev Biol, May 3, 2007, 307:340-55.*
Merkle et al, Methods in Enzymol, 1987, 138:232-259.*
Frostberg et al, Cancer Biochem Biophys, 1987, 9:155-168.*
Abbott et al., "Focused glycomic analysis of the N-linked glycan biosynthetic pathway in ovarian cancer," Aug. 2008 *Proteomics* 8(16):3210-3220.
Abbott et al., "Focused glycomic analysis of the N-linked glycan biosynthetic pathway in ovarian cancer," Aug. 2008 *Proteomics* 8(16):3210-3220; online Supporting Information available online at: <http://www.wiley-vch.de/contents/jc_2120/2008/pro200800157_s.pdf> ; _pages.

Aoki et al., "Dynamic developmental elaboration of N-linked glycan complexity in the Drosophila melanogaster embryo," Mar. 23, 2007 *J. Biol. Chem.* 282:9127-42. Available online on Jan. 29, 2007.
Auersperg et al., "Ovarian surface epithelium: biology, endocrinology, and pathology," Apr. 2001 *Endocr. Rev.* 22:255-288.
Bensi et al., "Structure and expression of the human haptoglobin locus," Jan. 1985 *EMBO J.* 4:119-26.
Bentz et al., "Purification and characterization of a unique osteoinductive factor from bovine bone," Dec. 5, 1989 *J Biol. Chem.* 264:20805-10.
Berking et al., "Transforming growth factor-beta1 increases survival of human melanoma through stroma remodeling," Nov. 15, 2001 *Cancer Res.* 61:8306-16.
Bhaumik et al., "Progression of hepatic neoplasms is severely retarded in mice lacking the bisecting N-acetylglucosamine on N-glycans: evidence for a glycoprotein factor that facilitates hepatic tumor progression," Jul. 1, 1998 *Cancer Res.* 58:2881-2887.
Bignotti et al., "Gene expression profile of ovarian serous papillary carcinomas: identification of metastasis-associated genes," Mar. 2007 *Am. J Obstet. Gynecol.* 196: 245.e1-11.
Blumer et al., "Identification and location of bone-forming cells within cartilage canals on their course into the secondary ossification centre," Jun. 2006 *J. Anat.* 208:695-707.
Brahimi-Horn et al., "Hypoxia and cancer," Dec. 2007 *J. Mol. Med.* 85: 1301-1307. Available online on Nov. 20, 2007.
Buckhaults et al., "Transcriptional regulation of N-acetylglucosaminyltransferase V by the src oncogene," Aug. 1, 1997 *J Biol. Chem.* 272:19575-81.
Burleson et al., "Disaggregation and invasion of ovarian carcinoma ascites spheroids," Jan. 24, 2006 *J Transl. Med.* 4:6; 16 pages.
Celis et al., "Proteomic characterization of the interstitial fluid perfusing the breast tumor microenvironment: a novel resource for biomarker and therapeutic target discovery," Apr. 2004 *Mol. Cell. Proteomics* 3:327-44. Available online on Jan. 30, 2004.
Cheung et al., "Metabolic homeostasis and tissue renewal are dependent on β1,6GlcNAc-branched N-glycans," Aug. 2007 *Glycobiology* 17:828-37. Available online on May 4, 2007.
Corsi et al., "Phenotypic effects of biglycan deficiency are linked to collagen fibril abnormalities, are synergized by decorin deficiency, and mimic Ehlers-Danlos-like changes in bone and other connective tissues," Jul. 2002 *J. Bone Miner. Res.* 17:1180-9. Available online on Jul. 1, 2002.
Cummings and Kornfeld, "Characterization of the structural determinants required for the high affinity interaction of asparagine-linked oligosaccharides with immobilized *Phaseolus vulgaris* leukoagglutinating and erythroagglutinating lectins," Oct. 10, 1982 *J Biol. Chem.* 257:11230-4.
Cummings and Kornfeld, "Fractionation of asparagine-linked oligosaccharides by serial lectin-Agarose affinity chromatography. A rapid, sensitive, and specific technique,"Oct. 10, 1982 *J. Biol. Chem.* 257:11235-40.
Dennis and Laferte, "Oncodevelopmental expression of—GlcNAcβ1-6Manα1-6Manβ1—branched asparagine-linked oligosaccharides in murine tissues and human breast carcinomas," Feb. 15, 1989 *Cancer Res.* 49:945-50.

(Continued)

*Primary Examiner* — Mark Halvorson
(74) *Attorney, Agent, or Firm* — Mueting Raasch & Gebhardt, P.A.

(57) ABSTRACT

The invention relates to glycoproteins having a cancer-specific glycoform. Cancer-specific glycoforms are useful in diagnostics and therapeutics.

11 Claims, 16 Drawing Sheets

(56) References Cited

OTHER PUBLICATIONS

Desruisseau et al., "Determination of TGFβ1 protein level in human primary breast cancers and its relationship with survival," Jan. 30, 2006 *Br. J. Cancer* 94:239-46.

Fernandes et al., "β1-6 Branched oligosaccharides as a marker of tumor progression in human breast and colon neoplasia," Jan. 15, 1991 *Cancer Res.* 51:718-723.

Gillan et al., "Periostin secreted by epithelial ovarian carcinoma is a ligand for αVβ3 and αVβ5 integrins and promotes cell motility," Sep. 15, 2002 *Cancer Res.* 62:5358-5364.

Gomis et al., "C/EBPβ at the core of the TGFβ cytostatic response and its evasion in metastatic breast cancer cells," Sep. 2006 *Cancer Cell* 10:203-14.

Grigoriadis et al., "Establishment of the epithelial-specific transcriptome of normal and malignant human breast cells based on MPSS and array expression data," Oct. 2, 2006 *Breast Cancer Res* 8:R56; 15 pages.

Guo et al., "Aberrant N-glycosylation of β1 integrin causes reduced α5β1 integrin clustering and stimulates cell migration," Dec. 1, 2002 *Cancer Res.* 62:6837-6845.

Guo et al., "N-acetylglucosaminyltransferase V expression levels regulate cadherin-associated homotypic cell-cell adhesion and intracellular signaling pathways," Dec. 26, 2003 *J. Biol. Chem.* 278:52412-52424. Available online on Oct. 15, 2003.

Guo et al., "Inhibition of a specific N-glycosylation activity results in attenuation of breast carcinoma cell invasiveness-related phenotypes: inhibition of epidermal growth factor-induced dephosphorylation of focal adhesion kinase," Jul. 27, 2007 *J Biol. Chem.* 282:22150-22162. Available online on May 30, 2007.

Handerson et al., "β1,6-branched oligosaccharides are increased in lymph node metastases and predict poor outcome in breast carcinoma," Apr. 15, 2005 *Clin. Cancer Res.* 11:2969-73.

Hayat et al., "Cancer statistics, trends, and multiple primary cancer analyses from the Surveillance, Epidemiology, and End Results (SEER) Program," Jan. 2007 *Oncologist* 12:20-37.

Huse et al., "Generation of a large combinatorial library of the immunoglobulin repertoire in phage lambda," Dec. 1989 *Science* 246:1275-1281.

Inamori et al., "N-Acetylglucosaminyltransferase IX acts on the GlcNAcβ1,2-Manα1-Ser/Thr moiety, forming a 2,6-branched structure in brain O-mannosyl glycan," Jan. 23, 2004 *J. Biol. Chem.* 279:2337-2340. Available online on Nov. 14, 2003.

Kang and Massague, "Epithelial-mesenchymal transitions: twist in development and metastasis," Aug. 4, 2004 *Cell* 118:277-9.

Kobata and Amano, "Altered glycosylation of proteins produced by malignant cells, and application for the diagnosis and immunotherapy of tumours," Aug. 2005 *Immunol. Cell Biol.* 83:429-439.

Kohler and Milstein, "Continuous cultures of fused cells secreting antibody of predefined specificity," Aug. 7, 1975 *Nature* 256:495-497.

Kuhajda et al., "Expression of haptoglobin-related protein and its potential role as a tumor antigen," Feb. 1989 *Proc. Natl. Acad. Sci. USA* 86:1188-92.

Kui Wong et al., "Characterization of the oligosaccharides associated with the human ovarian tumor marker CA125," Aug. 1, 2003 *J. Biol. Chem.* 278:28619-28634. Available online on May 6, 2003.

Lagana et al., "Galectin binding to Mgat5-modified N-glycans regulates fibronectin matrix remodeling in tumor cells," Apr. 2006 *Mol. Cell Biol.* 26:3181-93.

Lau et al., "Complex N-glycan number and degree of branching cooperate to regulate cell proliferation and differentiation," Apr. 6, 2007 *Cell* 129:123-134.

Lee, "GRP78 induction in cancer: therapeutic and prognostic implications," Apr. 15, 2007 *Cancer Res.* 67:3496-3499.

Massague and Gomis, "The logic of TGFbeta signaling," May 22, 2006 *FEBS Lett.* 580:2811-20. Available online on Apr. 21, 2006.

Nairn et al., "Regulation of glycan structures in animal tissues: transcript profiling of glycan-related genes," Jun. 20, 2008 *J. Biol. Chem.* 283:17298-17313. Available online on Apr. 14, 2008.

Norris et al., "Identification and detection of the periostin gene in cardiac development," Dec. 2004 *Anat. Rec. A* 281:1227-33.

Orlandi et al., "Cloning immunoglobulin variable domains for expression by the polymerase chain reaction," May 1989 *Proc. Nat'l Acad. Sci. USA* 86: 3833-3837.

Orsulic et al., "Induction of ovarian cancer by defined multiple genetic changes in a mouse model system," Feb. 2002 *Cancer Cell* 1:53-62.

Ozols et al., "Focus on epithelial ovarian cancer," Jan. 2004 *Cancer Cell* 5:19-24.

Pierce, James Michael, "GLCNACT-V Regulation of Cell Surface Structure/Function," Grant Abstract, Grant No. R01CA064462. National Cancer Institute, National Institutes of Health. Project dates Sep. 30, 1995 to Feb. 28, 2011. Available online [retrieved on Jul. 18, 2012]. Retrieved from the Internet: <http://projectreporter.nih.gov/pr_Prj_info_desc_dtls.cfm?aid=7576910&icde=13165614&ddparam=&ddvalue=&ddsub=&cr=1&csb=default&cs=ASC&print=yes >; 2 pages.

Pierce, James Michael, "Tumor Glycomics Laboratory for Discovery of Pancreatic Cancer Markers," Grant Abstract, Grant No. U01CA128454. National Cancer Institute, National Institutes of Health. Project dates Jul. 25, 2007 to Jun. 30, 2012. Available online [retrieved on Jul. 18, 2012]. Retrieved from the Internet: <http://projectreporter.nih.gov/pr_Prj_info_desc_dtls.cfm?aid=8106193&icde=13165568&ddparam=&ddvalue=&ddsub=&cr=1&csb=default&cs=ASC&print=yes >; 2 pages.

Pierce and Arango, "Rous sarcoma virus-transfolined baby hamster kidney cells express higher levels of asparagine-linked tri- and tetraantennary glycopeptides containing [GlcNAc-β(1,6)Man-α(1,6)Man] and poly-N-acetyllactosamine sequences than baby hamster kidney cells," Aug. 15, 1986 *J. Biol. Chem.* 261:10772-10777.

Reinboth et al., "βig-h3 interacts directly with biglycan and decorin, promotes collagen VI aggregation, and participates in ternary complexing with these macromolecules," Mar. 24, 2006 *J. Biol. Chem.* 281:7816-24. Available online on Jan. 24, 2006.

Ruhl et al., "Soluble collagen VI drives serum-starved fibroblasts through S phase and prevents apoptosis via down-regulation of Bax," Nov. 26, 1999 *J. Biol. Chem.* 274:34361-8.

Saldova et al., "Ovarian cancer is associated with changes in glycosylation in both acute-phase proteins and IgG," Dec. 2007 *Glycobiology* 17:1344-1356. Available online on Sep. 20, 2007.

Seales et al., "Ras oncogene directs expression of a differentially sialylated, functionally altered beta1 integrin," Oct. 16, 2003 *Oncogene* 22:7137-7145.

Sellers et al., "Association of single nucleotide polymorphisms in glycosylation genes with risk of epithelial ovarian cancer," Feb. 2008 *Cancer Epidemiol. Biomarkers Prev.* 17:397-404.

Seppo et al., "Zwitterionic and acidic glycosphingolipids of the *Drosophila melanogaster* embryo," Jun. 2000 *Eur. J Biochem.* 267:3549-58.

Shao et al., "Acquired expression of periostin by human breast cancers promotes tumor angiogenesis through up-regulation of vascular endothelial growth factor receptor 2 expression," May 2004 *Mol. Cell Biol.* 24:3992-4003.

Shibukawa et al., "Down-regulation of hydrogen peroxide-induced PKCδ activation in N-acetylglucosaminyltransferase III-transfected HeLaS3 cells," Jan. 31, 2003 *J. Biol. Chem.* 278:3197-3203. Available online on Nov. 8, 2002.

Shin et al., "Global profiling of the cell surface proteome of cancer cells uncovers an abundance of proteins with chaperone function," Feb. 28, 2003 *J. Biol. Chem.* 278:7607-7616. Available online on Dec. 18, 2002.

Singer et al., "Optimal humanization of 1B4, an anti-CD18 murine monoclonal antibody, is achieved by correct choice of human V-region framework sequences," Apr. 1, 1993 *J. Immun.* 150: 2844-57.

Storey et al., "Endometrioid epithelial ovarian cancer: 20 years of prospectively collected data from a single center," May 2008 *Cancer* 112:2211-2220.

(56) References Cited

OTHER PUBLICATIONS

Taniguchi et al., "Remodeling of cell surface glycoproteins by N-acetylglucosaminyltransferase III gene transfection: modulation of metastatic potentials and down regulation of hepatitis B virus replication," Oct. 1996 *Glycobiology* 6:691-694.
Tao et al., "Lectin microarrays identify cell-specific and functionally significant cell surface glycan markers," Oct. 2008 *Glycobiology* 18(10):761-769. Available online on Jul. 14, 2008.
Verhoeyen et al., "Reshaping human antibodies: grafting an antilysozyme activity," Mar. 25, 1988 *Science* 239:1534-6.
Wang et al., "Core fucosylation regulates epidermal growth factor receptor-mediated intracellular signaling," Feb. 3, 2006 *J. Biol. Chem.* 281:2572-2577. Available online on Nov. 29, 2005.
Warrenfeltz et al., "Gene expression profiling of epithelial ovarian tumours correlated with malignant potential," Oct. 7, 2004 *Mol. Cancer* 3:27; 17 pages.
Wimmerova et al., "Crystal structure of fungal lectin: six-bladed beta-propeller fold and novel fucose recognition mode for *Aleuria aurantia* lectin," Jul. 18, 2003 *J. Biol. Chem.* 278:27059-27067. Available online on May 5, 2003.
Yamashita et al., "Carbohydrate binding properties of complex-type oligosaccharides on immobilized *Datura stramonium* lectin," Feb. 5, 1987 *J. Biol. Chem.* 262:1602-1607.
Yang et al., "Twist, a master regulator of morphogenesis, plays an essential role in tumor metastasis," Jun. 25, 2004 *Cell* 117:927-39.
Yang et al., ","Multilectin affinity chromatography for characterization of multiple glycoprotein biomarker candidates in serum from breast cancer patients Oct. 2006 *Clin. Chem.* 52:1897-1905. Available online on Aug. 17, 2006.
Yoshimura et al., "Suppression of lung metastasis of B16 mouse melanoma by N-acetylglucosaminyltransferase III gene transfection," Sep. 12, 1995 *Proc. Natl. Acad. Sci. USA* 92:8754-8758.
Cummings and Etzler, "Antibodies and Lectins in Glycan Analysis," in *Essentials of Glycobiology Second Edition*, Varki et al. (Eds.); Cold Spring Harbor Press: Cold Spring Harbor, NY; 2009. Title page, publisher's page, table of contents, and pp. 633-648. Available online [retrieved on Feb. 1, 2013]; retrieved from the Internet: <www.ncbi.nlm.nih.gov/books/NBK1908/>; 22 pages.
Di Virgilio, "High performance lectin affinity chromatography for fractionation and sequence determination of oligosaccharides," paper presented at the *17th International Lectin Meeting* in Wurzburg, Germany; Sep. 24-27, 1997. Paper available online [retrieved on Nov. 11, 2008]; retrieved from the Internet: <plab.ku.dk/tcbh/Lectins12/DiVirgilio/paper.htm>; 28 pages.
Di Virgilio, "The synthesis of oligo-N-acetyllactosamines and their interaction with galectin-1, as studied by proton NMR," meeting abstract No. 27. *17th International Lectin Meeting* in Wurzburg, Germany; Sep. 24-27, 1997. Proceedings published in: *Eur. J. Cell. Biol.* Suppl. 46(vol. 74):9.
Di Virgilio et al., "Enzymatic synthesis of natural and $^{13}C$ enriched linear poly-N-acetyllactosamines as ligands for galectin-1," Apr. 1999 *Glycobiology* 9:353-364.
Mechref et al., "Glycoprotein enrichment through lectin affinity techniques," in *Methods Mol. Biol. Volume 454 2D PAGE: Sample Preparation and Fractionation* (Anton Posch, Ed.) Humana Press: Totowa, NJ; 2008. Cover page, publisher's page and pp. 373-396.
Pierce, "Cancer Glycomics," in *Handbook of Glycomics* (Cummings and Pierce, Eds). Elsevier Inc., San Diego: 2009. pp. 399-429.
Taeda et al., "Expression of L-PHA-binding proteins in breast cancer: reconstitution and molecular characterization of β1-6 branched oligosaccharides in three-dimensional cell culture," 1996 *Breast Cancer Research and Treatment* 38:313-324.
Abbott et al., "Evidence for Nuclear Factor-KappaB-Mediated Transcriptional Regulation of the β1,6-N-Acetylglucosaminyltransferase GnT-VB," Meeting abstract #190; presented at the *2005 Meeting of the Society for Glycobiology*; Nov. 9-12, 2005: Boston, MA. Published in Nov. 2005 *Glycobiology* 15:1234.
Abbott et al., "GnT-Vb Expression Increases O-Mannosyl-Linked HNK-1 Epitope Leading to Changes in Neuronal Cell Adhesion and Migration," Meeting Abstract #36 presented at the *2006 Meeting of the Society for Glycobiology*; Nov. 15-19, 2006: Universal City, CA. Published in Nov. 2006 *Glycobiology* 16:1111.
Abbott et al., "Integrin-dependent neuroblastoma cell adhesion and migration on laminin is regulated by expression levels of two enzymes in the O-mannosyl-linked glycosylation pathway, PomGnT1 and GnT-Vb," Sep. 10, 2006 *Exp. Cell Res.* 312:2837-2850. Available online on Jun. 21, 2006.
Abbott et al., "Identification of Glycoproteins Associated with Invasive Human Breast Cancer Using Lectin Glycoproteomics," poster presented at *Advances in Proteomics in Cancer Research* (sponsored by the American Associate for Cancer Research): Feb. 27-Mar. 2, 2007; Amelia Island, FL.
Abbott et al., "Targeted glycoproteomic identification of biomarkers for human breast carcinoma," Apr. 2008 *J. Prot. Res.* 7(4):1470-1480. Available online on Feb. 14, 2008.
Abbott et al., Supporting Information for "Targeted glycoproteomic identification of biomarkers for human breast carcinoma," Apr. 2008 *J. Prot. Res.* 7(4):1470-1480. Available online at: <http://pubs.acs.org/doi/suppl/10.1021/pr700792g/suppl_file/pr700792g-file004.pdf>; 5 pages.
Abbott et al., "Receptor tyrosine phosphatase β (RPTPβ) activity and signaling are attenuated by glycosylation and subsequent cell surface galectin-1 binding," Nov. 28, 2008 *J. Biol. Chem.* 283:33026-35. Available online on Oct. 6, 2008.
Abbott et al, "Identification of candidate biomarkers with cancer-specific glycosylation in the tissue and serum of endometrioid ovarian cancer patients by glycoproteomic analysis," Feb. 2010 *Proteomics* 10:470-481.
Akama et al., "N-acetylglucosaminyltransferase III expression is regulated by cell-cell adhesion via the E-cadherin-catenin-actin complex," Aug. 2008 *Proteomics* 8: 3221-3228.
An et al., "Profiling of glycans in serum for the discovery of potential biomarkers for ovarian cancer," Jul. 2006 *J. Proteome Res.* 5:1626-1635.
Brooks et al., "Validation of a simple avidin-biotin detection method for Helix pomatia lectin (HPA) binding as a prognostic marker in cancer," Jan. 1, 2003 *Acta Histochemica* 105:205-212.
Chen et al., "The her-2/neu oncogene stimulates the transcription of N-acetylglucosaminyltransferase V and expression of its cell surface oligosaccharide products," Oct. 22, 1998 *Oncogene* 17:2087-2093.
Cho et al., "Use of glycan targeting antibodies to identify cancer-associated glycoproteins in plasma of breast cancer patients," Jul. 15, 2008 *Anal. Chem.* 80:5286-5292. Available online on Jun. 18, 2008.
Ciucanu and Costello, "Elimination of oxidative degradation during the per-O-methylation of carbohydrates," Dec. 31, 2003 *J. Am. Chem. Soc.* 125:16213-9.
Clarke-Pearson, "Clinical practice. Screening for ovarian cancer," Jul. 9, 2009 *N. Engl. J. Med.* 361:170-177.
Comunale et al., "Identification and development of fucosylated glycoproteins as biomarkers of primary hepatocellular carcinoma," Feb. 2009 *J. Prot. Res.* 8: 595-602.
Danes et al., "14-3-3 zeta down-regulates p53 in mammary epithelial cells and confers luminal filling," Mar. 15, 2008 *Cancer Res.* 68:1760-1767.
De Santis et al., "E-cadherin directly contributes to PI3K/AKT activation by engaging the PI3K-p85 regulatory subunit to adherens junctions of ovarian carcinoma cells," Mar. 5, 2009 *Oncogene* 28: 1206-1217. Available online on Jan. 19, 2009.
Dinulescu et al., "Role of K-ras and Pten in the development of mouse models of endometriosis and endometrioid ovarian cancer," Jan. 2005 *Nat. Med.* 11:63-70. Available online on Dec. 26, 2004.
Droguett et al., "Extracellular proteoglycans modify TGF-beta bioavailability attenuating its signaling during skeletal muscle differentiation," Aug. 2006 *Matrix Biol.* 25:332-41. Available online on Apr. 27, 2006.
Fawcett et al., "Identification of the products of the haptoglobin-related gene," Apr. 6, 1990 *Biochim Biophys Acta* 1048:187-93.
Freire et al., "Enzymatic large-scale synthesis of MUC6-Tn glycoconjugates for antitumor vaccination," May 1, 2006 *Glycobiology* 16:390-401. Available online on Jan. 31, 2006.
Fry et al., "Cancer-associated glycoforms of gelatinase B exhibit a decreased level of binding to galectin-3," Dec. 26, 2006 *Biochem.* 45:15249-15258. Available online on Dec. 6, 2006.

(56) References Cited

OTHER PUBLICATIONS

Fu et al., "14-3-3 proteins: structure, function, and regulation," 2000 *Annu. Rev. Pharmacol. Toxicol.* 40:617-47.

Guo et al., "Opposing changes in N-acetylglucosaminyltransferase-V and -III during the cell cycle and all-trans retinoic acid treatment of hepatocarcinoma cell line," Feb. 28, 2000 *Biochim. Biophys. Acta* 1495:297-307.

Hakomori, "Antigen structure and genetic basis of histo-blood groups A, B and O: their changes associated with human cancer," Dec. 6, 1999 *Biochim. Biophys. Acta* 1473:247-266.

Harlow and Lane (Eds.), *Antibodies: A Laboratory Manual*. Cold Spring Harbor Laboratory: Cold Spring Harbor, NY; 1988. Cover page, publisher's page, and table of contents; 9 pages.

Hudelist et al., "Proteomic analysis in human breast cancer: identification of a characteristic protein expression profile of malignant breast epithelium," Mar. 2006 *Proteomics* 6:1989-2002.

Hufleijt et al., "Glycan array identifies specific signatures of antiglycan autoantibodies in sera of breast cancer patients: diagnostic, prognostic and therapeutic opportunities," Meeting Abstract No. 2008 from the *28th Annual San Antonio Breast Symposium*: Dec. 8-11, 2005. Published Dec. 1, 2005 *Breast Cancer Research and Treatment* 94(sup 1):585.

Irving et al., "Synchronous endometrioid carcinomas of the uterine corpus and ovary: alterations in the β-catenin (CTNNB1) pathway are associated with independent primary tumors and favorable prognosis," Jun. 2005 *Hum. Pathol.* 36:605-619.

Ishibashi et al., "N-acetylglucosaminyltransferase III in human serum, and liver and hepatoma tissues: increased activity in liver cirrhosis and hepatoma patients," Dec. 15, 1989 *Clin. Chim. Acta* 185:325-332.

Iskratsch et al., "Specificity analysis of lectins and antibodies using remodeled glycoproteins," Mar. 15, 2009 *Anal. Biochem.* 386:133-146. Available online on Dec. 14, 2008.

Jankovic and Milutinovic, "Glycoforms of CA125 antigen as a possible cancer marker," 2008 *Cancer Biomark.* 4:35-42.

Kamar et al., "Analysis of the site-specific N-glycosylation of beta1,6 N-acetylglucosaminyltransferase V," Jul. 2004 *Glycobiology* 14:583-592. Available online on Apr. 14, 2004.

Kaneko et al., "A novel beta(1,6)-N-acetylglucosaminyltransferase V (GnT-VB)(1)," Nov. 20, 2003 *FEBS Letters* 554:515-519.

Kelly et al. "Differential Lectin Binding Discrimiates Human Chorionic Gonadotropin (HCG) Produced During Pregnancy from that Produced During Choriocarcinoma," Meeting Abstract #LB-227 from the 2003 Annual Meeting of the AACR: Jul. 11-14, 2003; Washington, D.C. Published Jul. 11, 2003 *Proceedings of the Annual Meeting of the American Association for Cancer Research* 44:1373.

Kim and Varki, "Perspectives on the significance of altered glycosylation of glycoproteins in cancer," Aug. 1997 *Glycoconj. J.* 14:569-76.

Kim et al., "Lectin precipitation using phytohemagglutinin-L(4) coupled to avidin-agarose for serological biomarker discovery in colorectal cancer," Aug. 2008 *Proteomics* 8:3229-3235.

Kobata et al., "Structural changes induced in the sugar chains of glycoproteins by malignant transformation of producing cells and their clinical application," Nov. 1, 1988 *Biochimie* 70:1575-1585.

Kolasa et al., "PTEN mutation, expression and LOH at its locus in ovarian carcinomas. Relation to TP53, K-RAS and BRCA1 mutations," Nov. 2006 *Gynecol. Oncol.* 103:692-697. Available online on Jun. 21, 2006.

Kumar and Tatu, "Stress protein flux during recovery from simulated ischemia: induced heat shock protein 70 confers cytoprotection by suppressing JNK activation and inhibiting apoptotic cell death," Apr. 2003 *Proteomics* 3:513-526.

Lee et al., "The X-lectins: A new family with homology to the *Xenopus laevis* oocyte lectin XL-35," Aug. 2004 *Glycoconjugate J.* 21:443-450.

Lee et al., "A homolog of N-acetylglucosaminyltransferase V (GnT-V) Shows High Expression Levels in Mouse and Human Brain," Meeting abstract #342; presented at the *Joint Meeting of the Society for Glycobiology and the Japanese Society for Carbohydrate Research*; Nov. 17-20, 2004: Honolulu, HI. Published in Nov. 2004 *Glycobiology* 14:1149.

Lee et al., "N-acetylglucosaminyltranferase VB expression enhances β1 integrin-dependent PC12 neurite outgrowth on laminin and collagen," May 2006 *J. Neurochem.* 97:947-56. Available online on Apr. 5, 2006.

Lee et al., "A candidate precursor to serous carcinoma that originates in the distal fallopian tube," Jan. 2007 *J. Pathol.* 211:26-35.

Liu et al., "Human Plasma N-Glycoproteome Analysis by Immunoaffinity Subtraction, Hydrazide Chemistry, and Mass Spectrometry," Dec. 2005 *J. Proteome Res.* 4:2070-2080. Available online on Oct. 26, 2005.

Meezan et al., "Comparative studies on the carbohydrate-containing membrane components of normal and virus-transformed mouse fibroblasts. II. Separation of glycoproteins and glycopeptides by sephadex chromatography," Jun. 1969. *Biochemistry* 8:2518-2524.

Mehta and Block, "Fucosylated glycoproteins as markers of liver disease," 2008 *Dis. Markers* 25: 259-265.

Mitchell et al., "Do HPA and PHA-L have the same binding pattern in metastasizing human breast and colon cancer?" Jan. 16, 1998 *Cancer Lett.* 123:113-119.

Nagata et al., "Crystallization and characterization of a lectin obtained from a mushroom, *Aleuria aurantia*," Jan. 29, 1991 *Biochim. Biophys. Acta* 1076:187-190.

Nairn et al., "Glycomics of proteoglycan biosynthesis in murine embryonic stem cell differentiation," Nov. 2007 *J. Proteome Res.* 6:4374-4387. Available online on Oct. 4, 2007.

Nakagawa et al., "Glycomic analysis of alpha-fetoprotein L3 in hepatoma cell lines and hepatocellular carcinoma patients," Jun. 2008 *J. Proteome Res.* 7:2222-2233. Available online on May 15, 2008.

Nan et al., "Alteration of N-acetylglucosaminyltransferases in pancreatic carcinoma," Oct. 1998 *Glycoconj. J.* 15:1033-1037.

Oshima et al., "A novel mechanism for the regulation of osteoblast differentiation: transcription of periostin, a member of the fasciclin I family, is regulated by the bHLH transcription factor, twist," 2002 *J Cell Biochem.* 86:792-804.

Osumi et al., "Core fucosylation of E-cadherin enhances cell-cell adhesion in human colon carcinoma WiDr cells," May 2009 *Cancer Sci.* 100: 888-895. Available online on Mar. 11, 2009.

Peng et al., "Evaluation of multidimensional chromatography coupled with tandem mass spectrometry (LC/LC-MS/MS) for large-scale protein analysis: the yeast proteome," Jan.-Feb. 2003 *J. Proteome Res.* 2:43-50.

Pierce, James Michael, "Integrated Technology Resource for Biomedial Glycomics," Grant Abstract, Grant No. P41RR018502 [online]. National Center for Research Resources, National Institutes of Health. Project dates Sep. 1, 2003 to May 31, 2012. Available online [retrieved on Aug. 21, 2012]. Retrieved from the Internet: <http://projectreporter.nih.gov/pr_Prj_info_desc_dtls.cfm?aid=8310466&icde=13510635&ddparam=&ddvalue=&ddsub=&cr=1&csb=default&cs=ASC&print=yes >; 2 pgs.

Pierce, James Michael, "Breast Carcinoma Glycoprotein Changes Caused by Oncogene Expression," Grant Abstract, Grant No. P41RR018502; sub-Project ID: 0029 [online]. National Center for Research Resources, National Institutes of Health. Project dates Ju. 1, 2005 to Jun. 30, 2006. Available online [retrieved on Aug. 21, 2012]. Retrieved from the Internet: <http://projectreporter.nih.gov/pr_Pij_info_desc_dtls.cfm?aid=7183124&icde=13510635&ddparam=&ddvalue=&ddsub=&cr=45&csb=default&cs=ASC&print=yes>; 1 pg.

Pierce, James Michael, "Human Neuroblastoma Glycoproteins Expressing HNK-1 Epitope," Grant Abstract, Grant No. P41RR018502; sub-Project ID: 8840 [online]. National Center for Research Resources, National Institutes of Health. Project dates Jul. 1, 2007 to Jun. 30, 2008. Available online [retrieved on Aug. 21, 2012]. Retrieved from the Internet: <http://projectreporter.nih.gov/pr_Prj_info_desc_dtls.cfm?aid=7602798&icde=13510635&ddparam=&ddvalue=&ddsub=&cr=36&csb=default&cs=ASC&print=yes>; 1 pg.

(56) References Cited

OTHER PUBLICATIONS

Pierce, James Michael, "Breast Carcinoma Glycoprotein Changes Caused by Oncogene Expression," Grant Abstract, Grant No. P41RR018502; sub-Project ID: 8829 [online]. National Center for Research Resources, National Institutes of Health. Project dates Jul. 1, 2007 to Jun. 30, 2008. Available online [retrieved on Aug. 21, 2012]. Retrieved from the Internet: <http://projectreporter.nih.gov/pr_Prj_info_desc_dtls.cfm?aid=7602787&icde=13510635&ddparam=&ddvalue=&ddsub=&cr=31&csb=default&cs=ASC&print=yes>; 1 pg.

Pierce, James Michael, "Human Neuroblastoma Glycoproteins Expressing HNK-1 Epitope," Grant Abstract, Grant No. P41RR018502; sub-Project ID: 8739 [online]. National Center for Research Resources, National Institutes of Health. Project dates Aug. 8, 2008 to May 31, 2009. Available online [retrieved on Aug. 21, 2012]. Retrieved from the Internet: <http://projectreporter.nih.gov/pr_Prj_info_desc_dtls.cfm?aid=7722629&icde=13510635&ddparam=&ddvalue=&ddsub=&cr=27&csb=default&cs=ASC&print=yes>; 1 pg.

Pierce, James Michael, "Breast Carcinoma Glycoprotein Changes Caused by Oncogene Expression," Grant Abstract, Grant No. P41RR018502; sub-Project ID: 8730 [online]. National Center for Research Resources, National Institutes of Health. Project dates Aug. 8, 2008 to May 31, 2009. Available online [retrieved on Aug. 21, 2012]. Retrieved from the Internet: <http://projectreporter.nih.gov/pr_Prj_info_desc_dtls.cfm?aid=7722620&icde=13510635&ddparam=&ddvalue=&ddsub=&cr=22&csb=default&cs=ASC&print=yes>; 1 pg.

Pierce, James Michael, "Breast Carcinoma Glycoprotein Changes Caused by Oncogene Expression," Grant Abstract, Grant No. P41RR018502; sub-Project ID: 6227 [online]. National Center for Research Resources, National Institutes of Health. Project dates Jun. 1, 2009 to May 31, 2010. Available online [retrieved on Aug. 21, 2012]. Retrieved from the Internet: <http://projectreporter.nih.gov/pr_Prj_info_desc_dtls.cfm?aid=7955988&icde=13510635&ddparam=&ddvalue=&ddsub=&cr=15&csb=default&cs=ASC&print=yes>; 1 pg.

Pierce, James Michael, "Identification of a Pancreatic Carcinoma-Specific N-Linked Glycan Epitope," Grant Abstract, Grant No. P41RR018502; sub-Project ID: 7233 [online]. National Center for Research Resources, National Institutes of Health. Project dates Jun. 1, 2011 to May 31, 2012. Available online [retrieved on Aug. 21, 2012]. Retrieved from the Internet: <http://projectreporter.nih.gov/pr_Prj_info_desc_dtls.cfm?aid=8363124&icde=13510635&ddparam=&ddvalue=&ddsub=&cr=8&csb=default&cs=ASC&print=yes>; 1 pg.

Pierce, James Michael, "Identification of Potential Glycan Markers of Mouse Mammary Cancer Stem Cells," Grant Abstract, Grant No. P41RR018502; sub-Project ID: 7231 [online]. National Center for Research Resources, National Institutes of Health. Project dates Jun. 1, 2011 to May 31, 2012. Available online [retrieved on Aug. 21, 2012]. Retrieved from the Internet: <http://projectreporter.nih.gov/pr_Prj_info_desc_dtls.cfm?aid=8363122&icde=13510635&ddparam=&ddvalue=&ddsub=&cr=6&csb=default&cs=ASC&print=yes>; 1 pg.

Pierce, James Michael, "Comparing Glycans of HER-2 Mouse Mammary Tumors to Non-Diseased Mammary Tissue," Grant Abstract, Grant No. P41RR018502; sub-Project ID: 7230 [online]. National Center for Research Resources, National Institutes of Health. Project dates Jun. 1, 2011 to May 31, 2012. Available online [retrieved on Aug. 21, 2012]. Retrieved from the Internet: <http://projectreporter.nih.gov/pr_Prj_info_desc_dtls.cfm?aid=8363121&icde=13510635&ddparam=&ddvalue=&ddsub=&cr=5&csb=default&cs=ASC&print=yes>; 1 pg.

Pierce et al., "Regulation of N-acetylglucosaminyltransferase V and Asn-linked oligosaccharide β(1,6) branching by a growth factor signaling pathway and effects on cell adhesion and metastatic potential," Aug. 1997 *Glycoconj. J.* 14:623-630.

Pierce, "Discover of Cancer Markers Using Glycoproteomics," Slides accompanying Oral Presentation from Georgia Cancer Coalition Symposium; May 12, 2008: Atlanta, GA. Available online [retrieved Aug. 14, 2012]. Meeting Agenda retrieved from the Internet: <http://www.georgiacancer.org/res-symp-agenda.php>; Slides retrieved from the Internet: <http://www.georgiacancer.org/res-symposium/glycoproteomics.pdf>; 25 pages total.

Pucci-Minafra et al., "Expanding the protein catalogue in the proteome reference map of human breast cancer cells," Apr. 2006 *Proteomics* 6:2609-25.

Puglisi et al., "Expression of periostin in human breast cancer," 2008 *J. Clin. Path.* 61:494-498. Available online on Oct. 15, 2007.

Saldova et al., "Glycosylation changes on serum glycoproteins in ovarian cancer may contribute to disease pathogenesis," 2008 *Dis. Markers* 25:219-232.

Smith et al., "Patterns of Expression of the DS6-Glycoform of Muc1 Correlates with Known Prognostic Indicators in Breast Cancer," Meeting Abstract #1051 from the 2004 Annual Meeting of the AACR: Mar. 27-31, 2004; Orlando, FL. Published Jan. 1, 2004 *Proceedings of the Annual Meeting of the American Association for Cancer Research* 45:239.

Sodek et al., "Identification of pathways associated with invasive behavior by ovarian cancer cells using multidimensional protein identification technology (MudPIT)," Jul. 2008 *Mol. Biosyst.* 4:762-773. Available online on Apr. 17, 2008.

Srivastava et al., "Recognition of oligosaccharide substrates by N-acetyl-glucosaminyltransferase-V," Aug. 15, 1988 *Carbohydrate Res.* 179:137-161.

Stanley, "Biological consequences of overexpressing or eliminating N-acetylglucosaminyltransferase-TIII in the mouse," Dec. 19, 2002 *Biochim. Biophys. Acta* 1573:363-368.

Tabb et al., "MyriMatch: highly accurate tandem mass spectral peptide identification by multivariate hypergeometric analysis," Feb. 2007 *J. Proteome Res.* 6:654-661.

Takahashi et al., "α1,6fucosyltransferase is highly and specifically expressed in human ovarian serous adenocarcinomas," Dec. 15, 2000 *Int. J. Cancer* 88:914-919.

Takahashi et al., "Core fucose and bisecting GlcNAc, the direct modifiers of the N-glycan core: their functions and target proteins," Aug. 17, 2009 *Carbohydr. Res.* 344: 1387-1390. Available online on May 4, 2009.

Tiemeyer, Michael, "Mechanisms Regulating Glycan Expression and Function," Grant Abstract, Grant No. R01GM072839 [online] National Institute of General Medical Sciences, National Institutes of Health. Project dates Jul. 1, 2005 to Jun. 30, 2010. Available online [retrieved on Aug. 21, 2012]. Retrieved from the Internet: <http://projectreporter.nih.gov/pr_Prj_info_desc_dtls.cfm?aid=7468449&icde=13511220&ddparam=&ddvalue=&ddsub=&cr=1&csb=default&cs=ASC&print=yes>; 2 pgs.

Wang et al., "Altered mRNA expressions of sialyltransferases in ovarian cancers," Dec. 2005 *Gynecologic Oncol.* 99:631-639. Available online on Aug. 19, 2005.

Wang et al., "Phenotype changes of Fut8 knockout mouse: core fucosylation is crucial for the function of growth factor receptor(s)," 2006 *Methods Enzymol.* 417:11-22.

Winter and Harris, "Humanized antibodies," Jun. 1993 *Immunol. Today* 14:243-246.

Yamamoto et al., "β1,6-N-acetylglucosamine-bearing N-glycans in human gliomas: implications for a role in regulating invasivity," Jan. 1, 2000 *Cancer Res.* 60:134-142.

Yates et al., "Method to correlate tandem mass spectra of modified peptides to amino acid sequences in the protein database," Apr. 15, 1995 *Anal. Chem.* 67:1426-36.

Yeung et al., "Glucose-regulated protein 78 as a novel effector of BRCA1 for inhibiting stress-induced apoptosis," Dec. 4, 2008 *Oncogene* 27:6782-6789. Available online on Sep. 8, 2008.

Zhang et al., "Proteomic parsimony through bipartite graph analysis improves accuracy and transparency," Sep. 2007 *J. Proteome Res.* 6:3549-57. Available online on Aug. 4, 2007.

(56) References Cited

OTHER PUBLICATIONS

Zhao et al., "Comparative serum glycoproteomics using lectin selected sialic acid glycoproteins with mass spectrometric analysis: application to pancreatic cancer serum," Jul. 2006 *J. Proteome Res.* 5:1792-802.

International Preliminary Report on Patentability issued Jun. 15, 2010, in regard to International Patent Application No. PCT/US2008/013658, filed Dec. 12, 2008.

International Search Report mailed Jun. 22, 2009, in regard to International Patent Application No. PCT/US2008/013658, filed Dec. 12, 2008.

Written Opinion of the International Searching Authority mailed Jun. 22, 2009, in regard to International Patent Application No. PCT/US2008/013658, filed Dec. 12, 2008.

* cited by examiner

GLYCOPROTEIN CANCER BIOMARKER

CONTINUING APPLICATION DATA

This application is a continuation-in-part of International Application PCT/US2008/013658, with an international filing date of Dec. 12, 2008, which in turn claims the benefit of U.S. Provisional Application Ser. No. 61/007,442, filed Dec. 12, 2007, each of which is incorporated by reference herein.

STATEMENT OF GOVERNMENT RIGHTS

This invention was made with government support under grants from the National Center for Research Resources of the National Institutes of Health (Grant No. P41RR018502) and the National Cancer Institute of the National Institutes of Health (Grant Nos. RO1CA064462 and UO1CA128454). The U.S. Government has certain rights in this invention.

BACKGROUND

Breast carcinoma is the second leading cause of cancer deaths among women in the U.S. (Jemal et al., 2005. *CA Cancer J Clin* 55:10-30). Early detection and diagnosis of breast cancer significantly improves 5-year survival rates (Ries et al., 2005. SEER Cancer statistics review. National Cancer Institute, Bethesda, Md.). Currently the only approved screening method for the detection for breast cancer is mammography.

In the past few years, several large-scale proteomic studies have begun to characterize the proteome of breast cancer (Pucci-Minafra et al., 2006. *Proteomics* 6:2609-25; Celis et al., 2004. *Mol Cell Proteomics* 3:327-44; Hudelist et al., 2006. *Proteomics* 6:1989-2002). This high-throughput strategy leads to complex data sets that, while rich in information, are often not very useful in predicting proteins that may be sensitive and specific biomarkers for the disease.

Epithelial ovarian cancer is the deadliest reproductive tract malignancy of women in Western countries (Ozols et al., 2004. *Cancer Cell* 5:19-24). Ovarian cancer survival rates at years are only 30% for women diagnosed with distant metastases; however, the percentage survival climbs to 90% for women diagnosed with disease confined to the ovary (Hayat et al., 2007. *Oncologist* 12:20-37). Unfortunately, fewer than 25% of women are diagnosed when the disease is confined, due primarily to the lack of screening tests capable of detecting ovarian cancers early.

Reliable biomarkers are not available for the majority of cancers and precancerous conditions. Specifically, there is a lack of secreted biomarkers that can be detected through non-invasive assays such as blood tests. Without convenient and easily accessible screening tests for cancers and precancerous conditions, diagnostic delays will continue to plague the health care system and thwart efforts to detect and treat malignancies in their earliest stages.

SUMMARY OF THE INVENTION

The present invention is directed to cancer biomarkers, particularly glycoprotein biomarkers. A preferred cancer biomarker according to the invention is a cancer-specific glycoform of a glycoprotein. The present invention additionally provides methods for identifying glycoproteins possessing a cancer-specific glycoform, as well as diagnostic and therapeutic methods and compositions related to glycoprotein cancer biomarkers. Cancer biomarkers of the invention can be specific for any cancer, without limitation. Preferred cancer biomarkers and are specific for breast cancer, ovarian cancer, colorectal cancer, pancreatic cancer and liver cancer.

In one aspect, the invention provides a diagnostic method for evaluating the presence, absence, nature or extent of cancer or a precancerous condition in a subject. The subject can be any mammalian subject, and is preferably a human or a domestic animal. In one embodiment, the diagnostic method involves detecting the presence of a cancer-specific glycoform of a glycoprotein in a biological sample obtained from the subject, wherein the cancer-specific glycoform comprises glycan that is indicative of the presence of cancer or a precancerous condition. The biological sample can include, without limitation a biological fluid, such as blood, serum or plasma, or it can be a tissue or organ sample.

Any convenient method can be used to detect the cancer-specific glycoform. In one embodiment, the cancer-specific glycoform can be detected by contacting the biological sample with a glycan-binding molecule specific for the glycan, under conditions that permit binding of the cancer-specific glycoform of the glycoprotein to the glycan-binding molecule. Exemplary and preferred glycan-binding molecules include a lectin, a glycospecific antibody, a glycospecific aptamer, a glycospecific peptide, and a glycospecific small molecule. In other embodiments, other detection methods can be used, for example mass analysis methods such mass spectrometry.

In an embodiment of the diagnostic method wherein cancer or a precancerous condition of the breast is evaluated, exemplary glycoprotein breast cancer biomarkers include glycoproteins set forth in Table 4, including periostin and osteoglycin. Examples of glycans that can be detected on a breast cancer-specific glycoprotein glycoform include a GlcNAc β(1,6) Man branched N-linked glycan and a branched N-linked glycan extended with N-acetyllactosamine. A preferred glycan-binding molecule for use in evaluating breast cancer is the lectin leukoagglutinating phytohemagglutinin (L-PHA).

In an embodiment of the diagnostic method wherein cancer or a precancerous condition of the ovary is evaluated, exemplary glycoprotein ovarian cancer markers include glycoproteins set forth in Table 8. Examples of glycans that can be detected on an ovarian cancer-specific glycoprotein glycoform include a glycan containing α(1,6)-fucose linked to core N-acetylglucosamine (core fucosylation), and a GlcNAc β(1, 4) Man bisected N-linked glycan. Preferred glycan-binding molecules for use in evaluating ovarian cancer include erythroagglutinating phytohemagglutinin (E-PHA), *Aleuria aurantia* lectin (AAL) and *Datura stramonium* lectin (DSL).

In another aspect, the invention provides a method for identifying a biomarker associated with cancer. In one embodiment, a biological test sample from a subject having cancer or a precancerous condition is contacted with a glycan-binding molecule specific for a glycan, under conditions that permit binding of the glycan-binding molecule to the glycan, when present, yielding a bound glycoprotein/glycan-binding molecule complex. The biological sample is preferably a tissue or organ sample; for example obtained from a cancerous tumor.

A reference or control sample (a noncancerous biological sample) is preferably analyzed and compared with the test sample from the subject with cancer or a precancerous condition. The noncancerous biological sample can be from the same subject, a different subject, or it can be a pooled sample from a number of disease-free subjects. The noncancerous biological sample can be contacted with the glycan-binding molecule specific for the glycan, under conditions that permit binding of the glycan-binding molecule to the glycan, when present, to yield a bound glycoprotein/glycan-binding molecule complex. The presence of a cancer-specific glycoform can be evaluated by determining whether the amount of bound glycoprotein from the tumor sample is greater than the amount of bound glycoprotein from the noncancerous sample, wherein a greater amount in the tumor sample indicates the presence of a cancer-specific glycoform of the glycoprotein. Preferred glycan-binding molecules include those that are preferred for use in the diagnostic method of the invention, but are not limited thereto. Preferred glycans that can be detected with a glycan-binding molecule according to the identification method of the invention a GlcNAc β(1,6) Man branched N-linked glycan, a GlcNAc β(1,4) Man bisected N-linked glycan, a glycan containing α(1,6) fucose linked to a core N-acetylglucosamine, and a branched N-linked glycan extended with N-acetyllactosamine.

In another aspect, the invention includes glycoprotein cancer biomarkers identified using methods as described herein. Exemplary glycoprotein cancer biomarkers are set forth in Tables 4 and 6, and include a cancer-specific glycoform of periostin, preferably including a GlcNAc β(1,6) Man branched N-linked glycan component, and a cancer-specific glycoform of osteoglycin, preferably including GlcNAc β(1, 6) Man branched N-linked glycan component. Cancer-specific glycoforms of glycoproteins included in the present invention include but are not limited to cancer-specific glycoforms possessing one or more of the following glycan components or structural features: a GlcNAc β(1,6) Man branched N-linked glycan component and a branched N-linked glycan extended with N-acetyllactosamine, a GlcNAc β(1,4) Man bisected N-linked glycan component, and an α(1,6) fucose linked to a core N-acetylglucosamine.

The diagnostic methods of the invention and the biomarker identification method of the invention are both amenable to multiplexing. For example, a multiplexed diagnostic method for evaluating the presence, absence, nature or extent of cancer or a precancerous condition in a subject can include providing a biological sample obtained from the subject, wherein the biological sample includes a plurality of glycoproteins; and, for each of the plurality of glycoproteins, determining the presence, absence or amount of a cancer-specific glycoform of the glycoprotein in the biological sample, wherein the presence, absence or amount of the cancer-specific glycoform is indicative of cancer or a precancerous condition. In a multiplexed breast cancer diagnostic method, preferably the plurality of glycoproteins evaluated includes at least two proteins independently selected from the proteins set forth in Table 4. More preferably, the multiplexed breast cancer detection method detects cancer-specific glycoforms of periostin and osteoglycin. In a multiplexed ovarian cancer diagnostic method, preferably the plurality of glycoproteins evaluated includes at least two proteins independently selected from the proteins set forth in Table 8.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 18A is a lectin blot analysis of POSTN immunoprecipitations. POSTN was immunoprecitated from 500 μg of total cell lysate using a polyclonal antibody (Abeam, Cambridge, Mass.) prior to separation on 4-12% polyacrylamide gel and transfer to PVDF membrane. Blots were probed with biotinylated lectins (1:5,000) and detected using streptavidin coupled horseradish peroxidase (1:5,000) and chemiluminescent development. FIG. 18B is a lectin blot analysis of LAMP-1 immunoprecipitation reactions. LAMP-1 was immunoprecipitated from 500 μg of total cell lysates (normal-NL, and tumor-TU) using a monoclonal antibody (E-Biosciences, San Diego, Calif.) detected by lectin blot as described above.

FIG. 19A is a visualization of normalized microarray data (performed at the Georgia Institute of Technology and The Ovarian Cancer Institute) for glycoproteins from Table 10 selected for possible serum validation. The averaged fold-increase in expression levels in tumor tissue relative to normal tissue are shown below. Gene name abbreviations and IPI accessions are provided in Table 10. FIG. 19B shows a Western blot analysis of serum lectin precipitation reactions. The following antibodies were used: POSTN (Abeam, 1:1,000), THBS1 (Santa Cruz, 1:250), and α1-acid GP (Abeam, 1:1, 000). FIG. 19C shows cumulative Western blot data from 2 experiments was analyzed by densitometry using the Image J. Averaged scaled densitometry values for POSTN and THBS1 were added.

DETAILED DESCRIPTION OF ILLUSTRATIVE EMBODIMENTS

Figure 1:
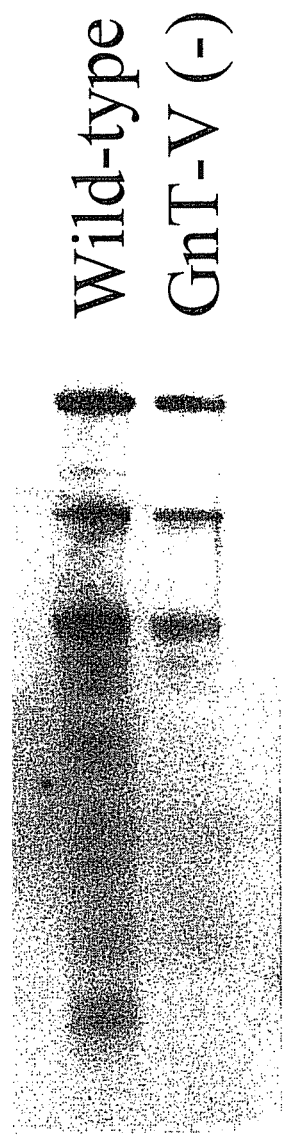
FIG. 1 shows a lectin blot demonstrating the reactivity of L-PHA toward proteins extracted from wild-type and GnT-V (−) MDA-MB231 invasive breast carcinoma cells.

The present invention is based upon the discovery that there exist cancer-specific glycoforms of various glycoproteins, and that these glycoforms can be identified, detected, and distinguished through the use of glycan-binding molecules such as lectins. Cancer-specific glycoforms serve as useful biological markers, i.e., biomarkers, of cancer or precancerous conditions. The cancer-specific biomarkers of the invention can be used to detect or monitor the progression of cancer or precancerous conditions, as well as to distinguish cancerous or precancerous conditions from each other and from benign (non-cancerous) disease states. The cancer-specific biomarker may be specific for a disease stage, hormone receptor status, lymph node status and her2/new status. The present invention provides both individual biomarkers as well as a panel of biomarkers useful for cancer screening.

Surprisingly, the invention allows detection of a cancer biomarker protein that may be present in equal or indistinguishable protein levels in diseased and normal samples. Although the total protein level or abundance may be equal as between the two samples, the invention facilitates discrimination between a protein glycoform that is present in the diseased and a different protein glycoform present in the normal sample.

Advantageously, cancer-specific biomarkers of the invention include glycoproteins that are present in blood or blood components, such as serum and/or plasma, or that have been secreted into other biological fluids. Biomarkers that are present in bodily fluids are especially well-suited for high throughput screening and early detection efforts. Blood and other bodily fluids present a readily accessible format for early detection. The identification of fluid biomarkers and development of a non-invasive screening test for cancers and precancerous conditions represents a significant medical advance.

Exemplary cancer-specific biomarkers of the invention include periostin and osteoglycin (also known as mimecan), each of which possesses at least one cancer-specific glycoform.

The invention also provides a method for identifying cancer-specific biomarkers. The identification method of the invention represents a targeted glycoproteomic approach to biomarker identification. The method makes use of a glycan-binding molecule, such as a glycospecific antibody, an a glycospecific aptamer, or a lectin, to identify a glycoform of a glycoprotein that is enriched in a biological sample containing cancer cells compared to a normal biological sample, and is thus cancer-specific. In some instances, the identification method may find a cancer-specific glycoprotein that is not found at all in normal samples. In other instances, the identification method may find a cancer-specific protein that is not a glycoprotein, but associates with a glycoprotein that binds to the glycan-binding molecule and is as a result affinity-enriched. In other instances, the identification method may find a cancer-specific glycoprotein, which is not glycosylated in its normal form but becomes glycosylated during oncogenic transformation. Typically, however, the method identifies a cancer-specific glycoform of a glycoprotein, with different glycoforms of the glycoprotein being found in healthy and cancerous tissues or fluids.

Lectins and other glycan-binding molecules can be used in the diagnostic methods of the invention to detect the presence of cancer-specific biomarker glycoforms, but it should be understood that cancer-specific glycoforms of glycoproteins can be detected using other detection methods as well. Furthermore, in addition to having utility in diagnostic methods, the cancer-specific biomarkers of the invention may serve as or may further suggest additional therapeutic targets.

Cancer-Specific Biomarker

A biomarker is a molecular, biological, or physical characteristic that can be measured or otherwise evaluated as an indicator of a normal biologic process, disease state, or response to a therapeutic intervention. The biomarker of the invention is a "cancer-specific" biomarker, i.e., it is indicative of cancer or a precancerous condition. Biomarkers of the invention include, but are not limited to, an RNA transcript, a protein, or a modified protein such as a glycoprotein. Biomarkers are detectable and/or measurable by any of a variety of methods such as biochemical and/or molecular assays.

The cancer-specific biomarker may be indicative of cancer or a precancerous condition by its presence, absence, increase in amount, decrease in amount, or differential glycosylation. Advances in proteomic methods now enable one to quantify a biomarker such that increases or decreases in the abundance of the biomarker, in addition to the complete presence or absence of the biomarker, may be indicative of the presence of cancer or a precancerous condition. Amounts of biomarker can be determined in absolute or relative terms. Accordingly, a glycoprotein biomarker may indicate the presence of cancer or a precancerous condition simply by its presence, absence or amount compared to a noncancerous sample or a predetermined level; however, the cancer-specific glycoprotein biomarker preferably takes the form of a cancer-specific glycoform of the glycoprotein. In another embodiment, the cancer-specific biomarker is an enzyme that catalyzes the particular linkage characterizing, and preferably specific to, the cancer-specific glycoform.

The cancer-specific biomarker of the invention is preferably a protein, more preferably a post-translationally modified protein, and even more preferably, a glycoprotein. The term "protein," as used herein, refers broadly to a polymer of two or more amino acids joined together by peptide bonds. The term "protein" does not imply a particular polymer length and thus includes peptides, oligopeptides, and polypeptides. The term protein also includes molecules which contain more than one peptide joined by a disulfide bond, or complexes of peptides that are joined together, covalently or noncovalently, as multimers (e.g., dimers, tetramers). The term "glycoprotein" includes any molecule that contains both a protein component and a carbohydrate component. The carbohydrate component is commonly referred to as a "glycan." As used herein, the term glycoprotein is inclusive of a glycopeptide, a glycopolypeptide and a proteoglycan. A glycan may contain one monosaccharide, or it may contain two or more monosaccharides linked by glycosidic bonds. A glycan can include nonrepeating or repeating monosaccharides, or both.

As used herein, the term "glycan" is interchangeable with the term saccharide, which includes a monosaccharide, a disaccharide or a trisaccharide; it can include an oligosaccharide or a polysaccharide. An oligosaccharide is an oligomeric saccharide that contains two or more saccharides. The structure of an oligosaccharide is typically characterized by particular identity, order, linkage positions (including branch points), and linkage stereochemistry ($\alpha$, $\beta$) of the monomers, and as a result has a defined molecular weight and composition. An oligosaccharide typically contains about 2 to about 20 or more saccharide monomers. In a polysaccharide, the identity, order, linkage positions (including branch points) and/or linkage stereochemistry can vary from molecule to molecule. Polysaccharides typically contain a larger number of monomeric components than oligosaccharides and thus have higher molecular weights. The term "glycan" as used herein is inclusive of both oligosaccharides and polysaccharides, and includes both branched and unbranched polymers as defined herein.

The glycan component of a glycoprotein can be N-linked or O-linked. An N-glycan is attached to a nitrogen atom, for example, at the side chain nitrogen atom of an asparagine amino acid within the peptide. An O-linked glycan is attached to an oxygen atom, for example at the side chain hydroxyl oxygen of a hydroxylysine, hydroxyproline, serine, or threonine amino acid within the peptide.

"Glycosylation" refers to the covalent attachment of at least one saccharide moiety to a molecule. Glycosidic linkages include O-glycosidic linkages, N-glycosidic linkages, S-glycosidic linkages and C-glycosidic linkages. An O-glycosidic linkage is formed between the anomeric carbon (C1) of a saccharide and an oxygen atom of another molecule (such as another saccharide or a polypeptide), while an N-glycosidic linkage is formed between the anomeric carbon (C1) of a saccharide and a nitrogen atom of another molecule. Likewise, S-glycosidic linkages and C-glycosidic linkages involve a sulphur and carbon atom from another molecule, respectively. In addition, glycosidic linkages are classified according to the ring position of the carbon atoms participating in the bond. For example, a 1,4 glycosidic linkage is formed between the first carbon (C1) on a first saccharide and the fourth carbon (C4) on a second saccharide while a 1,6 glycosidic linkage is formed between the first carbon (C1) on a first saccharide and the sixth carbon (C6) on a second saccharide. Glycosidic linkages are further classified as α-glycosidic or β-glycosidic according to whether the substituent groups on the carbons flanking the oxygen in the saccharide are pointing in the same or opposite directions. The term "glycosylation" as used herein should be broadly construed so as to encompass the covalent linkage of any other carbohydrate moieties such as fucose and sialic acid, and as such includes fucosylation or sialylation. Most N-linked glycans share a common structure, referred to as a core, which typically contains three mannose, and two N-acetylglucosamine residues. The core may contain modifications such as sulfation or phosphorylation; the core may be intact or it may be truncated. Terminal modifications and core modifications of a glycan can include glycosylations. Core glycosylation refers to the addition of glycosyl moieties to a core N-acetylglucosamine. Core fucosylation refers to the addition of a fucose residue to the core N-acetylglucosamine.

Figure 8:
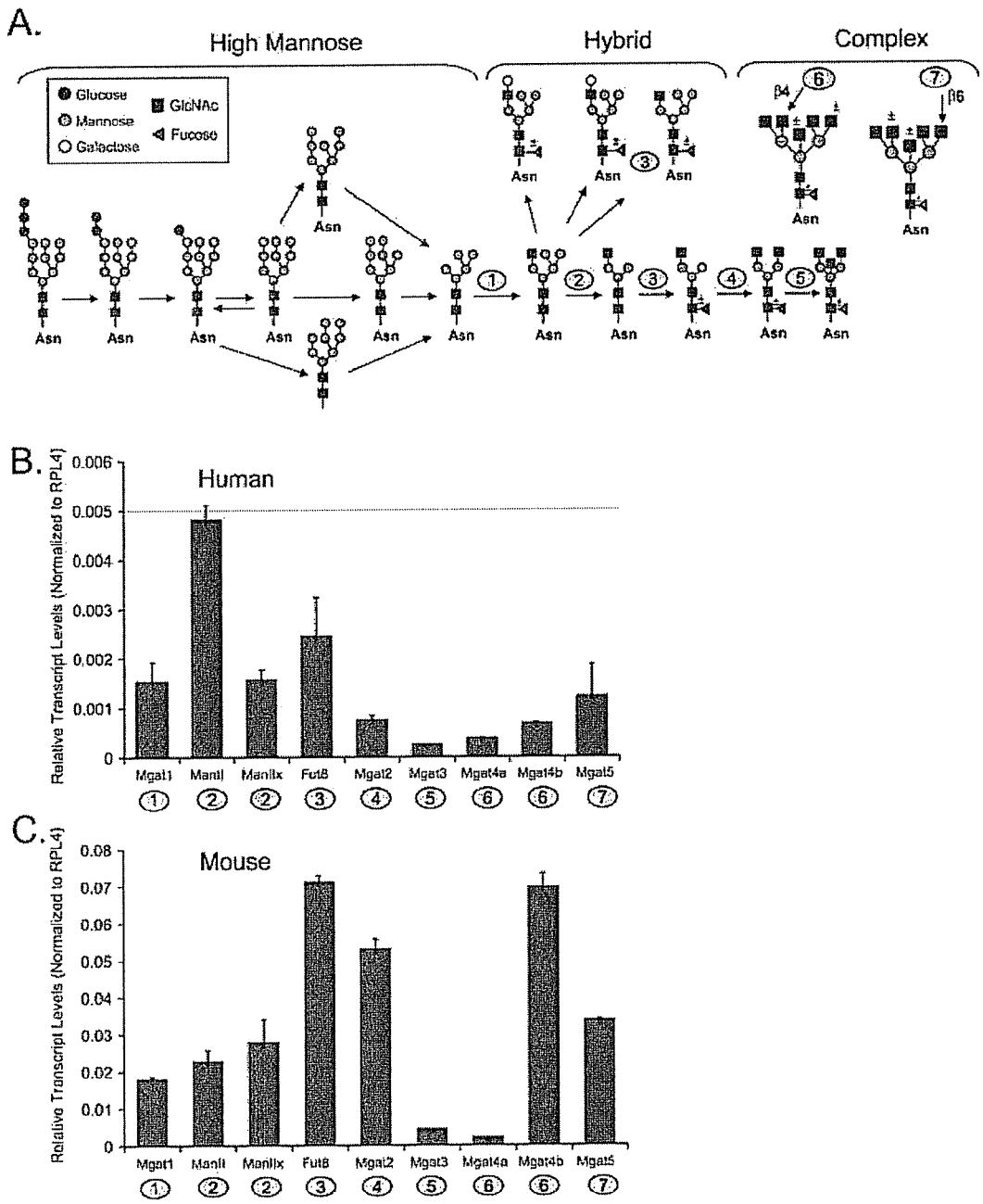
FIG. 8 shows transcript analysis of enzymes acting in the N-linked pathway for normal ovary. (A) N-linked glycosylation pathway with enzymes included in analysis numbered as follows: 1, MGAT1; 2, MAN2A1 (Man II) or MAN2A2 (Man IIx); 3, FUT8; 4, MGAT2; 5, MGAT3; 6, MGAT4a or MGAT4b; 7, MGAT5. (B) Relative transcript levels for normal human ovary tissue, average Ct for two pooled cases. Error bars represent the SD from the mean for triplicate Ct values. (C) Relative transcript levels for normal mouse ovary, average Ct for six pooled normal ovaries. Error bars represent the SD from the mean for triplicate Ct values.

A glycan can be branched or unbranched. A complex glycan is a glycan that contains at least one branch point. In a complex or branched glycan, the monosaccharide at the branch point is covalently linked to two other saccharides at carbons other than C1. For example, a branch point monosaccharide may be linked to other monosaccharides at C4 and C6, in addition to being linked to another monosaccharide or to an amino acid at C1. A complex glycan may be, without limitation, biantennary, triantennary, or tetraantennary. Additionally or alternatively, a complex glycan may be bisected (see, e.g., the structure catalyzed by MGAT3 in reaction 5 in FIG. 8).

Cancer-Specific Glycoforms

Glycosylation is a dynamic, post-translational modification that can be altered during the development and progression of a cancer or a precancerous condition. As a result, the same glycoprotein ("same" in the sense that it contains the same or essentially the same amino acid sequence; for example protein isoforms are considered to be the same protein) may be expressed both before and after oncogenic transformation, but the glycosylation of the glycoprotein before and after oncogenic transformation may be different. Glycoproteins having the same or essentially the same protein sequence, but exhibiting a difference in glycosylation, are termed "glycoforms." A cancer-specific glycoform is thus distinguishable from other (e.g., normal) glycoform(s) by a difference in glycosylation.

Differences in glycosylation that can produce distinct glycoforms include the removal of a glycan component, the addition of a glycan component, a change in the glycan component such as the substitution of one glycan component for another, and the rearrangement of one or more glycan components on the glycoprotein, as where a glycan component is shifted from one position on the polypeptide sequence to another.

Differences in glycosylation can be detected, according to the present invention, by utilizing a glycan-binding molecule, such as a glycospecific antibody, a glycospecific aptamer, or a lectin as further described herein, that is selective and/or specific for the cancer-specific glycoform. A particularly preferred glycospecific antibody is one that binds to an epitope that includes portions of both the polypeptide sequence and the glycan. Differences in glycosylation can also be detected spectroscopically. For example mass spectrometry can be used to characterize the glycan component and distinguish glycoforms.

As used herein, the terms "cancer-specific glycoform" and "tumor-specific glycoform" are used interchangeably and refer to a glycoform of a glycoprotein which is found in a subject affected with cancer or a precancerous condition and which differs from a glycoform found in noncancerous tissue. The presence, absence or expression level of the cancer-specific glycoform is indicative of the presence, absence, nature, or extent of a cancer or a precancerous condition. In a cancer-specific glycoform, the protein component is the same as that found in the normal glycoform, but the glycan component is specific to a cancer or a precancerous condition. In other words, an exemplary cancer-specific glycoform is differentially glycosylated relative to the glycoform present in a normal or non-diseased sample. As shown in the following examples, a cancer-specific glycoform may be characterized by, for example, a GlcNAc β(1,6) Man branched N-linked glycan component, a GlcNAc β(1,4) Man bisected N-linked glycan component, an α(1,6) fucose linked to a core N-acetylglucosamine, or a branched N-linked glycan extended with N-acetyllactosamine. For example, a subject having cancer or a precancerous disease may express a glycoprotein containing a β(1,6) branched N-linked glycan component while this β(1,6) structure is absent from the analogous glycoprotein in a subject not having cancer or a precancerous condition. In this instance, the glycoprotein having the β(1,6) branched N-linked glycan structure is the cancer-specific glycoform of that glycoprotein, and the detection of the cancer-specific glycoform is indicative of the presence of a cancer or a pre-cancerous condition.

Note that the designation β(1,6) as in a β(1,6) branched N-linked glycan is beta(1,6); the designation β(1,4) as in β(1,4) bisected N-linked glycan is beta(1,4); and the designation α(1,6) as in α(1,6) fucose linked to a core N-acetylglucosamine is alpha(1,6).

In some cases, the cancer-specific glycoform may be present in a disease-free individual, but expression of the cancer-specific glycoform may be elevated or reduced in an individual having cancer or a precancerous condition, in which case it is the change in expression level that is indicative of cancer or a precancerous condition. In other cases, the cancer-specific glycoform may be present only in a patient having cancer or a precancerous condition, and a different glycoform may be detectable in nonaffected individuals. In yet other cases, the glycoprotein itself (the cancer-specific biomarker), which in this case may exist only as a single glycoform may be found only in patients having cancer or a precancerous condition, and may not be detectable in nonaffected individuals.

Cancer-specific glycoprotein glycoforms of the invention can be structurally characterized or identified by one or more of their protein sequence, their ability to bind one or more glycan-binding molecules, and the chemical structure of their glycan component. An example of a cancer-specific glycoform is L-PHA reactive periostin, which can be identified or distinguished by, for example, sequential or concurrent contact with L-PHA lectin and an anti-periostin antibody. The ability of a cancer-specific glycoform to bind a particular glycan-binding molecule, e.g., a lectin, provides structural information about the glycoform in that it indicates that the glycoform possesses one or more structural features, such as a particular glycosidic linkage, necessary to bind the glycan-binding molecule. One of skill in the art can, if desired, isolate and further characterize the glycoform, for example by performing a structural analysis to determine monosaccharide composition, linkage positions, branching, or sequence of the glycan component, but such structural characterization of the glycan component is not necessary in order to practice the invention.

Examples of cancer-specific glycoprotein biomarkers that have been identified according to the identification method of the invention and which are particularly useful are described in more detail below and include, without limitation, periostin, osteoglycin (also called mimecan), lysosomal-associated membrane glycoprotein 1 (LAMP-1), and lectin galactosidase soluble binding protein 3 (GALS3BP). Advantageously, cancer-specific glycoforms of these glycoproteins may be secreted or show residency on the outer surface of the cell from which they may be shed and find their way into the bloodstream or a bodily discharge.

Glycan-Binding Molecules

The present invention makes use of glycan-binding molecules to detect glycoprotein glycoforms. The term "glycan-binding molecule" refers to any molecule that is capable of binding to a glycan component of a glycoprotein. Preferably, the glycan-binding molecule is glycoform-specific; that is, it selectively binds the glycan of one glycoform of a glycoprotein but not another, such that it can be used to distinguish different glycoforms of the glycoprotein. A glycoform-specific glycan-binding molecule is referred to herein as a "glycospecific." A glycan-binding molecule can be natural or synthetic. Examples of glycan-binding molecules include, without limitation, a lectin, a glycospecific antibody, a glycospecific aptamer, a glycospecific peptide, or a glycospecific small molecule. The term "aptamer" includes an RNA aptamer, a DNA aptamer, and a peptide aptamer, without limitation.

In a particularly preferred embodiment, the glycan-binding molecule selectively binds to a combination of the glycan component and the peptide component. For example, in the case of a glycan-binding molecule that is an antibody, the epitope includes portions of the glycan moiety as well as portions of the polypeptide sequence. This enhanced selectivity allows a single glycan-binding molecule to distinguish a glycoprotein from other proteins as well as from other glycoforms of the same protein. It also allows discrimination between glycoforms that have identical or essentially identical composition (i.e., same polypeptide sequence and glycan component) but wherein the glycan is attached at different locations in the polypeptide sequence as between the two glycoforms. In other words, the glycan-binding molecule can detect site-specific differences in glycosylation.

Preferably, the method of the invention utilizes a lectin to identify or detect a cancer-specific glycoprotein glycoform. Lectins are proteins or glycoproteins that bind to all or part of a glycan structure. Typically, lectins are non-enzymatic in action and are non-immune in origin. A lectin may bind to a glycan moiety which is part of a glycoprotein or another glycan-containing molecule such as glycolipids, glycophosphatidylinositols, and glycosaminoglycans. Lectins occur ubiquitously in nature and are found in both prokaryotes and eukaryotes, including bacteria, protozoa, fungi, plants and animals. Exemplary lectins include, without limitation, P-lectins, I-lectins, C-lectins, S-lectins (galectins), selectins, microbial carbohydrate proteins, glycosamineglycan binding proteins, and plant lectins. Lectins may also be produced synthetically by methods commonly used in the art such as recombinant DNA technology. A lectin useful in the method of the invention may be isolated from any source and may be naturally or synthetically produced, without limitation.

Importantly, lectins are capable of binding to specific glycans. Advantageously, the high specificity of a lectin for a particular glycan moiety enables the use of a lectin-glycoprotein binding to precipitate, isolate and/or detect glycoproteins (such as a cancer-specific glycoform of a glycoprotein) from or in a biological sample. For example, a type of N-linked glycosylation that is often increased in tumors, including breast and colon carcinoma, is the N-linked $\beta(1,6)$ branched glycan. This glycan structure associated with the transition to malignancy is recognized by the lectin L-PHA, particularly when the glycan also expresses a distal $\beta(1,4)$ linked galactose.

Figure 10:
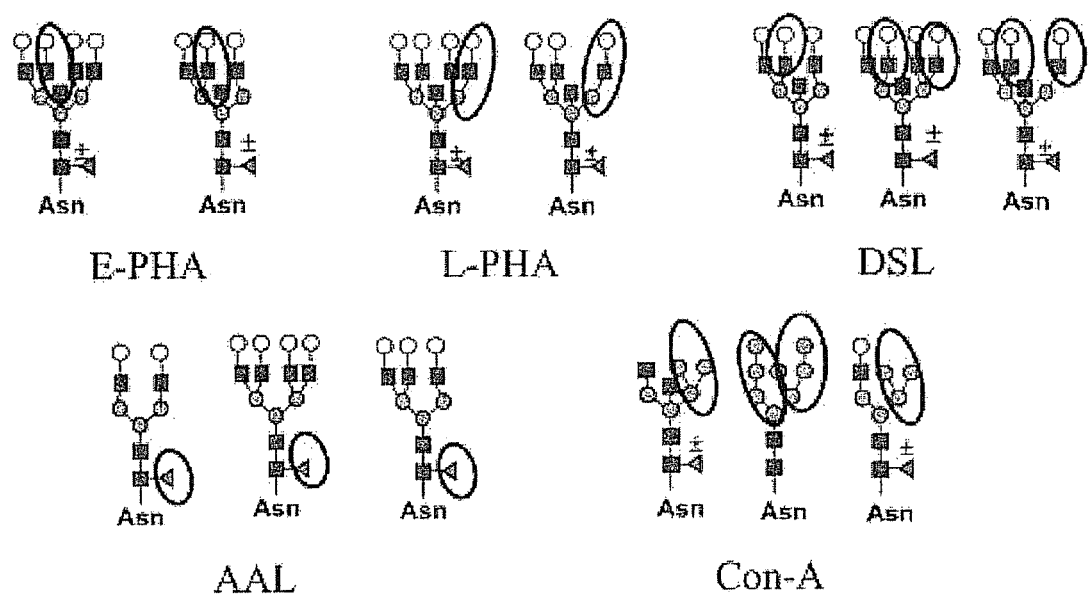
FIG. 10 shows oligosaccharides determinants for lectin binding affinity. Examples of structures with important binding determinants from each lectin circle.

Lectins and their specificities are widely known in the art (see Cummings and Etzler, "Antibodies and Lectins in Glycan Analysis," in *Essentials of Glycobiology Second Edition*, Varki et al. (Eds.); Cold Spring Harbor Press: Woodbury, N.Y.; 2009 and Tao et al., 2008 Glycobiology 18(10):761-769). Table 1 shows exemplary lectins and their binding specificities. It should be understood that Table 1 is illustrative only, and is not comprehensive with respect to either known lectins or with respect to the specificities shown for a particular lectin. FIG. 10 also shows exemplary lectin specifities.

TABLE 1

Examples of lectin specificities

| Lectin | Abbreviation | glycan | schematic of glycan specificity* (determinants involved in binding are boxed) |
|---|---|---|---|
| *Aleuria aurantia* lectin | AAL | α (1,2), (1,3), or (1,6)-linked Fucose | |

TABLE 1-continued

Examples of lectin specificities

| Lectin | Abbreviation | glycan | schematic of glycan specificity* (determinants involved in binding are boxed) |
|---|---|---|---|
| Concanavalin A (jack bean) | Con A | oligomannose-type N-glycan | |
| | | hybrid-type N-glycan | |
| | | biantennary complex-type N-glycan | |
| *Datura stramonium* lectin | DSL | tri, tetraantennary complex-type N-glycan | |

TABLE 1-continued

Examples of lectin specificities

| Lectin | Abbreviation | glycan | schematic of glycan specificity* (determinants involved in binding are boxed) |
|---|---|---|---|
| *Phaseolus vulgaris* lectin (red kidney bean; erythroagglutinin) | E-PHA | bisected di-, triantennary complex-type N-glycan | 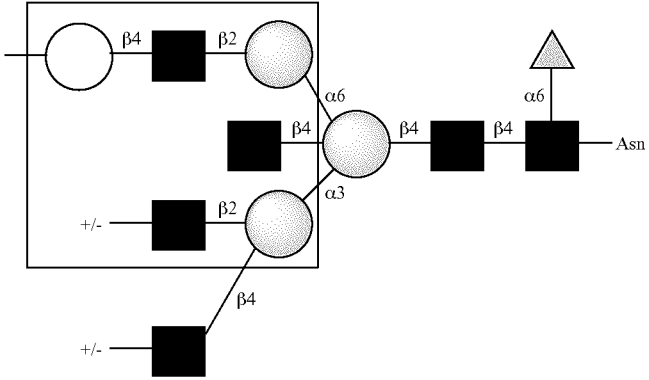 |
| *Phaseolus vulgaris* lectin (red kidney bean; leukoagglutinin) | L-PHA | tri-, tetraantennary complex-type N-glycan | 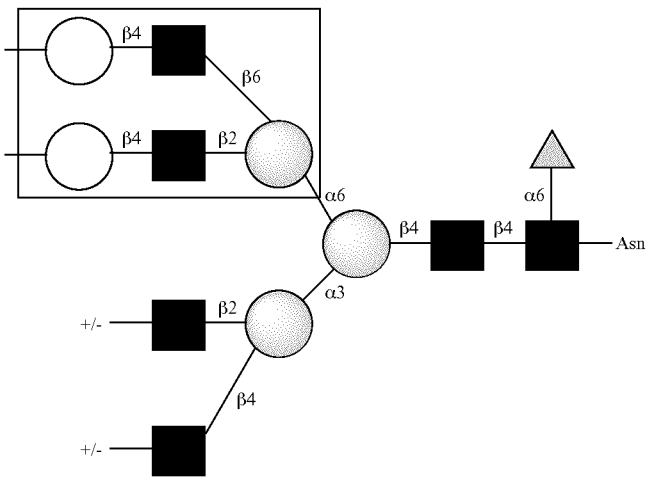 |
| *Maackia amurensis* agglutinin | MAA | Neu5Acα2-3Gal | 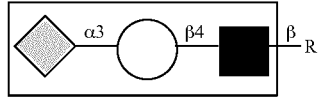 |
| *Sambucus nigra* agglutinin (Elderberry bark) | SNA | Neu5Acα2-6Gal or Neu5Acα2-6GalNAc | 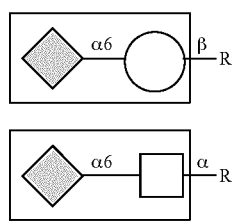 |

*shading and shapes for the glycan structures reflect standard nomenclature adopted by the Consortium for Functional Glycomics. Specific structures shown and are as follows:

 is fucose,  is galactose,  is glucose, is mannose.

** Information adapted from Cummings and Etzler, "*Antibodies and Lectins in Glycan Analysis*," in *Essentials of Glycobiology* Second Edition. Varki et al., (Eds.); Cold Spring Harbor Press: Woodbury, NY; 2009 and Tao et al., 2008 *Glycobiology* 18(10):761-769.

Generally, in the biomarker identification method of the invention, any lectin may be used, without limitation. In the diagnostic method of the invention, a lectin that is specific for the cancer-specific biomarker (e.g., glycoform) to be detected can be used. Preferred lectins for use in the present invention include, but are not limited to, *Aleuria aurantia* lectin (AAL), concanavalin A (Con A), *Datura stramonium* lectin (DSL; also known as DHA, *Datura stramonium* agglutinin), *Phaseolus vulgaris* erythroagglutinin (E-PHA), *P. vulgaris* leukoagglutinin (L-PHA), *Maackia amurensis* agglutinin (MAA), and *Sambucus nigra* agglutinin (SNA, inclusive of SNAI and SNAII).

Identification of a Biomarker

Included in the invention is a method for identifying a biomarker, preferably a cancer-specific glycoform of a glycoprotein.

In one embodiment of the method, a glycan-binding molecule, such as a lectin, is combined with a biological sample obtained from a patient with cancer or a precancerous condition, or from a cancer cell culture or animal with cancer or a precancerous condition (animal model), under conditions that allow the lectin to bind to a glycoprotein to faun a lectin-glycoprotein complex. A control experiment is also performed. This lectin enrichment step coupled with a protein identification strategy identifies specific glycoproteins from the disease sample that are not enriched in the corresponding control sample. More particularly, the binding levels between the two samples are compared, and if they differ, the lectin-glycoprotein complex is optionally isolated, and the glycoprotein biomarker is identified. It should be noted that the presence, absence, increase in amount, decrease in amount, or differential glycosylation of the glycoprotein in the sample from the patient with cancer or a precancerous condition, compared to the analogous glycoprotein in the control sample, is indicative of the presence of a cancer-specific biomarker. The identification of cancer-specific biomarkers that selectively bind to a cancer-specific glycoform of the glycoprotein (thereby causing different binding levels based on differential glycosylation of a glycoprotein found in both normal and disease samples) is particularly preferred.

Optionally, the glycan-binding molecule used in the method of identifying a biomarker may be tagged. The reasons and methods for tagging proteins are well known in art. For example, a protein may be tagged in order to facilitate isolation or tracking. Various types of tags that facilitate isolation or purification of the tagged biomolecule are commercially available and well known in the art and include, for example, beads (magnetic, sepharose, glass, agarose etc.), fusion peptides (hemagglutin, 6-histadine, c-myc, fluorescent proteins, GST, etc.), or antibody-based technologies such as biotin-avidin. A tag may include a detectable marker. Detectable markers are widely used in the art and may be used for visualization. Examples or detectable markers include, but are not limited to, enzymatic reactions such as horseradish peroxidase, colorimetic readouts such as 3,3'-diaminobenzidine tetrahydrochloride (DAB), and the use of fluorescence, radioactivity, or chemiluminescence.

Methods for detecting proteins, and thereby methods for detecting lectin-glycoprotein binding, are also well known in the art include, for example, immunohistochemistry, immunocytochemistry, ELISA, immunoblotting (i.e. Western blotting). Methods of isolating a protein are well known in the art and include, for example, immunoprecipitation (IP), sodium dodecyl sulphate polyacrylamide gel electrophoresis (SDS-PAGE), or 2D gel electrophoresis.

The glycoproteins isolated in the lectin-glycoprotein complex may be identified by a number of different means that are commonly used in the art. Optionally, the components of the lectin-glycoprotein complex may be cleaved from each other prior to analysis through chemical or enzymatic cleavage. Preferably, the cleavage is enzymatic. Both the glycan and the protein components may be identified through methods that are routine in the field and well known in the art. Protein identification and sequencing methods are well known in the art and include, without limitation, Edman degradation and mass spectrometry. Typically, protein sequencing is followed by comparison of the protein sequence against databases such as Entrez (available at the National Center for Biotechnology Information website found on the World Wide Web at www.ncbi.nlm.nih.gov/) and UniProt (available at the European Bioinformatics Institute website found on the World Wide Web at www.ebi.ac.uk/uniprotf). These databases are publically available and the methods of using them are well known in the art.

Optionally, the method may include identifying or characterizing the glycan moiety present on the glycoprotein. The glycan component may be structurally identified by deglycosylating the isolated glycoprotein and subjecting the glycan component to methods commonly used to elucidate saccharide structures such as chemical analysis, mass spectrometry and high performance liquid chromatography (HPLC).

The method for identifying a biomarker optionally utilizes a panel of lectins. A "panel of lectins" is to be broadly understood to encompass one or more lectins, for example, at least 2 lectins, at least 5 lectins, or at least 10 lectins. The lectins used in the panel may have the same glycan specificity, similar glycan specificity or disparate specificity. Preferably, the panel of lectins consists of lectins having specificity for glycans containing branch points. More preferably, the panel of lectins consists of lectins having specificity for outer-branched glycans. A preferred panel of lectins contains at one, two, three, four, five, six or all seven lectins selected from AAL, ConA, DSL, E-PHA, L-PHA, MAA, and SNA, and optionally, additional lectins. A particularly preferred panel of lectins includes one or more of E-PHA, AAL, DSL, and/or L-PHA.

One of skill in the art will recognize that while the identification method is preferably performed using a lectin as the glycan-binding molecule, the method can be performed using any molecule capable of binding the glycan component of a glycoprotein, preferably a glycospecific molecule capable of selectively binding a glycoform of a protein. Such glycospecific molecules include, without limitation, a lectin, a glycospecific antibody, a glycospecific aptamer, a glycospecific peptide, a glycospecific peptidomimetic or other small glycospecific molecule.

The biological sample used in the biomarker identification method of the invention is preferably a sample obtained from an organ or tissue, or a fluid associated with an organ or tissue, although it may also be a biological fluid such as blood or blood components, a bodily discharge, aspirate, and the like. More preferably, the biological sample of the method for identifying a biomarker is a tissue biopsy. The biological sample obtained from the patient having cancer or a precancerous condition preferably contains cancer cells. The sample may be pre-treated such that the cells are lysed, and partially purified to isolate, for example, a protein fraction or glycoprotein fraction prior to contact with the glycan-binding molecule. An example of an optional purification step is delipidation of the sample. The method therefore encompasses combining a glycan-binding molecule with one or more glycoproteins thus purified, partially purified or isolated from a biological sample (candidate biomarkers) to assay the particular glycoprotein(s) for cancer-specificity. Differential binding of the glycoprotein(s) in the biological sample compared to a control sample is indicative of the presence of a candidate biomarker.

Material from an experimental model (including both animal models and culture systems) can also be used to identify a cancer-specific biomarker. In experimental models and cultures, carcinogenic properties or the cancer or precancerous condition may be spontaneously present or may be induced. One of skill in the art is familiar with methods for transforming cells and inducing tumors in experimental models.

A biological sample also includes in vitro culture constituents derived from organ, tissue, or cell culture including, but not limited to, conditioned media, tissue homogenates, whole cells, cell lysates, and cellular fractions or components. However, it is important to note that the cellular mechanisms and processes of in vitro cultures may not accurately represent the cellular mechanisms and processes of cells that have been isolated from an in vivo setting in which the cellular microenvironment plays in important role in the maintenance of cellular mechanisms and processes, thus the use of biological samples obtained directly from a patient is preferable.

A control sample useful in the biomarker identification method of the invention includes a biological sample which is obtained from an experimental model (including both animal models and culture systems) that does not exhibit carcinogenic properties or from a subject without cancer or a precancerous condition. The control sample may also be referred to as a non-diseased sample. Preferably, the control sample is obtained from the same source as the biological sample having cancer or a precancerous condition. For example, typically multiple biopsy samples are taken in parallel such that one sample contains tissue exhibiting cancer or a precancerous disease while a second or subsequent sample contains adjacent, non-diseased tissue. Alternatively, tissue may be examined histologically and tissue exhibiting cancer or precancerous condition and non-diseased tissue present in the same tissue sample may be separated by techniques such as, but not limited to, laser capture microdissection. Control samples obtained from the same source are often referred to as tissue-matched controls. For example, when practicing the biomarker identification method to identify breast cancer specific biomarkers, control samples are preferably obtained from the same patient using disease-free samples outside the tumor margin.

In some instances, a control sample may not be obtainable from the same source as the biological sample having exhibiting cancer or a precancerous condition. A control sample may be obtained from a second model or subject that does not exhibit carcinogenic properties or from a subject without cancer or a precancerous condition. Optionally, the control sample may be a pool of samples from multiple models that do not exhibit carcinogenic properties or from multiple subjects without cancer or precancerous conditions. For example, when practicing the biomarker identification method to identify ovarian cancer specific biomarkers, control samples (and optionally the experimental samples as well) are typically pooled samples.

In some embodiments, the control sample may be obtained from an experimental model or a subject exhibiting a particular disease state. A number of cancers are characterized by progressive disease states, such as those characterized by inflammation, dysplasia, hyperplasia, or cancer stages. In some tissues or organs, various disease states are distinct from one another. For example, a non-diseased pancreas may progress to either pancreatitis or to a pancreatic cancer. However, in other tissues or organs, there is a distinct disease progression. For example, non-diseased endometria may progress to endometrial hyperplasia which further progresses to endometrial cancer. In addition, non-diseased breast tissue may develop into breast hyperplasia that often progresses into a breast cancer. Thus, the method of the invention may be used to identify biomarkers specific to each stage of cancer or to specific disease states.

It will be appreciated that an enzyme that catalyzes a particular linkage specific to a cancer-specific glycoform of a glycoprotein (as compared with a normal glycoform) can also be cancer-specific biomarker. That is, once a cancer-specific glycoform of a glycoprotein has been identified, and the differential glycosylation has been characterized, enzymes such as glycosyltransferases (GT) and glycosylhydrolases (GH) that catalyze the cancer-specific glycosylation can also serve as cancer-specific biomarkers. For example, expression of MGAT3 is increased in human ovarian tumor samples relative to normal ovarian tissue (Example III). Additional examples of such enzymes include, without limitation, alpha-(1,6)-fucosyltransferase encoded by the FUT8 gene, the mannoside acetylglucosaminyltransferase enzymes encoded by the Mgat genes (or the GnT genes), and the mannosidases encoded by the ManII genes.

A number of cancer-specific biomarkers have been identified using the biomarker identification method of the invention. They include periostin, osteoglycin (also called mimecan), lysosomal-associated membrane glycoprotein 1 (LAMP-1), and lectin galactosidase soluble binding protein 3 (GALS3BP). Each of these biomarkers has a cancer-specific glycoform, which can be selectively detected using a lectin, as illustrated in the following Examples. Proteins involved in certain metabolic pathways are particularly preferred as breast cancer biomarkers, including those involved in urokinase plasminogen activator pathway and the TGFβ pathway (such as the extracellular proteoglycans decorin and biglycan), as well as binding proteins related to cell adhesion, cell-cell communication, organ development and metabolism, and proteins that respond to external stimulus.

Preferred glycoproteins for use as biomarkers specific to breast cancer include, but are not limited to, proteins listed in Table 4 and in Table 5 (Example II). Breast cancer biomarkers that have glycoforms containing a β(1,6) branched N-linked glycan component are preferred. Breast cancer biomarkers are preferably L-PHA reactive. In a preferred embodiment, a breast cancer biomarker is periostin (POSTN), osteoglycin (mimecan; OGN), haptoglobin-related protein (HPR), apo-A1 precursor (APOA-1), collagen VI α3 (COL6A3), collagen α1 VI chain precursor (COL6A1), collagen α1 VI isoform 2C2 (COL6A2), tubulin α6 (TUBA1C), variable Ig (IGLV4-3), triosphosphate iso (TPI1), α-1 antitrypsin inhibitor (SERPINA1), vimentin-like 50 kDA (VM), or 14-3-3-zeta protein (KCIP-1). Abbreviations are used in the following examples and are provided here for convenience and ease of reference only. It is believed that neither osteoglycin nor 14-3-3-zeta protein have been previously associated with breast cancer, and further that this is the first report of a difference in glycosylation between the faun of periostin found in normal breast tissue, and the form of periostin found in breast cancer tissue.

Preferred glycoproteins for use as biomarkers specific to ovarian cancer include, but are not limited to, proteins listed in Table 8 (Example IV) and in Tables 10 and 11 (Example VII). Ovarian cancer biomarkers that have glycoforms containing glycans that exhibit core fucosylation and bisected (also referred to as "bisecting") glycans, preferably bisected complex N-glycans, are preferred. Ovarian cancer biomarkers are preferably E-PHA reactive, AAL reactive, or DSL reactive. More preferably, ovarian cancer biomarkers may be selected from the group including periostin (POSTN), biglycan (BGN), heparan sulfate proteoglycan 2 (HSPG2), lactate dehydrogenase A (LDHA), thrombospondin 1 (THBS1) serine protease inhibitor H1 (SERPINH1), lysosomal-associated membrane glycoprotein 1 (LAMP1), lectin galactosidase soluble binding protein 3 (LGALS3BP), complement factor B (CFB), fibulin 5 (FBLN5), mucin 5b (MUC5b), and lactotransferrin (LTF). Particularly preferred biomarkers include periostin, thrombospondin 1, and lysosomal-associated membrane glycoprotein 1. For example, the cancer-specific form of periostin is E-PHA reactive and possesses bisected N-linked glycans. LAMP-1 cancer-specific forms are DSL-reactive and/or AAL-reactive.

In another aspect, the glycoprotein of the invention is used to produce a polyclonal or monoclonal antibody that recognizes the cancer-specific biomarker. Preferably the antibody is a glycospecific antibody as previously defined. Briefly, the glycospecific antibody recognizes differences in glycosylation of a glycoprotein. More preferably, the antibody recognizes a cancer-specific glycoform of a glycoprotein. In a preferred embodiment, the antibody recognizes and/or selectively binds to a combination of the glycan component and the peptide component of the cancer-specific biomarker. Antibodies of the invention include but are not limited to those that recognize cancer-specific glycoforms of periostin, osteoglycin/mimecan, or thrombospondin 1. The invention encompasses the method of making said antibodies, as well as the antibodies themselves and hybridomas that produce monoclonal antibodies of the invention.

For preparation of an antibody of the present invention, any technique which provides for the production of antibody molecules by continuous cell lines in culture may be used. For example, the hybridoma technique originally developed by Kohler and Milstein (256 Nature 495-497 (1975)) may be used. See also Ausubel et al., Antibodies: a Laboratory Manual, (Harlow & Lane eds., Cold Spring Harbor Lab. 1988); Current Protocols in Immunology, (Colligan et al., eds., Greene Pub. Assoc. & Wiley Interscience N.Y., 1992-1996).

The present invention also provides for a hybridoma cell line that produces a monoclonal antibody, preferably one that has a high degree of specificity and affinity toward its antigen. Such cell lines can be produced artificially using known methods and still have the characteristic properties of the starting material. For example, they may remain capable of producing the antibodies according to the invention or derivatives thereof, and secreting them into the surrounding medium. Optionally, the hybridoma cell lines may occur spontaneously. Clones and sub-clones of hybridoma cell lines are to be understood as being hybridomas that are produced from the starting clone by repeated cloning and that still have the main features of the starting clone.

Antibodies can be elicited in an animal host by immunization with a cancer-specific biomarker as identified herein, or can be formed by in vitro immunization (sensitization) of immune cells. For example, the host or cell can be immunized using a three-component carbohydrate vaccine that consists essentially of three main components: at least one carbohydrate component that contains a B-epitope; at least one peptide component that contains a helper T-epitope; and at least one lipid component which functions as a built-in adjuvant. Preferably, the three-component carbohydrate vaccine has as its B-epitope, its T-epitope, or both, the glycospecific region of the cancer-specific biomarker of the invention. Advantageously, the three-component carbohydrate vaccine is thus able to elicit both a humoral response to the B-epitope and a cellular immune response to T-epitope enabling the production of high-titer IgG antibodies that recognize the cancer-specific biomarker of the invention. Exemplary three-component carbohydrate vaccines and methods of making them are described in, for example, WO 2007/079448, US Patent Publication 2009/0041836 A1, and WO 2010/002478.

The antibodies can also be produced in recombinant systems in which the appropriate cell lines are transformed, transfected, infected or transduced with appropriate antibody-encoding DNA. Alternatively, the antibodies can be constructed by biochemical reconstitution of purified heavy and light chains.

Once an antibody molecule has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences known in the art to facilitate purification.

The term "antibody" is used in the broadest sense and specifically covers monoclonal antibodies (including full length monoclonal antibodies) and antibody fragments so long as they exhibit the desired biological activity. "Antibody fragments" comprise a portion of a full length antibody, generally the antigen binding or variable region thereof. Examples of antibody fragments include, but are not limited to Fab, Fab', and Fv fragments; diabodies; linear antibodies; and single-chain antibody molecules. The term "monoclonal antibody" as used herein refers to antibodies that are highly specific, being directed against a single antigenic site. The term "antibody" as used herein also includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains as described by Huse et al. (Science 246:1275-1281 (1989)). These and other methods of making functional antibodies are well known to those skilled in the art (Winter and Harris, Immunol. Today 14:243-246 (1993); Ward et al., Nature 341:544-546 (1989); Harlow and Lane, supra, 1988); Hilyard et al., Protein Engineering: A practical approach (IRL Press 1992); Borrabeck, Antibody Engineering, 2d ed. (Oxford University Press 1995)).

In all mammalian species, antibody peptides contain constant (i.e., highly conserved) and variable regions, and, within the latter, there are the complementarity determining regions (CDRs) and the so-called "framework regions" made up of amino acid sequences within the variable region of the heavy or light chain but outside the CDRs. Preferably the antibody of the present invention has been humanized. As used herein, the term "humanized" antibody refers to antibodies in which non-human CDRs are transferred from heavy and light variable chains of the non-human immunoglobulin into a variable region designed to contain a number of amino acid residues found within the framework region in human IgG. Similar conversion of mouse/human chimeric antibodies to a humanized antibody has been described before. General techniques for cloning murine immunoglobulin variable domains are described, for example, by the publication of Orlandi et al., Proc. Nat'l Acad. Sci. USA 86: 3833 (1989), which is incorporated by reference in its entirety. Techniques for producing humanized MAbs are described, for example, by Jones et al., Nature 321: 522 (1986), Riechmann et al., Nature 332: 323 (1988), Verhoeyen et al., Science 239: 1534 (1988), and Singer et al., J. Immun. 150: 2844 (1993), each of which is hereby incorporated by reference.

Methods of using the antibody that recognizes and/or selectively binds to a cancer-specific biomarker are also encompassed by the invention. Uses for the antibody of the invention include, but are not limited to, diagnostic, therapeutic, and research uses. In a preferred embodiment, the antibody can be used for diagnostic purposes. Because differential glycosylation is associated with a variety of disease states, detection of changes in the levels glycan modifications may be interpreted as early indicators of the onset of such diseases. For example, the presence of β(1,6) branched N-linked glycosylation on periostin is a marker of breast cancer (Example II and Example V). Therefore, identifying an increased level of β(1,6) branched N-linked glycosylation in a biological sample of breast tissue relative to a non-disease control sample may be indicative of the presence of cancer.

Detection of Cancers and Precancerous Diseases

The goal of cancer screening is to find cancers and precancerous conditions prior to the development of symptoms. As used herein the term "screening" refers to tests and examinations used to evaluate the presence, absence, nature or extent of a cancer or a precancerous condition. The term "early detection" refers to specific screening processes that allow detection and evaluation of a cancer or precancerous condition at an early point in disease progression. For example, early detection allows the evaluation of a cancer or a precancerous condition in subjects who do not yet display symptoms of the cancer or precancerous condition. Cancers or precancerous conditions that are detected due to the manifestation of symptoms tend to be late-stage cancers that are relatively advanced and may have spread beyond the primary tumor site. In contrast, cancers found during early detection screens are more likely to be in an early stage and still be confined to the primary tumor site. It is widely understood and documented in the art that cancers that are detected early and remain as small, primary tumors are more easily treated and have better prognoses than cancers that are detected at later stages in which the tumors are large and have likely metastasized.

Diagnostic Assay

Included in the present invention is a method for detecting a cancer or a pre-cancerous condition in a subject. The method utilizes the biomarkers of the invention, as described herein, and can be used alone or in combination with other procedures commonly used to detect or evaluate cancer or a precancerous condition. The method for detecting a cancer or a precancerous condition in a subject includes assaying for the presence of a biomarker and is useful for, among other things, diagnosing the presence of, evaluating the stage of, and determining prognosis of a cancer of precancerous condition.

In embodiments of the diagnostic assay wherein the biomarker is a glycoprotein glycoform, the diagnostic assay makes use of a glycan-binding molecule, such as a lectin, to discriminate among different glycans and thereby glycoforms, and optionally a second binding molecule, typically an antibody specific for the polypeptide component of the glycoprotein (regardless of isoform), to identify the glycoprotein. The antibody specific for the polypeptide component is referred to herein as a "protein antibody." For example, a cancer-specific glycoform of the cancer biomarker periostin can be recognized by the lectin L-PHA, but L-PHA is not specific for periostin, as it can recognize the same glycan on other glycoproteins. The L-PHA reactive periostin can be unequivocally identified as periostin through the use of a periostin antibody, which is commercially available from, for example, Abcam. Advantageously, the glycan-binding molecule and/or the protein antibody can be detectably labelled. A preferred detectable label is biotin.

In a preferred embodiment of the diagnostic method of the invention, the biomarker is a cancer-specific glycoform of a glycoprotein. Exemplary glycoprotein glycoforms are set forth elsewhere herein. It should be understood that the invention is generally applicable detection of any cancer-specific glycoform, without limitation. Cancer-specific glycoprotein glycoforms can include, for example, contain glycan components that include, for example, a GlcNAc β(1,6) Man branched N-linked glycan component, a GlcNAc β(1,4) Man bisected N-linked glycan component, an α(1,6) fucose linked to a core N-acetylglucosamine, or a branched N-linked glycan extended with N-acetyllactosamine.

The diagnostic assays of the invention are described below with reference to a lectin, but it should be understood that any glycan-binding molecule, such as a glycospecific antibody, a glycospecific aptamer, a glycospecific peptide, or a glycospecific small molecule, can be used in place of a lectin.

In one embodiment of the diagnostic method of the invention, a glycan-specific molecule, such as a lectin, is combined with a biological sample isolated from a subject, under conditions to allow lectin-glycan binding, yielding a lectin-glycoprotein complex. The resulting lectin-glycoprotein complex is isolated, and the lectin-reactive glycoprotein biomarker is detected, wherein detection of the biomarker is indicative of presence of cancer or a precancerous condition. Methods of detecting or measuring the levels of a protein, including a glycoprotein, are well known in the art and include, without limitation, immunoprecipitation, immunohistochemistry, immunocytochemistry, ELISA, and immunoblotting (i.e. Western blotting). The glycoprotein biomarker can be conveniently detected using a detectably labelled antibody specific for the protein (a protein antibody). Optionally, the method may further include comparing the amount of biomarker to the amount of biomarker in a reference sample, or to a reference level, to determine whether the amount of the biomarker is indicative of the presence of cancer or a precancerous condition.

In an alternative embodiment of the diagnostic method of the invention, the glycan specific molecule is a glycospecific antibody. The method includes combining a glycospecific antibody with a biological sample isolated from a subject, under conditions to allow antibody-glycan binding, yielding an antibody-glycoprotein complex, and the antibody-reactive glycoprotein biomarker is detected, wherein detection of the biomarker is indicative of presence of cancer or a precancerous condition. Methods of detecting or measuring the levels of a protein, including a glycospecific antibody, are well known in the art and have been previously described.

In cases where glycosylation is altered in the disease state, an antibody that is specific to either the disease state or the non-disease state may be used. Preferably, the antibody is specific to the disease state and binding of the antibody to the protein or peptide is indicative of the presence of the disease state in the subject. In cases where the antibody is specific to the non-disease state, a lack of binding of the antibody to the protein or peptide is indicative of the presence of the disease state in the subject. Alternatively, glycosylation may be present in the disease state and absent in the non-disease state or glycosylation may be absent in the disease state and present in the non-disease state. Optionally, the method may further include incubating a second, non-diseased, biological sample with an antibody of the invention, detecting binding of the antibody to a protein or peptide, and comparing antibody binding in the first and second samples.

Additionally, for protein and peptides where glycosylation is present in both the disease state and the non-disease state, but is altered (i.e. increased or decreased) in the disease state, the method may further include quantitating the level of antibody binding in the first sample, quantitating the level of antibody binding in the second, non-diseased sample, and comparing the binding levels. A change in antibody binding in the first sample compared to the non-diseased sample is indicative of the presence of the infection, disease or disorder in the subject.

Any biological sample can be tested, without limitation. Advantageously, the invention permits detection of the biomarker in bodily fluids, providing a convenient, low-cost screening option. Biological samples that can be tested in the diagnostic method of the invention include, without limitation, organs, tissues (including biopsies), fecal matter, bone marrow, lymph tissue, biological fluids, and bodily discharges obtained from a human or veterinary subject. Biological fluids may include, without being limited to, blood (including components of blood such as serum or plasma), urine, bile, spinal fluid, lymph fluid, ascites fluid, pancreatic ductal fluid, sputum, pleural fluid, tears, saliva, mucus, breast milk and bodily discharges (such as vaginal discharge, nasal discharge, and nipple aspirate). A biological fluid is also intended to include breath in both a vaporous and liquid form. Preferably, the biological sample is obtained from a subject having cancer or a precancerous condition, although the screening method of the invention contemplates that both diseased and nondiseased subjects will be screened. Preferably, the biological sample in the diagnostic method of the invention is a biological fluid. More preferably, the biological sample is serum, vaginal discharge, or nipple aspirate. Even more preferably, the biological sample is serum.

In another embodiment, the diagnostic method includes combining a glycoform-specific lectin with one or more purified or partially purified glycoproteins obtained from a biological sample, enabling lectin-glycan binding to form a lectin-glycoprotein complex, and detecting a cancer-specific glycoform of the glycoprotein, wherein detection of the cancer-specific glycoform is indicative of presence of cancer or a precancerous condition. Isolation or purification of the glycoprotein(s) prior to contact with the lectin can be accomplished by fractionating the sample using any convenient method, for example by contacting the sample with a lectin with lesser specificity (e.g., concanavalin A, which binds high mannose, hybrid, and complex biantennary glycans). Likewise, the biological sample can be first contacted with a protein antibody to isolate the glycoprotein, and then contacted with the glycoform-specific molecule, such as a lectin, to determine whether the isolated glycoprotein is a cancer-specific glycoform of the glycoprotein. Optionally, the method may further include comparing the amount of biomarker to a reference, wherein altered glycosylation or altered expression of the biomarker relative to the reference is indicative of the presence of cancer or a precancerous condition.

In a particularly preferred embodiment of the diagnostic method of the invention, the glycan-binding molecule selectively binds to a combination of the glycan component and the peptide component. For example, in the case of a glycan-binding molecule that is an antibody, the epitope includes portions of the glycan moiety as well as portions of the polypeptide sequence. This enhanced selectivity allows a single glycan-binding molecule to distinguish a glycoprotein from other proteins as well as from other glycoforms of the same protein, thereby performing in a single step the functions of the glycan discrimination and protein identification.

Furthermore, it should be understood that detection of a cancer-specific glycoform or other biomarker in the diagnostic assay of the invention is not limited to chemical or immunochemical binding methods but includes any method of detection, without limitation, including for example spectroscopic detection such as mass spectrometric analysis, fluorescence, magnetic, electromagnetic or optical methods, or chemical analysis.

In another embodiment of the diagnostic method of the invention, a subject's bodily fluids, tissues or organs can be assayed for the presence of an autoimmune response to cancer or a precancerous condition. More specifically, the subject can be screened for the presence of circulating antibodies to one or more cancer biomarkers of the invention. For example, antigen that include a peptide sequence and glycan component that characterize a cancer-specific glycoform of a glycoprotein can be synthesized, and the subject's bodily fluid, tissue or organ can be contacted with the antigen to determine the presence of an antibody that binds thereto. The diagnostic assay is readily scalable and amenable to multiplexing in order to facilitate cancer screening using a multiplicity of synthetic cancer biomarkers.

In embodiments of the diagnostic assay wherein the biomarker is a glycosyltransferase (GT) or a glycosylhydrolyase (GE) enzyme that catalyzes the formation of a cancer-specific glycoprotein glycoform, the diagnostic assay typically measures RNA transcript levels for the enzyme, or enzyme activity.

Accordingly, in another embodiment, the diagnostic method involved detecting an enzyme biomarker that catalyzes a particular linkage characterizing a cancer-specific glycoform of a glycoprotein. Detection of an enzyme may occur at either a protein or a transcript level. Methods of detecting a protein include, without limitation, immunoprecipitation, immunohistochemistry, immunocytochemistry, ELISA, and immunoblotting (i.e. Western blotting). Examples of assays that may be used to detect a transcript are well known in the art and include, for example, Northern blot assays, reverse transcription polymerase chain reactions, RNase protection assays, and the like. Optionally, the method for detecting a biomarker in a subject, wherein the biomarker is an enzyme that catalyzes the particular linkage characterizing the cancer-specific glycoform of a glycoprotein may further include comparing the amount of biomarker to a reference, wherein altered expression of the biomarker is indicative of the presence of cancer or a precancerous condition.

Preferred enzyme biomarkers include, without limitation, enzymes encoded by the genes listed in Table 6 (Example III). Particularly preferred biomarkers include, without limitation N-acetyl glucosaminyltransferase V (GnT-V), fucosyltransferase 8 (FUT8), mannosidase N-acetylglucosaminyltransferase 3 (MGAT3), MGAT4a, MGAT4b, MGAT5, and MGAT5b. GnT-V catalyzes the addition of $\beta(1,6)$ branched N-linked glycans. FUT8 catalyzes the addition of core fucosylated N-linked glycans. MGAT3 catalyzes the addition of bisected N-linked glycans. MGAT4a and MGAT4b catalyze the addition of outer-branched N-linked $\beta(1,4)$ glycans. MGAT5 catalyzes the addition of outer branched N-linked $\beta(1,4)$ glycans. These glycan moieties are recognized by preferred lectins of the invention such as AAL, ConA, DSL, E-PHA, L-PHA, MAA, and SNA.

A "reference" includes, without limitation, a control sample (as previously defined) that may be used in comparison against the biological sample isolated from a subject. For example, the reference may be obtained from a subject without cancer or a precancerous condition. Optionally, the reference may be a pool of samples obtained from at least two subjects without cancer or a precancerous condition. Alternatively, the reference may be obtained from a subject having a cancer or a pre-cancerous condition at a determined stage. Alternatively, the reference may be a previously obtained biological sample from the subject. Alternatively, the reference may be a published or commonly known level of the biomarker (Galen, *Beyond Normality: the predictive value and efficiency of medical diagnosis*, Wiley & Sons: New York, N.Y.; 1975). For example, prostatic states such as non-diseased prostate, benign prostatic hyperplasia (BPH), and prostate cancer each exhibit a particular range of the prostate specific antigen (PSA) biomarker and the level of PSA associated with each state is commonly accepted by clinicians and used as a reference in diagnostic assays.

As used herein, the terms "cancer" and "pre-cancerous condition" refer to any uncontrolled and/or undesired growth of cells. The cancer or pre-cancerous condition is intended to include a hyperplastic growth, a benign tumor, a malignant tumor, or a metastasized tumor. A tumor is not limited to a solid tumor, but is intended to include any uncontrolled and/or undesired growth of cells including, for example, blood tumors that do not form a solid mass. The tumor may consist of, without being limited to, epithelial cells, stromal cells, undifferentiated cells, or any combination thereof. An epithelial cell is any cell that covers a surface, or lines a cavity or the like, and that, in addition, performs the functional aspect of the tissue such as any secretory, transporting, or regulatory function. Epithelial cells may be further classified as, for example, endothelial or mesothelial cells. Nonlimiting examples of epithelial cells include squamous, cuboidal, columnar, transitional, simple, stratified, and secretory. A stromal cell, also referred to as a mesenchymal cell, provides support for or surrounds tissues and organs. Nonlimiting examples of stromal cells include fibroblasts, immune cells, pericytes, endothelial cells and inflammatory cells. A carcinoma is a tumor derived from or consisting primarily of epithelial cells. Preferably, the cancer of pre-cancerous condition of the present invention is a carcinoma. Exemplary carcinomas for use in the present invention include, but are not limited to, breast, ovarian, colon, rectal, colorectal, pancreatic, or liver carcinomas.

This diagnostic method of the invention is highly amenable to multiplexing. For example, a panel of glycoform-specific (glycospecific) binding molecules (binding elements), such as lectins, glycospecific antibodies, or glycospecific aptamers, can be used to assay the biological sample for the presence or absence of cancer-specific glycoform biomarkers. The glycoform-specific binding molecules selected for use in the multiplexed assay preferably, but need not, bind cancer-specific glycoforms of a plurality of different glycoproteins, e.g., periostin and osteoglycin. The glycoproteins present in the glycoprotein/lectin complexes can then be identified using protein-specific antibodies. In another example, a panel of protein-specific antibodies (binding elements) can be used to assay the biological sample for the presence or absence of different glycoproteins that are known to possess a cancer-specific glycoform, then the bound glycoprotein/antibody complexes can be further assayed for the presence of cancer-specific glycoforms by contacting them with a plurality of glycospecific molecules such as lectins, glycospecific aptamers, or glycospecific second antibodies known to selectively bind the cancer-specific glycoforms.

A multiplexed panel is to be broadly understood to encompass a multiplicity of binding elements. A multiplexed panel can include 2, 3, 4, 5, 6, 7, 8, 9, 10, 11, 12, 13, 14, 15, 16, 17, 18, 19, 20 or more biomarkers. Preferably, the biomarker panel includes at least two biomarkers selected from periostin, osteoglycin, lysosomal-associated membrane glycoprotein 1, and lectin galactosidase soluble binding protein 3. More preferably, the biomarker panel includes at least periostin and osteoglycin.

Preferably, the method for identifying a biomarker is a high-throughput assay. High throughput assays allow numerous samples to be reviewed rapidly and simultaneously for the presence of one or more particular glycan components. Typically, a high-throughput assay is performed in a microtiter plate that enables the review of, for example, at least 6, at least 24, at least 96, at least 384, at least 1536, or at least 3456 samples. Assays that use micro-titer plates are well known in the art and are capable of, for example, detecting molecular interactions, detecting cell growth, detecting enzymatic activity, nucleic acid quantitation, and immunoassays. Detection methods commonly used in such assays include, but are not limited to absorbance, fluorescence intensity, and luminescence. Preferably, the method of identifying a biomarker utilizes enzyme-linked immunosorbent assay (ELISA) to detect lectin-glycoprotein binding. Alternatively, a high-throughput assay may include any assay that simultaneously evaluates a large number or samples, such as microarray technologies.

Therapeutic Applications

Also included in the invention is a therapeutic method and pharmaceutical composition for treating a subject having cancer or a precancerous condition. The method and pharmaceutical composition for treating a subject having cancer or a precancerous condition can be used alone or in combination with other procedures commonly used to treat cancer or a precancerous condition such as chemotherapy, surgery, and radiation therapy.

Cancer-specific glycoforms contain aberrant glycan moieties relative to the glycoform present in a non-diseased subject. Glycosylation and the resulting glycan moiety affect the ability of the protein to transduce normal cellular signals. For example, the glycan moiety present on a cancer-specific glycoform may cause a physical block of a typical binding interaction, prevent typical migration, induce atypical migration, or otherwise interfere with the normal signal transduction of the glycoprotein to result in mis-regulated cellular signaling that can result in the development of cancer or a precancerous condition. Therefore, inhibiting the production of or the function of a cancer-specific glycoform may restore normal signal transduction pathways to treat or prevent cancer or a precancerous disease.

In one embodiment, the method for treating a subject having cancer or a precancerous condition may include administering a therapeutic agent capable of targeting a biomarker, wherein the biomarker is a cancer-specific glycoform of a glycoprotein. Administration of the therapeutic agent can be prophylactic or, alternatively, can be initiated after the development of a cancer or a precancerous condition. Treatment that is prophylactic, for instance, initiated before a subject manifests symptoms of a cancer or a precancerous condition, is referred to herein as treatment of a subject that is "at risk" of developing the condition. Treatment initiated after the development of a cancer or a precancerous condition may result in decreasing the severity of the symptoms of one of the conditions, or completely removing the symptoms.

The term "therapeutic agent," as used herein, refers to a molecule capable of inhibiting a cancer-specific glycoform of the glycoprotein. Inhibition may occur at a number of different levels. For example, one could prevent transcription, prevent translation, prevent posttranslational modification, or prevent function of the cancer-specific glycoform. Methods for preventing transcription are well known in the art and include, without limitation, and short hairpin RNAs (shRNAs), morpholinos, and anti-sense DNA-hybridizing probes. Methods for preventing translation are well known in the art and include, without limitation, RNA interference (RNAi), and small interfering RNAs (siRNA). Methods for preventing posttranslational modification include inhibiting the enzyme that catalyzes the particular linkage characterizing the cancer-specific glycoform by any of the inhibition methods listed herein. Methods for preventing the function of the cancer-specific glycoform are well known in the art and include, without limitation, antibody technology, peptidomimetics, and small molecule inhibitors. Preferably, the therapeutic agent of the invention prevents the aberrant glycosylation of the cancer-specific glycoform of a glycoprotein.

Also included in the invention is a composition containing the therapeutic agent. A composition may be prepared by methods well known in the art of pharmacy. In general, a composition can be formulated to be compatible with its intended route of administration. Typically, the composition further contains a pharmaceutically acceptable carrier. The term "pharmaceutically acceptable," as used herein, means that the therapeutic agent so described is suitable for use in contact with a subject without undue toxicity, incompatibility, instability, allergic response, and the like. Typically, pharmaceutically acceptable carriers include saline, solvents, dispersion media, coatings, antibacterial and antifungal agents, isotonic and absorption delaying agents, and the like, compatible with pharmaceutical administration.

The therapeutic agent may be administered by a number of methods including, but not limited to, oral and systemic administration. Therapeutic amounts are amounts which eliminate or reduce the patient's tumor burden, or which prevent or reduce the proliferation of metastatic cells. Oral compositions generally include an inert diluent or an edible carrier. For the purpose of oral therapeutic administration, the therapeutic agent can be incorporated with excipients and used in the form of tablets, troches, or capsules, e.g., gelatin capsules. For administration by inhalation, the active compounds are delivered in the form of an aerosol spray from a pressured container or dispenser which contains a suitable propellant, e.g., a gas such as carbon dioxide, or a nebulizer. Systemic administration includes transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

Preferably the therapeutic agent is a glycan-binding molecule including, but not limited to lectins, glycospecific antibodies, and any small molecules capable of specifically binding to the cancer-specific glycoform. More preferably, the therapeutic agent is a lectin or a glycan-specific antibody.

Optionally, the method may further include conjugating the therapeutic agent to a cytotoxic agent, further enhancing toxicity to targeted cells. Such agents include, but are not limited to, known chemotherapeutic agents, immunotherapeutic agents, and radiotherapeutic agents.

In another embodiment, the invention may include a method for treating a subject having cancer or a precancerous condition, wherein the glycan moiety present on the cancer-specific glycoform of the glycoprotein is a targeting moiety. Glycans are typically maintained on the cell surface. Therefore, the cancer-specific glycoform of a glycoprotein provides a novel target for delivering therapeutic agents to the tumor. Currently, one of the major issues in cancer therapies is effectively targeting the tumor cells. Consequently, a majority of the cancer therapies currently available are toxic to many healthy cells as well as to cancer cells.

The method for treating a subject having cancer or a precancerous condition, wherein the glycan moiety present on the cancer-specific glycoform of the glycoprotein is a targeting moiety may include administering a glycan-binding molecule conjugated to a therapeutic agent to a subject having cancer or a precancerous condition, wherein the glycan-binding molecule or glycopeptide binding specifically targets the glycan moiety on the cancer-specific glycoform of the glycoprotein.

It should be noted that although the invention is described primarily with respect to cancer and precancerous conditions in humans, it is equally applicable to all mammalian subjects and, in that regard, has application in veterinary and research settings as well as in human medical contexts. Preferably, the subject is a mammal. A mammal may include, without limitation, domestic animals (such as cats, dogs, horses, and cattle), laboratory animals (such as mice, rats, rabbits, and monkeys), and humans. More preferably, the subject is a human.

The present invention is illustrated by the following examples. It is to be understood that the particular examples, materials, amounts, and procedures are to be interpreted broadly in accordance with the scope and spirit of the invention as set forth herein.

EXAMPLES

Example I

Identification of Glycoproteins Associated with Invasive Human Breast Cancer Using Lectin Glycoproteomics Glycosylation is a dynamic post-translational modification that changes during the development and progression of various malignancies. Oncogenically transformed cells demonstrate defined changes in glycan structures, in particular they show increased amount of a specific type of N-linked structure known as the $\beta(1,6)$ branch (Pierce et al., 1997 *Glycoconj J* 14:623-630). The enzyme known as N-acetylglucosaminyl-transferase V (GnT-V) adds GlcNAc in a $\beta(1,6)$ linkage to form the branch that leads to the formation of complex poly-lactosamine structures. During the oncogenesis of breast carcinoma, GnT-V transcript levels and activity are increased due to activated oncogenic signaling pathways. Elevated GnT-V levels leads to increased $\beta(1,6)$ branched N-linked glycan structures on glycoproteins that can be measured by the binding of a specific lectin, L-PHA. L-PHA immunohistochemical staining on paraffin sections of normal breast carcinoma, ductal hyperplasia, and carcinoma in situ reveal that L-PHA staining was qualitative at the point cells are progressing to carcinoma in situ (Fernandes et al., *Cancer Res.*, 1991. 51:718-723). The L-PHA staining of breast carcinoma frequently shows a coarse granular type punctate staining pattern. L-PHA does not bind to non-diseased breast epithelial cells, but during the progression to invasive carcinoma, cells show a progressive increase in L-PHA binding.

We have developed a procedure for intact protein L-PHA-affinity enrichment followed by electrospray ionization mass spectrometry (ESI-MS) to identify potential biomarkers for the early detection of breast carcinoma. We have characterized the media from the invasive breast cancer cell line MBAMB231 for L-PHA-reactive proteins, and found that this methodology clearly detects glycoproteins with β(1,6) branched glycan structures as well as proteins that are associated with these glycoproteins. Our results identified proteins participating in the urokinase plasminogen activator pathway and the TGFb pathway.

In example II we analyzed matched normal and malignant tissue from patients with invasive breast ductal carcinoma. L-PHA enrichment coupled with ESI-MS identified specific glycoproteins from the tumor tissue that are not enriched in the corresponding normal tissue sample for the same patient. These results indicate that lectin enrichment strategies that target glycan changes known to occur during the oncogenesis of a particular tumor can be a powerful method of biomarker discovery.

Methods

Cells were cultured in serum-free media. Proteins secreted from cultured cells were collected from the media, concentrated, and the buffer was exchanged. Biotinylated L-PHA lectin was added to the proteins. Magnetic streptavidin particles were then added to the solution containing both the proteins and the biotinylated L-PHA. Lectin-bound glycoproteins were captured using a magnetic stand, washed, and eluted in urea/DTT. The eluted proteins were carboxyamidomethylated and subjected to a tryptic digestion and C18 reverse phase chromatography.

CID fragmentation was carried out on an LTQ. All experiments were performed using nanospray of eluent from a reverse-phase C18 capillary column (75 mM by 10 cm) using an increasing gradient of acetonitrile in formic acid. Data was stringently filtered using Turbo Sequest to achieve a false positive rate of less than 1.5% for any single peptide (protein false positive rate of less than 0.3% with 2+ peptides) using an inverted database.

Results

Defining the specificity of L-PHA binding. GnT-V is the only glycosyltransferase in breast cancer cells that adds the branched β(1,6) glycan structure required for L-PHA binding. Therefore to test the specificity of the L-PHA lectin we have suppressed the expression of GnT-V using RNA interference. FIG. 1 is a lectin blot showing the reactivity of L-PHA toward total cellular proteins extracted from wild-type and GnT-V(−) MDA-MB231 invasive breast carcinoma cells (the three bold bands are non-specific bands resulting from the streptavidin-horseradish peroxidase detection).

L-PHA affinity enriched secreted glycoproteins identified by ESI-MS from MDA-MB231 cells. Glycoproteins that were bound by L-PHA and isolated from the serum-free media of cultured cells are shown in Table 2.

TABLE 2

L-PHA affinity enriched secreted glycoproteins from serum-free media of cultured cells.

| Protein | Function | presence of secretion signal |
|---|---|---|
| A4 amyloid protein precursor | binds cationic trypsinogen to inhibit activity | yes |
| alpha actinin | actin binding protein promotes cell migration | possible |
| alpha enolase | glycolytic enzyme can serve as a plasminogen receptor | yes |
| annexin A1 | part of plaminogen activator system | yes |
| annexin A2 | part of plaminogen activator system | yes |
| annexin A5 | part of plaminogen activator system | yes |
| ARCN1 protein | coatamer protein | yes |
| ATP citrate lyase isoform 2 | cell growth | no |
| cathepsin D | protease found in lamellar granules | yes |
| cationic trypsinogen | cell proliferation | yes |
| follistatin-related protein | regulator of activin and TGF-beta signaling | yes |
| galectin 3 binding protein | tumor antigen associated with metastasis | yes |
| lysosomal membrane glycoprotein-2 (lamp-2) | adhesive glycoprotein, ligand of galectin-3 promotes tumor cell growth and invasion | yes |
| neonatal thrombolytic agent | plasminogen activator promotes tumor metastasis | no |
| PAI precursor | promotes tumor cell invasion by degrading extracellular matrix-part of the plasminogen activator system | yes |
| pyruvate kinase 3 isoform 2 | glycolytic enzyme | yes |
| S100 calcium binding protein | calcium dep membrane binding protein interacts with annexin proteins | |
| tenascin C | promotes tumor growth and angiogenesis | yes |
| thrombospondin 1 precursor | multifunctional matrix glycoprotein influences tumor growth | yes |
| TRAP1 (INF-1 receptor associated) | chaperone activity activation of TNF alpha | yes |
| vimentin | cytoskeletal protein found in mesenchymal tissue mainly, except in migrating endothelial cells | no |

Conclusions

GnT-V glycosylation correlates with transition from normal breast epithelium to carcinoma in situ. GnT-V glycosylation can be identified by the specific and high affinity binding of the lectin L-PHA. In this evaluation of secreted L-PHA reactive glycoproteins from an invasive breast carcinoma cell line we have specifically captured, identified, and initiated mapping of N-glycosylated peptides using mass spectrometry. Our results have identified several glycoproteins implicated in cell proliferation and cell migration control mechanisms. In Example II we show the use of this lectin affinity method to pull out β(1,6) branched glycoproteins from matched normal and ductal invasive carcinoma tissue samples, correlate the results and identify potential biomarkers for the development of a serum-based breast cancer screening assay as illustrated in Example V.

Example II

Targeted Glycoproteomic Identification of Biomarkers for Human Breast Carcinoma

Glycosylation is clearly the most complex set of post-translational modifications that proteins undergo during biosynthesis, and several specific types of glycan epitopes have been shown to be associated with various types of cancer (Kim and Varki, 1997. Glycoconj J 14:569-76; Hakomori, 2001. *Adv Exp Med Biol* 491:369-402). The glycosylation patterns of cell surface glycoproteins play important roles in mediating cell-cell and cell-matrix interactions. During oncogenesis, distinct signal transduction pathways are altered, leading to the differential expression of numerous genes. Genes known as glycosyltransferases (GT) and glycosyihydrolases (GH), responsible for the addition and removal of sugars on proteins in the ER and Golgi apparatus, can change activity during oncogenesis, causing different oligosaccharide structures to emerge on cell surface glycoproteins (Pierce and Arango, 1986. *J. Biol. Chem.* 261:10772-10777; Meezan et al., 1969. *Biochemistry* 8:2518-2524). These glycan changes can have potent effects on the tumor microenvironment, promoting tumor invasion and metastasis (Guo et al., 2002. *Cancer Res.* 62:6837-6845; Guo et al., 2003. *J. Biol. Chem.* 278:52412-52424; Guo et al., 2007. *J. Biol. Chem.* 282:22150-22162; Abbott et al., 2006. *Exp. Cell Res.* 312: 2837-2850). Factors contributing to the regulation of glycosylation include: nucleotide sugar donor availability, substrate availability, sequential reactions, and transcriptional regulation of GT and GH. Studies examining the dynamics of the glycome during differentiation of stem cells have found that changes in GT and GH mRNA levels correlate well with glycan structures observed (Nairn et al., 2007. *J. Proteome Res.* 6:4374-4387). Therefore, despite the complexity of factors influencing glycosylation, transcriptional regulation of the enzymes involved in the synthesis and catabolism of glycans seems to be the one of the primary mechanisms to control glycan structures on the cell surface. Comparative studies examining the differences in GT and GH expression patterns between normal and tumor tissue could direct the discovery of tumor-specific glycosylation changes associated with particular malignancies, which could then be exploited to develop diagnostic and cell targeting reagents.

Figure 2:
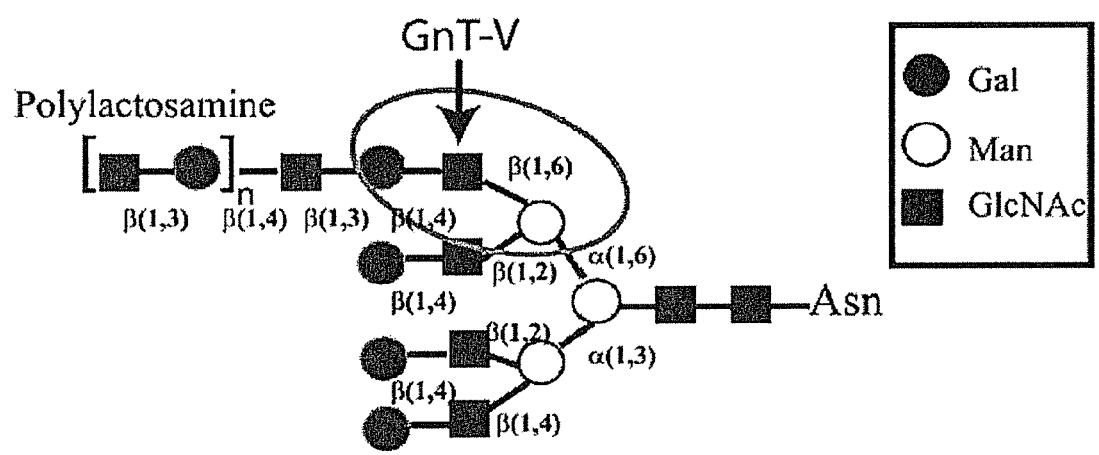
FIG. 2 shows a tetra-antennary N-linked oligosaccharide showing the GnT-V β(1,6) GlcNAc addition that leads to the formation of polylactosamine structures. The L-PHA recognition site is circled.

A particular type of N-linked glycosylation that is often increased in tumors is the N-linked β(1,6) branched glycan (Pierce and Arango, 1986. *J Biol Chem* 261:10772-7) that is bound by the lectin, L-PHA, when the glycan also expresses a distal β(1,4) linked galactose (circled in FIG. 2; Cummings and Kornfeld, 1982. *J Biol Chem* 257:11235-40; Cummings and Kornfeld, 1982. *J Biol Chem* 257:11230-4). For example, staining of normal breast epithelia shows insignificant reactivity with L-PHA; yet, in breast carcinoma, staining by this lectin significantly increases (Fernandes et al., 1991. *Cancer Res* 51:718-23; Dennis and Laferte, 1989. *Cancer Res* 49:945-50). Expression of β(1,6) branched glycan structures in both breast and colon carcinoma appears to be a qualitative change exhibited at the transition to malignancy, which is likely caused by up-regulation of the glycosyltransferase known as GnT-V (GnT-Va, Mgat5a) that synthesizes the N-linked β(1,6) branch (Buckhaults et al., 1997. *J Biol Chem* 272:19575-81). This glycosylation is often a step toward the formation of more complex poly N-acetyllactosamine glycan structures (FIG. 2) which serve as ligands for the class of animal lectin known as galectins that are often elevated in metastatic carcinoma (Lagana et al., 2006. *Mol Cell Biol* 26:3181-93). A recent study staining more than 700 primary breast tumors with L-PHA found that β(1,6) branched oligosaccharides were an independent prognostic indicator for poor outcome in primary node-negative tumors (Handerson et al., 2005. *Clin Cancer Res* 11:2969-73).

Experimental modulation of GnT-V activity, both in vivo and in vitro, results in changes in carcinoma invasiveness and metastasis, supporting the conclusion that increases in the posttranslational modification of proteins by GnT-V is a mechanism by which tumor cell malignancy may increase (Guo et al., 2002. *Cancer Res* 62:6837-45; Guo et al., 2003. *J Biol Chem* 278:52412-24; Cheung et al., 2007. *Glycobiology* 17:828-37; Guo et al., 2007. *J Biol Chem* 282:22150-62).

In this example, we show the development of a simple glycoproteomic strategy to identify the glycoproteins from breast tissue that bind to a specific carbohydrate binding protein or lectin known as L-PHA (L-phytohemagglutinin). Glycosylation is a dynamic post-translational modification that changes during the development and progression of various malignancies. During the oncogenesis of breast carcinoma, the glycosyltransferase known as N-acetylglucosaminyltransferase Va (GnT-Va) transcript levels and activity are increased due to activated oncogenic signaling pathways. Elevated GnT-V levels leads to increased β(1,6) branched N-linked glycan structures on glycoproteins that can be measured using L-PHA. L-PHA does not bind to non-diseased breast epithelial cells, but during the progression to invasive carcinoma, cells show a progressive increase in L-PHA binding. Our experimental design utilizes intact proteins and allows for the identification of glycoproteins whose glycans are bound by the lectin L-PHA, as well as those proteins/glycoproteins that may associate with the bound glycoproteins (Abbott et al., April 2008 *J. Prot. Res.* 7(4):1470-1480; Abbott et al., April 2008 *J. Prot. Res.* 7(4):1470-1480 online Supporting Information is available on the World Wide Web at pubs.acs.org/doi/suppl/10.1021/pr700792a/suppl_file/pr700792g-file004.pdf).

Here we describe a procedure for intact protein L-PHA-affinity enrichment, followed by nanospray ionization mass spectrometry (NSIMS/MS), and subsequent proteomic data analysis to identify potential biomarkers for breast carcinoma. Our results demonstrate that this technique can be an effective method to identify proteins with tumor-specific glycosylation changes. We identified L-PHA reactive glycoproteins from matched normal (non-diseased) and malignant tissue isolated from patients with invasive ductal breast carcinoma. Comparison analysis of the data identified 34 proteins that were enriched by L-PHA fractionation in tumor relative to normal for at least 2 cases of ductal invasive breast carcinoma (Table 4). Of these 34 L-PHA tumor enriched proteins, 12 (periostin, haptoglobin-related protein, apo-A1 precursor, osteoglycin, collagen VI α3, tubulin α6, collagen α1 VI chain precursor, collagen α1 VI isoform 2C2, variable Ig, triosphosphate iso, α-1 antitrypsin inhibitor and vimentin-like 50 kDa) are common to all 4 matched cases analyzed. These results indicate that lectin enrichment strategies targeting a particular glycan change associated with malignancy can be an effective method of identifying potential biomarkers for breast carcinomas with diverse clinical features.

Materials and Methods

Specimens.

Tissue specimens, matched normal and tumor, from patients with histologically proven invasive ductal breast carcinoma were collected in accordance with approved institutional review board Human subject's guidelines at Emory University Hospital, Atlanta, Ga. Board certified clinical oncologists and pathologists carried out all clinical and histological analysis of the biopsies. All specimens for this study were immediately frozen at −70° C. until proteomic analysis. For the initial validation of our L-PHA affinity enrichment method we analyzed 4 patients with matched normal and malignant breast tissue (Table 3).

Sample Processing, L-PHA Enrichment, and MS.

Frozen tissue samples were processed as follows: 100 mg of tissue was de-lipidated using a mixture of chloroform/methanol/water (4:8:3, v/v/v) as described previously (Seppo et al., 2000. *Eur J Biochem* 267:3549-58; Aoki et al., 2007. *J Biol Chem* 282:9127-42). Delipidated and precipitated proteins were pelleted by centrifugation and the pellet was given an additional wash with acetone and water (4:1) on ice for 15 minutes. Intact proteins were extracted from the delipidated tissues using a mild detergent solution as follows: 5 mg of delipidated protein powder was dissolved in 300 μl of 50 mM Tris-Cl pH 7.5, 0.1% NP40, 150 mM NaCl, 0.4 mM EDTA, 1 protease inhibitor tablet, the sample was sonicated 3 times for 10 second pulses at setting 5 (Vertis Virsonic microtip). The supernatant was taken after centrifugation at 10,000 rpm at 4° C. for 10 minutes. The protein concentration of the sample was determined by BCA assay and 600 μg of total protein lysate was dialyzed overnight at 4° C. into 40 mM ammonium bicarbonate using a 4,000 MWCO tube-O-dialyzer (GBiosciences). The sample was adjusted to 150 mM NaCl, 5 mM CaCl2, and 5 mM MgCl2 before the addition of the lectin. Biotinylated L-PHA (Vector Labs, Burlingame, Calif.) (10 μg) was added and the sample was rotated at 4° C. overnight. Bound L-PHA reactive proteins were captured using 100 μl paramagnetic streptavidin particles (Promega) at 4° C. for 2 hours. After extensive washing in 1×PBS, captured proteins were eluted with 200 μl of 2M Urea/0.2 mM DTT/40 mM ammonium bicarbonate at 52° C. for 1 hour. The eluted fraction was separated from the paramagnetic streptavidin particles using a magnetic stand. Eluted proteins were carboxyamidomethylated by adding an equal volume of iodoacetamide (10 mg/ml in 40 mM ammonium bicarbonate) in the dark for 45 minutes and digested with 5 μg of sequencing grade trypsin (Promega) at 37° C. overnight. Tryptic peptides were acidified with 200 μl of 1% trifluoroacetic acid and desalting was performed using C18 spin columns (Vydac Silica C18, The Nest Group, Inc.). Eluted peptides were dried in the speed vac and resuspended in 78 μl buffer A (0.1% formic acid) and 2 μl of buffer B (80% acetonitrile/0.1% formic acid) and filtered through a 0.2 μM filter (nanosep, PALL). Samples were loaded off-line onto a nanospray column/emitter (75 μm×8.5 cm, New Objective) self-packed with C18 reverse-phase resin in a nitrogen pressure bomb for 10 minutes. Peptides were eluted via a 160-minute linear gradient of increasing B at a flow rate of approximately 250 nl/min. directly into a linear ion trap (LTQ, Thermo Co. San Jose, Calif. equipped with a nanoelectrospray ion source). The top eight ions from the full MS (300-2000M/Z) were selected for CID fragmentation at 34% with a dynamic exclusion of 2.

Permethylation of Glycans.

To facilitate the analysis of oligosaccharides by MS, N-linked glycans released by N-glycanase were permethylated as described previously (Aoki et al., 2007. *J Biol Chem* 282:9127-42). Briefly, following extraction from tissue samples, delipidated proteins were digested with trypsin and chymotrypsin. The resulting digests were enriched for glycopeptides, which were then treated with PNGaseF (Prozyme) to release N-linked glycans. Contaiminants, buffer, salts, and residual peptides were removed from the released glycans by Sep-Pak C18 chromatography and the resulting glycan preparation was permethylated prior to analysis by nanospray ionization mass spectrometry using a linear ion trap (LTQ; Thermo Finnagan). The total ion mapping (TIM) functionality of the Xcalibur software package (version 2.0) was used to obtain total glycan profiles for each sample. Through TIM analyses, automated MS and MS/MS spectra are obtained in small mass increments across a broad range of m/z values. For the analysis of tissue samples, TIM analysis was performed from m/z=500–2000. This mass range collects MS profiles and MS/MS fragmentation spectra for glycans detected from their 1+ to 4+ charge states. Following data collection, resulting TIM profiles are filtered for the presence of characteristic glycan fragments in the associated MS/MS spectra. By plotting the signal intensity of characteristic fragments as a function of elapsed scan time, a TIM chromatogram is generated that indicates the relative prevalence of specific glycan structures. For assessing the presence of β(1,6)-branched glycans extended with at least two N-acetyllactosamine repeats, TIM scans were filtered for the loss of a Hex-HexNAc-Hex-Hex-NAc fragment from the parent ion.

Proteomic Data Analysis.

The raw peptide data was converted to mzXML using ReAdW. MS/MS spectra were searched against the International Protein Index (IPI) human sequence database (IPI.HUMAN.v.3.26; available on the World Wide Web at http://www.ebi.ac.uk/IPI/Databases.html, 67,665 sequences) using MyriMatch (Hakomori, 1999. *Biochim. Biophys. Acta* 1473: 247-266). The MyriMatch search criteria included only tryptic peptides, all cysteines were presumed carboxyamidomethylated, and methionines were allowed to be oxidized. MyriMatch searches allowed a precursor error of up to 1.25 m/z and a fragment ion limit of within 0.5 m/z. All ambiguous identifications that matched to multiple peptide sequences were excluded. The identified proteins (2+ peptides required) from each individual tumor and normal sample were filtered and grouped using IDPicker software (Zhang et al., 2007. *J Proteome Res.* 6:3549-57). IDPicker software incorporates searches against a reverse database, probability match obtained from MyriMatch, and DeltCN scores to achieve false discovery rates typically<5%. Information about IDPicker tools can be found at http://www.mc.vanderbilt.edu/msrc/bioinformatics/. The raw data files were also analyzed using the TurboSequest algorithm (Peng et al., 2003. *J Proteome Res* 2:43-50; Yates et al., 1995. Anal Chem 67:1426-36; Yates et al., 1996. *Analyst* 121:65 R-76R) to achieve a false discovery rate of less than 0.3% for proteins assigned by 2+ peptides using an inverted database (BioWorks 3.1, Thermo Finnigan). Our results indicate that the final MyriMatch/IDPicker proteins list and TurboSequest proteins list showed near complete agreement. All proteins reported in this manuscript were identified using both methods. We found no evidence of amino acid carbamylation following urea elution and DTT reduction.

Biological Function Annotation.

Proteins (defined by 2 or more peptides) showing differential binding to L-PHA for tumor compared to normal in at least 2 cases were converted to gene symbols and uploaded to DAVID 2007 (the Database for Annotation, Visualization and Integrated Discovery) for analysis.

Western Blot Experiments.

One hundred micrograms of delipidated protein powder were solubilized in 1×TBS/1% triton X-100/protease inhibitor tablet for precipitation using antiperiostin (Abcam) (1 μg). Bound proteins were captured using protein G plus agarose or streptavidin paramagnetic particles before gel electrophoresis and transfer to PVDF membrane prior to probing using biotinylated L-PHA (1:5,000). For L-PHA precipitations 500 μg of delipidated protein powder was solubilized in 1×TBS/ 1% tritonX-100/protease inhibitors before adding 10 μg of biotinylated L-PHA and mixing overnight at 4° C. Magnetic streptavidin beads (100 μl) were used to pull down the L-PHA bound complexes. After washing the beads, proteins were released by boiling in sample loading buffer and separated on 4-12% NuPage Bis-Tris gels and transferred to PVDF membrane before detection using either anti-periostin Ab (1:1, 000) (Abcam) or anti-haptoglobin Ab (1:200) (Santa Cruz Biotechnology). Blots were incubated with anti-rabbit HRP (1:5,000) (Santa Cruz Biotechnology) or anti-mouse HRP (1:5,000) (Santa Cruz Biotechnology) or streptavidin-HRP (1:5,000) (Vector Labs) before washing and detection using Western Lightening Plus (Perkin Elmer).

Results

Figure 3:
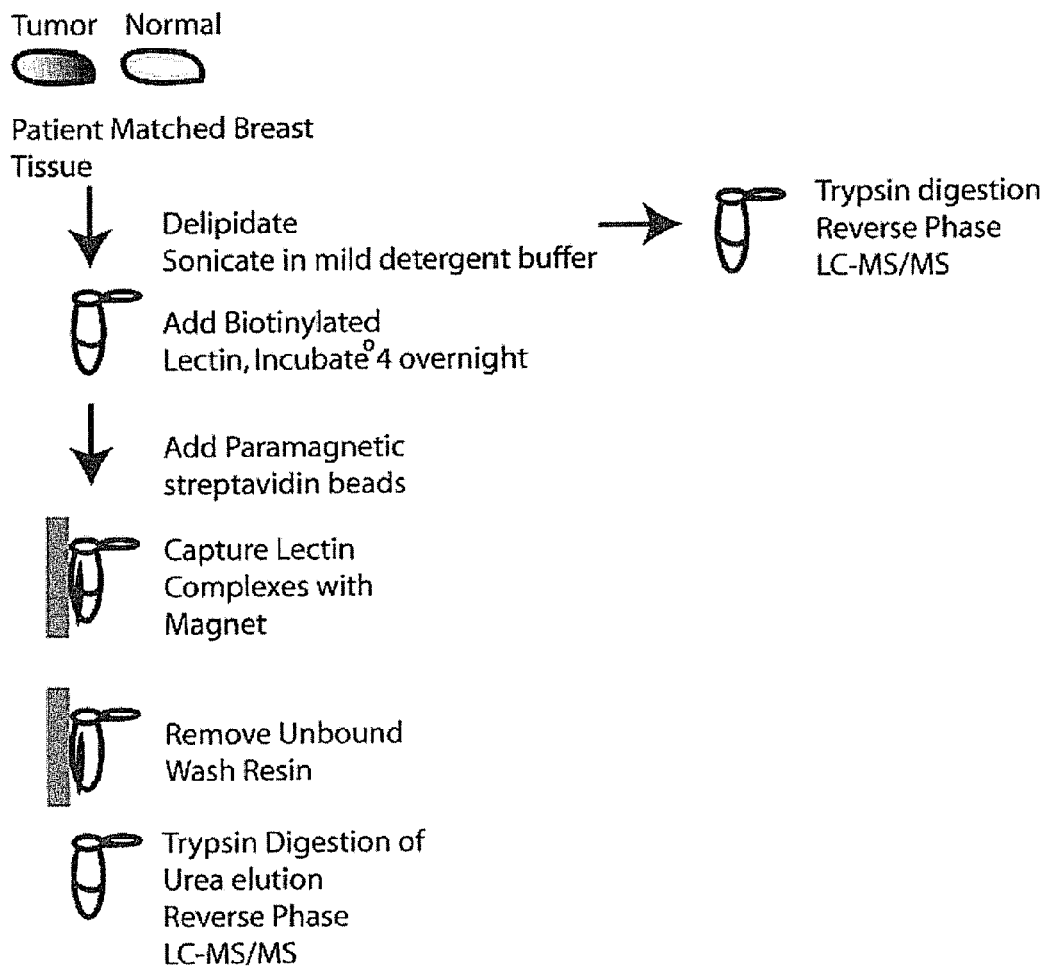
FIG. 3 shows a schematic flow diagram for the L-PHA enrichment protocol (B).

An initial set of 5 human ductal invasive breast carcinoma tissue samples were used to evaluate the use of the lectin L-PHA to bind and enrich for potential glycoprotein biomarkers to distinguish breast cancer from normal tissue. As shown in Table 3 these cases represent metastatic and non-metastatic disease, cases positive and negative for amplified her2/neu, and cases that were both estrogen receptor (ER) and progesterone receptor (PR) positive and negative. Our approach is to analyze breast tissue, comparing normal and tumor tissue from the same patient, to identify potential glycoproteins that react with the lectin L-PHA. All cases showed increased levels of L-PHA binding indicative of β(1,6) branched N-linked glycans except case 10406, therefore, case 10406 was not analyzed by NSI-MS. We conclude that 4 out of 5 cases or 80% of the tumor tissue analyzed had proteins with increased levels of β(1,6) branched N-linked glycan structures relative to normal breast tissue. To isolate these L-PHA reactive glycoproteins, we developed a method using intact proteins for the lectin binding, which differs from the more common method of using glycopeptides (FIG. 3). In addition, we found that delipidation of the breast tissue prior to analysis significantly improved MS/MS results (FIG. 3) (Aoki et al., 2007. *J Biol Chem* 282:9127-42).

reactivity that were analyzed by MS/MS. For each of the 258 unique proteins identified, we examined the number of peptides identified for that protein from NSI-MS/MS analysis of normal tissue and tumor tissue before and after L-PHA fractionation. Differences in protein abundance between normal and tumor were normalized by determining the ratio of peptides identified in patient matched normal and tumor tissue prior to L-PHA fractionation. Proteins were eliminated in each case if they did not show a minimum of 1.5 fold increase in peptides identified from tumor relative to normal after L-PHA fractionation. From the list of proteins showing at least a 1.5 fold increase in tumor relative to normal, proteins were considered "enriched" following LPHA fractionation if they were identified from at least 2 cases. A total of 34 proteins had increased peptides and spectra present in L-PHA fractionations isolated from tumor compared with normal tissue for at least 2 separate cases of ductal invasive breast carcinoma (Table 4, number of spectra in parenthesis). The peptide sequences for these proteins are provided in Table 5. As expected, the majority of these proteins are predicted to be glycoproteins by searching databases such as GenBank and IPI. Since we do not compete L-PHA bound proteins from the magnetic beads using a competitive sugar hapten, we have identified some proteins that are predicted to be non-glyco-

TABLE 3

Summary of cases analyzed

| Case | Unique Proteins Total NL | Unique Proteins Total TU | Unique Proteins L-PHA-NL | Unique Proteins L-PHA-TU | Tumor Grade | HER2 Status | ER Status | PR Status | LN Status | L-PHA Level |
|---|---|---|---|---|---|---|---|---|---|---|
| 10406 | ND | ND | ND | ND | II, moderate | Positive | 3+ Positive | Negative | Yes | 1 |
| 10119 | 362 | 363 | 88 | 80 | II, moderate | Negative | 3+ Positive | 3+ Positive | No | 4 |
| 11827 | 349 | 515 | 70 | 118 | III, poor | ND | ND | ND | Yes | 4 |
| 2417 | 347 | 491 | 53 | 214 | III, poor | 2+ Positive | Negative | Negative | Yes | 10 |
| 2207 | 362 | 476 | 145 | 193 | III, poor | 2+ Positive | 3+ Positive | 3+ Positive | No | 9 |

Figure 4:
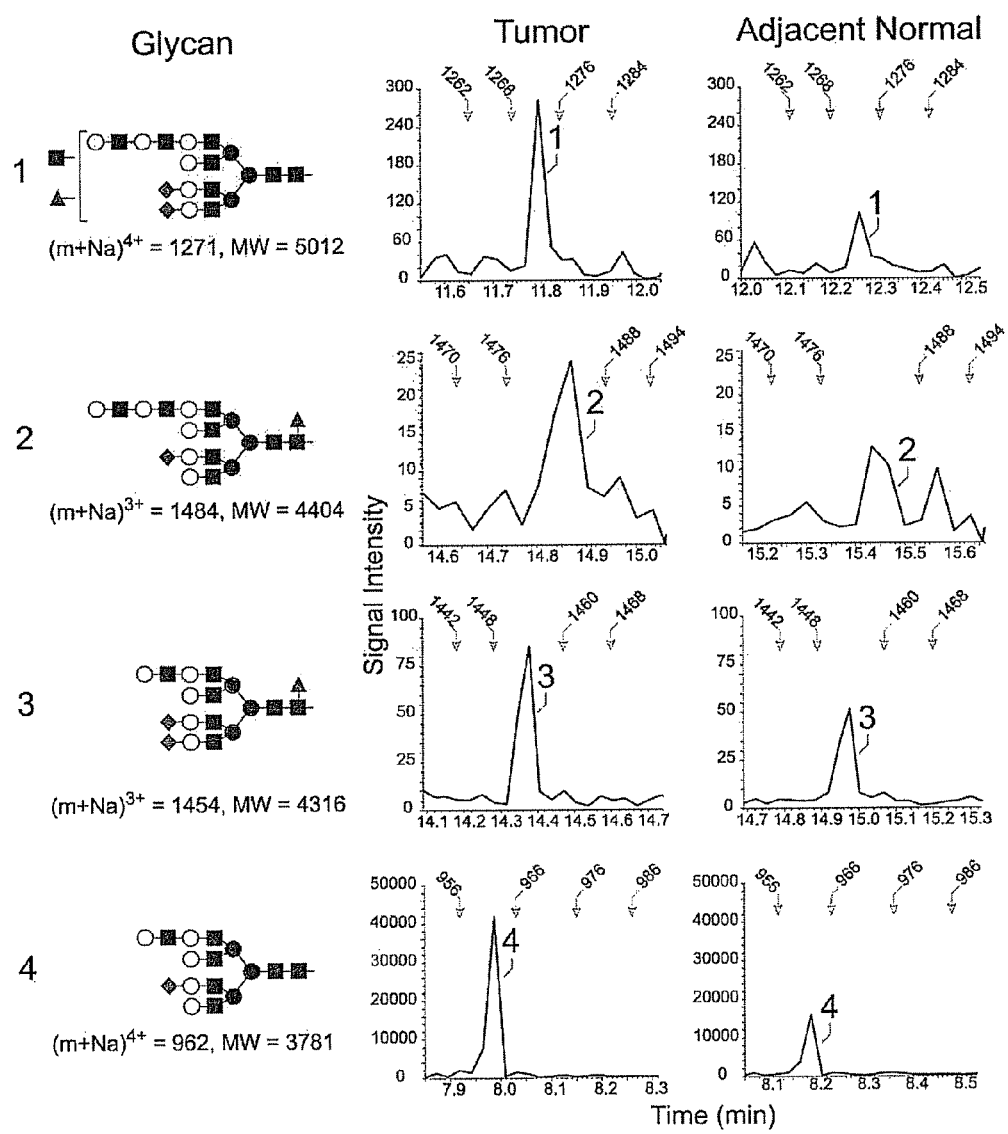
FIG. 4 shows enrichment of tetra-antennary glycans extended with N-acetyllactosamine in tumor and adjacent normal tissue from case 2417. The four indicated N-linked glycans (1-4) were detected by NSI-MS/MS. In the profiles shown at the right of each glycan, the MS/MS spectra associated with the TIM scan for the indicated tissue were filtered to present the detected signal intensity of a signature tetrasaccharide fragment (Hex-HexNAc-Hex-HexNAc). The presence of this fragment indicates the detection of a glycan extended with at least two N-acetyllactosamine repeats at a scan time which predicts the m/z ratio for the parent ion. For reference, the scan time for specific m/z values are indicated by arrows in each filtered profile. The shading and shapes for the glycan structures reflect standard nomenclature adopted by the Consortium for Functional Glycomics (CFG; N-Acetylglucosamine, GlcNAc, square; galactose, Gal, open circle, mannose, Man, filled circle; fucose, Fuc, triangle, N-Acetylneuraminic acid, NeuAc, diamond).

To verify that L-PHA binding accurately reports intrinsic differences in glycan expression between tumor and adjacent normal tissue, total N-linked glycans were profiled for tissues taken from case 2417, which exhibited the greatest relative increase in tumor-associated L-PHA recognition (Table 3). The prevalence of glycans carrying a β(1,6) branch extended with N-acetyllactosamine was compared in tumor and adjacent normal preparations by quantifying the signal intensity of a specific fragment ion detected in TIM analysis. By filtering TIM profiles for the presence of a permethylated Hex-HexNAc-Hex-HexNAc fragment, the relative abundances of several β(1,6) branched parent ions were measured and compared. The most prevalent of the detected glycans extended with N-acetyllactosamine was increased more than 2.5-fold in tumor tissue relative to adjacent normal tissue, compared using equivalent protein amounts as starting material (FIG. 4). The trimmed, high mannose glycan Man5GlcNAc2, that serves as an early precursor for complex terminal modifications including β(1,6) branching, was found in equal prevalence between the two tissues (data not shown). Therefore for case 2417, the increased abundance of L-PHA reactive proteins identified by MS/MS from tumor tissue compared with normal tissue correlates with increases in β(1,6) branched N-glycan structures, confirming the specificity of the lectin enrichment analysis.

Proteins Showing Tumor-Specific Increased Reactivity with L-PHA.

Figure 5:
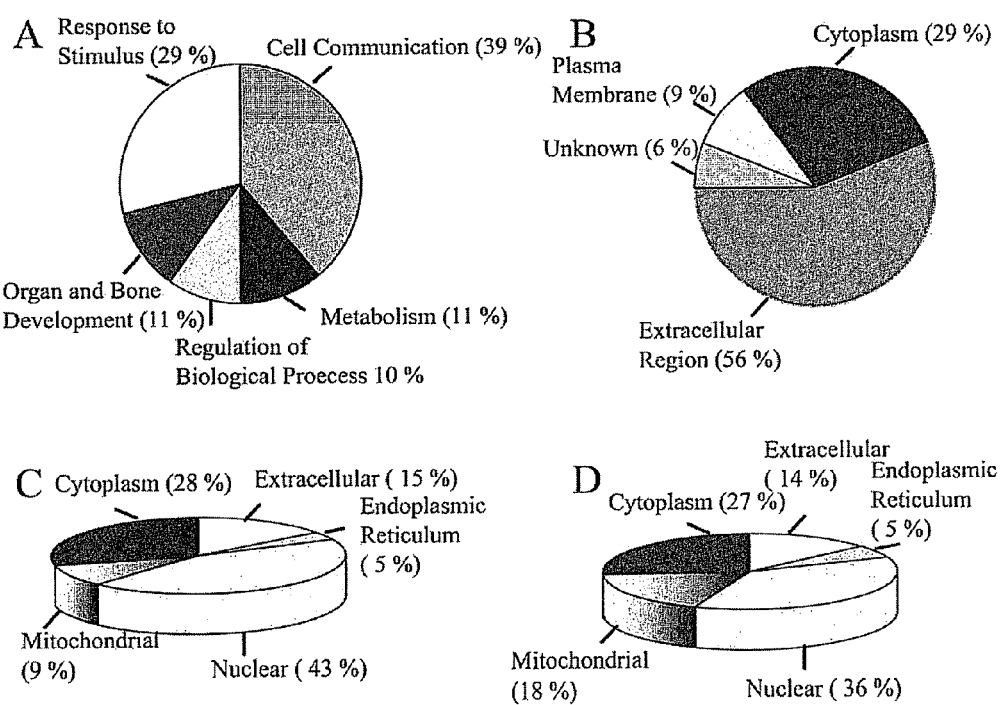
FIG. 5 shows the functional annotation and distribution of the L-PHA enriched proteins identified from breast carcinoma. (A) Biological function of proteins listed in Table 2 as annotated by DAVID 2007 (B) Cellular compartment for L-PHA enriched proteins assigned based on GO consortium (C) Cellular compartment of proteins identified from normal breast tissue by total MS/MS analysis assigned by the Gene Ontology (GO) consortium. (D) Cellular compartment of proteins identified from tumor breast tissue assigned by GO consortium.

We detected a total of 258 L-PHA reactive proteins (2 or more peptides) from the 4 tumors showing elevated L-PHA sylated and are likely binding to L-PHA reactive glycosylated proteins. We utilized DAVID 2007 (Database for Annotation, Visualization and Integrated Discovery) to annotate the function of the proteins listed in Table 4 (FIG. 5A). The top 2 functional classifications of glycoproteins showing differential binding to L-PHA in ductal invasive breast carcinoma relative to normal breast tissue are (i) binding proteins related to cell adhesion and cell-communication, and (ii) proteins that respond to external stimulus. These results indicate that largest group of proteins showing increases in β(1,6) branched glycosylation function in mediating communication of the tumor cell with the extracellular matrix (COL6A1, COL6A2, COL6A3, COL14A1) and neighboring cells (HPX, BGN, DCN, VIM, POSTN, VTN, THBS1, OGN). The second highest group of proteins with elevated L-PHA reactive glycoproteins participates in the response of the tumor cells to environmental stress. This group includes the members of the lectin-induced complement pathway (C3 and C4B), activators of complement (HPR), immunoglobulin/MHC complex (IGHA1, IGLV4-3, IGHM), enzyme inhibitors (SERPINA1, 14-3-3 zeta/delta, COL6A3, THBS1), enzyme activators of MMP (HPX), and enzymes that detoxify (PRDX1). This information contributes to our knowledge of the functions of glycoproteins acquiring β(1,6) branched N-linked glycan structures in breast carcinoma and offers insights into how the acquisition of these structures may be associated with breast cancer progression. Several of the proteins enriched by L-PHA are predicted to participate in the development of the skeletal system and organ development (POSTN, ANXA2, DCN, COL6A3, PRDX1, and OGN).

There are also several enzymes that participate in the glycolytic pathway that are enriched by L-PHA (PGK1, TPI1, ENO1, LDHA, and PKM2). Overall, these results suggest that proteins that are participating in cell communication, organ development, and metabolism derive β(1,6) branched N-linked glycan structures in breast tumors. The abnormal elevated expression of these glycan structures on these proteins in breast epithelial cells may play roles in tumor progression and invasion (Guo et al., 2007. *J Biol Chem* 282: 22150-62).

TABLE 4

L-PHA reactive proteins with elevated peptides and spectra in tumor relative to normal for at least 2 cases.

| Abb name | Name | 10119-NL | 10119-TU | 11827-NL | 11827-TU | 2207-NL | 2207-TU | 2417-NL | 2417-TU | Function | Cell Compartment |
|---|---|---|---|---|---|---|---|---|---|---|---|
| PRDX1 | Perosiredoxin-1 | 0 | 0 | 0 | 1(1) | 1(2) | 2(3) | 0 | 0 | proliferation | Unknown |
| POSTN | Periostin | 0 | 4(9) | 0 | 6(14) | 0 | 11(26) | 1(1) | 10(51) | adhesion | Ext |
| BGN | Biglycan | 4(7) | 1(3) | 0 | 0 | 3(7) | 6(12) | 1(3) | 7(14) | binding | Ext |
| CLIC1 | Chloride intracellular channel protein | 0 | 0 | 0 | 0 | 0 | 1(2) | 0 | 1(2) | CI transport | PM |
| DCN | Decorin | 3(7) | 1(5) | 0 | 0 | 4(14) | 6(18) | 2(6) | 8(18) | organ morpho | Ext |
| KCIP-1 | 14-3-3 zeta/delta | 0 | 1(1) | 0 | 3(5) | 0 | 3(6) | 0 | 0 | binding | Cyto |
| APOA-1 | Apo-A1 precursor | 1(1) | 2(4) | 3(7) | 2(4) | 4(7) | 1(1) | 1(1) | 5(8) | binding | Ext |
| HPX | Hemopexin | 0 | 0 | 0 | 0 | 3 | 5 | 0 | 6 | binding | Ext |
| OGN | Osteoglycin | 3(7) | 5(8) | 0 | 1(2) | 0 | 8(25) | 0 | 7(12) | proliferation | Unknown |
| COL6A3 | Collagen VI alpha 3 | 22(56) | 25(47) | 10(14) | 7(10) | 40(105) | 60(167) | 26(167) | 86(290) | adhesion | Ext |
| C3 | 187 kD protein | 4(8) | 1(2) | 0 | 0 | 4(6) | 11(18) | 0 | 25(44) | binding | Ext |
| PGK1 | Phosphoglycerate kinase 1 | 0 | 0 | 0 | 1(2) | 0 | 2(3) | 0 | 3 | catalytic | Cyto |
| COL14A1 | Collagen 14 isoform 1 | 1(2) | 9(15) | 0 | 0 | 14(43) | 22(72) | 6(13) | 28(98) | cell-cell adhesion | Ext |
| PROF1 | Profilin | 0 | 0 | 0 | 1(2) | 0 | 1(4) | 0 | 2(3) | binding | Cyto |
| LDHA | Lactate Dehydrogenase isoform 1 | 0 | 0 | 0 | 1(2) | 0 | 3(6) | 0 | 1(1) | catalytic | Ext |
| TUBA1C | Tubulin alpha 6 | 0 | 1( ) | 0 | 2(5) | 3(3) | 7(18) | 1(1) | 7(12) | binding | Cyto |
| COL6A1 | Collagen alpha 1 VI chain precursor | 6(13) | 5(0) | 1(2) | 2(3) | 7(23) | 13(36) | 2(3) | 14(43) | adhesion | Ext |
| THBS1 | Thrombospondin-1 | 0 | 0 | 0 | 3(4) | 0 | 0 | 0 | 1(2) | motility | Ext |
| VTN | Vitronectin | 0 | 1(1) | 0 | 1(1) | 0 | 0 | 0 | 2(3) | adhesion | Ext |
| COL6A2 | Collagen alpha 1 VI isoform 2C2 | 7(19) | 8(15) | 5(7) | 3(7) | 10(22) | 12(31) | 5(13) | 14(62) | cell-cell adhesion | Ext |
| HSPA1 | Heat Shock 70 kDa | 0 | 0 | 0 | 1(1) | 0 | 1(1) | 0 | 0 | unfolded protein | Ext |
| ANXA5 | Annesin A5 | 0 | 0 | 0 | 2(2) | 0 | 1(2) | 0 | 0 | binding | Cyto |
| IGLV4-3 | variable Ig | 0 | 1(1) | 0 | 1(1) | 3(5) | 5(12) | 0 | 8(32) | immune res | Ext |
| C4B | C4B complement | 0 | 0 | 0 | 0 | 1(2) | 3(7) | 0 | 3(5) | binding | Ext |
| PPIA | Peptidyl prolyl isomerase A | 0 | 0 | 0 | 2(5) | 0 | 0 | 0 | 1(2) | catalytic | |
| IGHA1 | MHC Class 1 protein | 0 | 0 | 0 | 0 | 2(5) | 4(10) | 2(2) | 7(14) | binding | Ext |
| ANXA2 | Annexin A2 | 0 | 0 | 1(1) | 2(2) | 2(3) | 5(14) | 0 | 0 | enzyme inhibitor | PM |
| TPI1 | Triosphosphate iso | 0 | 1(1) | 0 | 1(2) | 4(3) | 3(4) | 0 | 3(3) | carb metabolism | Cyto |
| ENO1 | Alpha enolase | 0 | 0 | 0 | 3(5) | 4(17) | 3(5) | 0 | 5(10) | glycolytic | Cyto |
| IGHM | IGHM protein | 0 | 0 | 0 | 0 | 8(37) | 10(54) | 6(13) | 11(63) | immune res | PM |
| HPR | Haptoglobin-related protein precursor Isoform-1 | 0 | 1(1) | 0 | 1(2) | 0 | 1(2) | 0 | 3(4) | defense | Ext |
| PKM2 | Pyruvate kinase M2 | 0 | 0 | 0 | 0 | 1(1) | 5(12) | 0 | 3(9) | binding | Cyto |
| SERPINA1 | Alpha-1 antitrypsin inhibitor | 0 | 1( ) | 2(4) | 2(4) | 4(11) | 4(12) | 1(1) | 8(17) | binding | Ext |
| VM | Vimentin like 50 kDa | 1(1) | 3(6) | 6(9) | 6(12) | 2(3) | 5(8) | 0 | 5(6) | motility | Cyto |

[a]International protein index database # of spectra in parenthesis beside the number of peptides
[b]Gene function determined by the Gene Ontology Consortium

TABLE 5

Proteins with increased peptides and spectra present in L-PHA fractions isolated from tumors.

| Number | IPI | Name | M Wt (kDa) | # Unique Peptides | % Coverage | Peptide Sequence | SEQ ID NO: | Spectra |
|---|---|---|---|---|---|---|---|---|
| 1 | IPI00000874 | PRDX1 | 22.1 | 2 | 9.5 | ADEGISFR | 1 | 1 |
|   | IPI00000874 | PRDX1 | 22.1 | 2 | 9.5 | QITVNDLPVGR | 2 | 3 |
| 2 | IPI00022488 | HPX | 51.6 | 7 | 22 | NFPSPVDAAFR | 3 | 1 |
|   |   |   |   |   |   | LLQDEFPGIPSPLDAAVECHR | 4 | 1 |
|   |   |   |   |   |   | YYCFQGNQFLR | 5 | 2 |
|   |   |   |   |   |   | GGYTLVSGYPK | 6 | 1 |
|   |   |   |   |   |   | EVGTPHGIILDSVDAAFICPGSSR | 7 | 1 |
|   |   |   |   |   |   | RLWWLDLK | 8 | 1 |
|   |   |   |   |   |   | SGAQATWTELPWPHEK | 9 | 4 |
| 3 | IPI00007960 | POSTN | 93.3 | 11 | 21.8 | DQGPNVCALQQILGTK | 10 | 2 |
|   |   |   |   |   |   | LREEIEGK | 11 | 1 |
|   |   |   |   |   |   | VLTQIGTSIQDFIEAEDDLSSFR | 12 | 18 |
|   |   |   |   |   |   | AAAITSDILEALGR | 13 | 7 |
|   |   |   |   |   |   | DGHFTLFAPTNEAFEK | 14 | 9 |
|   |   |   |   |   |   | DIVTNNGVIHLIDQVLIPDSAK | 15 | 5 |
|   |   |   |   |   |   | VGLNELYNGQILETIGGK | 16 | 8 |
|   |   |   |   |   |   | FSTFLSLLEAADLK | 17 | 7 |
|   |   |   |   |   |   | ELLTQPGDWTLFVPTNDAFK | 18 | 10 |
|   |   |   |   |   |   | LLYPADTPVGNDQLLEILNK | 19 | 11 |
|   |   |   |   |   |   | IIDGVPVEITEK | 20 | 2 |
| 4 | IPI00216691 | PROF1 | 15 | 2 | 20 | DSPSVWAAVPGK | 21 | 1 |
|   |   |   |   |   |   | TFVNITPAEVGVLVGK | 22 | 8 |
| 5 | IPI00072917 | COL6A3 | 322 | 77 | 36.2 | VGLVQFSDTPVTEFSLNTYQTK | 23 | 2 |
|   |   |   |   |   |   | SDILGHLR | 24 | 2 |
|   |   |   |   |   |   | TLSGTPEESKR | 25 | 2 |
|   |   |   |   |   |   | AAPLQGLPGLLAPLR | 26 | 4 |
|   |   |   |   |   |   | LLPYIVGVAQR | 27 | 2 |
|   |   |   |   |   |   | MKPLDGSALYTGSALDFVR | 28 | 1 |
|   |   |   |   |   |   | NNLFTSSAGYR | 29 | 8 |
|   |   |   |   |   |   | LLVLITGGK | 30 | 2 |
|   |   |   |   |   |   | SLDEISQPAQELK | 31 | 6 |
|   |   |   |   |   |   | GADQAELEEIAFDSSLVFIPAEFR | 32 | 3 |
|   |   |   |   |   |   | DILFLFDGSANLVGQFPVVR | 33 | 11 |
|   |   |   |   |   |   | IIDELNVKPEGTR | 34 | 4 |
|   |   |   |   |   |   | IAVAQYSDDVKVESR | 35 | 3 |
|   |   |   |   |   |   | FDEHQSKPEILNLVK | 36 | 5 |
|   |   |   |   |   |   | ALNLGYALDYAQR | 37 | 16 |
|   |   |   |   |   |   | SSDRVDGPASNLK | 38 | 5 |
|   |   |   |   |   |   | VDGPASNLK | 39 | 1 |
|   |   |   |   |   |   | QSGVVPFIFQAK | 40 | 3 |
|   |   |   |   |   |   | NADPAELEQIVLSPAFILAAESLPK | 41 | 14 |
|   |   |   |   |   |   | IGDLHPQIVNLLK | 42 | 4 |
|   |   |   |   |   |   | DVVFLLDGSEGVR | 43 | 4 |
|   |   |   |   |   |   | SGFPLLK | 44 | 4 |
|   |   |   |   |   |   | VVESLDVGQDR | 45 | 9 |
|   |   |   |   |   |   | VAVVQYSDR | 46 | 4 |
|   |   |   |   |   |   | QLTLLGGPTPNTGAALEFVLR | 47 | 9 |
|   |   |   |   |   |   | NILVSSAGSR | 48 | 11 |
|   |   |   |   |   |   | ITEGVPQLLIVLTADR | 49 | 9 |
|   |   |   |   |   |   | SGDDVRNPSVVVK | 50 | 6 |
|   |   |   |   |   |   | QLGTVQQVISER | 51 | 9 |
|   |   |   |   |   |   | VTQLTR | 52 | 1 |
|   |   |   |   |   |   | LQPVLQPLPSPGVGGK | 53 | 9 |
|   |   |   |   |   |   | DVVFLIDGSQSAGPEFQYVR | 54 | 15 |
|   |   |   |   |   |   | LVDYLDVGFDTTR | 55 | 29 |
|   |   |   |   |   |   | VAVIQFSDDPK | 56 | 4 |
|   |   |   |   |   |   | VEFLLNAHSSKDEVQNAVQR | 57 | 1 |
|   |   |   |   |   |   | DEVQNAVQR | 58 | 4 |
|   |   |   |   |   |   | QINVGNALEYVSR | 59 | 12 |
|   |   |   |   |   |   | IEEGVPQFLVLISSGK | 60 | 8 |
|   |   |   |   |   |   | SDDEVDDPAVELK | 61 | 8 |
|   |   |   |   |   |   | QFGVAPFTIAR | 62 | 3 |
|   |   |   |   |   |   | NADQEELVK | 63 | 14 |
|   |   |   |   |   |   | ISLSPEYVFVSTFR | 64 | 7 |
|   |   |   |   |   |   | LLTPITTLTSEQIQK | 65 | 14 |
|   |   |   |   |   |   | RLNIGPSK | 66 | 8 |
|   |   |   |   |   |   | LNIGPSK | 67 | 1 |
|   |   |   |   |   |   | VGVVQFSNDVFPEFYLK | 68 | 7 |
|   |   |   |   |   |   | SQAPVLDAIR | 69 | 11 |
|   |   |   |   |   |   | ALEFVAR | 70 | 2 |

TABLE 5-continued

Proteins with increased peptides and spectra present in L-PHA fractions isolated from tumors.

| Number | IPI | Name | M Wt (kDa) | # Unique Peptides | % Coverage | Peptide Sequence | SEQ ID NO: | Spectra |
|---|---|---|---|---|---|---|---|---|
| | | | | | | IEDGVPQHLVLVLGGK | 71 | 5 |
| | | | | | | SSGIVSLGVGDR | 72 | 5 |
| | | | | | | NIDRTELQTITNDPR | 73 | 2 |
| | | | | | | TELQTITNDPR | 74 | 7 |
| | | | | | | LVFTVR | 75 | 2 |
| | | | | | | DSFQEVLR | 76 | 9 |
| | | | | | | RQIIDAINK | 77 | 1 |
| | | | | | | VGLEHLR | 78 | 3 |
| | | | | | | VNHFVPEAGSR | 79 | 1 |
| | | | | | | VPQIAFVITGGK | 80 | 10 |
| | | | | | | SVEDAQDVSLALTQR | 81 | 9 |
| | | | | | | VFAVGVR | 82 | 10 |
| | | | | | | NIDSEEVGK | 83 | 10 |
| | | | | | | IASNSATAFR | 84 | 5 |
| | | | | | | ACNLDVILSFDGSR | 85 | 6 |
| | | | | | | DQNVFVAQK | 86 | 8 |
| | | | | | | VSVVANTPSGPVEAFDFDEYQPEMLEK | 87 | 3 |
| | | | | | | SQHPYVLTEDTLK | 88 | 5 |
| | | | | | | VVIHFTDGADGDLADLHR | 89 | 5 |
| | | | | | | ALILVGLER | 90 | 9 |
| | | | | | | VVNLER | 91 | 7 |
| | | | | | | LNLLDLDYELAEQLDNIAEK | 92 | 18 |
| | | | | | | GETGDDGRDGVGSEGR | 93 | 5 |
| | | | | | | GDSIDQCALIQSIK | 94 | 1 |
| | | | | | | DVVLSIVNDLTIAESNCPR | 95 | 6 |
| | | | | | | VAVVTYNNEVTTEIR | 96 | 14 |
| | | | | | | NLQVALTSK | 97 | 4 |
| | | | | | | VAVFFSNTPTR | 98 | 2 |
| | | | | | | ALGSAIEYTIENVFESAPNPR | 99 | 7 |
| | | | | | | LLDSFVSSENAFYLSPDIR | 100 | 6 |
| 6 | IPI00218343 | TUBA1C | 49.8 | 9 | 30.5 | LIGQIVSSITASLR | 101 | 2 |
| | | | | | | TIQFVDWCPTGFK | 102 | 1 |
| | | | | | | LISQIVSSITASLR | 103 | 6 |
| | | | | | | TIGGGDDSFNTFFSETGAGK | 104 | 2 |
| | | | | | | AVFVDLEPTVIDEVR | 105 | 10 |
| | | | | | | EIIDLVLDR | 106 | 4 |
| | | | | | | NLDIERPTYTNLNR | 107 | 1 |
| | | | | | | FDGALNVDLTEFQTNLVPYPR | 108 | 8 |
| | | | | | | VGINYQPPTVVPGGDLAK | 109 | 4 |
| 7 | IPI00025465 | OGN | 33.9 | 7 | 29.2 | DFADIPNLR | 110 | 9 |
| | | | | | | RLDFTGNLIEDIEDGTFSK | 111 | 9 |
| | | | | | | LSLLEELSLAENQLLK | 112 | 11 |
| | | | | | | LPVLPPK | 113 | 1 |
| | | | | | | LIHLQFNNIASITDDTFCK | 114 | 2 |
| | | | | | | DRIEEIR | 115 | 2 |
| | | | | | | LEGNPIVLGK | 116 | 10 |
| 8 | IPI00477597 | HPR | 39 | 3 | 8.6 | DIAPTLTLYVGK | 117 | 1 |
| | | | | | | NPANPVQR | 118 | 1 |
| | | | | | | VTSIQDWVQK | 119 | 7 |
| 9 | IPI00479186 | PKM2 | 57.9 | 6 | 18.6 | LDIDSPPITAR | 120 | 2 |
| | | | | | | NTGIICTIGPASR | 121 | 2 |
| | | | | | | TATESFASDPILYRPVAVALDTK | 122 | 2 |
| | | | | | | LAPITSDPTEATAVGAVEASFK | 123 | 10 |
| | | | | | | APIIAVTR | 124 | 3 |
| | | | | | | GIFPVLCKDPVQEAWAEDVDLR | 125 | 2 |
| 10 | IPI00465248 | ENO1 | 47.1 | 4 | 20 | AAVPSGASTGIYEALELR | 126 | 6 |
| | | | | | | DATNVGDEGGFAPNILENKEGLELLK | 127 | 1 |
| | | | | | | YISPDQLADLYK | 128 | 6 |
| | | | | | | SGETEDTFIADLVVGLCTGQIK | 129 | 2 |
| 11 | IPI00164623 | C3 | 187.3 | 24 | 19.9 | TIYTPGSTVLYR | 130 | 2 |
| | | | | | | AYYENSPQQVFSTEFEVK | 131 | 6 |
| | | | | | | EYVLPSFEVIVEPTEK | 132 | 5 |
| | | | | | | IPIEDGSGEVVLSR | 133 | 4 |
| | | | | | | VLLDGVQNPR | 134 | 1 |
| | | | | | | VPVAVQGEDTVQSLTQGDGVAK | 135 | 2 |
| | | | | | | TKKQELSEAEQATR | 136 | 1 |
| | | | | | | TELRPGETLNVNFLLR | 137 | 1 |
| | | | | | | EPGQDLVVLPLSITTDFIPSFR | 138 | 2 |

TABLE 5-continued

Proteins with increased peptides and spectra present in
L-PHA fractions isolated from tumors.

| Number | IPI | Name | M Wt (kDa) | # Unique Peptides | % Coverage | Peptide Sequence | SEQ ID NO: | Spectra |
|---|---|---|---|---|---|---|---|---|
| | | | | | | LVAYYTLIGASGQR | 139 | 2 |
| | | | | | | IWDVVEK | 140 | 2 |
| | | | | | | ASHLGLAR | 141 | 1 |
| | | | | | | SNLDEDIIAEENIVSR | 142 | 5 |
| | | | | | | LPYSVVR | 143 | 2 |
| | | | | | | NEQVEIR | 144 | 6 |
| | | | | | | SSLSVPYVIVPLK | 145 | 3 |
| | | | | | | TGLQEVEVK | 146 | 6 |
| | | | | | | ILLDGTPVAQMTEDAVDAER | 147 | 1 |
| | | | | | | DFDFVPPVVR | 148 | 3 |
| | | | | | | VHQYFNVELIQPGAVK | 149 | 2 |
| | | | | | | ACEPGVDYVYK | 150 | 1 |
| | | | | | | VQLSNDFDEYIMAIEQTIK | 151 | 1 |
| | | | | | | SGSDEVQVGQQR | 152 | 3 |
| | | | | | | DTWVEHWPEEDECQDEENQK | 153 | 2 |
| 12 | IPI00021841 | APOA1 | 30.7 | 4 | 18.9 | DYVSQFEGSALGK | 154 | 4 |
| | | | | | | LLDNWDSVTSTFSK | 155 | 4 |
| | | | | | | QGLLPVLESFK | 156 | 5 |
| | | | | | | VSFLSALEEYTK | 157 | 4 |
| 13 | IPI00021263 | KCIP-1 | 27.7 | 4 | 23 | SVTEQGAELSNEER | 158 | 5 |
| | | | | | | DICNDVLSLLEK | 159 | 2 |
| | | | | | | YLAEVAAGDDKK | 160 | 1 |
| | | | | | | TAFDEAIAELDTLSEESYK | 161 | 4 |
| 14 | IPI00010790 | BGN | 41.6 | 8 | 26.9 | VVQCSDLGLK | 162 | 3 |
| | | | | | | EISPDTTLLDLQNNDISELR | 163 | 8 |
| | | | | | | NHLVEIPPNLPSSLVELR | 164 | 7 |
| | | | | | | GVFSGLR | 165 | 1 |
| | | | | | | DLPETLNELHLDHNK | 166 | 1 |
| | | | | | | IQAIELEDLLR | 167 | 9 |
| | | | | | | LGLGHNQIR | 168 | 2 |
| | | | | | | VPSGLPDLK | 169 | 3 |
| 15 | IPI00012119 | DCN | 39.7 | 8 | 29.8 | DFEPSLGPVCPFR | 170 | 4 |
| | | | | | | VVQCSDLGLDKVPK | 171 | 1 |
| | | | | | | DLPPTTLLDLQNNK | 172 | 23 |
| | | | | | | ITEIKDGDFK | 173 | 1 |
| | | | | | | NLHALILVNNK | 174 | 4 |
| | | | | | | VSPGAFTPLVK | 175 | 2 |
| | | | | | | VPGGLAEHK | 176 | 3 |
| | | | | | | ASYSGVSLFSNPVQYWEIQPSTFR | 177 | 1 |
| 16 | IPI00382938 | IGLV4 | 25.9 | 5 | 33.3 | AAPSVTLFPPSSEELQANK | 178 | 16 |
| | | | | | | AGVETTTPSK | 179 | 9 |
| | | | | | | ATLVCLISDFYPGAVTVAWK | 180 | 3 |
| | | | | | | YAASSYLSLTPEQWK | 181 | 5 |
| | | | | | | SYSCQVTHEGSTVEK | 182 | 4 |
| 17 | IPI00418163 | C4B | 192.7 | 5 | 4.2 | LNMGITDLQGLR | 183 | 1 |
| | | | | | | VGDTLNLNLR | 184 | 2 |
| | | | | | | SFFPENWLWR | 185 | 1 |
| | | | | | | VTASDPLDTLGSEGALSPGGVASLLR | 186 | 5 |
| | | | | | | VLSLAQEQVGGSPEK | 187 | 3 |
| 18 | IPI00430842 | IGHA1 | 52.8 | 7 | 16.8 | DASGVTFTWTPSSGK | 188 | 4 |
| | | | | | | SAVQGPPER | 189 | 2 |
| | | | | | | TFTCTAAYPESK | 190 | 2 |
| | | | | | | TPLTATLSK | 191 | 5 |
| | | | | | | WLQGSQELPR | 192 | 5 |
| | | | | | | YLTWASR | 193 | 2 |
| | | | | | | QEPSQGTTTFAVTSILR | 194 | 2 |
| 19 | IPI00465028 | TPI1 | 30.7 | 2 | 9.4 | VVLAYEPVWAIGTGK | 195 | 5 |
| | | | | | | SNVSDAVAQSTR | 196 | 5 |
| 20 | IPI00472610 | IGHM | 52.6 | 14 | 45 | GPSVFPLAPSSK | 197 | 6 |
| | | | | | | GTTVTVSSASTK | 198 | 5 |
| | | | | | | THTCPPCPAPELLGGPSVFLFPPKPK | 199 | 1 |
| | | | | | | TPEVTCVVVDVSHEDPEVK | 200 | 12 |
| | | | | | | FNWYVDGVEVHNAK | 201 | 9 |
| | | | | | | TTPPVLDSDGSFFLYSK | 202 | 23 |
| | | | | | | STSESTAALGCLVK | 203 | 2 |

TABLE 5-continued

Proteins with increased peptides and spectra present in
L-PHA fractions isolated from tumors.

| Number | IPI | Name | M Wt (kDa) | # Unique Peptides | % Coverage | Peptide Sequence | SEQ ID NO: | Spectra |
|---|---|---|---|---|---|---|---|---|
| | | | | | | GFYPSDIAVEWESNGQPENNYK | 204 | 17 |
| | | | | | | TPEVTCVVVDVSHEDPEVQFK | 205 | 1 |
| | | | | | | WYVDGVEVHNAK | 206 | 2 |
| | | | | | | VVSVLTVLHQDWLNGK | 207 | 2 |
| | | | | | | DTLMISR | 208 | 10 |
| | | | | | | GPSVFPLAPCSR | 209 | 1 |
| | | | | | | NQCSLTCLVK | 210 | 4 |
| 21 | IPI00827679 | VIM | 50 | 10 | 27.8 | SLYASSPGGVYATR | 211 | 1 |
| | | | | | | LLQDSVDFSLADAINTEFK | 212 | 6 |
| | | | | | | VELQELNDR | 213 | 1 |
| | | | | | | ILLAELEQLK | 214 | 6 |
| | | | | | | EEAENTLQSFR | 215 | 1 |
| | | | | | | QDVDNASLAR | 216 | 1 |
| | | | | | | NLQEAEEWYK | 217 | 6 |
| | | | | | | FADLSEAANR | 218 | 5 |
| | | | | | | QVQSLTCEVDALK | 219 | 2 |
| | | | | | | ISLPLPNFSSLNLR | 220 | 3 |
| 22 | IPI00169383 | PGK1 | 44.6 | 3 | 11 | YSLEPVAVELK | 221 | 1 |
| | | | | | | ACANPAAGSVILLENLR | 222 | 2 |
| | | | | | | QIVWNGPVGVFEWEAFAR | 223 | 2 |
| 23 | IPI00176193 | COL14A1 | 193.5 | 26 | 18.9 | TNQLNLQNTATK | 224 | 8 |
| | | | | | | HFLENLVTAFDVGSEK | 225 | 6 |
| | | | | | | DEVIEAVR | 226 | 10 |
| | | | | | | IGILITDGK | 227 | 4 |
| | | | | | | SQDDIIPPSR | 228 | 4 |
| | | | | | | ASAHAITGPPTELITSEVTAR | 229 | 11 |
| | | | | | | WDAVTGASGYLILYAPLTEGLAGDEK | 230 | 1 |
| | | | | | | ISNVGSNSAR | 231 | 4 |
| | | | | | | IVYNNADGTEINEVEVDPITTFPLK | 232 | 8 |
| | | | | | | NLVVGDETTSSLR | 233 | 6 |
| | | | | | | WDISDSDVQQFR | 234 | 5 |
| | | | | | | VTVTPIYTDGEGVSVSAPGK | 235 | 14 |
| | | | | | | TLPSSGPQNLR | 236 | 7 |
| | | | | | | VSEEWYNR | 237 | 2 |
| | | | | | | ITWDPPSSPVK | 238 | 4 |
| | | | | | | TLFLGVTNLQAK | 239 | 7 |
| | | | | | | VVIESLQDR | 240 | 5 |
| | | | | | | IISFLYSTVGALNK | 241 | 4 |
| | | | | | | TKETLLDAIK | 242 | 4 |
| | | | | | | DTLFTAESGTR | 243 | 6 |
| | | | | | | VIVVITDGR | 244 | 4 |
| | | | | | | HVFFVDDFDAFK | 245 | 2 |
| | | | | | | DGIDLAGFK | 246 | 4 |
| | | | | | | ILPDTPQEPFALWEILNK | 247 | 11 |
| | | | | | | NSDPLVGVILDNGGK | 248 | 13 |
| 24 | IPI00217966 | LDHA | 36.6 | 2 | 8.1 | DLADELALVDVIEDK | 249 | 4 |
| | | | | | | VIGSGCNLDSAR | 250 | 4 |
| 25 | IPI00291136 | COL6A1 | 108.5 | 17 | 24.8 | DAEEAISQTIDTIVDIK | 251 | 1 |
| | | | | | | RFIDNLR | 252 | 2 |
| | | | | | | FIDNLR | 253 | 1 |
| | | | | | | YLIVVTDGHPLEGYKEPCGGLEDAVNEAK | 254 | 3 |
| | | | | | | VFSVAITPDHLEPR | 255 | 4 |
| | | | | | | LSIIATDHTYR | 256 | 3 |
| | | | | | | SGDEGPPGSEGAR | 257 | 6 |
| | | | | | | SLQWMAGGTFTGEALQYTR | 258 | 3 |
| | | | | | | IALVITDGR | 259 | 9 |
| | | | | | | DTTPLNVLCSPGIQVVSVGIK | 260 | 5 |
| | | | | | | DVFDFIPGSDQLNVISCQGLAPSQGRPGLSLVK | 261 | 3 |
| | | | | | | ENYAELLEDAFLK | 262 | 8 |
| | | | | | | LLLFSDGNSQGATPAAIEK | 263 | 21 |
| | | | | | | AGIEIFVVVGR | 264 | 1 |
| | | | | | | TAEYDVAYGESHLFR | 265 | 6 |
| | | | | | | VPSYQALLR | 266 | 8 |
| | | | | | | GVFHQTVSR | 267 | 2 |
| 26 | IPI00296099 | THBS1 | 129.3 | 4 | 5.1 | IEDANLIPPVPDDKFQDLVDAVR | 268 | 2 |
| | | | | | | FVFGTTPEDILR | 269 | 1 |
| | | | | | | TIVTTLQDSIR | 270 | 2 |
| | | | | | | KVTEENKELANELR | 271 | 1 |

TABLE 5-continued

Proteins with increased peptides and spectra present in L-PHA fractions isolated from tumors.

| Number | IPI | Name | M Wt (kDa) | # Unique Peptides | % Coverage | Peptide Sequence | SEQ ID NO: | Spectra |
|---|---|---|---|---|---|---|---|---|
| 27 | IPI00298971 | VTN | 54.3 | 2 | 5.6 | DVWGIEGPIDAAFTR | 272 | 4 |
| | | | | | | FEDGVLDPDYPR | 273 | 1 |
| 28 | IPI00304840 | COL6A2 | 108.5 | 13 | 15.2 | NLQGISSFR | 274 | 10 |
| | | | | | | LFAVAPNQNLK | 275 | 12 |
| | | | | | | DIASTPHELYR | 276 | 7 |
| | | | | | | NDYATMLPDSTEIDQDTINR | 277 | 3 |
| | | | | | | NFVINVVNR | 278 | 6 |
| | | | | | | NLEWIAGGTWTPSALK | 279 | 14 |
| | | | | | | VFAVVITDGR | 280 | 7 |
| | | | | | | DDDLNLR | 281 | 9 |
| | | | | | | HESENLYSIACDKPQQVR | 282 | 1 |
| | | | | | | LGEQNFHK | 283 | 9 |
| | | | | | | FVEQVAR | 284 | 6 |
| | | | | | | RDDDPLNAR | 285 | 12 |
| | | | | | | AAVFHEKDYDSLAQPGFFDR | 286 | 2 |
| 29 | IPI00304925 | HSPA1 | 70 | 2 | 6.8 | DAGVIAGLNVLR | 287 | 1 |
| | | | | | | ELEQVCNPIISGLYQGAGGPGPGGFGAQGPK | 288 | 1 |
| 30 | IPI00419585 | PPIA | 18 | 2 | 10.9 | VSFELFADK | 289 | 3 |
| | | | | | | FEDENFILK | 290 | 4 |
| 31 | IPI00553177 | SERPINA1 | 46.7 | 8 | 24.8 | SVLGQLGITK | 291 | 3 |
| | | | | | | VFSNGADLSGVTEEAPLK | 292 | 10 |
| | | | | | | ITPNLAEFAFSLYR | 293 | 1 |
| | | | | | | AVLTIDEK | 294 | 1 |
| | | | | | | VVNPTQK | 295 | 1 |
| | | | | | | TLNQPDSQLQLTTGNGLFLSEGLK | 296 | 11 |
| | | | | | | LQHLENELTHDIITK | 297 | 5 |
| | | | | | | SASLHLPK | 298 | 2 |
| 32 | IPI00010896 | CLIC1 | 26.9 | 2 | 14.5 | LAALNPESNTAGLDIFAK | 299 | 2 |
| | | | | | | FLDGNELTLADCNLLPK | 300 | 2 |
| 33 | IPI00455315 | ANXA2 | 38.6 | 5 | 20 | GVDEVTIVNILTNR | 301 | 4 |
| | | | | | | TPAQYDASELK | 302 | 5 |
| | | | | | | GLGTDEDSLIEIICSR | 303 | 2 |
| | | | | | | TNQELQEINR | 304 | 4 |
| | | | | | | TDLEKDIISDTSGDFRK | 305 | 1 |
| 34 | IPI00329801 | ANXA5 | 35.9 | 2 | 8.7 | GLGTDEESILTLLTSR | 306 | 1 |
| | | | | | | DLLDDLKSELTGK | 307 | 2 |

Interestingly, many of the proteins identified in Table 4 are connected with TGFβ signaling pathways. A recent manuscript identifies increased TGFβ protein levels in breast tumor tissue as a factor that correlates with shorter disease-free survival (Desruisseau et al., 2006. *Br J Cancer* 94:239-46). Many of the proteins we identified after L-PHA enrichment in tumor tissue are either induced by TGFβ (POSTN, COL6A3, SERPINA1) or are known to bind TGFβ with nanomolar affinities (BGN, DCN). It will be interesting to determine how β(1,6) branched N-linked glycosylation influences the binding of TGFβ to these proteins.

L-PHA Capture Facilitates the Identification of Biomarkers Likely to be Found in Serum.

We have examined the predicted cellular distribution of proteins enriched by L-PHA listed in Table 4. The distribution is primarily extracellular (56%) and cytoplasmic (29%) with the remainder of proteins localized on the plasma membrane (9%) or unknown (6%) (FIG. 5B). L-PHA-affinity enrichment significantly concentrates proteins identified from the extracellular region. For comparison, only 14-15% of the total proteins isolated from normal and tumor before L-PHA enrichment are extracellular (FIGS. 5C and 5D).

L-PHA Enrichment can Identify Novel Markers for Breast Carcinoma.

Approximately 73% of the 34 tumor L-PHA enriched proteins have been previously reported in breast cancer studies (n=25); while 29% (n=9) have not been previously cited for breast cancer (Table 4). One of the novel, tumor-specific L-PHA reactive glycoproteins that we identified, known as osteoglycin (OGN), was present at similar levels of peptide abundance in normal and tumor breast tissue before L-PHA fractionation. However, OGN is consistently identified from tumor tissue after L-PHA fractionation. Osteoglycin has not been identified as a potential marker for breast cancer previously, likely due to the consistent levels of protein present in normal and tumor. Another interesting protein not previously associated with breast cancer is the 14-3-3 zeta protein. This protein is not predicted to be glycosylated and is probably enriched by L-PHA due to association with a protein that binds L-PHA. 14-3-3 zeta functions as an adapter protein that binds with other proteins controlling cell growth and proliferation. The cellular localization of 14-3-3 zeta protein has been reported to be largely cytoplasmic, but it has been reported to be present on the plasma membrane and in the Golgi (Fu et al., 2000. *Annu Rev Pharmacol Toxicol* 40:617-47). We find in 3 out of the 4 cases significant tumor-specific association with L-PHA for 14-3-3 zeta. Similar levels of 14-3-3 zeta present in normal and tumor tissue probably prevented previous identification of this protein as a marker for breast cancer. We conclude that selective enrichment using the lectin L-PHA has enabled the identification of novel markers for breast carcinoma and adds an additional level of biomarker selection.

L-PHA Enrichment Increases the Identification of Markers Common to Breast Carcinoma Cases with Diverse Clinical Features.

Figure 6:
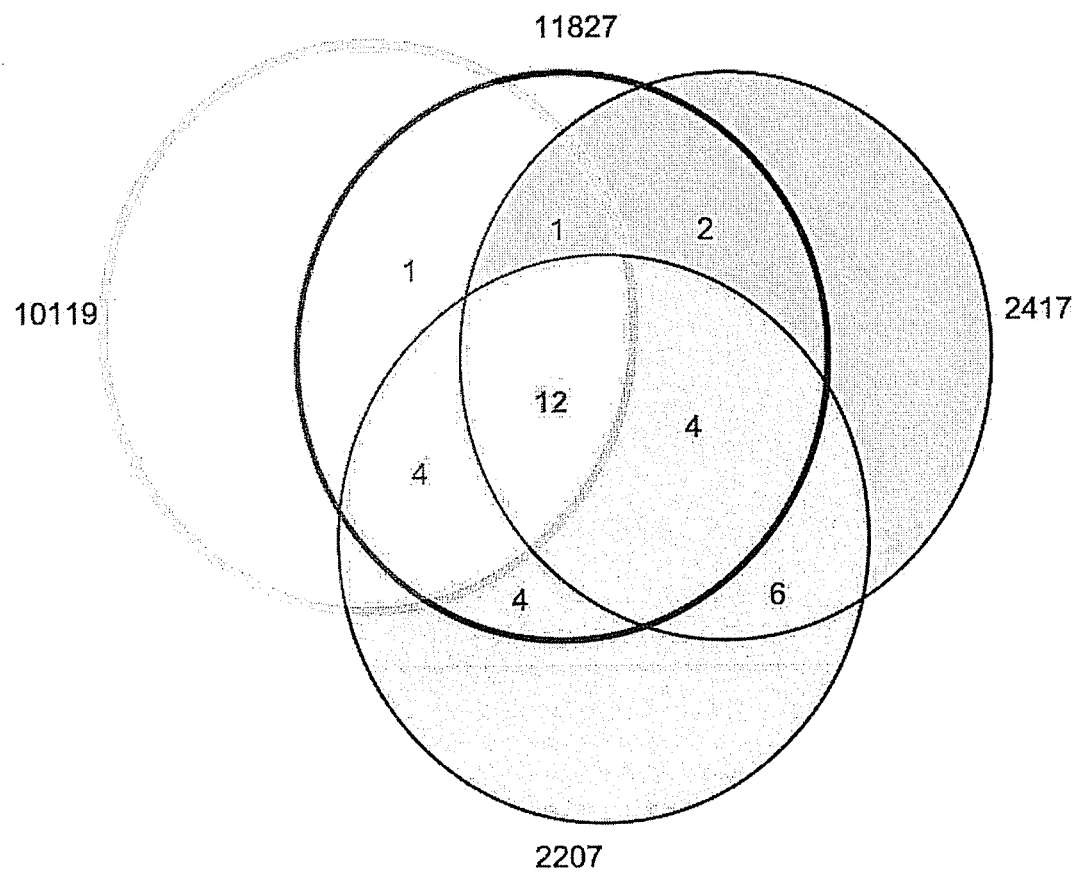
FIG. 6 shows a Venn diagram showing the number of L-PHA enriched proteins identified in common for each case.

The quest to identify markers for the early detection of many tumors has been hampered by tumor heterogeneity. Our approach, focusing on a specific post-translational modification that increases in parallel with malignant progression, has enabled the identification of 12 markers common to all 4 cases of breast carcinoma analyzed (FIG. 6). A key element of our success is the targeting of β(1,6) branched N-linked glycan structures that are normally expressed at a low level in non-diseased breast epithelial cells. This targeted approach has enabled the identification of proteins that change glycosylation only in breast carcinoma tumor tissue.

Validation of Glycoproteins with Differential L-PHA Reactivity in Normal and Tumor Tissue.

We have selected 2 markers for further validation from Table 4. These glycoproteins were selected due to enrichment in tumor tissue for all cases analyzed in Table 4.

Periostin.

Figure 7:
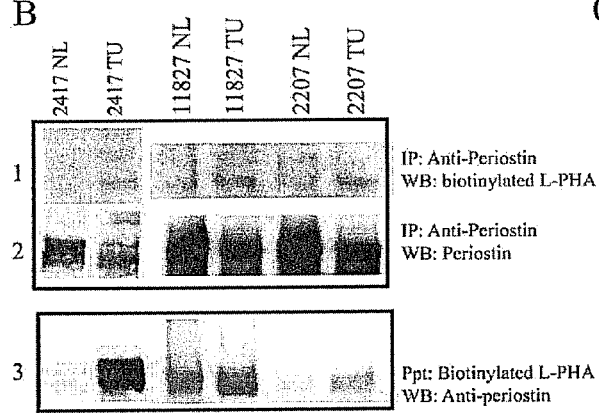
FIG. 7 shows an analysis of periostin and haptoglobin-related protein by Western blot. (A) Number of peptides identified for periostin before L-PHA fractionation (total) and after lectin fractionation (L-PHA). (B) Precipitation of periostin using an anti-periostin antibody followed by detection using biotinylated L-PHA and streptavidin HRP (panel 1). Total levels of periostin precipitated are confirmed by detection of the blot using anti-periostin antibody (panel 2). Reverse precipitation with L-PHA first followed by detection using an anti-periostin antibody (panel 3). (C) Densitometry quantification of the relative increase in L-PHA reactive periostin normalized for total periostin. (D) Number of peptides identified for haptoglobin-related protein (HPR) precursor by MS/MS before (total) and after L-PHA fractionation (L-PHA). (E) L-PHA precipitation followed by detection using an anti-haptoglobin antibody shows increased reactivity for the beta chains of tumor HPR for cases 2417 and 2207 and in all cases a migratory shift to a higher molecular weight. (F) Relative levels of L-PHA reactive haptoglobin were determined following densitometric analysis normalizing to the total levels of haptoglobin on 10% input blots (data not shown).
Figure 7:
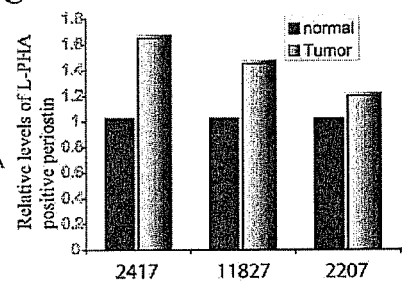
Figure 7:
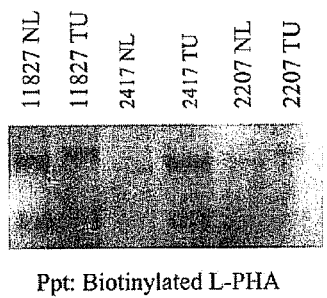
Figure 7:
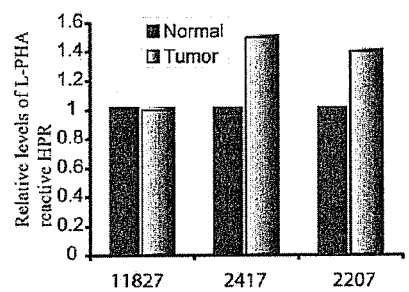

Periostin (POSTN) has been identified as a possible factor promoting breast cancer progression through induction of angiogenesis (Shao et al., 2004. *Mol Cell Biol* 24:3992-4003). Previous studies analyzing mRNA levels by pooled RNA sampling and immunohistochemistry arrays indicated that POSTN mRNA and protein levels were increased in malignant breast epithelial cells (Shao et al., 2004. *Mol Cell Biol* 24:3992-4003; Grigoriadis et al., 2006. *Breast Cancer Res* 8:R56). We found in the total MS/MS analysis of matched normal and malignant breast tissue before L-PHA fractionation that there were roughly twice as many POSTN peptides identified from tumor tissue compared with normal tissue for cases 10119 and 2207. For case 11827, we did not detect POSTN before L-PHA fractionation and for 2417 we found equivalent levels of POSTN peptides identified in normal and tumor tissue before L-PHA enrichment using NSI-MS/MS (FIG. 7A). These results are not quantitative and are only a qualitative assessment of abundance. However, they suggest that examining alterations in the abundance of POSTN protein alone would not be a selective marker for breast carcinoma. However, we identified POSTN peptides after L-PHA enrichment and MS/MS analysis in all 4 of the tumor tissues analyzed with only 1 peptide identified in normal tissue for case 2417 (FIG. 7A). The high degree of tumor-specific association of POSTN with LPHA suggests that the presence of β(1,6) branched N-linked glycosylation on POSTN is a marker of breast cancer. To confirm these results, we have immunoprecipitated POSTN from normal and tumor breast tissue using an anti-periostin antibody and probed the blot using biotinylated LPHA. Tissue amounts were limiting for case 10119 preventing further analysis of this case. For each case analyzed, POSTN reactivity with L-PHA is higher compared with the matched normal tissue control (FIG. 7B, panel 1). To normalize for total periostin protein, we probed the membrane using the anti-periostin antibody (FIG. 7B panel 2). To confirm these results, we precipitated using biotinylated L-PHA followed by detection using the anti-periostin antibody (FIG. 7B panel 3). To quantitate the relative increase in L-PHA reactive periostin, films for total periostin and LPHA reactive periostin were scanned and analyzed by densitometry (FIG. 7C). Overall, our results indicate that POSTN acquires increased levels of β(1,6) branched N-linked structures in the breast tumor tissue relative to normal breast tissue.

Haptoglobin-Related Protein Precursor.

Haptoglobin-related precursor protein (HPR) has 90% sequence identity to the conventional form of haptoglobin (HP) found in serum. The adult liver expresses low levels of HPR mRNA (Bensi et al., 1985. *EMBO J* 4:119-26) and very little HPR protein has been detected in serum (Fawcett et al., 1990. *Biochim Biophys Acta* 1048:187-93), suggesting that the HPR we detected in breast carcinoma tissue is likely expressed by breast cancer epithelial cells. HPR shares antigenic epitopes with the pregnancy-associated plasma protein-A that is secreted from uterine epithelial cells or placenta during pregnancy and has been reported as an independent prognostic factor useful for detecting the recurrence of breast cancer (Kuhajda et al., 1989. *Proc Natl Acad Sci USA* 86:1188-92; Kuhajda et al., 1989. *N Engl J Med* 321:636-41). To validate the identification of L-PHA reactive HPR as a breast tumor-specific marker we performed L-PHA precipitation followed by Western blotting. Due to the fact that we did not detect HPR prior to L-PHA affinity enrichment (FIG. 7D) we have chosen to validate using L-PHA precipitation followed by detection using an anti-haptoglobin antibody that recognizes HP as well as HPR (FIG. 7E). Our results revealed an increased association of the beta chain of haptoglobin with L-PHA for the tumor tissue compared with normal breast tissue in cases 2417 and 2207. For case 11827, we observed a similar intensity in beta haptoglobin between normal and tumor on the Western blot. In all 3 cases, the tumor haptoglobin displayed a shift to a larger molecular weight compared with normal breast tissue from the same patient. Therefore, we conclude that in agreement with our MS/MS data, tumor haptoglobin has elevated β(1,6) branched N-linked glycan structures compared with normal.

Discussion

Elevation of β(1,6) branched N-linked glycans in breast cancer has been previously cited as a poor prognostic indicator (Handerson et al., 2005. *Clin Cancer Res* 11:2969-73). In this study we have used L-PHA, a lectin that specifically recognizes these glycan structures, to pull out potential biomarkers for breast carcinoma. Using this type of targeted glycoproteomic approach enabled us to identify markers common to breast cancer tissues with different stages, hormone receptor status, lymph node status, and her2/neu status. Our ability to analyze the relative abundance of biomarkers in normal and tumor tissue from the same patient, before and after L-PHA fractionation, eliminates possible bias that may be introduced from differences in individual gene expression profiles. Our targeted glycoproteomic approach has enabled the identification of several potential markers for breast carcinoma. Therefore, future studies focused on defining the normal and tumor glycome of various tissues can be useful for the development of new lectin targeting strategies to identify glycoproteins with tumor-specific glycan alterations.

TGFβ Connection.

We have identified several proteins either induced by TGFβ, or known to associate with TGFβ, suggesting a link between β(1,6) branched N-linked glycosylation in breast tumors and the TGFβ pathway. Changes in downstream signaling controlled by TGFβ have been documented for breast cancer (Gomis et al., 2006. *Cancer Cell* 10:203-14). However, unlike other types of malignancy that have evaded the normal growth-inhibitory functions of TGFβ through inactivating mutations in TGFβ receptors, the mechanisms of breast cancer resistance to TGFβ-mediated growth inhibition remain poorly understood (Massague and Gomis, 2006. *FEBS Lett* 580:2811-20). We have found increased β(1,6) branched N-linked glycosylation on several extracellular proteins known to interact with TGFβ. Differential glycosylation of these ligands may initiate alterations in TGFβ signaling. The extracellular proteoglycans decorin and biglycan have been shown to bind TGFβ reducing its bio-availability for TGFβRI and TGFβRII during skeletal muscle differentiation (Droguett et al., 2006. Matrix Biol 25:332-41). Therefore, it may be possible that the aberrant glycosylation of small leucine-rich proteoglycans such decorin (DCN) and biglycan (BGN) increases the amount of TGFβ sequestered in the extracellular matrix complexes making less TGFβ available for canonical TGFβ receptor activation. Increased expression of TGFβ in fibroblasts has been shown to induce the expression of several glycoproteins implicated in the pathogenesis of breast cancer such as collagen VI α3, tenascin, and PAI-1 (Berking et al., 2001. *Cancer Res* 61:8306-16). In this study, we have identified collagen VI α3 (COL6A3) as one of the proteins enriched by L-PHA in tumor tissue. Collagen VI upregulation and secretion is associated with increased cell survival via resistance to apoptosis through down-regulation of Bax and prevention of β1 integrin-mediated apoptosis (Ruhl et al., 1999. *J Biol Chem* 274:34361-8). Logically, increased levels of TGFβ in the tumor should initiate the cytostatic effect often associated with TGFβ signaling. However, elevated TGFβ levels in the tumor can have an opposite effect by inducing collagen VI expression that can oppose cytostatic effects by blocking apoptosis (Ruhl et al., 1999. *J Biol Chem* 274:34361-8). Interestingly, collagen VI has been shown to associate in a ternary complex with DCN, and BGN by co-immunoprecipitation experiments (Reinboth et al., 2006. *J Biol Chem* 281:7816-24). COL6A3, DCN, and BGN were enriched by L-PHA in at least 2 cases (Table 4) suggesting a possible link between the formation of this complex and the presence of β(1,6) branched N-linked glycans. Experiments investigating the impact of β(1,6) branched glycosylation on the formation of this complex and the resulting effect on cell survival in breast epithelial cells will be necessary to evaluate this hypothesis as a possible mechanism for breast tumor cells evasion of TGFβ-induced cytostatic response.

An Enrichment of L-PHA Reactive Glycoproteins that have Functions in the Skeletal System.

Many of the proteins that were enriched by L-PHA in tumor tissue have proposed functions in the skeletal system and a gene encoding one of these proteins, periostin (POSTN), has been identified as a gene expressed in the myoepithelial cells of breast tumors (Grigoriadis et al., 2006. *Breast Cancer Res* 8:R56). This gene has also been reported to be expressed in normal bone chondrocytes and pre-osteoblasts; both are mesenchymal cell types (Blumer et al., 2006. *J Anat* 208:695-707). We find in our analysis of breast tissue after L-PHA fractionation that we detect POSTN almost exclusively in the tumor. This is the first identification of a difference in the glycosylation of POSTN for breast cancer tissue relative to normal breast tissue. Prior to L-PHA fractionation we detect POSTN in both normal and tumor tissue, likely due to stromal expression. We do not separate epithelial and stromal cells before L-PHA fractionation, therefore, our data strongly support the notion that POSTN with complex β(1,6) branched N-linked glycan structures is expressed mainly in the breast tumor epithelial cells since there is very little L-PHA reactive POSTN isolated from normal breast tissue. The activation of POSTN expression in osteoblasts has been linked to twist, a bHLH transcription factor that controls the expression of embryonic mesenchymal genes during development (Oshima et al., 2002. *J Cell Biochem* 86:792-804). Twist expression has been reported to be increased in lobular infiltrating breast cancer (Yang et al., 2004. *Cell* 117:927-39; Kang and Massague, 2004. *Cell* 118:277-9). Therefore, these observations may explain how POSTN is expressed in breast epithelial cells. Also, TGFβ has been shown to increase the expression of POSTN in cardiac development providing another possible explanation for how POSTN may be expressed in breast cancer epithelial cells (Norris et al., 2004. *Anat Rec A Discov Mol Cell Evol Biol* 281:1227-33).

GnT-V, the gene that adds the β(1,6) GlcNAc branch leading to the formation of β(1,6) branched N-linked glycans has recently been implicated in the maintenance of bone density as GnT-V (−/−) mice show a loss of bone mineral density (Cheung et al., 2007. *Glycobiology* 17:828-37). It is possible that POSTN may be a preferred substrate for GnT-V in osteoblasts and chondrocytes during development. Therefore, the abnormal expression of both GnT-V and POSTN in breast carcinoma epithelial cells would lead to significant changes in breast epithelial cell adhesion and migration, promoting tumor progression.

Another protein, osteoglycin (OGN), which was enriched by L-PHA in breast tumor tissue relative to normal tissue was originally identified in bone as an osteoinductive factor (Bentz et al., 1989. *J Biol Chem* 264:20805-10). OGN along with DCN and BGN are members of a group of small lecuine-rich repeat proteoglycans (SLRPs) that are important during skeletal development. BGN and DCN are also involved in the development and maintenance of bone. More pronounced loss of bone mass is present in the double knockout of BGN and DCN than for each individual gene knockout suggesting that both of these SLRPs play a role in the maintenance of bone (Corsi et al., 2002. *J Bone Miner Res* 17:1180-9). Interestingly, DCN is also found to be expressed in the myoepithelial cells of the breast (Grigoriadis et al., 2006. *Breast Cancer Res* 8:R56). Exactly how the presence of β(1,6) branched N-linked glycosylation on these proteins within the breast tissue may influence malignancy is unknown. One can postulate that increased β(1,6) branched N-linked glycans may influence the formation of collagen fibrils making it easier for tumor cells to migrate and invade through the basement membrane. Many proteins that we have identified as highly L-PHA reactive in tumor tissue relative to normal tissue have reported functions in skeletal development. This suggests that L-PHA reactive N-linked structures may be promoting mesenchymal functions within breast epithelial cells. Future experiments will test if GnT-V expression levels can affect the epithelial to mesenchymal transition (EMT).

Example III

Focused Glycomic Analysis of the N-linked Glycan Biosynthetic Pathway in Ovarian Cancer Epithelial ovarian cancer is the deadliest female reproductive tract malignancy in Western countries. Less than 25% of cases are diagnosed when the cancer is confined, pointing to the critical need for early diagnostics for ovarian cancer. Identifying the changes that occur in the glycome of ovarian cancer cells may provide an avenue to develop a new generation of potential biomarkers for early detection of this disease. Epithelial ovarian cancers are comprised of five major subtypes (serous, endometrioid, mucinous, clear cell, and transitional adenocarcinomas), with serous and endometrioid being the two most common types. Epithelial ovarian cancer arises in humans from the ovarian surface epithelium (OSE), epithelial inclusion cysts, or the tubal fimbria (Lee et al., 2007. *J. Pathol.* 211:26-35; Auersperg et al., 2001. *Endocr. Rev.* 22:255-288). Several oncogenes have been implicated in ovarian cancer development including: c-myc, k-ras, erbB2, egfr, p53, b-catenin, brca1/2, pten, and others (Orsulic et al., 2002. *Cancer Cell* 1:53-62; Aunoble et al., 2000. *Int. J. Oncol.* 16:567-576; Dinulescu et al., 2005. *Nat. Med.* 11:63-70). Utilizing this knowledge, a mouse model of human epithelial endometrioid ovarian carcinoma was developed by adenoviral infection of the Cre recombinase in the OSE of conditional mice engineered to activate oncogenic k-ras and inactivate pten (Dinulescu et al., 2005. Nat. Med. 11:63-70). The combination of these mutations leads to the induction of malignant epithelial endometrioid ovarian carcinoma lesions that recapitulate the morphology and histology of the human disease (Dinulescu et al., 2005. *Nat. Med.* 11:63-70). Several clinical studies have recently validated these genetic results by identifying the first cases of human ovarian carcinomas with synchronous k-ras and pten mutations (Irving et al., 2005. *Hum. Pathol.* 36:605-619; Kolasa et al., 2006. *Gynecol. Oncol.* 103:692-697).

We performed a glycotranscriptomic analysis of endometrioid ovarian carcinoma using human tissue, as well as a newly developed mouse model that mimics this disease. Our results show that the N-linked glycans expressed in both nondiseased mouse and human ovarian tissues are similar; moreover, malignant changes in the expression of N-linked glycans in both mouse and human endometrioid ovarian carcinoma are qualitatively similar. We have used a quantitative real-time PCR approach (qRT-PCR) to quantitatively measure changes in the expression levels of enzymes in the N-linked biosynthetic pathway for mouse and human epithelial ovarian endometrioid carcinomas. Comparative lectin blot analysis was used to confirm changes in glycan structures predicted by qRT-PCR results. Lectin reactivity was used as a means for rapid validation of glycan structural changes in the carcinomas that were predicted by the glycotranscriptome analysis. Among several changes in glycan expression noted, the increase of bisected N-linked glycans and the transcripts of the enzyme responsible for its biosynthesis, GnT-III, was the most significant. This study provides evidence that glycotranscriptome analysis can be an important tool in identifying potential cancer biomarkers (Abbott et al., August 2008 *Proteomics* 8(16):3210-3220; Abbott et al., August 2008 *Proteomics* 8(16):3210-3220 online Supporting Information available at http://www.wiley-vch.de/contents/jc_2120/2008/pro200800157_s.pdf.

Materials and Methods

Tumor samples.

Endometrioid ovarian tumors (N=3) and normal ovaries (N=6) were obtained from the previously described mouse model (Dinulescu et al., 2005. *Nat. Med.* 11:63-70). Tumors were graded and assessed based on established histopathology analysis (Dinulescu et al., 2005. *Nat. Med.* 11:63-70). Human endometrioid ovarian cancers (N=3) (0.90% tumor) were obtained from women as frozen tissue from the Ovarian Cancer Institute (Atlanta, Ga.). Institutional Review Board approval was obtained for this research. Human normal adjacent ovary RNA samples (N=2) were purchased from BioChain Institute (Heyward, Calif.). Human normal ovary tissue lysates was purchased from Protein Biotechnologies (Ramona, Calif.).

qRT-PCR.

Samples (50 mg tissue for tumor, entire normal ovaries) were extracted using 0.8 mL TriZol (Invitrogen, Carlsbad, Calif.) with polytron homogenization at setting 3 for 1 min. Total RNA was isolated according to the manufacturer's instructions. After DNase treatment, RNA (2 mg) was reverse-transcribed using Superscript III (Invitrogen) with random hexamers and Oligo (dT). Primer pairs for assay genes and control genes were designed within a single exon using conditions described in Nairn et al. (2008. *J. Biol. Chem.* 283:17298-17313) and listed in Table 6. Primers were validated with respect to primer efficiency and single product detection. The control gene, Ribosomal Protein L4 (RPL4, NM_024212) was included on each plate to control for run variation and to normalize individual gene expression. Samples were run with negative control templates prepared without reverse transcription to ensure amplification is specific to cDNA. Triplicate Ct values for each gene were averaged and the SD from the mean was calculated. Data were converted to linear values and normalized as described previously (Nairn et al., 2007. *J. Proteome Res.* 6:4374-4387).

Lectin Analysis.

Tissue (50 mg) isolated from the same tumors used for qRT-PCR analysis were lysed in RIPA buffer (16PBS, 1% NP-40, 0.5% DOC, 0.1% SDS) containing a mini complete protease inhibitor tablet (Roche, Indianapolis, Ind.) using a polytron at setting 3 for 1 min. The lysate was cleared by centrifugation at 10 000× g for 10 min. Protein concentrations were determined by BCA assay (Pierce, Rockford, Ill.). Biotinylated lectin (Con A, Vector Labs, Burlingame, Calif.) (2 mg) was added to 50 mg cleared lysate at 47° C. for 2 h. Paramagnetic streptavidin beads (50 mL) were added to separate Con A bound and unbound proteins. Unbound fractions, 10 mg, were separated on 4-12% NuPage Bis Tris gels and transferred to PVDFinembrane at 25 V for 1.5 h. Membranes were blocked overnight in 3% BSA/TBST buffer before lectin blot detection using a 1:5000 dilution of the following biotinylated lectins: (*Phaseolus vulgaris leucoagglutinin* (L-PHA), *P. vulgaris erythroagglutinin* (E-PHA), *Aleuria aurantia* (AAL), and *Datura stramonium* (DSL), Vector Labs). Bound lectin was detected using a 1:5000 dilution of streptavidin-HRP (Vector Labs) before washing and detection using Western Lightening Plus (Perkin Elmer).

TABLE 6

Primer pairs for qRT-PCR assay genes and control genes.

| Gene | Abbrev. | Species | Accession # | Forward Primer (5' to 3') | SEQ ID NO: | Reverse Primer (5' to 3') | SEQ ID NO: |
|---|---|---|---|---|---|---|---|
| Mannoside acetylglucosaminyltransferase 1 | Mgat1 | mouse | NM_010794 | CCCTTCACCCAGTTGGACCTG | 308 | GCACCATAGACCTGGGCGAG | 328 |
| | | human | NM_002406 | GTGATTCCCATCCTGGTCAT | 309 | TAATGCAGCAGCTTGTCCAG | 329 |
| Mannoside acetylglucosaminyltransferase 2 | Mgat2 | mouse | NM_146035 | TGCTGGAGACTGTGGTATGC | 310 | ACTCAATTTGGGCACTCTGG | 330 |
| | | human | NM_002408 | AGCAAGAGTGCCCTGAATGT | 311 | TGCCATAGAAACTGCGACTG | 331 |

TABLE 6-continued

Primer pairs for qRT-PCR assay genes and control genes.

| Gene | Abbrev. | Species | Accession # | Forward Primer (5' to 3') | SEQ ID NO: | Reverse Primer (5' to 3') | SEQ ID NO: |
|---|---|---|---|---|---|---|---|
| Mannoside acetylglucosaminyltransferase 3 | Mgat3 | mouse | NM_010795 | GCGTGATGGTGTGCTGTTCC | 312 | ACAGGGACTTCCGCATGTGG | 332 |
| | | human | NM_002409 | CGAGGGCATCTACTTCAAGC | 313 | CGCTTGTCCTCGTAGTCACC | 333 |
| Mannoside acetylglucosaminyltransferase 4, isoenzyme A | Mgat4a | mouse | NM_173870 | GCGACAGACAGAAGGCAAACC | 314 | CCGACAGAGACGAGTGTAGGC | 334 |
| | | human | NM_012214 | AAGGTCTACCAAGGGCATACG | 315 | TATCGGTGTGATAGCCCAGAA | 335 |
| Mannoside acetylglucosaminyltransferase 4, isoenzyme B | Mgat4b | mouse | NM_145926 | AGGTGACGTGGTGGACATTT | 316 | GCTTCAGGCTCTCTTGCTCA | 336 |
| | | human | NM_014275 | TGCACTCGTACCTGACTGACA | 317 | GACCGAGTCCTCCTTCTCCT | 337 |
| Mannoside N-acetylglucosaminyltransferase V | Mgat5 | mouse | NM_145128 | CCCTGGAAGTTGTCCTCTCA | 318 | TCCTCTGCCAGTGCCTTAAT | 338 |
| | | human | NM_002410 | AGCCTGAAAGCAGCTCCAT | 319 | GCCAGTGCCTTGATGTACCT | 339 |
| Mannosidase 2, alpha 1 (Man2a1) | ManII | mouse | NM_008549 | CTCTGGTGTCCGTGCTGGTG | 320 | AATAGGCAGGACTGGCGAACC | 340 |
| | | human | NM_002372 | GAGTGAGTCTGTGGAGGATGG | 321 | GAAGATGTGAGCCAGCACCT | 341 |
| Mannosidase 2, alpha 2 (Man2a2) | ManIIx | mouse | NM_172903 | AAGCAGGTGACGGTGTGTGG | 322 | TGCACTCGGTCCAGCATAAGG | 342 |
| | | human | NM_006122 | GCCCAGCTTCTTCTCCATCT | 323 | TGCAGCTCTGGCTTCTGAC | 343 |
| Fucosyltransferase 8 | Fut8 | mouse | NM_016893 | AACAGAAGCAGCCTTCCACCC | 324 | CATTCTGCGTGCGAGAAGCTG | 344 |
| | | human | NM_178154 | GGTCGAGCTTCCCATTGTAG | 325 | GCGAGGTCTTCTGGTACAGC | 345 |
| Ribosomal Protein L4* | RPL4 | mouse | NM_024212 | GACAGCCCTATGCCGTCAGTG | 326 | GCCACAGCTCTGCCAGTACC | 346 |
| | | human | NM_000968 | AGAAGGCTGCTGTTGGTGTT | 327 | TGGTTTCTTGGTAGCTGCTG | 347 |

*Normalization control gene

Results

Expression Data from the N-Linked Biosynthetic Pathway for Normal Ovary.

Enzymes from the N-linked glycosylation pathway (FIG. 8A) were chosen for analysis based on low levels of redundancy and the previous correlations of transcript levels with glycan structural analysis in mouse tissues (Nairn et al., 2008. J. Biol. Chem. 283:17298-17313). Before analyzing tumor tissues, we examined the relative transcript abundance of these enzymes using pooled RNA isolated from normal mouse and human ovarian tissue. The development of epithelial endometrioid ovarian tumors in the model developed by Dinulescu et al. (2005. Nat. Med. 11:63-70) utilizes adenoviral infection of the Cre recombinase into the outer epithelial layer of the ovary to initiate tumor formation. This technique allows the noninfected ovary within the same animal to serve as a normal control. From the group of genes analyzed, there are both similarities and differences in transcript expression profiles between mouse and human normal ovary. Transcripts present in higher abundance for both species are: FUT8, MGAT1 (human) or MGAT2 (mouse), and MOATS (FIGS. 8B and C). These enzymes are involved in the branching (MGAT1, MGAT2, MGAT5) or core fucosylation (FUT8) of N-linked glycans (FIG. 8A). Due to the higher levels of these transcripts, core fucosylated hybrid type or core fucosylated complex branched N-linked glycans are likely to be abundant in both mouse and human ovary. The MGAT3 transcripts are present at low levels in both mouse and human ovaries (FIGS. 8B and C). The lower levels of MGAT3 transcripts suggest that bisecting N-linked glycans may be present at lower levels in normal mouse and human ovary tissue. Interestingly, the levels of MGAT4b transcripts are very high in mouse compared with human. However, for both mouse and human the MGAT4a levels are lower. These genes are both capable of adding N-acetylglucosamine in β(1,4) linkage (FIG. 8A). Considering the levels of both MGAT4a and MGAT4b, along with abundant MGAT5 levels, tri- and tetra-antennary complex N-linked glycans should be present in normal ovary. Enzymes showing differences in transcript abundance in mouse and human are the mannosidases, MAN2A1 (Man II) is more abundant in human ovary, while MAN2A1 (Man II) and MAN2A2 (Man IIx) are equally abundant in mouse ovary. Overall, for this subset of genes participating in the N-linked pathway, transcript levels in both mouse and human normal ovary show a high degree of species conservation.

Comparative Analysis of Normal and Epithelial Endometrioid Ovarian Carcinoma.

To investigate possible differences in the expression of GT and GH in malignant epithelial ovarian tissue, RNA from mouse endometrioid and human endometrioid carcinoma was analyzed by qRT-PCR. Total RNA from age-matched human normal ovary was purchased from a commercial source. Human normal ovarian tissue samples were averaged for comparison with the qRT-PCR results from individual human tumor tissues. The mouse normal samples qRT-PCR results were also averaged to enable comparison with qRT-PCR results from individual mouse tumor tissues. The levels of MGAT1 and MGAT2 transcripts were increased above normal for both mouse and human tumors suggesting increased complex N-linked glycans (FIGS. 9A and B). The transcripts encoding FUT8, the enzyme responsible for α(1,6) fucosylation of the core N-linked glycan, increased on average 1.5-2-fold relative to normal for mouse tumor tissues (FIG. 9A). However, in human endometrioid ovarian tumors, an increase in FUT8 transcripts occurred in only one of three cases analyzed (FIG. 9B). These results indicate that the factors regulating transcript levels of FUT8 may be more complex in human ovarian cancer. The transcript levels for MGAT3 in both mouse and human tumor samples were increased significantly (average of 18-fold for human and 16-fold for mouse) relative to normal ovarian tissue. The lower transcript abundance of MGAT3 observed for mouse and human normal ovary (FIGS. 8B and C) contrast with the large increase in MGAT3 transcripts observed for all cases of epithelial endometrioid carcinoma analyzed in both mouse and human (FIGS. 9A and B). The commonality of this change for mouse and human tumor samples along with the magnitude of the change predict the possibility of isolating glycoproteins with complex bisecting N-linked glycans as markers for endometrioid ovarian cancer. Transcripts encoding enzymes that perform outer branching of complex N-linked glycans such as MGAT4a, MGAT4b, and MGAT5 are increased in mouse and human ovarian cancer relative to normal. MGAT4a transcripts are increased at a higher level relative to normal for mouse compared with human (2-6-fold and 1.5-4-fold, respectively). However, levels of MGAT4b were also elevated in human tumor tissue, while mouse MGAT4b transcript levels in mouse tumor were not significantly increased. The different regulation of MGAT4b transcripts in mouse and human ovarian tumor tissue may highlight a possible species-specific difference in the transcriptional regulation of this gene. However, the cumulative effect of increases in MGAT4a, MGAT4b, and MGAT5 predict more branched complex N-linked glycan structures present in endometrioid ovarian cancer relative to normal.

Comparative Lectin Analysis.

To investigate whether the tumor-specific changes in GT transcript levels correlate with glycan structures found on glycoproteins, we used lectin separation and blotting techniques. The carbohydrate binding preferences for lectins are diverse, allowing the selection of lectins to detect a wide range of oligosaccharide structures. Lectins (E-PHA, LPHA, DSL, and AAL) recognizing the oligosaccharide products of FUT8, MGAT3, MGAT4a, MGAT4b, MGAT5, and MGAT5b are shown in FIG. 10. These are only examples of oligosaccharide structures that these lectins can bind to and are not intended to be a complete list of all structures capable of binding the lectins. Sugar residues previously described as a determinant for binding of each lectin are circled (Nagata et al., 1991. *Biochim. Biophys. Acta* 1076:187-190; Wimmerova et al., 2003. *J. Biol. Chem.* 278:27059-27067; Cummings and Kornfeld, 1982. *J. Biol. Chem.* 257:11235-11240; Cummings and Kornfeld, 1982. *J. Biol. Chem.* 257:11230-11234; Yamashita et al., 1987. *J. Biol. Chem.* 262:1602-1607). Con A is a lectin that recognizes branched mannose residues with high affinity (FIG. 10), and this lectin was used to separate the high-mannose, hybrid, and complex biantennary oligosaccharides from the complex tri- and tetra-antennary N-linked glycans prior to lectin blot detection (Cummings and Kornfeld, 1982. *J. Biol. Chem.* 257:11235-11240). Total cell lysates from the three mouse tumors were pooled for lectin analysis due to the high degree of correspondent changes observed in the qRT-PCR experiments.

Increased Core Fucosylation in Ovarian Tumors.

Figure 9:
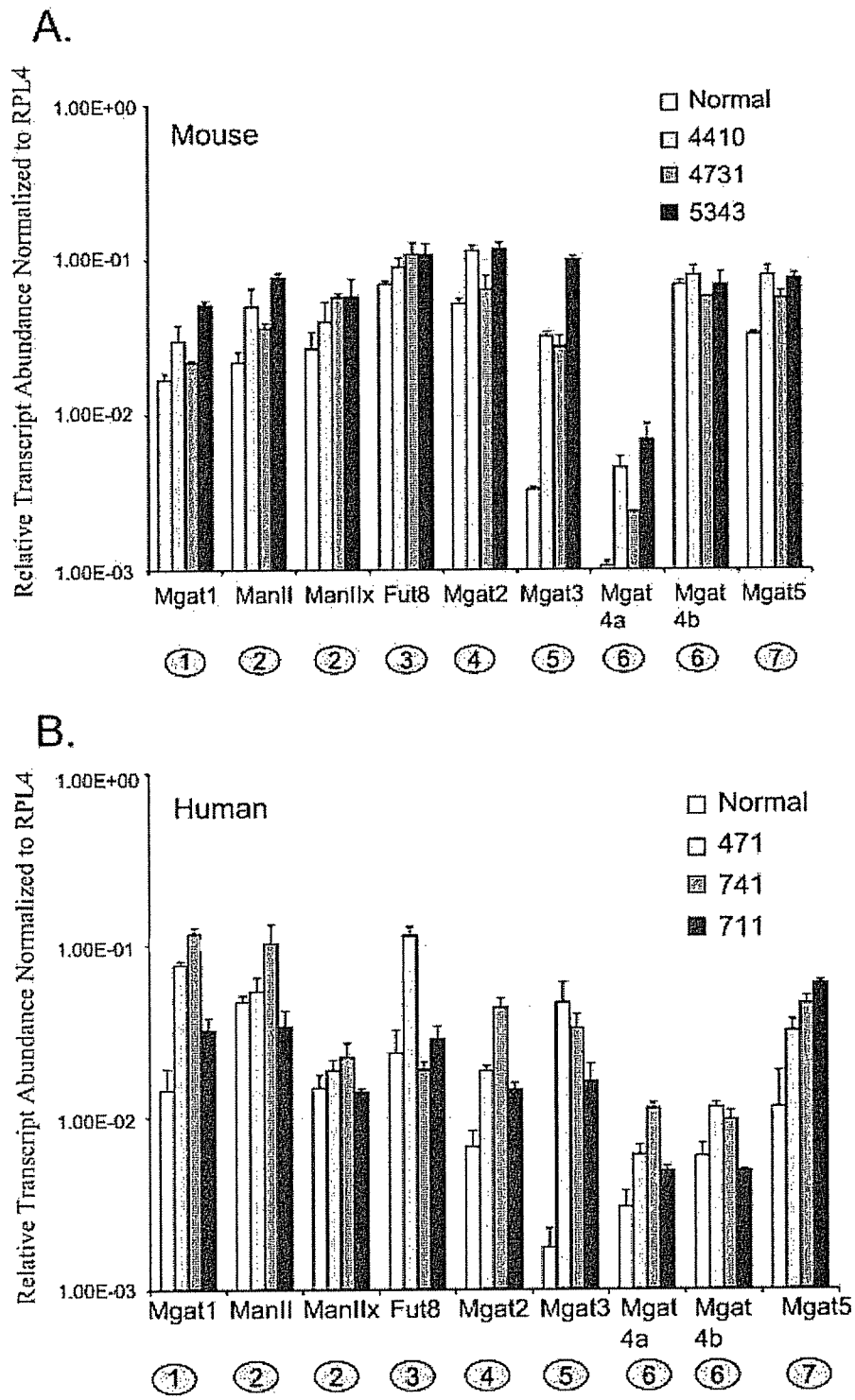
FIG. 9 shows comparative analysis of normal and endometrioid ovarian carcinoma. (A) Relative transcript abundance for mouse normal and ovarian tumors plotted on a log scale. Error bars represent the SD from the mean for triplicate Ct values. (B) Relative transcript abundance for human normal and ovarian tumors plotted on a log scale. Error bars represent the SD from the mean for triplicate Ct values.
Figure 11:
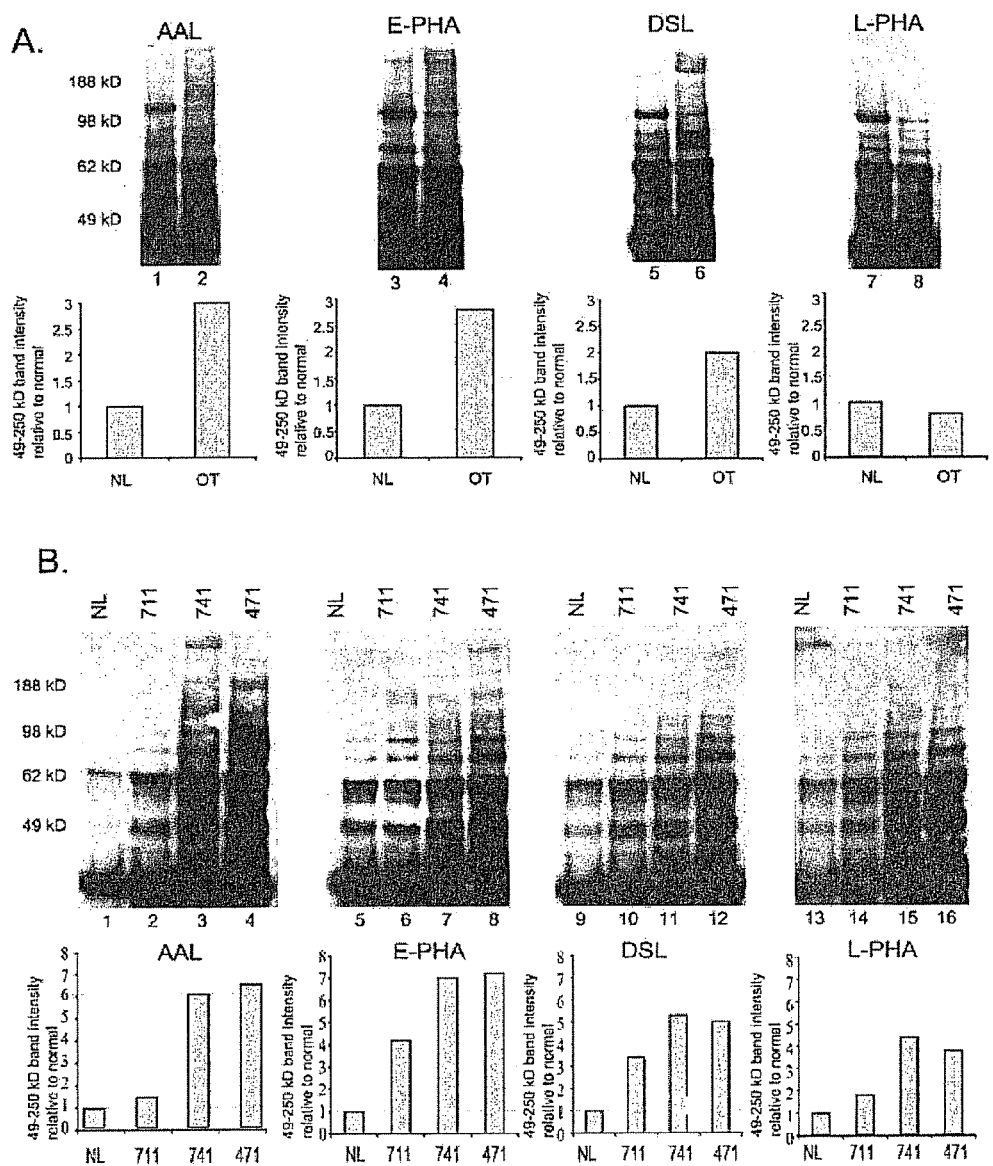
FIG. 11 shows lectin blot analysis of glycoproteins from mouse and human endometrioid ovarian carcinoma. (A) Glycoproteins extracted from mouse endometrioid ovarian tumors (lanes 2, 4, 6, and 8) or normal mouse ovary (lanes 1, 3, 5, and 7) that were nonadherent to Con A were separated on 4-12% Bis-Tris gels before transfer to PVDF membrane and detection using biotinylated lectins and streptavidin-HRP. Panel below shows the densitometry analysis of bands from normal (NL) or ovarian tumor (OT) in the 49-250 kDa range from the blots shown above with normal set at 1.0 for comparison. Fold increase was adjusted for lectin pull-down inputs based on the levels of ERK2 on a 10% input blot (data not shown). (B) Glycoproteins nonadherent to Con A from human endometrioid ovarian cancer cases (711, 741, and 471) and normal human ovary (NL) were separated on 4-12% Bis-Tris gels before lectin blot detection as described. The panel below represents the densitometry results for glycoproteins 49-250 kDa relative to normal set at 1.0. Increases relative to normal were adjusted for input using ERK2 analysis form 10% input blots (data not shown).

All three mouse endometrioid ovarian tumors analyzed showed elevated levels of FUT8 transcripts (FIG. 9). The lectin AAL has a high affinity for the core α(1,6) fucose linked product that would result from FUT8 activity (Nagata et al., 1991. Biochim. Biophys. Acta 1076:187-190). Core fucosylation can be found on hybrid type N-linked glycans as well as complex bi-, tri-, and tetra-antennary oligosaccharides. However, no differences in AAL binding to Con A bound fractions were observed between normal and tumors, suggesting that the levels of core fucosylation do not change significantly on hybrid type and complex biantennary N-linked glycans for ovarian tumors (data not shown). AAL binding to the unbound Con A fraction increases significantly to glycoproteins isolated from ovarian tumors compared to normal ovarian tissue (FIG. 11A lanes 1 and 2). These results indicate that the core fucosylation of complex tri- and tetra-branched oligosaccharides increased for tumors relative to normal. To analyze human ovarian cancer tissues, individual samples were analyzed due to the differences in qRT-PCR results for these cases for FUT8. AAL binding to glycoproteins isolated from human endometrioid ovarian tumors was similar to the levels predicted by qRT-PCR results for case 471. Case 471 had a 0.4-fold increase in FUT8 mRNA compared with normal and shows seven-fold increase in the level of AAL binding relative to normal (FIGS. 9B and 11B, lane 4). Case 711 had similar levels of FUT8 transcripts and shows levels of AAL reactivity similar to the normal control sample (FIGS. 9B and 11B, lane 2). Case 741 had lower levels of FUT8 expression compared with normal (FIG. 9B), yet AAL binding was significantly increased (FIG. 11B, lane 3). To better evaluate the fucosylation of this case we used qRT-PCR to analyze all known fucosyltransferases and fucosidases. Our results indicate a two-fold reduction in the levels of a-L-fucosidase (FUCA2) expression (data not shown). We did not observe this decrease in FUTA2 for cases 711 and 471, suggesting that this may be contributing to the increased levels of core a-1,6-fucosylation for case 741. Our data suggest that in the majority of cases for both mouse and human, core fucosylation levels are elevated. Therefore, glycoproteomic studies targeting the core fucose could potentially lead to the isolation of tumor-specific markers for ovarian cancer.

Ovarian Tumors have Increased Levels of Bisecting Complex N-Linked Glycans.

N-glycans containing a bisecting N-acetylglucosamine are produced by the activity of MGAT3 (FIG. 8A). This enzyme showed the largest increases in expression in ovarian tumor tissues compared with normal ovary tissue (FIGS. 9A and B). Lectin analysis of mouse tissues using the lectin E-PHA, whose binding is dependent on the presence of bisecting GlcNAc (FIG. 10), shows 0.2× the levels of E-PHA binding for tumor relative to normal (FIG. 11A, lanes 3 and 4). Human ovarian tumor glycoproteins analyzed for E-PHA binding showed positive correlation with qRT-PCR results for each case. For example, case 471 and 741 had the highest and second highest increases in MGAT3 transcript levels (FIG. 9B) and these cases also have the highest levels of EPHA binding (FIG. 11B, lanes 7 and 8). Case 711 had a lower increase in MGAT3 transcripts measured by qRT-PCR and shows a lower level of E-PHA binding than cases 471 and 741. In every endometrioid ovarian tumor analyzed, mouse and human, there were elevated bisecting complex N-linked glycans compared with normal controls. Although the datasets are small, these results strongly suggest that the presence of bisecting complex N-glycans is a marker for ovarian tumors.

Tri- or Tetra-Antennary Complex N-Linked Glycans are Increased in Ovarian Tumors.

The lectins known as DSL and L-PHA recognize the outer branches of complex N-linked glycans (MGAT4a, MGAT4b, MGAT5, and MGAT5b) (FIG. 10). L-PHA is specific for the β(1,6) branched, galactosylated product of MGAT5; while DSL can recognize the β(1,4) branch added by MGAT4a and MGAT4b as well as the MGAT5 branch (FIG. 10). MGAT4a and MGAT4b transcript levels were elevated for human endometrioid ovarian tumors and MGAT4a transcripts were amplified for mouse tumors (FIGS. 9A and B). These genes can perform the same glycosyltransferase reactions and their elevations predict the existence of more β(1,4) branched glycans and increased DSL binding. Indeed, analysis of unbound Con A fractions indicate elevated levels of DSL binding to mouse tumor glycoproteins compared with glycoproteins from normal mouse ovary (FIG. 11A, lanes 5 and 6). The levels of DSL binding to tumor glycoproteins isolated from human ovarian tumors were lower compared with AAL or E-PHA binding (FIG. 11B, lanes 9-12) and this correlates with a lower change in transcript levels for MGAT4 (FIG. 9B). Interestingly, L-PHA binding levels for mouse ovarian tumor tissues were not increased above normal, despite increases in MGAT5 transcripts (FIGS. 9A and 11A, lanes 7 and 8). Human tumor samples had higher levels of MGAT5 transcripts compared with normal and do show a slight increase in LPHA binding compared with normal (FIGS. 9B and 11B, lanes 13-16). Mouse ovarian tumors had a two-fold increase in MGAT5 and human ovarian tumors had a three- to five-fold increase in MGAT5 expression (FIGS. 9A and B and Table 7). Based on these findings elevated L-PHA binding would be expected. However, we find no increase in L-PHA binding for mouse ovarian tumors (FIG. 11A) and a lower than expected increase in L-PHA reactivity to glycoproteins from human ovarian tumors. These results may indicate that the MGAT3 elevated activity may inhibit MGAT5 activity and this will be discussed further in the discussion. Overall, the DSL lectin is useful for capturing glycoproteins with the MGAT4 or MGAT5 branch, and based on our analysis, would be an effective lectin for isolating glycoprotein markers with elevated β(1,4) or β(1,6) complex branched glycans for endometrioid ovarian tumors.

*Chem.* 261:10772-10777; Meezan et al., 1969. *Biochemistry* 8:2518-2524; Kobata and Amano, 2005. *Immunol. Cell Biol.* 83:429-439; Hakomori, 1999. *Biochim. Biophys. Acta* 1473: 247-266). For breast cancer, increased β(1,6) branched glycans emerged qualitatively from the transition to malignancy due to elevated expression of the MOATS gene (Buckhaults et al., 1997. *J. Biol. Chem.* 272:19575-19581; Fernandes et al., 1991. *Cancer Res.* 51:718-723). Few studies have evaluated glycosylation changes for ovarian cancer (An et al., 2006. *J. Proteome Res.* 5:1626-1635; Saldova et al., 2007. *Glycobiology* 17:1344-1356; Kui Wong et al., 2003. *J. Biol. Chem.* 278:28619-28634; Wang et al., 2005. *Gynecol. Oncol.* 99:631-6390). However, from the small group of studies conducted, Rudd and coworkers (Saldova et al., 2007. *Glycobiology* 17:1344-1356) found increased levels of bisecting core fucosylated complex N-linked glycans in the serum of ovarian cancer patients compared with normal serum. This result agrees with our data showing increased core fucosylation and bisecting glycans in endometrioid ovarian tumor tissues. Therefore, there is a high probability of isolating and identifying glycoproteins shed into serum from ovarian carcinomas with differences in glycosylation. Lebrilla (An et al., 2006. *J. Proteome Res.* 5:1626-1635) have monitored changes in glycan structures in the serum of ovarian cancer patients using MALDI-FTMS and find several tumor-specific changes for neutral oligosaccharides in MALDI spectra. This study employed a β-elimination procedure to remove oligosaccharides; therefore the neutral glycans changing in the serum could correspond to N- or O-linked glycans. Our data suggest

TABLE 7

Genes analyzed by qRT-PCR.

| Symbol | Average fold change mouse | Average fold change human | Chromosome location | Mouse | Human |
|---|---|---|---|---|---|
| Fut8 | (+) 1.5 | (+) 2.3 | 14q24.3 | NM_016893 | NM_178154 |
| Mgat1 | (+) 2.0 | (+) 5.2 | 5q31 or 5q35 | NM_010794 | NM_002406 |
| Mgat2 | (+) 1.9 | (+) 3.8 | 14q21 | NM_146035 | NM_002408 |
| Mgat3 | (+) 16.0 | (+) 18.2 | 22q13.1 | NM_010795 | NM_002409 |
| Mgat4a | (+) 4.4 | (+) 2.5 | 2q12 | NM_173870 | NM_012214 |
| Mgat4b | no change | (+) 1.5 | 5q35 | NM_145926 | NM_014275/NM_054013 |
| Mgat5 | (+) 2.2 | (+) 4.0 | 2q21 | NM_145128 | NM_002410 |
| MAN2A1 | (+) 2.5 | (+) 1.4 | 5q21 | NM_008549 | NM_002372 |
| MAN2A2 | (+) 1.9 | (+) 1.2 | 15q25 | NM_172903 | NM_006122 |

Discussion

In this report we have used a glycotranscriptome approach to characterize the N-linked glycan profiles of normal ovary and endometrioid ovarian carcinoma. Our results provide several significant findings: (i) mouse and human normal ovarian tissues have a similar expression profile for certain enzymes participating in the formation of N-linked glycans suggesting some degree of species conservation, (ii) enzymes changing in expression for tumors isolated from the mouse model of human endometrioid ovarian cancer correspond qualitatively with changes observed for human tumors of the same malignancy, (iii) E-PHA, AAL, and DSL reactivity levels were elevated in endometrioid ovarian tumors relative to normal indicating that these lectins could be useful together for biomarker discovery or to improve the specificity of existing ovarian tumor markers.

Glycosylation Changes Observed for Reproductive Malignancies.

Analysis of glycoprotein glycosylation patterns is emerging as a powerful tool to discriminate normal glycoproteins from glycoproteins marking diseases such as cancer. Over 20 years ago, researchers began to observe glycosylation changes occurring on cell surface glycoproteins following oncogenic transformation (Pierce and Arango, 1986. *J. Biol.* that neutral glycans from the N-linked biosynthetic pathway such as core fucosylation and bisecting N-acetylglucosamine are increased significantly in ovarian tumor tissue relative to normal. Therefore, it should be possible to identify the glycoproteins that have these neutral N-linked glycan alterations from patient serum. In conclusion, our data in addition to these previous studies indicate that like breast cancer, ovarian tumor formation results in distinct altered glycan structures.

Comparison of Changes in Glycosylation Between a Mouse-Model of Endometrioid Ovarian Cancer and Human Endometrioid Ovarian Cancer.

Ovarian tumors derived from the mouse model of human endometrioid ovarian cancer developed by Dinulescu et al. (2005. Nat. Med. 11:63-70) are well differentiated and recapitulate human ovarian cancer histologically. The benefits of mouse models are numerous, including: stable genetics, controlled environmental factors such as diet, and most importantly, the ability to sample tissue and serum at different stages of tumor development. Our data demonstrate that the glycomic changes occurring in the N-linked pathway for mouse-derived epithelial endometrioid ovarian tumors show corresponding changes in human ovarian endometrioid tumors.

Increased Knowledge about the N-Linked Glycan Pathway.

The N-linked glycosylation pathway consists of a series of sequential reactions (FIG. 8A). The qRT-PCR approach enabled the quantization of the transcript levels for several enzymes with a wide dynamic range. The total pathway approach offers a chance to learn more about how synchronous oncogenic signaling changes can influence glycosylation. A summary of the average fold changes in expression measured for each enzyme analyzed is provided in Table 7. Some interesting findings that have resulted from this study include: (i) increased variability in FUT8 levels for human ovarian cancer versus mouse tumors, suggesting more complex influences controlling the levels of core fucosylation, (ii) lower levels of L-PHA reactivity for glycoproteins with elevated MGAT5 mRNA levels suggests possible inhibition of MGAT5 activity by MGAT3.

Genetic factors influencing glycosylation patterns have not been extensively studied. Although there has been a study recently published examining the effect of single nucleotide polymorphisms in genes involved in the mucin-type glycosylation of MUC1 (Sellers et al., 2008. *Cancer Epidemiol. Biomarkers Prev.* 17:397-404). This study found that genetic polymorphisms within glycosylation enzymes analyzed for MUC1 may be playing a role in the underglycosylation of this protein in ovarian cancer patients suggesting that genetic factors can affect glycosylation. Several of the GT and GH enzymes included in this study are located in similar regions of the chromosomes (Table 7). MGAT1 and MGAT4b are located on the same chromosome in close proximity and show very different expression profiles for ovarian cancer. This seems to suggest that elevations in MGAT1 expression are probably not related to gain of chromosome copy, or MGAT4b would be increased in a similar manner. The changes in expression observed for GT enzymes in ovarian cancer could be due to differences in factors regulating GT promoters.

The small sample size of human endometrioid carcinoma cases analyzed in our study suggests that FUT8 expression and activity are more variable. Due to the lack of variability in the mouse model, we postulate that in humans there may be unknown factors in ovarian tumors either genetic or epigenetic that are capable of influencing core fucosylation. The FUT8 variability in human ovarian tumors contrasts with MGAT1, MGAT2, and MGAT3 which seems to be unaffected by genetic differences. More studies examining the glycomic changes in human cancer samples performed in conjunction with murine models are needed to better understand the possible role of genetic regulation on glycosylation.

The product of MGAT3 activity, the bisecting N-acetylglucosamine structure, has been reported to inhibit the activity of MGAT5 (Yoshimura et al., 1995. *Proc. Natl. Acad. Sci. USA* 92:8754-8758; Taniguchi et al., 1996. *Glycobiology* 6:691-694). We find that MGAT3 levels are substantially increased far above MGAT5 levels in ovarian tumors. Therefore, one possibility for why we observe less change in L-PHA reactivity for ovarian tumors (FIGS. 11A and B), despite increased levels of MGAT5 expression, may be that the addition of bisecting N-acetylglucosamine by MGAT3 prevented the addition of the β(1,6) branched oligosaccharide structure. Competition for the same nucleotide sugar donor (UDP-GlcNAc) does not seem to be a factor since MGAT4a and MGAT4b addition (evidenced by DSL binding) is unaffected by the large increase in MGAT3 activity. The addition of bisect bisecting N-acetylglucosamine to the trimannosyl core N-linked glycan has been reported to occur in opposition to β(1,6) branching performed by MGAT5 during the cell cycle (Guo et al., 2000. *Biochim. Biophys. Acta* 1495:297-307). In this study the authors found that the mRNA levels and protein levels for MGAT5 were not changing, yet there was less MGAT5 enzyme activity at stages of the cell cycle when MGAT3 activity levels were high. These data along with our data support the notion that increased MGAT3 activity inhibits the addition of β(1,6) branched glycans by MGAT5 and the mechanism of this inhibition is currently unknown.

Bisecting Oligosaccharides and Cancer.

Elevated levels of MGAT3 expression and an increase in bisecting glycans have been reported for pancreatic cancer and hepatoma (Ishibashi et al., 1989. *Clin. Chim. Acta* 185:325-332; Nan et al., 1998. *Glycoconj. J.* 15:1033-1037). Studies using diethylnitrosamine to induce liver tumor formation in mice null for MGAT3 showed reduced tumor formation (Wang et al., 2005. *Gynecol. Oncol.* 99:631-639; Bhaumik et al., 1998. *Cancer Res.* 58:2881-2887). However, if MGAT3 was overexpressed there is no induction or augmentation of tumor growth using diethylnitrosamine (Stanley, 2002. *Biochim. Biophys. Acta* 1573:363-368). This result suggests an indirect effect of MGAT3 overexpression on liver tumorigenesis. In ovarian tumors, bisecting glycan structures predominate as evidenced by increased MGAT3 mRNA (FIGS. 9A and B) and elevated EPHA binding (FIGS. 11A and B). Bisecting structures have also been documented on CA125 isolated from the ovarian cancer cell line OVCAR3 (Kui Wong et al., 2003. *J. Biol. Chem.* 278:28619-28634). Mice null for MGAT3 are viable and reproduce normally. This, along with the fact that MGAT3 is expressed at a low level in normal ovary, suggest that therapeutic strategies targeting MGAT3 could be useful for retarding ovarian tumor progression with minimal interruption of normal ovary functions.

In conclusion, the glycomic analysis presented in this manuscript provides a framework for future glycoproteomic studies. These studies will enable the identification of the proteins that express bisecting N-linked glycans and allow for the structural characterization of the bisecting oligosaccharides.

Example IV

Ovarian Cancer Biomarkers

Glycan changes present in ovarian cancer may differ from glycan changes present in breast cancer. Potential biomarkers of ovarian cancer, as shown in Table 8, were discovered in ovarian tissue using methods analogous to those described in Examples II and III, using lectins that recognize bisecting N-linked glycans (E-PHA), core-fucosylated (AAL), and β(1,4) branched glycans (DSL). As shown below, not all of the identified proteins were predicted to by glycosylated proteins (glycoproteins). These may associate with other, lectin-reactive glycoproteins or have acquired a glycan to become a glycoprotein as part of oncogenic transformation.

TABLE 8

Lectin-reactive proteins with elevated peptides and spectra in ovarian tumor relative to normal.

| Name | Tumor Total | Normal Total | Predicted Glycoprotein |
|---|---|---|---|
| Glucose-regulated protein 78 | 16 | 0 | No |
| heterogeneous nuclear ribonucleoprotein F | 7 | 0 | No |
| lysosomal-associated membrane protein 1 | 8 | 0 | Yes |
| periostin | 20 | 5 | Yes |
| adenylate cyclase-associated protein 1 (yeast) | 7 | 0 | No |
| protein disulfide isomerase family A, member 4 | 4 | 0 | No |

TABLE 8-continued

Lectin-reactive proteins with elevated peptides and spectra in ovarian tumor relative to normal.

| Name | Tumor Total | Normal Total | Predicted Glycoprotein |
|---|---|---|---|
| chaperonin containing TCP1, subunit 5 (epsilon) | 8 | 0 | No |
| biglycan | 22 | 8 | Yes |
| procollagen-proline, 2-oxoglutarate 4-dioxygenase (proline 4-hydroxylase) | 14 | 0 | No |
| Ceruloplasmin | 8 | 0 | Yes |
| transforming growth factor, beta-induced | 16 | 6 | No |
| myosin, heavy chain 9, non-muscle | 34 | 7 | No |
| complement factor B | 7 | 0 | Yes |
| myosin, heavy chain 11, smooth muscle | 21 | 5 | No |
| calreticulin | 14 | 3 | No |
| creatin kinase-brain | 7 | 0 | No |
| lectin, galactoside-binding, soluble, 3 binding protein | 8 | 0 | Yes |
| heparan sulfate proteoglycan 2 | 7 | 0 | Yes |
| myosin, heavy chain 11, smooth muscle | 21 | 5 | No |
| protein disulfide isomerase family A, member 3 | 16 | 0 | No |
| tenascin XB | 35 | 28 | Yes |
| heat shock 27 kDa protein 1 | 13 | 4 | No |
| glucose-6-phosphate isomerase | 7 | 0 | No |
| phosphoglycerate kinase 1 | 16 | 3 | No |
| elongation factor 2 | 10 | 3 | No |
| ADP-Ribosylation Factor 1 | 5 | 0 | No |
| ADP-Ribosylation Factor 3 | 5 | 0 | No |
| heterogeneous nuclear ribonucleoprotein K | 9 | 0 | No |
| heterogeneous nuclear ribonucleoprotein K | 9 | 0 | No |
| lactate dehydrogenase A | 18 | 2 | Yes |
| Isoform 2 of Periostin precursor | 20 | 5 | Yes |
| phosphogluconate dehydrogenase | 5 | 2 | No |
| glutathione S-transferase pi 1 | 6 | 4 | No |
| peroxiredoxin 6 | 5 | 0 | No |
| 14-3-3GAMMA | 5 | 0 | No |
| malate dehydrogenase 2, NAD (mitochondrial) | 6 | 0 | No |
| thrombospondin 1 | 22 | 0 | Yes |
| coagulation factor XIII, A1 polypeptide | 8 | 0 | Yes |
| chaperonin containing TCP1, subunit 2 (beta) | 4 | 0 | No |
| lactotransferrin | 4 | 0 | Yes |
| talin 1 | 9 | 0 | No |
| protein disulfide isomerase family A, member 6 | 15 | 0 | No |
| eukaryotic translation initiation factor 5A | 5 | 0 | No |
| fibulin 5 | 5 | 2 | Yes |
| immunoglobulin heavy constant gamma 2 (G2m marker) | 8 | 0 | Yes |
| periostin, osteoblast specific factor | 20 | 5 | Yes |
| eukaryotic translation initiation factor 5A | 5 | 0 | No |
| similar to hCG2038920 | 8 | 0 | Yes |
| XP_933498 similar to Phosphoglycerate | 5 | 0 | No |
| alpha-2-macroglobulin | 31 | 2 | Yes |
| heterogeneous nuclear ribonucleoprotein U | 5 | 0 | No |
| phosphoglycerate mutase 1 (brain) | 5 | 0 | No |
| transgelin 2 | 13 | 2 | No |
| periostin, osteoblast specific factor | 20 | 5 | Yes |
| biglycan | 22 | 8 | Yes |
| heterogeneous nuclear ribonucleoprotein U | 5 | 0 | No |
| heterogeneous nuclear ribonucleoprotein U | 5 | 0 | No |
| protein disulfide isomerase family A, member 6 | 15 | 0 | No |
| transgelin 2 | 13 | 2 | No |
| protein disulfide isomerase family A, member 3 | 16 | 0 | No |
| immunoglobulin lambda locus | 13 | 8 | Yes |
| myosin, heavy chain 11, smooth muscle | 21 | 5 | No |
| myosin, heavy chain 11, smooth muscle | 21 | 5 | No |
| phosphogluconate dehydrogenase | 5 | 2 | No |
| talin 1 | 9 | 0 | No |
| mucin 5B | 18 | 0 | Yes |
| lactotransferrin (truncated) | 4 | 0 | Yes |
| lactotransferrin (truncated) | 4 | 0 | Yes |
| lactotransferrin (truncated) | 4 | 0 | Yes |
| glutathione S-transferase pi 1 | 6 | 4 | No |
| glutathione S-transferase pi 1 | 6 | 4 | No |
| periostin, osteoblast specific factor | 20 | 5 | Yes |
| glutathione S-transferase pi 1 | 6 | 4 | No |
| heterogeneous nuclear ribonucleoprotein K | 9 | 0 | No |
| immunoglobulin heavy constant gamma 3 (G3m marker) | 6 | 0 | Yes |
| serpin H1 precursor (SERPINH1) | 20 | 8 | Yes |

Example V

Detection of Breast Cancer Biomarkers in Serum

Figure 12:
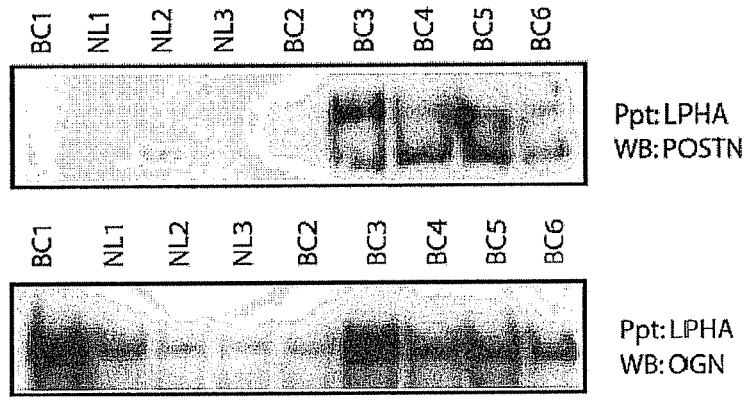
FIG. 12 shows a Western blot, using antibodies against periostin (POSTN) and osteoglycin (OGN), probed with L-PHA enriched serum from patients with breast cancer (BC) and healthy patients (NL).

Increased β(1, 6) branched glycans in breast cancer. Serum (5 μl) from patients with breast cancer (BC) and healthy patients (NL) was incubated with 10 μg of biotinylated LPHA in 300 μl of lectin binding buffer (50 mM Tris-Cl pH 7.5, 0.1% NP-40, 150 mM NaCl, 0.4 mM EDTA, and 1 protease inhibitor tablet) overnight at 4° C. Paramagnetic streptavidin beads were added and the reactions were incubated at room temperature for 1 hour. Bound complexes were captured using a magnet and washed with lectin binding buffer 3× before separating the proteins on a 4-12% NuPage Bis-Tris gel. Proteins were transferred to PVDF membrane and probed using the indicated antibodies, anti-periostin and anti-osteoglycin. Periostin (POSTN) from breast cancer (BC) cases (BC3, BC4, BC5 and BC6) show increased reactivity with LPHA compared with the POSTN from normal (NL) cases (FIG. 12). These cases also exhibit an additional isoform of periostin reacting with L-PHA that is of a higher molecular weight. Osteoglycin (OGN) from BC cases (BC1, BC3, BC4, BC5, and BC6) also shows increased reactivity with L-PHA compared with OGN from NL cases. Combining these results, serum from BC1, BC3, BC4, BC5, and BC6 have significant increases in L-PHA reactive POSTN and/or OGN compared to serum from healthy women. FIG. 12 thus provides evidence of increased β1,6 branched glycans on periostin (POSTN) and osteoglycin (OGN) (also referenced as mimecan) in serum from breast cancer (BC) cases compared with normal (NL) serum.

Example VI

Detection of Ovarian Cancer Biomarkers in Tissue and Serum

Figure 13:
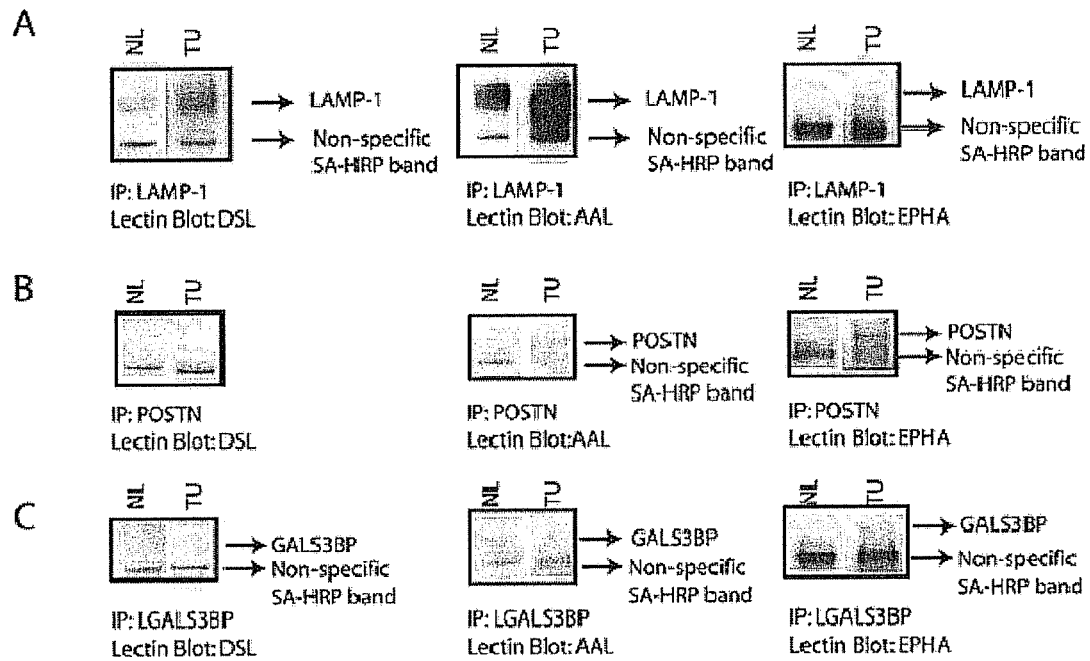
FIG. 13 shows Western blots for three different proteins immunoprecipiated from ovarian tumor tissue (TU) and benign ovarian tissue (NL), and probed with lectins DSL, AAL and E-PHA, (A) lysosomal-associated membrane glycoprotein 1 (LAMP-1), (B) periostin (POSTN), and (C) lectin galactosidase soluble binding protein 3 (GALS3BP).

Tumor-specific glycosylation in ovarian cancer. Markers were selected for validation based on results obtained using glycoproteomic analysis of endometrioid ovarian tumor (TU) tissue compared with benign (NL) ovary tissue (Example IV). Lysosomal-associated membrane glycoprotein 1 (LAMP-1) was immunoprecipitated from 500 μg of pre-cleared protein lysate obtained from ovarian tumor tissue or normal ovarian tissue in 300 μl of 1× Tris-buffered saline, 1% triton-X-100 using 2 μg of anti-LAMP-1 monoclonal antibody (E-Bioscience). Bound antibody complexes were captured using 50 μl of protein A/G plus agarose (Santa Cruz Biotechnology) at 4° C. for 2 hours. Complexes were washed stringently using 1×TBS/1% triton X-100 buffer before separating the proteins on 4-12% NuPage Bis-Tris gels prior to transfer to PVDF membrane for 2 hours at 25V. Membranes were blocked overnight at 4° C. in 3% BSA/1×TBST before detection using the indicated biotinylated lectin (DSL, AAL, E-PHA) (1:5,000 dilution) followed by streptavidin-HRP (1:5,000) incubation and Western Lightening Plus (Perkin Elmer) detection. LAMP-1 isolated from tumor tissue shows increased reactivity with the DSL and AAL lectins compared with LAMP-1 isolated from normal ovary (FIG. 13A). The lower band represents a non-specific reaction of the streptavidin-HRP with a protein from the tissue lysates. This band serves as a control for equivalent protein content in the immunoprecipitation reactions; confirming that the increased band density for LAMP-1 from tumor tissue compared with normal is due to increased glycosylation and not a difference in protein input. These results definitively demonstrate significantly elevated levels of branched N-linked glycans that have either α1,3 or α1,6 linked fucose on LAMP-1 in ovarian tumor tissue compared to benign ovarian tissue. POSTN was immunoprecipitated from 500 μg of pre-cleared protein lysate as described above using 2 μg of an anti-periostin polyclonal antibody (Abcam). There is no POSTN reacting with the DSL lectin. However, POSTN isolated from tumor tissue is reacting with the AAL and E-PHA lectins, while there is no detectable band present in the POSTN isolated from normal tissue (FIG. 13B). These results suggest that POSTN from ovarian tumor tissue has increased core fucosylation and increased levels of bisecting glycans compared with POSTN from normal ovary. The lower non-specific band again demonstrates an equivalent amount of protein present in the precipitation reactions. Lectin galactoside soluble binding protein 3 (LGALS3BP) was immunoprecipitated as described for LAMP-1 using a goat polyclonal antibody to LGALS3BP (Santa Cruz Biotechnology). LGALS3BP isolated from normal and tumor tissue shows no change in reactivity to DSL and AAL, however, there is an increased reactivity with E-PHA for LGALS3BP from ovarian tumor tissue compared to normal (FIG. 13C). These results suggest that LGALS3BP has increased bisecting N-linked glycans in ovarian tumor tissue relative to normal ovarian tissue.

Figure 14:
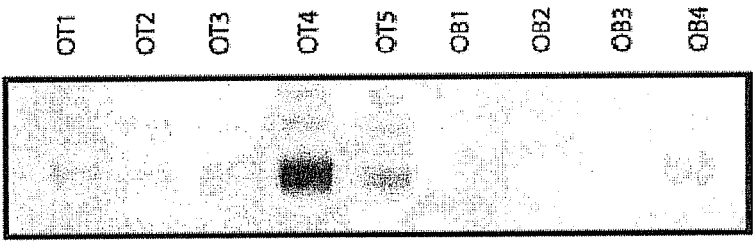
FIG. 14 shows Western blots, using antibodies against (A) periostin and a control, (B) α-1 acid glycoprotein, with E-PHA enriched serum from patients with ovarian cancer (OT) compared with serum from women with benign uterine conditions (OB).
Figure 14:
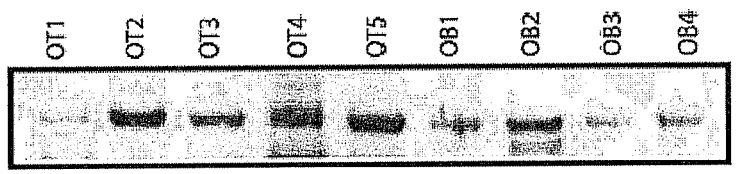

Increased bisecting glycans in ovarian cancer. Serum (5 μl) was incubated with 10 μg of biotinylated E-PHA in 300 μl of lectin binding buffer (50 mM Tris-Cl pH 7.5, 0.1% NP-40, 150 mM NaCl, 0.4 mM EDTA, and 1 protease inhibitor tablet) overnight at 4° C. Paramagnetic streptavidin beads were added and the reactions were incubated at room temperature for 1 hour. Bound complexes were captured using a magnet and washed with lectin binding buffer 3× before separating the proteins on a 4-12% NuPage Bis-Tris gel. Proteins were transferred to PVDF membrane and probed using the indicated antibodies, anti-periostin and anti-α-1 acid GP as a control. Ovarian tumors (OT) OT1, OT4, and OT5 have increased levels of periostin interacting with EPHA when compared to all benign cases analyzed (FIG. 14A). These cases also show evidence of multiple isoforms of periostin present after EPHA precipitation. These results indicate that POSTN present in the serum of patients with ovarian cancer have bisecting N-linked glycans while POSTN that may be present in the serum of women with benign gynecologic diseases does not have this glycan structure. These results correlate with the immunoprecipitation results obtained from ovarian cancer tissue compared with normal ovarian tissue (FIG. 13B). α-1 acid glycoprotein (α-1 acid GP) is a ubiquitous protein found in serum that does not show any changes in the abundance of bisecting N-linked glycans (FIG. 14B). These results demonstrate that equivalent levels of protein were present in the E-PHA precipitation reactions. Therefore, the absence of POSTN in the E-PHA precipitation from serum of women with benign gynecologic disease is not due to protein degradation or reduced protein input. These results provide evidence that the presence of bisecting N-linked glycans on periostin is an ovarian tumor-specific marker found in serum.

Increased Fucosylated Glycans on Lysosomal-Associated Glycoprotein 1 (LAMP-1).

Figure 15:
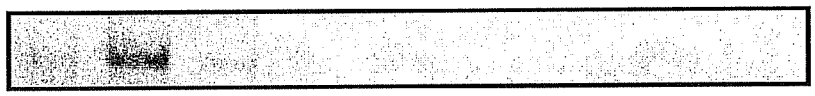
FIG. 15 shows evidence of increased fucosylated glycans on lysosomal-associated glycoprotein 1 (Lamp-1) present in serum from patients with ovarian cancer (OT) compared with serum from women with benign uterine conditions (OB).
Figure 15:

Serum (5 μl) was incubated with 10 μg of biotinylated AAL in 300 μl of lectin binding buffer (50 mM Tris-Cl pH 7.5, 0.1% NP-40, 150 mM NaCl, 0.4 mM EDTA, and 1 protease inhibitor tablet) overnight at 4° C. Paramagnetic streptavidin beads were added and the reactions were incubated at room temperature for 1 hour. Bound complexes were captured using a magnet and washed with lectin binding buffer 3× before separating the proteins on a 4-12% NuPage Bis-Tris gel. Proteins were transferred to PVDF membrane and probed using the indicated antibodies. Ovarian tumors (OT1, OT2, OT3, and OT5) have increased levels of Lamp-1 interacting with AAL compared to benign cases analyzed (FIG. 15). These cases also show evidence of a slower migrating form of Lamp-1, further evidence of a change in glycosylation. These results correlate with the immunoprecipitation results obtained from ovarian cancer tissue compared with normal ovarian tissue (FIG. 13A). The lower panel of FIG. 15 is a streptavidin (SA-HRP) interacting protein for each lane. These results demonstrate that equivalent levels of protein were present in the AAL precipitation reactions. Therefore, the increased abundance of Lamp-1 in the AAL precipitation from serum of women with ovarian cancer is not due to increased protein input. These results provide evidence that the fucosylation of N-linked glycans on Lamp-1 is an ovarian tumor-specific marker found in serum.

Example VII

Identification of Candidate Biomarkers with Cancer-Specific Glycosylation in the Tissue and Serum of Endometrioid Ovarian Cancer Patients by Glycoproteomic Analysis Epithelial ovarian cancer is diagnosed less than 25% of the time when the cancer is confined to the ovary, leading to 5 year survival rates of less than 30%. Therefore, there is an urgent need for early diagnostics for ovarian cancer. Our study using glycotranscriptome comparative analysis of endometrioid ovarian cancer tissue and normal ovarian tissue led to the identification of distinct differences in the transcripts of a restricted set of glycosyltransferases involved in N-linked glycosylation. Utilizing lectins that bind to glycan structures predicted to show changes, we observed differences in lectin-bound glycoproteins consistent with some of the transcript differences. In the present study, we have extended our observations by the use of selected lectins to perform a targeted glycoproteomic analysis of ovarian cancer and normal ovarian tissues. Our results have identified several glycoproteins that display tumor-specific glycosylation changes. We have verified these glycosylation changes on glycoproteins from tissue using immunoprecipitation followed by lectin blot detection. The glycoproteins that were verified were then analyzed further using existing microarray data obtained from benign ovarian adenomas, borderline ovarian adenocarcinomas, and malignant ovarian adenocarcinomas. Those verified glycoproteins found to be expressed above control levels in the microarray datasets were then screened for tumor-specific glycan modifications in serum from ovarian cancer patients. Results obtained from two of these glycoprotein markers, periostin and thrombospondin, have confirmed that tumor-specific glycan changes can be used to distinguish ovarian cancer patient serum from normal serum.

Epithelial ovarian cancer is the deadliest reproductive tract malignancy of women in Western countries (Ozols et al., Cancer Cell 2004. 5: 19-24). Approximately 22,000 new cases are diagnosed each year and about 45% of these women will be alive at 5 years (Hayat et al., Oncologist 2007. 12: 20-37). Methods useful for the early diagnosis of ovarian cancer could significantly improve survival rates. For example, ovarian cancer survival rates climb to greater than 90% for women diagnosed when the disease is confined to the ovary (Hayat et al., Oncologist 2007. 12: 20-37). In this study we are focusing on a specific type of ovarian cancer found to comprise 16-25% of ovarian cancer cases known as endometrioid ovarian cancer (Storey et al., Cancer 2008. 112: 2211-2220). This cancer arises from the outer epithelial lining of the ovary similar to other types of ovarian cancer such as serous adenocarcinoma of the ovary, clear cell carcinoma, and mucinous carcinoma. Many endometrioid ovarian cancers are diagnosed at an earlier stage, enabling the study of early malignant lesions.

Figure 16:
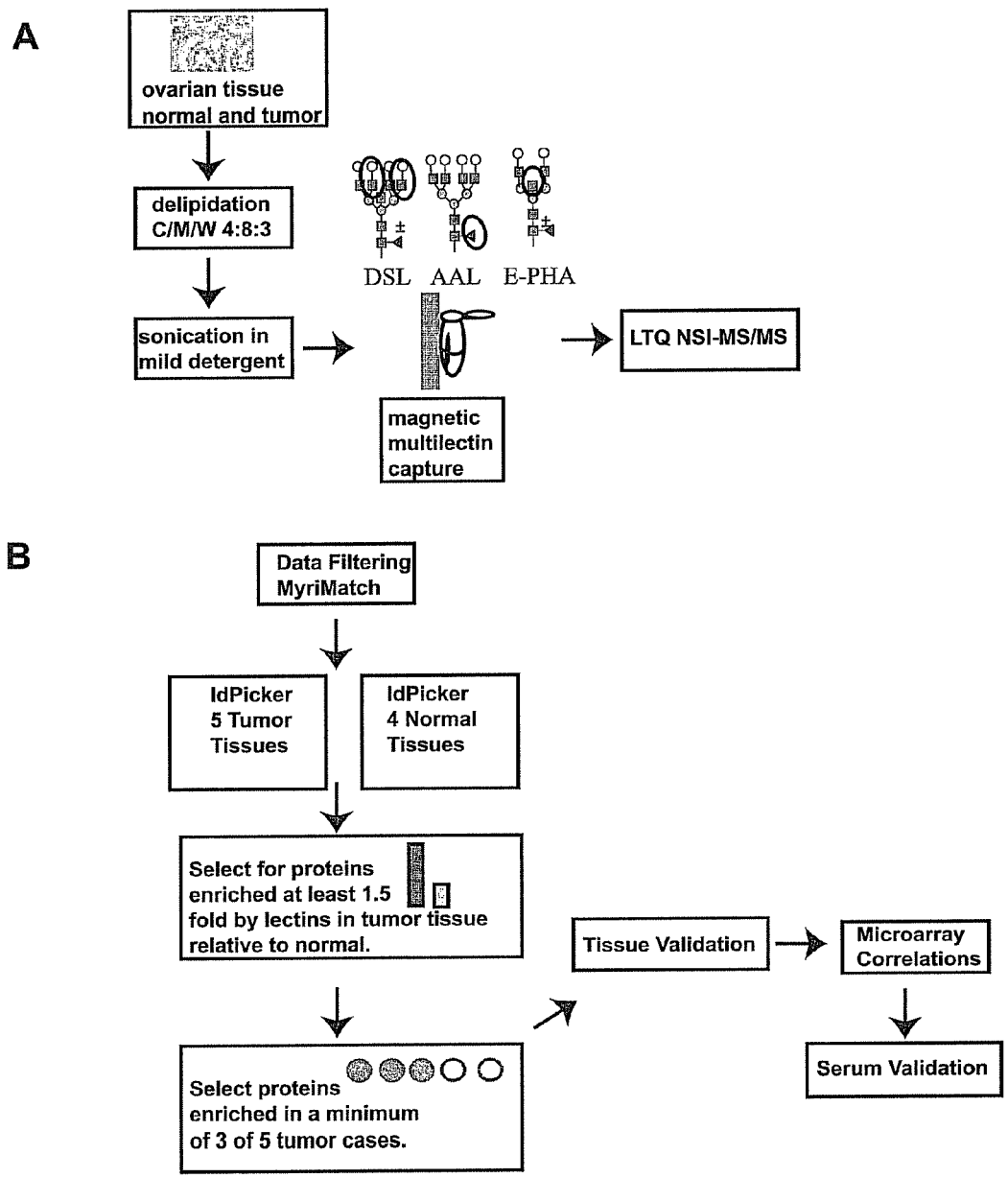
FIG. 16A shows a schematic flow of the multilectin glycoproteomic method used in this study. The glycan structures targeted are circled in the structures displayed.
FIG. 16B shows a flow diagram illustrating the data analysis and filtering methods.

Glycosyltransferase expression levels have been shown to change in certain tumors (Buckhaults et al., J Biol Chem 1997. 272: 19575-19581; Seales et al., Oncogene 2003. 22: 7137-7145; Takahashi et al., Int J Cancer 2000. 88: 914-919). Glycan structures that are added by these glycosyltransferases can be detected by specific lectins (FIG. 16A). In an earlier study, we used human endometrioid ovarian tissue, as well as a mouse model of human endometrioid ovarian cancer, and a quantitative real-time PCR approach (qRT-PCR) to measure quantitative changes in the expression levels of a set of enzymes in the N-linked biosynthetic pathway (Abbott et al., Proteomics 2008. 8: 3210-3220). We were able to identify glycosyltransferases within the N-linked pathway that had significantly increased transcript levels in the tumor tissues compared to normal. The use of lectins to fractionate complex biological samples such as tissue and serum for protein identification by mass spectrometry is becoming a sensitive method to isolate potential disease markers (Yang et al., Clin Chem 2006. 52: 1897-1905; Abbott et al., J Proteome Res 2008. 7: 1470-1480; Mechref et al., Methods Mol Biol 2008. 424: 373-396; Kim et al., Proteomics 2008. 8: 3229-3235; Pierce, "Cancer Glycomics." in Cummings and Pierce (Eds.), Handbook of Glycomics. Academic Press, San Diego 2009). Our approach targeting specific glycan structures that are changing in correlation with malignant disease has been used successfully for breast cancer (Abbott et al., J Proteome Res 2008. 7: 1470-1480). In this study, we have extended this technique for natural and malignant human ovarian tissue using fractionation with multiple lectins. Our mass spectrometry results have identified tumor-specific glycosylation changes on glycoprotein markers not previously identified for ovarian cancer. In addition, we have validated these glycan changes on glycoproteins in tissue and serum collected from the patients in this study. Our approach using tissue as the initial source for glycoproteomic analysis, followed by validation in serum, has enabled us to find novel tumor-specific glycoprotein markers that may be useful for the early diagnosis of ovarian cancer (Abbott et al, Proteomics 2010, 10:470-481).

Materials and Methods

Tumor Samples and Sample Preparation.

Human endometrioid ovarian cancers (n=5) and non-diseased human ovary tissue (n=4) were obtained from women as frozen tissue from the Ovarian Cancer Institute (Atlanta, Ga.). Institutional Review Board approval was obtained for this research from The Georgia Institute of Technology, The University of Georgia, and Northside Hospital (Atlanta, Ga.). Our analysis included frozen tissue (minimum of 50 mg) wet weight, which we were able to obtain from 5 tumor and 4 non-diseased age-matched ovary samples. Frozen tissue was made into a fine powder in the presence of liquid nitrogen using a mortar and pestle. Tissue powder was delipidated using a mixture of chloroform/methanol/water (4:8:3, v/v/v) as described previously (Aoki et al., J Biol Chem 2007. 282: 9127-9142). Delipidated protein pellets were given an additional wash with acetone and water (4:1) on ice for 15 minutes before drying under nitrogen. Delipidated pellets were stored at −80° C. until use.

Lectin Binding and MS Sample Processing.

Intact proteins were extracted from the delipidated tissues using a mild detergent solution as follows: 20 mg of delipidated protein powder was dissolved in 300 µl of 50 mM Tris-Cl pH 7.5, 0.1% NP-40, 150 mM NaCl, 0.4 mM EDTA, one protease inhibitor tablet, the sample was sonicated 3 times for 10 second pulses at setting 5 (Vertis Virsonic microtip). The supernatant was taken after centrifugation at 10,000 rpm at 4° C. for 10 minutes. The protein concentration of the sample was determined by BCA assay and 600 µg of total protein lysate was dialyzed overnight at 4° C. into 40 mM ammonium bicarbonate using a 4,000 MWCO tube-O-dialyzer (GBiosciences). Minimal loss of protein occurred following dialysis due to the use of neutral non-binding membrane, ≤5%. The sample was adjusted to 150 mM NaCl, 5 mM $CaCl_2$, and 5 mM $MgCl_2$ before the addition of the following lectins: biotinylated E-PHA (Phaseolus Vulgaris Erythroagglutinin), biotinylated AAL (*Aleuria Aurantia*), and biotinylated DSL (Datura Stramonium) (Vector Labs, Burlingame, Calif.) (10 µg each) was added and the sample was rotated at 4° C. overnight. Bound lectin reactive proteins were captured using 100 µl paramagnetic streptavidin particles (Promega) at 4° C. for 2 hours. After washing in 1×PBS, captured proteins were eluted with 200 µl of 2M Urea/4 mM DTT/40 mM ammonium bicarbonate at 52° C. for 1 hour. The eluted fraction was separated from the paramagnetic streptavidin particles using a magnetic stand. Eluted proteins were carboxyamidomethylated by adding an equal volume of iodoacetamide (10 mg/ml in 40 mM ammonium bicarbonate) in the dark for 45 minutes and digested with 5 µg of sequencing grade trypsin (1:50, Promega) at 37° C. overnight. Tryptic peptides were acidified with 200 µl of 1% trifluoroacetic acid and desalting was performed using C18 spin columns (Vydac Silica C18, The Nest Group, Inc.). Eluted peptides were dried in the speed vac and resuspended in 19.5 µl buffer A (0.1% formic acid) and 0.5 µl of buffer B (80% acetonitrile/0.1% formic acid) and filtered through a 0.2 µm filter (nanosep, PALL). Samples were loaded off-line onto a nanospray column/emitter (75 µm×13.5 cm, New Objective) self-packed with C18 reverse-phase resin in a nitrogen pressure bomb for 10 minutes. Peptides were eluted via a 160-minute linear gradient of increasing B at a flow rate of approximately 200 nl/min. directly into a linear ion trap mass spectrometer (LTQ, Thermo Co. San Jose, Calif. equipped with a nanoelectrospray ion source). The top eight ions from the full MS (300-2000 m/z) were selected for CID fragmentation at 36% with a dynamic exclusion of 2 repeat counts using an exclusion time of 30 seconds.

Proteomic Data Analysis.

The raw MS data was converted to mzXML using ReAdW, a software written at the Institute for Systems Biology in Seattle, Wash., which is available on the World Wide Web at http://www.systemsbiology.org. MS/MS spectra were searched against the International Protein Index (IPI) human sequence database (IPI.HUMAN.v.3.26; available on the World Wide Web at http://www.ebi.ac.uk/IPI/Databases.html) using MyriMatch (Tabb et al., J Proteome Res 2007. 6: 654-661). The MyriMatch search criteria included only tryptic peptides, all cysteines were presumed carboxyamidomethylated, and methionines were allowed to be oxidized. MyriMatch searches allowed a precursor error of up to 1.25 m/z and a fragment ion limit of within 0.5 m/z. All ambiguous identifications that matched to multiple peptide sequences were excluded. The identified proteins (2+ peptides required) from each individual tumor and normal sample were filtered and grouped using IDPicker software (Zhang et al., J Proteome Res 2007. 6: 3549-3557). IDPicker software incorporates searches against a separate reverse database, probability match obtained from MyriMatch, and DeltCN scores. Information about IDPicker tools can be found on the World Wide Web at http://www.mc.vanderbilt.edu/msrc/bioinformatics/. Variance for sample processing between normal and tumor samples were calculated by measuring the number of peptides identified for proteins that adhere to the lectins in a non-glycan dependent manner, such as serum albumin. Our results indicate 14.6%±0.16 variance between normal and tumor cases analyzed.

Western Blot Tissue Validation.

Tissue (50 mg frozen) samples were lysed in RIPA buffer (1× Phosphate buffered saline, 1% NP-40, 0.5% sodium deoxycholate, 0.1% SDS) containing a mini complete protease inhibitor tablet (Roche, Indianapolis, Tenn.) using a polytron at setting 3 for 1 minute. The lysate was cleared by centrifugation at 10,000× g for 10 minutes. Protein concentrations were determined by BCA assay (Pierce, Rockford, Ill.). Lysate (500 µg) was pre-cleared using protein A/G beads and normal IgG from the species of the primary antibody prior to immunoprecipitation. Antibodies to indicated biomarkers (2 µg) were added to 500 µg pre-cleared lysate at 4° C. for 2 hours. Protein A/G beads (50 µl) were added to separate antibody bound and unbound proteins. Proteins bound to protein A/G were separated on 4-12% NuPage Bis Tris gels and transferred to PVDF membrane at 25 V for 1.5 hours. Membranes were blocked overnight in 3% BSA/TBST buffer before lectin blot detection using a 1:5,000 dilution of the following biotinylated lectins: *Phaseolus vulgaris erythroagglutinin* (E-PHA), *Aleuria aurantia* (AAL), and *Datura stramonium* (DSL), Vector Labs, Burlingame, Calif.). Bound lectin was detected using a 1:5,000 dilution of streptavidin-HRP (Vector Labs, Burlingame, Calif.) before washing and detection using Western Lightening Plus (Perkin Elmer).

Serum Validation.

Serum (5 µl) was diluted in a 300 µl volume of 50 mM Tris-Cl pH 7.5, 0.1% NP-40, 150 mM NaCl, 5 mM $MgCl_2$, and 5 mM $CaCl_2$. Biotinylated lectins E-PHA, AAL, or DSL 10 µg were added and the reactions were incubated at 4° C. for 2 hours. Lectin reactive proteins were captured using 100 µl paramagnetic streptavidin particles (Promega) at 4° C. for 2 hours. Proteins were separated on 4-12% NuPage Bis Tris gels and transferred to PVDF membrane at 25 V for 1.5 hours. Membranes were blocked overnight in 5% nonfat milk before detection of specific proteins using the indicated antibodies.

Results

Multilectin Glycoproteomic Analysis

Lectins recognizing specific glycan structures within the N-linked glycosylation pathway (FIG. 16A) were chosen for glycoproteomic analysis based on our results demonstrating that the mRNA levels of the enzymes that synthesize these glycans were elevated 2-18 fold in ovarian cancer tissue relative to normal ovary (Abbott et al., Proteomics 2008. 8: 3210-3220). The enzymes showing the largest elevations in mRNA levels were MGAT 4a, MGAT4b, MGAT5, MGAT3, and FUT8. As shown circled in FIG. 16A, the lectin *Datura stramonium* (DSL) can recognize the β(1,4) branched N-acetylglucosamine (GlcNAc) added by the glycosyltransferases MGAT4a and MGAT4b, as well as the β(1,6) branched N-acetylglucosamine added by the glycosyltransferase MGAT5 (Wu et al., Glycoconj J 2008). The lectin *Aleuria aurantia* (AAL) has a high affinity for the core α(1,6) fucose-linked product that results from the activity of the FUT8 glycosyltransferase (Nagata et al., Biochim Biophys Acta 1991. 1076: 187-190; Iskratsch et al., Anal Biochem 2009. 386: 133-146). *Phaseolus vulgaris erythroagglutinin* (E-PHA) binds with the bisecting N-acetylglucosamine that is produced by the activity of the glycosyltransferase known as MGAT3.

TABLE 9

Patient Information and Proteins Detected Following Multilectin Proteomics of Ovarian Tissue

| Sample No | Histology | Tumor Stage | Tumor Grade | Unique Proteins |
|---|---|---|---|---|
| 1 | endometrioid | III-IV | 2 | 525 |
| 2 | endometrioid | IIIa | 3 | 416 |
| 3 | endometrioid | Ia | 2 | 306 |
| 4 | endometrioid | Ia-Ic | 2 | 328 |
| 5 | endometrioid | IIIb-IIIc | 3 | 416 |
| 6 | normal | n/a | n/a | 242 |
| 7 | normal | n/a | n/a | 258 |
| 8 | normal | n/a | n/a | 158 |
| 9 | normal | n/a | n/a | 213 |

Figure 17:
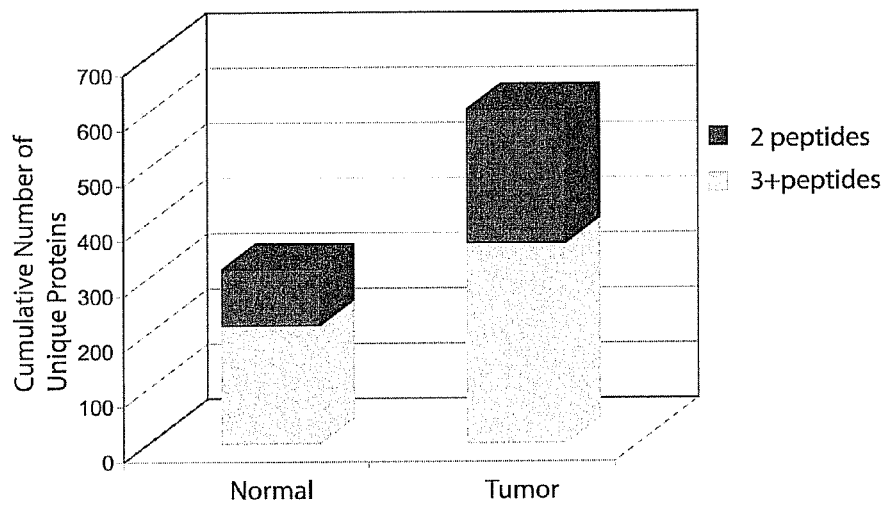
FIG. 17 shows a graphical presentation of cumulative proteomic data.

Intact glycoproteins were extracted from ovarian tissue (FIG. 16A) before isolating lectin reactive proteins using the lectins DSL, AAL, and E-PHA. The cases of ovarian cancer chosen for analysis are shown in Table 9: five cases of endometrioid ovarian cancer (2 early stage and 3 later stage) and four cases of normal ovary tissue (age matched with tumor cases). Following multiple lectin enrichment, eluted intact glycoproteins were processed to tryptic peptides prior to MS/MS analysis. MS/MS data for each tissue sample were analyzed using the flow diagram for outlined in FIG. 16B. Myrimatch searches were used to filter m/z data against the reverse human IPI database to achieve a false discovery rate of less than 2% for proteins identified with a minimum of 2 peptides. We identified cumulatively 504 unique proteins from the ovarian tumor tissue and 315 unique proteins from normal ovarian tissue after multilectin enrichment. As shown in FIG. 17, >60% of the unique protein identifications were made with 3 or more peptides. FIG. 17 also indicates that there was a 38% increase in the number of proteins enriched by lectins from tumor tissues relative to normal ovarian tissues. These results are expected due to the increased expression of the glycosyltransferases that add these glycan structures in ovarian cancer tissue versus non-diseased ovary (Abbott et al., Proteomics 2008. 8: 3210-3220). The proteins identified in tumor and non-diseased cases were then grouped using the IdPicker software. Proteins that were enriched in tumor cases at a spectral abundance of 1.5× (150%) above normal were selected. In addition, a second criterion that was applied required the protein to be present at a 1.5× increase in at least 3 of the 5 tumor cases analyzed. Table 10 lists select proteins that remained following both data filtering criteria. The peptide sequences for those proteins and additional identified proteins are provided in Table 11. Approximately 40% of the proteins in this list contain a signal sequence and are predicted to be glycoproteins. Since we do not elute proteins from the lectin column with sugar haptens, many of the proteins not predicted to be glycoproteins by sequence analysis may be associating with glycoproteins that have bound to the lectins.

The database DAVID (Database for Annotation, Visualization and Integrated Discovery) was used to annotate the function of the proteins shown in Table 10. The top 3 functional classifications of the proteins enriched by multilectin affinity chromatography of ovarian tumor tissue relative to non-diseased ovarian tissue were: antioxidant activity (3.2E-8), glucose metabolism (8.7E-7), and cellular adhesion (9.8E-3). Considering only glycoproteins containing signal sequences, the functional categories are dominated by the antioxidant (examples include: CP, LDHA, LTF, SERPINH1, CFB, and LAMP1) and cellular adhesion (examples include: POSTN, THBS1, FIBLN5, MUC5b, and HSPG2) categories. Glycoproteins in these functional categories play significant roles in the progression and metastatic spread of ovarian cancer. Therefore, strategies to co-target the glycan moieties on these glycoproteins as well as their peptide epitopes may contribute to new therapeutic strategies with greater specificities that could be useful to inhibit ovarian tumor cell adhesion and spread in the peritoneal cavity.

TABLE 10

Proteomic Analysis of Multilectin Enriched Proteins

| IPI Accession[a] | Gene Name | Mol. Wt. | Description | Cumulative Spectral Counts Tumor | Cumulative Spectral Counts Normal | Cellular Location | Predicted Glycoprotein? | In N-glycoprotein[b] plasma proteome study? |
|---|---|---|---|---|---|---|---|---|
| IPI00003362.2 | GRP78 | 72 | Glucose-regulated protein 78 | 16 | 0 | cell surface | No | No |
| IPI00003881.5 | HNRNPF | 45 | heterogeneous nuclear ribonucleoprotein F | 7 | 0 | cytoplasm | No | No |
| IPI00004503.5 | LAMP1 | 44 | lysosomal-associated membrane protein 1 | 8 | 0 | membrane | Yes | Yes |
| IPI00007960.4 | POSTN | 93 | periostin | 20 | 5 | extracellular | Yes | Yes |
| IPI00008274.7 | CAP1 | 51 | adenylate cyclase-associated protein 1 | 7 | 0 | membrane | Yes | Yes |
| IPI00009904.1 | PDIA4 | 72 | protein disulfide isomerase family A, | 4 | 0 | ER | No | No |
| IPI00010720.1 | CCT5 | 57 | chaperonin containing TCP1, subunit 5 (epsilon) | 8 | 0 | cytoplasm | No | No |
| IPI00010790.1 | BGN | 42 | Biglycan precursor | 34 | 8 | extracellular | Yes | No |
| IPI00010796.1 | P4HB | 122 | procollagen-proline, 2-oxoglutarate 4-dioxygenase | 14 | 0 | ER/Golgi | No | No |
| IPI00017601.1 | CP | 57 | Ceruloplasmin | 8 | 0 | extracellular | Yes | Yes |
| IPI00018219.1 | TGFBI | 75 | transforming growth factor, beta-induced | 16 | 6 | extracellular | No | No |
| IPI00019502.3 | MYH9 | 226 | myosin, heavy chain 9, non-muscle | 34 | 7 | cytoplasm | No | No |
| IPI00019591.1 | CFB | 86 | complement factor B | 7 | 0 | membrane | Yes | Yes |
| IPI00020501.1 | MYH11 | 227 | myosin, heavy chain 11, smooth muscle | 21 | 5 | cytoplasm | No | No |
| IPI00020599.1 | CRTC | 48 | calreticulin | 14 | 3 | ER | No | No |
| IPI00022977.1 | CKB | 42 | creatin kinase-brain | 7 | 0 | cytoplasm | No | No |
| IPI00023673.1 | LGALS3BP | 65 | lectin, galactoside-binding, soluble, 3 binding protein | 8 | 0 | extracellular | Yes | Yes |
| IPI00024284.4 | HSPG2 | 469 | heparan sulfate proteoglycan 2 | 7 | 0 | membrane | Yes | Yes |
| IPI00025252.1 | PDIA3 | 57 | protein disulfide isomerase A3 | 16 | 0 | ER | No | No |
| IPI00025512.2 | HSPB1 | 23 | heat shock 27 kDa protein | 13 | 4 | cell surface | No | No |
| IPI00027497.5 | GPI | 63 | glucose-6-phosphate | 7 | 0 | ER | No | No |
| IPI00032140.4 | SERPINH1 | 46 | Serine protease inhibitor H1 | 19 | 8 | ER/Golgi | Yes | No |
| IPI00169383.3 | PGK1 | 45 | phosphoglycerate kinase | 16 | 3 | cytoplasm | No | No |
| IPI00186290.6 | EEF2 | 93 | elongation factor 2 | 10 | 3 | cytoplasm | No | No |
| IPI00215914.5 | ARF1 | 21 | ADP-Ribosylation Factor | 5 | 0 | Golgi | No | No |
| IPI00216049.1 | HNRNPK | 51 | heterogeneous nuclear ribonucleoprotein K | 9 | 0 | cytoplasm | No | No |
| IPI00217966.7 | LDHA | 37 | lactate dehydrogenase A | 18 | 2 | cytoplasm | Yes | No |
| IPI00219525.10 | PGD | 53 | phosphogluconate dehydrogenase | 5 | 2 | cytoplasm | No | No |
| IPI00219713 | FIBG | 51 | Fibrinogen gamma | 17 | 2 | extracellular | Yes | No |
| IPI00220301.5 | PRDX6 | 25 | peroxiredoxin 6 | 5 | 0 | cytoplasm | No | No |
| IPI00220642.7 | YWHAG | 28 | 14-3-3 gamma | 5 | 0 | cytoplasm | No | No |
| IPI00291006.1 | MDH2 | 35 | malate dehydrogenase 2, NAD (mitochondrial) | 6 | 0 | mitochondrial | No | No |
| IPI00296099.6 | THBS1 | 129 | thrombospondin 1 | 22 | 0 | extracellular | Yes | Yes |
| IPI00297550.8 | F13A1 | 83 | coagulation factor XIII, A1 | 8 | 0 | extracellular | Yes | Yes |
| IPI00298860.5 | LTF | 78 | lactotransferrin | 4 | 0 | extracellular | Yes | No |
| IPI00298994.5 | TLN1 | 269 | talin 1 | 9 | 0 | membrane | No | No |

TABLE 10-continued

Proteomic Analysis of Multilectin Enriched Proteins

| IPI Accession[a] | Gene Name | Mol. Wt. | Description | Cumulative Spectral Counts Tumor | Cumulative Spectral Counts Normal | Cellular Location | Predicted Glycoprotein? | In N-glycoprotein[b] plasma proteome study? |
|---|---|---|---|---|---|---|---|---|
| IPI00299571.5 | PDIA6 | 54 | protein disulfide isomerase family A, | 15 | 0 | ER/Golgi | No | No |
| IPI00376005.2 | EIF5A | 20 | eukaryotic translation initiation factor 5A | 5 | 0 | cytoplasm | No | No |
| IPI00382428.6 | FBLN5 | 60 | fibulin 5 | 5 | 2 | extracellular | Yes | No |
| IPI00426051.3 | IGHG2 | 51 | similar to hCG2038920 | 8 | 0 | unknown | Yes | No |
| IPI00478003.1 | A2M | 163 | alpha-2-macroglobulin | 31 | 2 | extracellular | Yes | No |
| IPI00479217.1 | HNRNPU | 89 | heterogeneous nuclear ribonucleoprotein U | 5 | 0 | cell surface | No | No |
| IPI00549725.6 | PGAM1 | 29 | phosphoglycerate mutase 1 (brain) | 5 | 0 | cytoplasm | No | No |
| IPI00550363.3 | TAGLN2 | 24 | transgelin 2 | 13 | 2 | cytoplasm | No | No |
| IPI00759776.1 | ACTN1 | 103 | Actinin 1 isoform b | 14 | 0 | cytoplasm | No | No |
| IPI00719373.1 | IGL@ | 23 | immunoglobulin lambda locus | 13 | 8 | extracellular | Yes | No |
| IPI00787849.1 | MUC5B | 597 | mucin 5B | 18 | 0 | extracellular | Yes | No |

[a]International protein index database.
[b]Published analysis of the N-linked glycoproteins from human plasma Liu, et al., J. Prot. Res. (2005)4: 2070-2080.

TABLE 11

Peptides and spectra present in lectin-bound fractions isolated from ovarian cancer tumors.

| IPI Number | Code | Molecular Weight (kDa) | Unique Peptides | % Coverage | Peptide Sequences | SEQ ID NO: | Spectra |
|---|---|---|---|---|---|---|---|
| IPI00003362.2 | GRP78 | 72.43 | 8 | 16.3 | NQLTSNPENTVFDAK | 348 | 4 |
| | | | | | TWNDPSVQQDIK | 349 | 2 |
| | | | | | KSDIDEIVLVGGSTR | 350 | 1 |
| | | | | | SQIFSTASDNQPTVTIK | 351 | 4 |
| | | | | | ITITNDQNR | 352 | 1 |
| | | | | | NELESYAYSLK | 353 | 1 |
| | | | | | ELEEIVQPIISK | 354 | 1 |
| | | | | | IINEPTAAAIAYGLDK | 355 | 2 |
| IPI00003881.5 | HNRNPF | 45.68 | 2 | 8.27 | ITGEAFVQFASQELAEK | 356 | 4 |
| | | | | | ATENDIYNFFSPLNPVR | 357 | 4 |
| IPI00004503.5 | LAMP1 | 44.89 | 3 | 8.8 | TVESITDIR | 358 | 4 |
| | | | | | FFLQGIQLNTILPDAR | 359 | 3 |
| | | | | | ALQATVGNSYK | 604 | 1 |
| IPI00007960.4 | POSTN | 93.33 | 9 | 19.5 | GSFTYFAPSNEAWDNLDSDIR | 605 | 1 |
| | | | | | IIHGNQIATNGVVHVIDR | 606 | 1 |
| | | | | | VLTQIGTSIQDFIEAEDDLSSFR | 607 | 5 |
| | | | | | AAAITSDILEALGR | 608 | 4 |
| | | | | | DGHFTLFAPTNEAFEK | 609 | 1 |
| | | | | | DIVTNNGVIHLIDQVLIPDSAK | 610 | 2 |
| | | | | | VGLNELYNGQILETIGGK | 611 | 2 |
| | | | | | FSTFLSLLEAADLK | 612 | 1 |
| | | | | | LLYPADTPVGNDQLLEILNK | 613 | 6 |
| IPI00008274.7 | CAP1 | 51.86 | 2 | 7.01 | AGAAPYVQAFDSLLAGPVAEYLK | 614 | 5 |
| | | | | | VENQENVSNLVIEDTELK | 615 | 2 |
| IPI00009904.1 | PDIA4 | 72.94 | 2 | 4.52 | EVSQPDWTPPPEVTLVLTK | 616 | 2 |
| | | | | | VDATAETDLAK | 617 | 1 |
| IPI00010720.1 | CCT5 | 56.68 | 3 | 8.34 | IADGYEQAAR | 618 | 2 |
| | | | | | WVGGPEIELIAIATGGR | 619 | 2 |
| | | | | | LGFAGLVQEISFGTTK | 620 | 7 |
| IPI00010790.1 | BGN | 41.66 | 10 | 34.3 | EISPDTTLLDLQNNDISELR | 621 | 4 |
| | | | | | EISPDTTLLDLQNNDISELRK | 622 | 2 |
| | | | | | GLQHLYALVLVNNK | 623 | 1 |
| | | | | | NHLVEIPPNLPSSLVELR | 360 | 6 |
| | | | | | DLPETLNELHLDHNK | 361 | 1 |

TABLE 11-continued

Peptides and spectra present in lectin-bound fractions isolated from ovarian cancer tumors.

| IPI Number | Code | Molecular Weight (kDa) | Unique Peptides | % Coverage | Peptide Sequences | SEQ ID NO: | Spectra |
|---|---|---|---|---|---|---|---|
| | | | | | IQAIELEDLLR | 362 | 8 |
| | | | | | LGLGHNQIR | 363 | 6 |
| | | | | | VPSGLPDLK | 364 | 2 |
| | | | | | AYYNGISLFNNPVPYWEVQPATFR | 365 | 3 |
| | | | | | LAIQFGNYK | 366 | 1 |
| IPI00017601.1 | CP | 122.2 | 6 | 9.1 | ALYLQYTDETFR | 367 | 2 |
| | | | | | GAYPLSIEPIGVR | 368 | 1 |
| | | | | | NNEGTYYSPNYNPQSR | 369 | 2 |
| | | | | | DVDKEFYLFPTVFDENESLLLEDNIR | 370 | 1 |
| | | | | | KAEEEHLGILGPQLHADVGDK | 371 | 1 |
| | | | | | VNKDDEEFIESNK | 372 | 1 |
| IPI00010796.1 | P4HB | 57.12 | 7 | 21.37 | VDATEESDLAQQYGVR | 373 | 3 |
| | | | | | TGPAATTLPDGAAAESLVESSEVAVIGFFK | 374 | 5 |
| | | | | | QFLQAAEAIDDIPFGITSNSDVFSK | 375 | 1 |
| | | | | | YGLDKDGVVLFK | 376 | 1 |
| | | | | | THILLFLPK | 377 | 2 |
| | | | | | ILEFFGLK | 378 | 1 |
| | | | | | NFEDVAFDEKK | 379 | 1 |
| IPI00018219.1 | TGFBI | 74.69 | 7 | 16.35 | VISTITNNIQQIIEIEDTFETLR | 380 | 5 |
| | | | | | ILGDPEALR | 381 | 2 |
| | | | | | DILATNGVIHYIDELLIPDSAK | 382 | 2 |
| | | | | | TLFELAAESDVSTAIDLFR | 383 | 4 |
| | | | | | LTLLAPLNSVFK | 384 | 4 |
| | | | | | EGVYTVFAPTNEAFR | 385 | 3 |
| | | | | | SLQGDKLEVSLK | 386 | 1 |
| IPI00019502.3 | MYH9 | 226.59 | 19 | 13.8 | NFINNPLAQADWAAK | 387 | 4 |
| | | | | | VISGVLQLGNIVFK | 388 | 3 |
| | | | | | VVFQEFR | 389 | 1 |
| | | | | | ALELDSNLYR | 390 | 1 |
| | | | | | IAEFTTNLTEEEEK | 391 | 1 |
| | | | | | IRELESQISELQEDLESER | 392 | 2 |
| | | | | | DLGEELEALKTELEDTLDSTAAQQELR | 393 | 1 |
| | | | | | DFSALESQLQDTQELLQEENR | 394 | 4 |
| | | | | | DLEGLSQR | 395 | 1 |
| | | | | | LQQELDDLLVDLDHQR | 396 | 1 |
| | | | | | QAQQERDELADEIANSSGK | 397 | 1 |
| | | | | | IAQLEEELEEEQGNTELINDR | 398 | 1 |
| | | | | | ANLQIDQINTDLNLER | 399 | 1 |
| | | | | | IAQLEEQLDNETK | 400 | 1 |
| | | | | | QLEEAEEEAQR | 401 | 2 |
| | | | | | QLLQANPILEAFGNAK | 402 | 4 |
| | | | | | KEEELQAALAR | 403 | 1 |
| | | | | | KFDQLLAEEK | 404 | 3 |
| | | | | | TQLEELEDELQATEDAK | 405 | 3 |
| IPI00019591.1 | CFB | 85.55 | 3 | 5.14 | YGLVTYATYPK | 406 | 1 |
| | | | | | VSEADSSNADWVTK | 407 | 4 |
| | | | | | EAGIPEFYDYDVALIK | 408 | 2 |
| IPI00020501.1 | MYH11 | 227.39 | 14 | 9.92 | NFINSPVAQADWAAK | 409 | 1 |
| | | | | | VVSSVLQLGNIVFK | 410 | 1 |
| | | | | | VDYNASAWLTK | 411 | 1 |
| | | | | | HAQAVEELTEQLEQFKR | 412 | 1 |
| | | | | | DVASLSSQLQDTQELLQEETR | 413 | 2 |
| | | | | | LQDFASTVEALEEGK | 414 | 1 |
| | | | | | EIENLTQQYEEK | 415 | 1 |
| | | | | | LQQELDDLVVDLDNQR | 416 | 1 |
| | | | | | KATQQAEQLSNELATER | 417 | 1 |
| | | | | | IAQLEEQVEQEAR | 418 | 1 |
| | | | | | QLLQANPILEAFGNAK | 419 | 4 |
| | | | | | KEEELQAALAR | 420 | 1 |
| | | | | | KFDQLLAEEK | 421 | 3 |
| | | | | | TQLEELEDELQATEDAK | 422 | 3 |

TABLE 11-continued

Peptides and spectra present in lectin-bound fractions isolated from ovarian cancer tumors.

| IPI Number | Code | Molecular Weight (kDa) | Unique Peptides | % Coverage | Peptide Sequences | SEQ ID NO: | Spectra |
|---|---|---|---|---|---|---|---|
| IPI00020599.1 | CALR | 48.15 | 6 | 22.8 | TQLEELEDELQATEDAK | 423 | 4 |
| | | | | | FYGDEEKDK | 424 | 2 |
| | | | | | GLQTSQDAR | 425 | 1 |
| | | | | | FYALSASFEPFSNK | 426 | 4 |
| | | | | | IDNSQVESGSLEDDWDFLPPKK | 427 | 1 |
| | | | | | SGTIFDNFLITNDEAYAEEFGNETWGVTK | 428 | 3 |
| IPI00022977.1 | CKB | 42.65 | 4 | 19.9 | TDLNPDNLQGGDDLDPNYVLSSR | 429 | 1 |
| | | | | | LAVEALSSLDGDLAGR | 430 | 3 |
| | | | | | GTGGVDTAAVGGVFDVSNADR | 431 | 2 |
| | | | | | LGFSEVELVQMVVDGVK | 432 | 1 |
| IPI00023673.1 | LGALS3BP | 65.3 | 4 | 10.3 | LADGGATNQGR | 433 | 4 |
| | | | | | ELSEALGQIFDSQR | 434 | 1 |
| | | | | | TLQALEFHTVPFQLLAR | 435 | 1 |
| | | | | | IYTSPTWSAFVTDSSWSAR | 436 | 2 |
| IPI00024284.4 | HSPG2 | 468.92 | 5 | 1.6 | IPGDQVVSVVFIK | 437 | 1 |
| | | | | | VISSGSVASYVTSPQGFQFR | 438 | 1 |
| | | | | | ASYAQQPAESR | 439 | 3 |
| | | | | | IAHVELADAGQYR | 440 | 1 |
| | | | | | YELGSGLAVLR | 441 | 1 |
| IPI00024870.1 | MYH11 | 223.63 | 14 | 10.1 | NFINSPVAQADWAAK | 442 | 1 |
| | | | | | VVSSVLQLGNIVFK | 443 | 1 |
| | | | | | VDYNASAWLTK | 444 | 1 |
| | | | | | HAQAVEELTEQLEQFKR | 445 | 1 |
| | | | | | DVASLSSQLQDTQELLQEETR | 446 | 2 |
| | | | | | LQDFASTVEALEEGK | 447 | 1 |
| | | | | | EIENLTQQYEEK | 448 | 1 |
| | | | | | LQQELDDLVVDLDNQR | 449 | 1 |
| | | | | | KATQQAEQLSNELATER | 450 | 1 |
| | | | | | IAQLEEQVEQEAR | 451 | 1 |
| | | | | | QLLQANPILEAFGNAK | 452 | 4 |
| | | | | | KEEELQAALAR | 453 | 1 |
| | | | | | KFDQLLAEEK | 454 | 3 |
| | | | | | TQLEELEDELQATEDAK | 455 | 3 |
| IPI00025252.1 | PDIA3 | 56.76 | 11 | 30.2 | LAPEYEAAATR | 456 | 1 |
| | | | | | YGVSGYPTLK | 457 | 2 |
| | | | | | DGEEAGAYDGPR | 458 | 3 |
| | | | | | FISDKDASIVGFFDDSFSEAHSEFLK | 459 | 1 |
| | | | | | FAHTNVESLVNEYDDNGEGIILFR | 460 | 1 |
| | | | | | DLLIAYYDVDYEK | 461 | 1 |
| | | | | | TFSHELSDFGLESTAGEIPVVAIR | 462 | 1 |
| | | | | | FLQDYFDGNLK | 463 | 2 |
| | | | | | FLQDYFDGNLKR | 464 | 1 |
| | | | | | SEPIPESNDGPVK | 465 | 1 |
| | | | | | ELSDFISYLQR | 466 | 3 |
| IPI00025276.1 | TNXB | 464.5 | 4 | 1.28 | FDSFTVQYK | 467 | 1 |
| | | | | | LGELWVTDPTPDSLR | 468 | 1 |
| | | | | | LGPISADSTTAPLEK | 469 | 2 |
| | | | | | LSQLSVTDVTTSSLR | 470 | 1 |
| IPI00025512.2 | HSPB1 | 22.79 | 5 | 44.4 | LFDQAFGLPR | 471 | 5 |
| | | | | | LPEEWSQWLGGSSWPGYVRPLPPAAIESPAVAAPAYSR | 472 | 2 |
| | | | | | VSLDVNHFAPDELTVK | 473 | 2 |
| | | | | | TKDGVVEITGK | 474 | 2 |
| | | | | | LATQSNEITIPVTFESR | 475 | 3 |
| IPI00027497.5 | GPI | 63.16 | 2 | 5.57 | TLAQLNPESSLFIIASK | 476 | 4 |
| | | | | | TFTTQETITNAETAK | 477 | 3 |
| IPI00169383.3 | PGK1 | 44.62 | 8 | 20.6 | NNQITNNQR | 478 | 1 |
| | | | | | YSLEPVAVELK | 479 | 2 |
| | | | | | LGDVYVNDAFGTAHR | 480 | 1 |
| | | | | | ALESPERPFLAILGGAK | 481 | 3 |
| | | | | | ITLPVDFVTADKFDENAK | 482 | 2 |
| | | | | | YAEAVTR | 483 | 2 |
| | | | | | QIVWNGPVGVFEWEAFAR | 484 | 5 |
| | | | | | WNTEDKVSHVSTGGGASLELLEGK | 485 | 1 |

TABLE 11-continued

Peptides and spectra present in lectin-bound fractions
isolated from ovarian cancer tumors.

| IPI Number | Code | Molecular Weight (kDa) | Unique Peptides | % Coverage | Peptide Sequences | SEQ ID NO: | Spectra |
|---|---|---|---|---|---|---|---|
| IPI00186290.6 | EEF2 | 93.35 | 5 | 9.66 | STAISLFYELSENDLNFIK | 486 | 4 |
| | | | | | ALLELQLEPEELYQTFQR | 487 | 3 |
| | | | | | ARPFPDGLAEDIDKGEVSAR | 488 | 1 |
| | | | | | YEWDVAEAR | 489 | 1 |
| | | | | | AYLPVNESFGFTADLR | 490 | 2 |
| IPI00215914.5 | ARF1 | 20.7 | 2 | 18..6 | LGEIVTTIPTIGFNVETVEYK | 491 | 4 |
| | | | | | NISFTVWDVGGQDK | 492 | 2 |
| IPI00215917.3 | ARF3 | 20.6 | 2 | 18.7 | LGEIVTTIPTIGFNVETVEYK | 493 | 4 |
| | | | | | NISFTVWDVGGQDK | 494 | 2 |
| IPI00216049.1 | HNRNPK | 50.98 | 6 | 20.3 | TDYNASVSVPDSSGPER | 495 | 2 |
| | | | | | ILSISADIETIGEILK | 496 | 1 |
| | | | | | LLIHQSLAGGIIGVK | 497 | 1 |
| | | | | | IILDLISESPIK | 498 | 2 |
| | | | | | IDEPLEGSEDR | 499 | 1 |
| | | | | | IITITGTQDQIQNAQYLLQNSVK | 500 | 4 |
| IPI00216746.1 | HNRNPK | 51.04 | 6 | 20.3 | Same as IPI00216049.1 | | |
| IPI00217966.7 | LDHA | 36.69 | 8 | 25.8 | DQLIYNLLKEEQTPQNK | 501 | 2 |
| | | | | | DLADELALVDVIEDK | 502 | 5 |
| | | | | | DLADELALVDVIEDKLK | 503 | 2 |
| | | | | | TLHPDLGTDKDKEQWK | 504 | 1 |
| | | | | | QVVESAYEVIK | 505 | 1 |
| | | | | | VTLTSEEEAR | 506 | 2 |
| | | | | | SADTLWGIQK | 507 | 4 |
| | | | | | LNLVQR | 508 | 2 |
| IPI00218585.5 | POSTN | 87.03 | 9 | 20.9 | Same as IPI00007960.4 | | |
| IPI00219525.10 | PGD | 53.15 | 3 | 12.2 | LVPLLDTGDIIIDGGNSEYR | 509 | 2 |
| | | | | | GILFVGSGVSGGEEGAR | 510 | 1 |
| | | | | | WTAISALEYGVPVTLIGEAVFAR | 511 | 2 |
| IPI00219757.13 | GSTP1 | 23.36 | 2 | 16.5 | FQDGDLTLYQSNTILR | 512 | 6 |
| | | | | | DQQEAALVDMVNDGVEDLR | 513 | 1 |
| IPI00220301.5 | PRDX6 | 25.04 | 2 | 7.03 | LPFPIIDDR | 514 | 4 |
| | | | | | NFDEILR | 515 | 1 |
| IPI00220642.7 | YWHAG | 28.31 | 4 | 20.6 | NVTELNEPLSNEER | 516 | 1 |
| | | | | | YLAEVATGEK | 517 | 1 |
| | | | | | AYSEAHEISK | 518 | 1 |
| | | | | | TAFDDAIAELDTLNEDSYK | 519 | 2 |
| IPI00291006.1 | MDH2 | 35.54 | 3 | 13.6 | VAVLGASGGIGQPLSLLLK | 520 | 4 |
| | | | | | IFGVTTLDIVR | 521 | 1 |
| | | | | | VDFPQDQLTALTGR | 522 | 2 |
| IPI00296099.6 | THBS1 | 129.4 | 7 | 9.27 | IPESGGDNSVFDIFELTGAAR | 523 | 3 |
| | | | | | IEDANLIPPVPDDKFQDLVDAVR | 524 | 6 |
| | | | | | GGVNDNFQGVLQNVR | 525 | 3 |
| | | | | | FVFGTTPEDILR | 526 | 4 |
| | | | | | TIVTTLQDSIR | 527 | 4 |
| | | | | | QVTQSYWDTNPTR | 528 | 2 |
| | | | | | NALWHTGNTPGQVR | 529 | 2 |
| IPI00297550.8 | F13A1 | 83.28 | 5 | 9.25 | GTYIPVPIVSELQSGK | 530 | 1 |
| | | | | | KDGTHVVENVDATHIGK | 531 | 1 |
| | | | | | DGTHVVENVDATHIGK | 532 | 1 |
| | | | | | FQEGQEEER | 533 | 6 |
| | | | | | STVLTIPEIIIK | 534 | 2 |
| IPI00297779.7 | CCT2 | 57.5 | 3 | 9.95 | VQDDEVGDTTSVTVLAAELLR | 535 | 2 |
| | | | | | LGGSLADSYLDEGFLLDK | 536 | 1 |
| | | | | | GATQQILDEAER | 537 | 1 |
| IPI00298860.5 | LTF | 78.4 | 2 | 4.1 | DGAGDVAFIR | 538 | 1 |
| | | | | | IDSGLYLGSGYFTAIQNLR | 539 | 4 |

TABLE 11-continued

Peptides and spectra present in lectin-bound fractions isolated from ovarian cancer tumors.

| IPI Number | Code | Molecular Weight (kDa) | Unique Peptides | % Coverage | Peptide Sequences | SEQ ID NO: | Spectra |
|---|---|---|---|---|---|---|---|
| IPI00298994.5 | TLN1 | 269.83 | 7 | 4.81 | DPVQLNLLYVQAR | 540 | 1 |
| | | | | | AVSSAIAQLLGEVAQGNENYAGIAAR | 541 | 1 |
| | | | | | AVTQALNR | 542 | 1 |
| | | | | | LNEAAAGLNQAATELVQASR | 543 | 1 |
| | | | | | TLAESALQLLYTAK | 544 | 2 |
| | | | | | LAQAAQSSVATITR | 545 | 2 |
| | | | | | VGAIPANALDDGQWSQGLISAAR | 546 | 1 |
| IPI00299571.5 | PDIA6 | 53.91 | 6 | 18.8 | TGEAIVDAALSALR | 547 | 4 |
| | | | | | LAAVDATVNQVLASR | 548 | 4 |
| | | | | | ALDLFSDNAPPPELLEIINEDIAK | 549 | 3 |
| | | | | | NSYLEVLLK | 550 | 2 |
| | | | | | GSFSEQGINEFLR | 551 | 2 |
| | | | | | GSTAPVGGGAFPTIVER | 552 | 2 |
| IPI00376005.2 | EIF5A | 20.17 | 2 | 21.8 | NDFQLIGIQDGYLSLLQDSGEVR | 553 | 4 |
| | | | | | EDLRLPEGDLGKEIEQK | 554 | 1 |
| IPI00382428.6 | FBLN5 | 60.03 | 2 | 3.66 | DQPFTILYR | 555 | 2 |
| | | | | | YPGAYYIFQIK | 556 | 3 |
| IPI00399007.5 | IGHG2 | 46.07 | 3 | 13.1 | TTPPMLDSDGSFFLYSK | 557 | 2 |
| | | | | | VVSVLTVVHQDWLNGK | 558 | 1 |
| | | | | | GFYPSDIAVEWESNGQPENNYK | 559 | 19 |
| IPI00410241.2 | POSTN | 90.44 | 9 | 20.1 | Same as IPI00007960.4 | | |
| IPI00411704.9 | EIF5A | 16.83 | 2 | 26.1 | Same as IPI00376005.2 | | |
| IPI00426051.3 | IGHG2 | 51.1 | 3 | 11.8 | Same as IPI00399007.5 | | |
| IPI00453476.2 | PGAM1 | 28.8 | 2 | 9.54 | Same as IPI00549725.6 | | |
| IPI00478003.1 | A2M | 163.31 | 18 | 14 | NEDSLVFVQTDK | 560 | 2 |
| | | | | | IAQWQSFQLEGGLK | 561 | 3 |
| | | | | | QFSFPLSSEPFQGSYK | 562 | 3 |
| | | | | | TEHPFTVEEFVLPK | 563 | 1 |
| | | | | | FEVQVTVPK | 564 | 2 |
| | | | | | QGIPFFGQVR | 565 | 1 |
| | | | | | LLIYAVLPTGDVIGDSAK | 566 | 3 |
| | | | | | VSVQLEASPAFLAVPVEK | 567 | 2 |
| | | | | | DTVIKPLLVEPEGLEK | 568 | 1 |
| | | | | | LPPNVVEESAR | 569 | 1 |
| | | | | | AIGYLNTGYQR | 570 | 2 |
| | | | | | TAQEGDHGSHVYTK | 571 | 1 |
| | | | | | ALLAYAFALAGNQDK | 572 | 2 |
| | | | | | FQVDNNNR | 573 | 1 |
| | | | | | VSNQTLSLFFTVLQDVPVR | 574 | 1 |
| | | | | | NQGNTWLTAFVLK | 575 | 2 |
| | | | | | SSGSLLNNAIK | 576 | 1 |
| | | | | | YGAATFTR | 577 | 1 |
| IPI00479217.1 | HNRNPU | 89 | 2 | 4.6 | EKPYFPIPEEYTFIQNVPLEDR | 578 | 3 |
| | | | | | NFILDQTNVSAAAQR | 579 | 5 |
| IPI00549725.6 | PGAM1 | 28.81 | 2 | 9.55 | HGESAWNLENR | 580 | 2 |
| | | | | | ALPFWNEEIVPQIK | 581 | 3 |
| IPI00550363.3 | TAGLN2 | 22.4 | 4 | 28 | QMEQISQFLQAAER | 582 | 1 |
| | | | | | YGINTTDIFQTVDLWEGK | 583 | 5 |
| | | | | | DDGLFSGDPNWFPK | 584 | 4 |
| | | | | | NFSDNQLQEGK | 585 | 3 |
| IPI00641231.1 | POSTN | 90.16 | 9 | 20.1 | Same as IPI00007960.4 | | |
| IPI00643384.1 | BGN | 34.88 | 10 | 41 | Same as IPI00010790.1 | | |
| IPI00644079.2 | HNRNPU | 90.6 | 2 | 4.5 | Same as IPI00479217.1 | | |
| IPI00644224.1 | HNRNPU | 61.76 | 2 | 6.6 | Same as IPI00479217.2 | | |
| IPI00644989.2 | PDIA6 | 48.13 | 6 | 21 | Same as IPI00299571.5 | | |

TABLE 11-continued

Peptides and spectra present in lectin-bound fractions isolated from ovarian cancer tumors.

| IPI Number | Code | Molecular Weight (kDa) | Unique Peptides | % Coverage | Peptide Sequences | SEQ ID NO: | Spectra |
|---|---|---|---|---|---|---|---|
| IPI00647915.1 | TAGLN2 | 24.46 | 4 | 25.6 | Same as IPI00550363.3 | | |
| IPI00657680.1 | PDIA3 | Need Mw | | | Same as IPI00025252.1 | | |
| IPI00719373.1 | IGL@ | 23.07 | 6 | 40.5 | VTVLGQPK | 586 | 1 |
| | | | | | ANPTVTLFPPSSEELQANK | 587 | 14 |
| | | | | | FSGSNSGNTATLTISR | 588 | 2 |
| | | | | | YAASSYLSLTPEQWK | 589 | 9 |
| | | | | | LVITGNLITIFQER | 590 | 1 |
| | | | | | LISWYDNEFGYSNR | 591 | 9 |
| IPI00743857.1 | MYH11 | 228.14 | 14 | 9.88 | Same as IPI00020501.1 | | |
| IPI00744256.1 | MYH11 | 224.38 | 14 | 10 | Same as IPI00020501.2 | | |
| IPI00747533.1 | PGD | 56.51 | 3 | 11.5 | Same as IPI00219525.10 | | |
| IPI00784273.1 | TLN1 | 269.83 | 7 | 4.81 | Same as IPI00298994.5 | | |
| IPI00787849.1 | MUC5B | 596.7 | 9 | 2.23 | TFDGDVFR | 592 | 2 |
| | | | | | AAYEDFNVQLR | 593 | 3 |
| | | | | | LTPLQFGNLQK | 594 | 2 |
| | | | | | LTDPNSAFSR | 595 | 2 |
| | | | | | LFVESYELILQEGTFK | 596 | 3 |
| | | | | | SVVGDALEFGNSWK | 597 | 2 |
| | | | | | SEQLGGDVESYDK | 598 | 1 |
| | | | | | EEGLILFDQIPVSSGFSK | 599 | 2 |
| | | | | | VDIPALGVSVTFNGQVFQAR | 600 | 3 |
| IPI00788271.1 | LTF | Need Mw | 2 | | Same as IPI00298860.5 | | |
| IPI00789477.1 | LTF | 73.17 | 2 | 4.4 | Same as IPI00298860.6 | | |
| IPI00790669.1 | LTF | 78.4 | 2 | 4.1 | Same as IPI00298860.7 | | |
| IPI00793319.1 | GSTP1 | 19.48 | 2 | 19.8 | Same as IPI00219757.13 | | |
| IPI00795980.1 | | | | | | | |
| IPI00796076.1 | GSTP1 | Need Mw | | | Same as IPI00219757.13 | | |
| IPI00797227.1 | POSTN | Need Mw | | | Same as IPI00007960.4 | | |
| IPI00797321.1 | GSTP1 | Need Mw | | | Same as IPI00219757.13 | | |
| IPI00807545.1 | HNRNPK | 48.57 | 6 | 21.3 | Same as IPI00216049.1 | | |
| IPI00827754.1 | IGHG3 | 41.29 | 3 | 9.86 | WYVDGVEVHNAK | 601 | 1 |
| | | | | | VVSVLTVLHQDWLNGK | 602 | 5 |
| | | | | | GLEWVANIK | 603 | 1 |

Most of the glycoproteins listed in Tables 10 and 11 have never been exploited as potential biomarkers for ovarian cancer. The two proteins for which we are presenting further development, periostin (POSTN) and thrombospondin (THBS1), have been cited as being present in ovarian cancer (Gillan et al., Cancer Res 2002. 62: 5358-5364; Bignotti et al., Am J Obstet Gynecol 2007. 196: 245 e241-211). These proteins have not, however, been developed into potential diagnostic assays, likely due to their presence in the serum of normal patients. Our identification of tumor-specific glycosylation changes on POSTN and THBS1 for ovarian cancer tissue and patient serum appears to be novel. By extension, therefore, it is likely that other glycoproteins in Tables 10 and 11 may be useful as candidate ovarian cancer markers based on glycosylation differences.

Validation Studies

Glycoproteins from Table 10 were chosen for validation studies based on their reported identification in serum (Liu et al., J Proteome Res 2005. 4: 2070-2080). Since the glycoproteomic studies were performed with 3 lectins simultaneously, the glycoproteins markers listed in Table 10 likely have multiple, distinct glycan structures. A direct method to confirm and characterize glycan changes on glycoproteins is to immunoprecipitate the protein using an antibody directed against its polypeptide, followed by SDS-PAGE and Western blotting, then detection of the glycan of interest using a labeled lectin. In an effort to find markers for early stage disease, a single stage I case (sample 3, Table 9) was chosen for validation along with a non-diseased case (sample 7, Table 9). An example of validation is shown for the marker POSTN in FIG. 18A. Our results indicated that POSTN was reactive with the lectins AAL (panel 2, FIG. 18A) and E-PHA (panel 3, FIG. 18A) only in the tumor tissue. There was no reactivity of POSTN with the lectin DSL (panel 1, FIG. 18A). The tumor-selective reactivity of POSTN with AAL and E-PHA suggest that this marker would be a good candidate for serum validation.

Figure 18:
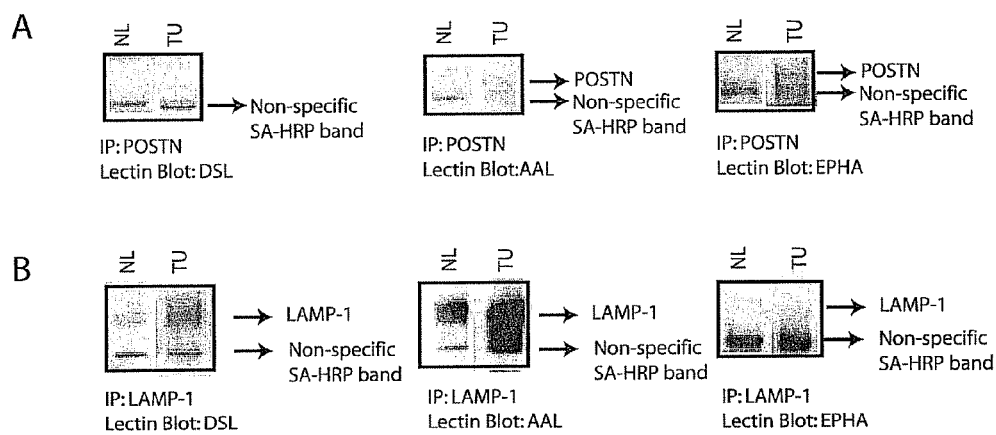
FIG. 18 shows a tissue validation.

By contrast to POSTN, the glycoprotein LAMP-1 (lysosomal-associated membrane protein-1) has elevated reactivity with DSL and AAL (panel 1 and 2, FIG. 18B) in tumor tissue relative to normal tissue but very little change in E-PHA reactivity (panel 3, FIG. 18B). Equivalent levels of protein were present in each immunoprecipitation for normal and tumor, evidenced by the detection of a streptavidin-reactive protein present on each blot which was observed without lectin present. These results confirm the ability of the lectins to recognize and bind to specific glycan structures and suggest that core fucosylation (AAL reactivity, panel 2) is the most significantly changing glycan structure on LAMP-1 in ovarian cancer tissue. Although we did not detect LAMP-1 in normal tissue by proteomic analysis (Table 10), the detection of LAMP-1 lectin reactivity in normal tissue (panel 1 and 2, FIG. 18B) by immunoprecipitation and Western blot suggest that this marker is not a prime candidate for further serum validation. A technical difference in the conditions that produced the MS/MS data in Table 10 and the Western blot data shown in FIG. 18 for LAMP-1 was the denaturation of the protein prior to lectin blot analysis and not prior to the lectin chromatography/MS analysis. LAMP-1 is a heavily N-glycosylated protein, at least 17 potential sites of glycosylation, and it is quite possible that denaturation could render glycosylation sites accessible for lectin binding that are not as exposed under the native conditions used for the multilectin affinity prior to MS/MS analysis.

During our studies, we also observed that when glycoproteins were highly reactive with E-PHA, there was low DSL reactivity; conversely, if the protein was highly positive for DSL reactivity, the E-PHA reactivity was low (compare DSL data in FIG. 18). These results suggest that the presence of a bisecting N-acetylglucosamine (detected by E-PHA) could either inhibit DSL lectin binding or that the presence of the bisecting glycan inhibited glycosylation reactions on the protein to which DSL binds. The marker POSTN has been shown to express elevated β(1,6) branched N-linked glycans in invasive ductal breast carcinoma (Abbott et al., J Proteome Res 2008. 7: 1470-1480). Our observation that E-PHA and DSL co-reactivity does not appear to exist in a single glycoprotein population suggests that the E-PHA-reactive form of POSTN may be a selective marker for ovarian cancer. Our results suggest, therefore, that it is possible for a single glycoprotein, POSTN, to be a marker for two different types of cancer depending on specific differences in the glycans that it expresses.

Figure 19:
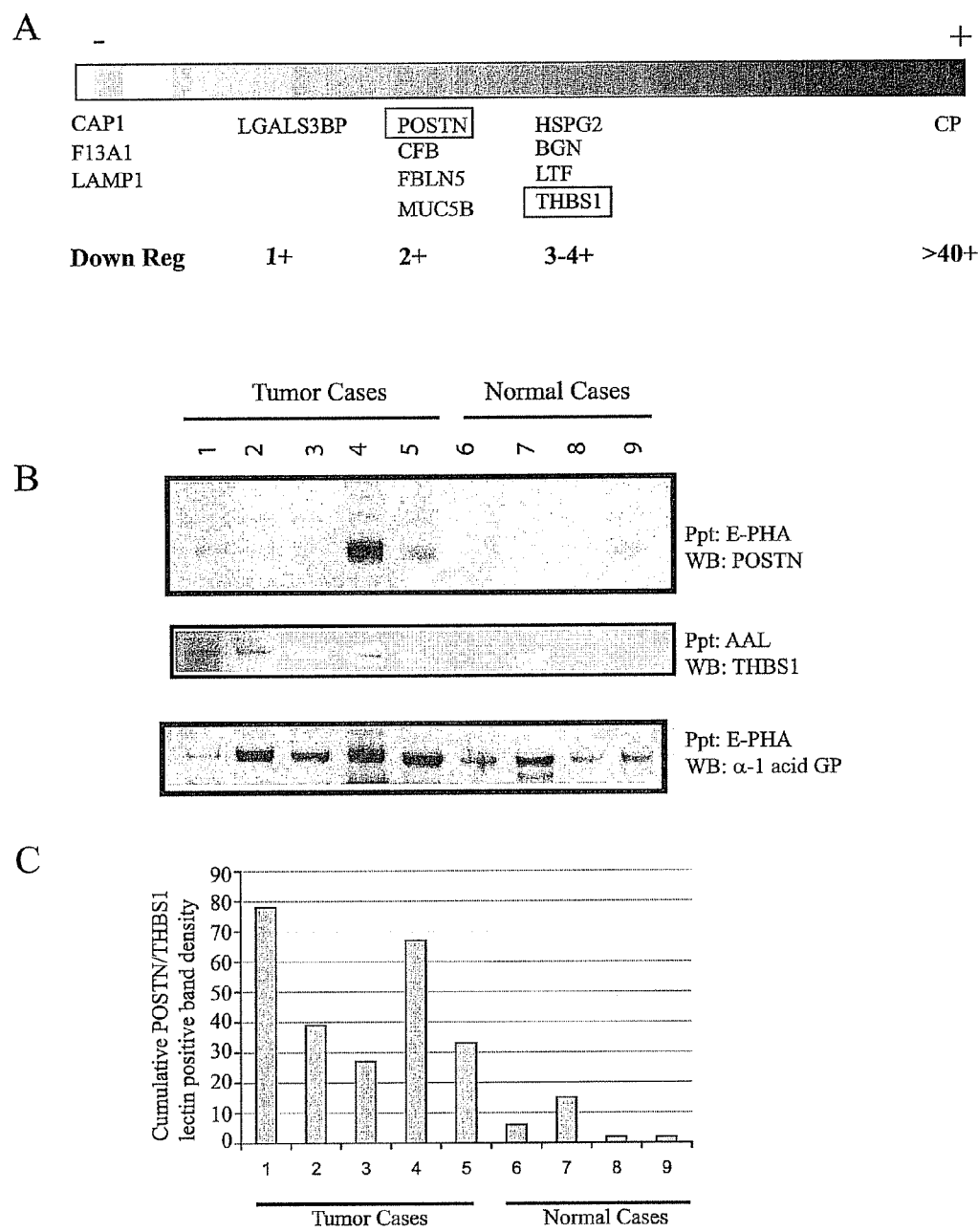
FIG. 19 shows microarray data and serum validation.

Our ultimate goal is to identify glycoprotein markers that can be used to detect early stage ovarian cancers. Ovarian cancers originate via diverse oncogenic signaling mechanisms (Aunoble et al., Int J Oncol 2000. 16: 567-576); therefore, potential markers identified by any study may not be present at detectable levels in serum from patients with a wide variety of histological types of ovarian tumors. In order to identify markers for serum validation studies that could have the broadest applicability, we consulted the extensive microarray dataset generated by The Ovarian Cancer Institute laboratory at The Georgia Institute of Technology. Microarray transcript expression profiling has been shown to discriminate benign and malignant ovarian tumors (Warrenfeltz et al., Mol Cancer 2004. 3: 27). Microarray expression data were analyzed for those glycoproteins in Table 10 whose sequences predicted that they could be secreted into serum. As shown in FIG. 19A, microarray expression data revealed that the majority of potential serum glycoprotein markers identified have increased mRNA expression levels in tumors above normal. Considering the microarray data, tissue verification data, and high abundance predicted by MS spectral count analysis in ovarian cancer cases, we chose POSTN and THBS1 for initial serum validation. To validate glycan changes on glycoproteins from serum, biotinylated lectins were coupled to magnetic streptavidin beads to isolate lectin-reactive proteins prior to Western blot detection using antibodies directed against specific proteins. The validation of two candidate markers in sera is presented: POSTN (2 fold increase in expression arrays) and THBS1 (4 fold increase in expression arrays) (FIG. 19A, boxed). The glycoprotein POSTN displays increased bisecting N-acetylglucosamine glycosylation and core fucosylation in ovarian tumor tissue, as evidenced by increased E-PHA and AAL reactivity, respectively (FIG. 18A panel 2 and 3). As shown in FIG. 19B, serum samples from four of five tumor cases have E-PHA-reactive POSTN detected above normal serum levels (FIG. 19B, panel 1, cases 1, 3, 4, 5). Initial validation results suggest, therefore, that expression of the bisecting N-linked structure on POSTN in serum is associated with ovarian cancer. Lower grade tumors such as those in cases 3 and 4 are positive as well as higher grade tumors. While only one band migrating at approximately 98 kD was observed in tissue (FIG. 18A panel 2 and 3), in serum we observed three bands migrating at approximately 98 kD, 80 kD, and 65 kD. The presence of smaller forms may also be due to proteolytic cleavage in serum. There is one potential N-linked glycosylation site, and it is located in the C-terminus of POSTN. The reactivity of these smaller forms of periostin with the lectin E-PHA indicates that N-terminal cleavage of POSTN may occur after release into serum. We observed that core fucosylated (AAL reactive) POSTN was present at variable levels in serum, and its presence in non-diseased and tumor serum showed no association with the presence of malignant. These results suggest that POSTN with AAL reactivity is released into the serum from a tissue other than ovary.

The candidate marker THBS1 shows increased core fucosylation in ovarian cancer tissue relative to normal, based on AAL reactivity. AAL precipitation and antibody analysis of THBS1 in serum samples indicates that in four of five tumor cases (cases 1-4), THBS1 was more reactive with AAL compared to non-diseased serum cases (FIG. 19B, panel 2). Again, both low grade and higher grade cases are positive for AAL reactivity with THBS1. We observed only one form of THBS1 from tissue migrating at approximately 135-140 kD. However, in serum we observed a form migrating at a slightly lower molecular weight ~125 kD, as shown in FIG. 19B. The higher molecular weight glycoform can be detected at a lower level of expression in some cases, such as case 1 and 2. THBS1 has three-four N-linked sequons, with two-three located toward the N-terminus region and one in the C-terminus region. The cleavage of THBS1 that may be occurring in serum does not affect its tumor-specific AAL reactivity, however. In these experiments, serum input amounts and quality were assessed by measuring the levels of E-PHA reactive alpha-1 acid glycoprotein (FIG. 19B, panel 3). Taken together, these results identify E-PHA-reactive POSTN and AAL-reactive THBS1 as candidate markers useful in the distinguishing of sera from endometrioid ovarian cancer patients and sera from non-diseased controls. Combining the Western blot results for both markers (FIG. 19C) all 5 tumor cases (samples 1-5) are more lectin reactive when compared with normal serum (cases 6-9). Therefore, the cumulative detection of both glycoproteins with their tumor-specific glycan structures can distinguish the serum of ovarian endometrioid cancer patients from normal serum in 5/5 cases tested.

Discussion

We have used a focused approach targeting N-linked glycan structures that appear to be increased in endometrioid ovarian cancer tissue relative to normal ovary to identify potential glycoprotein markers for this cancer. This strategy has led to the identification of 47 potential tumor-specific lectin-reactive markers. We have presented tissue and serum validation methods that add confidence that in many cases the tumor-specific glycoform detected in serum has originated from the tumor. The goal of future investigations is to develop a multi-glycoprotein-marker panel that when assayed together could provide an effective means for the early detection, prognosis, and monitoring of all types of ovarian cancer.

Bisecting Glycans and Core Fucosylation in Ovarian Cancer

The role of bisecting glycans in most epithelial cancers is thought to suppress metastasis by suppressing the addition of branched complex N-linked glycans that can promote tumor cell migration (Schachter, Adv Exp Med Biol 1986. 205: 53-85; Takahashi et al., Carbohydr Res 2009. 344: 1387-1390; Lau et al., Cell 2007. 129: 123-134). Epithelial ovarian cancer (EOC) is a unique type of epithelial cancer due to its origination from the outer epithelial surface of the ovary that exhibits both epithelial and mesenchymal characteristics (Lee et al., J Pathol 2007. 211: 26-35; Auersperg et al., Endocr Rev 2001. 22: 255-288). Cell-cell adhesive contacts are important in the regulation of cell signaling events that promote tumorigenesis. Most epithelial tumors have a loss of cell-cell adhesion due to decreased expression of E-cadherin. However, EOC maintain E-cadherin expression and cell-cell adhesion junctions during tumor development and progression (De Santis et al., Oncogene 2009. 28: 1206-1217). This observation leads to the hypothesis that a possible feedback loop connecting the expression of bisecting N-linked glycans added by GnT-III and E-cadherin expression in EOC. GnT-III expression is regulated by E-cadherin-mediated cell-cell adhesion in epithelial cells (Akama et al., 2008. 8: 3221-3228). Conversely, GnT-III can glycosylate E-cadherin, increasing the cell surface levels of E-cadherin and further stimulating GnT-III expression and activity[31]. The effect of increased E-cadherin on the cell surface would elevate the AKT/PI3K pathway promoting ovarian cancer cell growth and tumorigenesis (De Santis et al., Oncogene 2009. 28: 1206-1217). Another way that bisecting glycans could promote EOC tumorigenesis is through the inhibition of apoptosis. GnT-III over-expression in HeLa cells has been shown to suppress peroxide-induced apoptosis (Shibukawa et al., J Biol Chem 2003. 278: 3197-3203). Therefore, ovarian cancer cells under oxidative stress may activate apoptotic pathways that are then suppressed by GnT-III activity and the presence of bisecting glycans on cell surface receptors. The mechanisms of how GnT-III activity can suppress apoptosis are not fully understood, and specific acceptors of glycosylation responsible have not been identified, however. Future glycoproteomic studies on membrane glycoproteins isolated from ovarian tumor tissue could lead to the identification of cell surface glycoprotein receptors that may be potential therapeutic targets.

Core fucosylation, a common N-linked glycan modification, is increased in and serves as a marker for several cancers (Comunale and Mehta, Methods Mol Biol 2009. 520: 59-74; Comunale et al., J Proteome Res 2009. 8: 595-602; Mehta and Block, Dis Markers 2008. 25: 259-265; Inamori et al., J Biol Chem 2004. 279: 2337-2340; Nakagawa et al., J Proteome Res 2008. 7: 2222-2233). Increased core fucosylation on glycoproteins promotes growth factor signaling, since FUT8−/− mice are small and die during prenatal development (Wang et al., Methods Enzymol 2006. 417: 11-22). FUT8 expression has also been implicated in the regulation of EGFR and PDGF receptor internalization and signaling (Wang et al., J Biol Chem 2006. 281: 2572-2577). Core fucosylation has also been linked to enhanced E-cadherin-mediated cell-cell adhesion in colon cancer cells by reducing the turnover of cell surface E-cadherin (Osumi et al., Cancer Sci 2009. 100: 888-895). Therefore, the cumulative effect of increased bisecting N-acetylglucosamine and core fucosylation on E-cadherin would likely promote ovarian cancer tumorigenesis.

Cell Stress and Glycosylation Changes

Our glycoproteomic data has identified several non-N-linked-glycosylated proteins enriched by multi-lectin chromatography of ovarian tumor extracts. Many of these proteins are heat shock proteins and chaperones (GRP78, HSPB1, YWHAG, CCT5), protein disulfide isomerases (PDIA3, PDIA4, PDIA6), and glucose metabolism enzymes (GPI, PGK1, PGD, PGAM1). Tumor cells that are proliferating rapidly create a glucose-deprived, hypoxic environment (Brahimi-Horn et al., J Mol Med 2007. 85: 1301-1307). The classes of non-N-linked-glycosylated proteins observed to be enriched by multi-lectin chromatography may be managing this type of cellular stress. Many of these proteins such as GRP78 have been identified on the cell surface in previous proteomic studies (Shin et al., J Biol Chem 2003. 278: 7607-7616). GRP78 is induced by glucose deprivation and acts as a cell survival factor capable of inhibiting apoptosis in many tumors (Yeung et al., Oncogene 2008. 27: 6782-6789; Kumar and Tatu, Proteomics 2003. 3: 513-526). While GRP78 may not be an ideal biomarker for the diagnosis of ovarian cancer due to its increased levels in many different types of cancer, it may, however, be useful in directing therapeutics (Lee, Cancer Res 2007. 67: 3496-3499). Although GRP78 contains no predicted N-linked glycosylation sequons, we sought to test whether GRP78 isolated by immunoprecipitation would be bound directly by lectins. We immunoprecipitated GRP78 from ovarian cancer tissues, subjected the bound proteins to SDS-PAGE and Western blotting, but observed no reactivity with the lectins used in this study (data not shown). Therefore, GRP78 must be binding tightly enough to glycoproteins to be enriched by lectin affinity. Which glycoproteins GRP78 is binding with on the surface of ovarian cancer cells is currently unknown. Future studies identifying the cell surface glycoproteins GRP78 may be binding with may provide targets for peptide therapeutic strategies to block the anti-apoptotic activity of GRP78. Our approach solubilizing proteins in mild detergent would not allow for the identification of possible membrane glycoproteins that may be GRP78 cell surface binding partners.

Glycoprotein Markers and Potential Involvement in Ovarian Cancer Spread

Ovarian cancer cells typically form multicellular aggregates and may spread by attachment to the peritoneal abdominal wall lining (Burleson et al., J Transl Med 2006. 4: 6). This type of non-hematological tumor-spread may be influenced by the extracellular matrix proteins identified in this study, such as POSTN, BGN, HSPG2, THBS1, and FIBLN5, and corresponding interactions with their cell receptors. A recent proteomic study to identify expression profiles associated with invasive potential in ovarian cancer cell lines found that the most significantly enriched signaling pathway promoting invasivity was extracellular matrix receptor signaling (Sodek et al., Mol Biosyst 2008. 4: 762-773). The adhesive glycoproteins that we have validated as glycomarkers for ovarian cancer, POSTN and THBS1, have been implicated in promoting tumor spread (Gillan et al., Cancer Res 2002. 62: 5358-5364; Bignotti et al., Am J Obstet Gynecol 2007. 196: 245 e241-211). Future studies will focus on determining if increased core fucosylation and bisecting N-glycans on these glycoproteins augment ovarian cancer peritoneal adhesion with a focus on identifying potential mechanisms that could be targeted to block EOC peritoneal adhesion.

Relationship of the Results of this Study to CA-125, a Glycoprotein Marker for Ovarian Cancer The best known glycoprotein marker for ovarian cancer is CA-125 (MUC16). Serum protein levels of this marker may be used to monitor ovarian cancer patients during treatment; however, due to variable concentrations of CA-125 in benign diseases, this assay has not been routinely as a diagnostic assay (Clarke-Pearson, N Engl J Med 2009. 361: 170-177). CA-125 is a large mucin protein containing both N- and O-linked glycans, and its complexity has hampered detailed analysis of its glycan structures. However, the glycosylation patterns of CA-125 and certain acute-phase glycoproteins have been documented to change in ovarian cancer (Saldova et al., Glycobiology 2007. 17: 1344-1356; Saldova et al., Dis Markers 2008. 25: 219-232; Jankovic et al., Cancer Biomark 2008. 4: 35-42). For example, Jankovic et al., compared the glycans of CA-125 isolated from amniotic fluid to CA-125 from the OVCAR3 ovarian cancer cell line and found a significant increase in the reactivity of OVCAR3 CA-125 with the lectin E-PHA compared to CA-125 from amniotic fluid (Jankovic et al., Cancer Biomark 2008. 4: 35-42). These data agree with our finding that bisecting N-linked glycans are elevated in ovarian cancer tissue relative to normal ovary (Abbott et al., Proteomics 2008. 8: 3210-3220). Despite these findings, however, we were unable to detect CA-125 in our glycoproteomic analysis of endometrioid ovarian cancer tissue, which may reflect differences between endometrioid ovarian cancer and other adenocarcinomas of the ovary. We did identify another mucin, MUC5b, which showed increased binding to the lectins used in this study, suggesting that different types of ovarian cancers may secrete different dominate mucins. These data suggest that assays targeting mucin glycoproteins may not have sufficient sensitivity for a variety of histological types and grades of ovarian tumors. The ability to correlate focused glycoproteomic data with genomic microarray data from a diverse sampling of histological type ovarian tumors will likely lead to glycomarkers with increased sensitivity for many histological subtypes of ovarian cancer.

In conclusion, the glycoproteomic results presented offers initial validation that glycoproteins with tumor-specific glycan changes can be used to distinguish malignant ovarian tissue and serum from normal ovarian tissue and serum. The glycosylated candidate markers and non-glycosylated candidate markers identified with tumor-specific lectin affinity are promising for the detection and potential therapeutic intervention of endometrioid ovarian cancer and possibly other forms of ovarian cancer.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

Sequence Listing Free Text

| | |
|---|---|
| SEQ ID NOs: 1-307 | peptide fragments |
| SEQ ID NOs: 308-347 | oligonucleotide primer |
| SEQ ID NOs: 348-623 | peptide fragments |

What is claimed is:

1. A method for evaluating the presence, absence, nature or extent of breast cancer or a precancerous condition of the breast, the method comprising:
    providing a biological sample obtained from a subject, the biological sample comprising glycoproteins;
    contacting the biological sample with a glycan-binding molecule specific for a glycan, under conditions that permit binding of the glycan-binding molecule to a glycoprotein comprising said glycan, wherein the glycan comprises a GlcNAc β(1,6) Man branched N-linked glycan;
    contacting the glycoprotein with an anti-periostin antibody; and
    detecting binding of the glycan-binding molecule and the anti-periostin antibody to the glycoprotein to determine the presence, absence or amount of a cancer-specific glycoform of periostin in the biological sample, wherein said cancer-specific glycoform comprises the glycan and is indicative of breast cancer or a precancerous condition of the breast; and wherein the presence, absence or amount of the cancer-specific glycoform is indicative of the presence, absence, nature or extent of breast cancer or a precancerous condition of the breast.

2. The method of claim 1 wherein the glycan-binding molecule comprises a detectable label.

3. The method of claim 1 wherein the glycan-binding molecule is selected from the group consisting of a lectin, a glycospecific antibody, a glycospecific aptamer, a glycospecific peptide, and a glycospecific small molecule.

4. The method of claim 3 wherein the lectin comprises leukoagglutinating phytohemagglutinin (L-PHA).

5. The method of claim 1 wherein the glycan comprises a branched N-linked glycan extended with N-acetyllactosamine.

6. The method of claim 1 wherein the biological sample comprises a biological fluid.

7. The method of claim 1 wherein the biological sample comprises serum or plasma.

8. The method of claim 1 wherein the biological sample comprises tissue.

9. The method of claim 1 wherein the subject is a human.

10. A method for evaluating the presence, absence, nature or extent of breast cancer or a precancerous condition of the breast, the method comprising:
    contacting a biological sample obtained from a subject, with a glycan-binding molecule specific for a glycan under conditions that permit binding of the glycan-binding molecule to a glycoprotein comprising said glycan, wherein the glycan comprises a GlcNAc β(1,6) Man branched N-linked glycan;
    contacting the glycoprotein with an anti-periostin antibody; and
    detecting binding of the glycan-binding molecule and the anti-periostin antibody to the glycoprotein to determine the presence of a cancer-specific glycoform of periostin in the biological sample, wherein the cancer-specific glycoform comprises the glycan and is indicative of the presence of cancer or a precancerous condition.

11. A diagnostic composition comprising a biomarker comprising a isolated cancer-specific glycoform of periostin comprising a GlcNAc β(1,6) Man branched N-linked glycan component.

* * * * *

SEQUENCE LISTING

<160> NUMBER OF SEQ ID NOS: 623

<210> SEQ ID NO 1
<211> LENGTH: 8
<212> TYPE: PRT
<213> ORGANISM: artificial
<220> FEATURE:
<223> OTHER INFORMATION: peptide fragment present in lectin-bound fraction isolated from human breast carcinomas -continued

```
<400> SEQUENCE: 1

Ala Asp Glu Gly Ile Ser Phe Arg
1               5

<210> SEQ ID NO 2
<211> LENGTH: 11
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 2

Gln Ile Thr Val Asn Asp Leu Pro Val Gly Arg
1               5                   10

<210> SEQ ID NO 3
<211> LENGTH: 11
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 3

Asn Phe Pro Ser Pro Val Asp Ala Ala Phe Arg
1               5                   10

<210> SEQ ID NO 4
<211> LENGTH: 21
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 4

Leu Leu Gln Asp Glu Phe Pro Gly Ile Pro Ser Pro Leu Asp Ala Ala
1               5                   10                  15

Val Glu Cys His Arg
            20

<210> SEQ ID NO 5
<211> LENGTH: 11
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 5

Tyr Tyr Cys Phe Gln Gly Asn Gln Phe Leu Arg
1               5                   10

<210> SEQ ID NO 6
<211> LENGTH: 11
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 6

Gly Gly Tyr Thr Leu Val Ser Gly Tyr Pro Lys
1               5                   10
```

```
<210> SEQ ID NO 7
<211> LENGTH: 24
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 7

Glu Val Gly Thr Pro His Gly Ile Ile Leu Asp Ser Val Asp Ala Ala
1               5                   10                  15

Phe Ile Cys Pro Gly Ser Ser Arg
            20

<210> SEQ ID NO 8
<211> LENGTH: 8
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 8

Arg Leu Trp Trp Leu Asp Leu Lys
1               5

<210> SEQ ID NO 9
<211> LENGTH: 16
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 9

Ser Gly Ala Gln Ala Thr Trp Thr Glu Leu Pro Trp Pro His Glu Lys
1               5                   10                  15

<210> SEQ ID NO 10
<211> LENGTH: 16
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 10

Asp Gln Gly Pro Asn Val Cys Ala Leu Gln Gln Ile Leu Gly Thr Lys
1               5                   10                  15

<210> SEQ ID NO 11
<211> LENGTH: 8
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 11

Leu Arg Glu Glu Ile Glu Gly Lys
1               5

<210> SEQ ID NO 12
<211> LENGTH: 23
<212> TYPE: PRT
<213> ORGANISM: artificial
<220> FEATURE:
<223> OTHER INFORMATION: peptide fragment present in lectin-bound
      fraction isolated from human breast carcinomas
```

-continued

<400> SEQUENCE: 12

Val Leu Thr Gln Ile Gly Thr Ser Ile Gln Asp Phe Ile Glu Ala Glu
1               5                   10                  15

Asp Asp Leu Ser Ser Phe Arg
            20

<210> SEQ ID NO 13
<211> LENGTH: 14
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 13

Ala Ala Ala Ile Thr Ser Asp Ile Leu Glu Ala Leu Gly Arg
1               5                   10

<210> SEQ ID NO 14
<211> LENGTH: 16
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 14

Asp Gly His Phe Thr Leu Phe Ala Pro Thr Asn Glu Ala Phe Glu Lys
1               5                   10                  15

<210> SEQ ID NO 15
<211> LENGTH: 22
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 15

Asp Ile Val Thr Asn Asn Gly Val Ile His Leu Ile Asp Gln Val Leu
1               5                   10                  15

Ile Pro Asp Ser Ala Lys
            20

<210> SEQ ID NO 16
<211> LENGTH: 18
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 16

Val Gly Leu Asn Glu Leu Tyr Asn Gly Gln Ile Leu Glu Thr Ile Gly
1               5                   10                  15

Gly Lys

<210> SEQ ID NO 17
<211> LENGTH: 14
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 17

```
Phe Ser Thr Phe Leu Ser Leu Leu Glu Ala Ala Asp Leu Lys
1               5                   10

<210> SEQ ID NO 18
<211> LENGTH: 20
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 18

Glu Leu Leu Thr Gln Pro Gly Asp Trp Thr Leu Phe Val Pro Thr Asn
1               5                   10                  15

Asp Ala Phe Lys
            20

<210> SEQ ID NO 19
<211> LENGTH: 20
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 19

Leu Leu Tyr Pro Ala Asp Thr Pro Val Gly Asn Asp Gln Leu Leu Glu
1               5                   10                  15

Ile Leu Asn Lys
            20

<210> SEQ ID NO 20
<211> LENGTH: 12
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 20

Ile Ile Asp Gly Val Pro Val Glu Ile Thr Glu Lys
1               5                   10

<210> SEQ ID NO 21
<211> LENGTH: 12
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 21

Asp Ser Pro Ser Val Trp Ala Ala Val Pro Gly Lys
1               5                   10

<210> SEQ ID NO 22
<211> LENGTH: 16
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 22

Thr Phe Val Asn Ile Thr Pro Ala Glu Val Gly Val Leu Val Gly Lys
1               5                   10                  15
```

-continued

```
<210> SEQ ID NO 23
<211> LENGTH: 22
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 23

Val Gly Leu Val Gln Phe Ser Asp Thr Pro Val Thr Glu Phe Ser Leu
1               5                   10                  15

Asn Thr Tyr Gln Thr Lys
            20

<210> SEQ ID NO 24
<211> LENGTH: 8
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 24

Ser Asp Ile Leu Gly His Leu Arg
1               5

<210> SEQ ID NO 25
<211> LENGTH: 11
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 25

Thr Leu Ser Gly Thr Pro Glu Glu Ser Lys Arg
1               5                   10

<210> SEQ ID NO 26
<211> LENGTH: 15
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 26

Ala Ala Pro Leu Gln Gly Leu Pro Gly Leu Leu Ala Pro Leu Arg
1               5                   10                  15

<210> SEQ ID NO 27
<211> LENGTH: 11
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 27

Leu Leu Pro Tyr Ile Val Gly Val Ala Gln Arg
1               5                   10

<210> SEQ ID NO 28
<211> LENGTH: 19
<212> TYPE: PRT
<213> ORGANISM: artificial
<220> FEATURE:
<223> OTHER INFORMATION: peptide fragment present in lectin-bound
```

-continued fraction isolated from human breast carcinomas

<400> SEQUENCE: 28

Met Lys Pro Leu Asp Gly Ser Ala Leu Tyr Thr Gly Ser Ala Leu Asp
1               5                   10                  15

Phe Val Arg

<210> SEQ ID NO 29
<211> LENGTH: 11
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 29

Asn Asn Leu Phe Thr Ser Ser Ala Gly Tyr Arg
1               5                   10

<210> SEQ ID NO 30
<211> LENGTH: 9
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 30

Leu Leu Val Leu Ile Thr Gly Gly Lys
1               5

<210> SEQ ID NO 31
<211> LENGTH: 13
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 31

Ser Leu Asp Glu Ile Ser Gln Pro Ala Gln Glu Leu Lys
1               5                   10

<210> SEQ ID NO 32
<211> LENGTH: 24
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 32

Gly Ala Asp Gln Ala Glu Leu Glu Glu Ile Ala Phe Asp Ser Ser Leu
1               5                   10                  15

Val Phe Ile Pro Ala Glu Phe Arg
            20

<210> SEQ ID NO 33
<211> LENGTH: 20
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 33

Asp Ile Leu Phe Leu Phe Asp Gly Ser Ala Asn Leu Val Gly Gln Phe

```
                 1               5                  10                 15
Pro Val Val Arg
              20

<210> SEQ ID NO 34
<211> LENGTH: 13
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 34

Ile Ile Asp Glu Leu Asn Val Lys Pro Glu Gly Thr Arg
1               5                   10

<210> SEQ ID NO 35
<211> LENGTH: 15
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 35

Ile Ala Val Ala Gln Tyr Ser Asp Asp Val Lys Val Glu Ser Arg
1               5                   10                  15

<210> SEQ ID NO 36
<211> LENGTH: 15
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 36

Phe Asp Glu His Gln Ser Lys Pro Glu Ile Leu Asn Leu Val Lys
1               5                   10                  15

<210> SEQ ID NO 37
<211> LENGTH: 13
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 37

Ala Leu Asn Leu Gly Tyr Ala Leu Asp Tyr Ala Gln Arg
1               5                   10

<210> SEQ ID NO 38
<211> LENGTH: 13
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 38

Ser Ser Asp Arg Val Asp Gly Pro Ala Ser Asn Leu Lys
1               5                   10

<210> SEQ ID NO 39
<211> LENGTH: 9
<212> TYPE: PRT
<213> ORGANISM: artificial
```

```
<220> FEATURE:
<223> OTHER INFORMATION: peptide fragment present in lectin-bound
      fraction isolated from human breast carcinomas

<400> SEQUENCE: 39

Val Asp Gly Pro Ala Ser Asn Leu Lys
1               5

<210> SEQ ID NO 40
<211> LENGTH: 12
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 40

Gln Ser Gly Val Val Pro Phe Ile Phe Gln Ala Lys
1               5                   10

<210> SEQ ID NO 41
<211> LENGTH: 25
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 41

Asn Ala Asp Pro Ala Glu Leu Glu Gln Ile Val Leu Ser Pro Ala Phe
1               5                   10                  15

Ile Leu Ala Ala Glu Ser Leu Pro Lys
            20                  25

<210> SEQ ID NO 42
<211> LENGTH: 13
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 42

Ile Gly Asp Leu His Pro Gln Ile Val Asn Leu Leu Lys
1               5                   10

<210> SEQ ID NO 43
<211> LENGTH: 13
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 43

Asp Val Val Phe Leu Leu Asp Gly Ser Glu Gly Val Arg
1               5                   10

<210> SEQ ID NO 44
<211> LENGTH: 7
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 44

Ser Gly Phe Pro Leu Leu Lys
```

```
<210> SEQ ID NO 45
<211> LENGTH: 11
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 45

Val Val Glu Ser Leu Asp Val Gly Gln Asp Arg
1               5                   10

<210> SEQ ID NO 46
<211> LENGTH: 9
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 46

Val Ala Val Val Gln Tyr Ser Asp Arg
1               5

<210> SEQ ID NO 47
<211> LENGTH: 21
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 47

Gln Leu Thr Leu Leu Gly Gly Pro Thr Pro Asn Thr Gly Ala Ala Leu
1               5                   10                  15

Glu Phe Val Leu Arg
            20

<210> SEQ ID NO 48
<211> LENGTH: 10
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 48

Asn Ile Leu Val Ser Ser Ala Gly Ser Arg
1               5                   10

<210> SEQ ID NO 49
<211> LENGTH: 16
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 49

Ile Thr Glu Gly Val Pro Gln Leu Leu Ile Val Leu Thr Ala Asp Arg
1               5                   10                  15

<210> SEQ ID NO 50
<211> LENGTH: 13
<212> TYPE: PRT
<213> ORGANISM: artificial
```

```
<220> FEATURE:
<223> OTHER INFORMATION: peptide fragment present in lectin-bound
      fraction isolated from human breast carcinomas

<400> SEQUENCE: 50

Ser Gly Asp Asp Val Arg Asn Pro Ser Val Val Lys
1               5                   10

<210> SEQ ID NO 51
<211> LENGTH: 12
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 51

Gln Leu Gly Thr Val Gln Gln Val Ile Ser Glu Arg
1               5                   10

<210> SEQ ID NO 52
<211> LENGTH: 6
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 52

Val Thr Gln Leu Thr Arg
1               5

<210> SEQ ID NO 53
<211> LENGTH: 16
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 53

Leu Gln Pro Val Leu Gln Pro Leu Pro Ser Pro Gly Val Gly Gly Lys
1               5                   10                  15

<210> SEQ ID NO 54
<211> LENGTH: 20
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 54

Asp Val Val Phe Leu Ile Asp Gly Ser Gln Ser Ala Gly Pro Glu Phe
1               5                   10                  15

Gln Tyr Val Arg
            20

<210> SEQ ID NO 55
<211> LENGTH: 13
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 55

Leu Val Asp Tyr Leu Asp Val Gly Phe Asp Thr Thr Arg
```

```
<210> SEQ ID NO 56
<211> LENGTH: 11
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 56

Val Ala Val Ile Gln Phe Ser Asp Asp Pro Lys
1               5                   10

<210> SEQ ID NO 57
<211> LENGTH: 20
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 57

Val Glu Phe Leu Leu Asn Ala His Ser Ser Lys Asp Glu Val Gln Asn
1               5                   10                  15

Ala Val Gln Arg
            20

<210> SEQ ID NO 58
<211> LENGTH: 9
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 58

Asp Glu Val Gln Asn Ala Val Gln Arg
1               5

<210> SEQ ID NO 59
<211> LENGTH: 13
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 59

Gln Ile Asn Val Gly Asn Ala Leu Glu Tyr Val Ser Arg
1               5                   10

<210> SEQ ID NO 60
<211> LENGTH: 16
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 60

Ile Glu Glu Gly Val Pro Gln Phe Leu Val Leu Ile Ser Ser Gly Lys
1               5                   10                  15

<210> SEQ ID NO 61
<211> LENGTH: 13
<212> TYPE: PRT
<213> ORGANISM: artificial
```

```
<220> FEATURE:
<223> OTHER INFORMATION: peptide fragment present in lectin-bound
      fraction isolated from human breast carcinomas

<400> SEQUENCE: 61

Ser Asp Asp Glu Val Asp Asp Pro Ala Val Glu Leu Lys
1               5                   10

<210> SEQ ID NO 62
<211> LENGTH: 11
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 62

Gln Phe Gly Val Ala Pro Phe Thr Ile Ala Arg
1               5                   10

<210> SEQ ID NO 63
<211> LENGTH: 9
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 63

Asn Ala Asp Gln Glu Glu Leu Val Lys
1               5

<210> SEQ ID NO 64
<211> LENGTH: 14
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 64

Ile Ser Leu Ser Pro Glu Tyr Val Phe Val Ser Thr Phe Arg
1               5                   10

<210> SEQ ID NO 65
<211> LENGTH: 15
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 65

Leu Leu Thr Pro Ile Thr Thr Leu Thr Ser Glu Gln Ile Gln Lys
1               5                   10                  15

<210> SEQ ID NO 66
<211> LENGTH: 8
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 66

Arg Leu Asn Ile Gly Pro Ser Lys
1               5
```

```
<210> SEQ ID NO 67
<211> LENGTH: 7
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 67

Leu Asn Ile Gly Pro Ser Lys
1               5

<210> SEQ ID NO 68
<211> LENGTH: 17
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 68

Val Gly Val Val Gln Phe Ser Asn Asp Val Phe Pro Glu Phe Tyr Leu
1               5                   10                  15

Lys

<210> SEQ ID NO 69
<211> LENGTH: 10
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 69

Ser Gln Ala Pro Val Leu Asp Ala Ile Arg
1               5                   10

<210> SEQ ID NO 70
<211> LENGTH: 7
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 70

Ala Leu Glu Phe Val Ala Arg
1               5

<210> SEQ ID NO 71
<211> LENGTH: 16
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 71

Ile Glu Asp Gly Val Pro Gln His Leu Val Leu Val Leu Gly Gly Lys
1               5                   10                  15

<210> SEQ ID NO 72
<211> LENGTH: 12
<212> TYPE: PRT
<213> ORGANISM: artificial
<220> FEATURE:
<223> OTHER INFORMATION: peptide fragment present in lectin-bound
      fraction isolated from human breast carcinomas
```

```
<400> SEQUENCE: 72

Ser Ser Gly Ile Val Ser Leu Gly Val Gly Asp Arg
1               5                   10

<210> SEQ ID NO 73
<211> LENGTH: 15
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 73

Asn Ile Asp Arg Thr Glu Leu Gln Thr Ile Thr Asn Asp Pro Arg
1               5                   10                  15

<210> SEQ ID NO 74
<211> LENGTH: 11
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 74

Thr Glu Leu Gln Thr Ile Thr Asn Asp Pro Arg
1               5                   10

<210> SEQ ID NO 75
<211> LENGTH: 6
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 75

Leu Val Phe Thr Val Arg
1               5

<210> SEQ ID NO 76
<211> LENGTH: 8
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 76

Asp Ser Phe Gln Glu Val Leu Arg
1               5

<210> SEQ ID NO 77
<211> LENGTH: 9
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 77

Arg Gln Ile Ile Asp Ala Ile Asn Lys
1               5

<210> SEQ ID NO 78
<211> LENGTH: 7
<212> TYPE: PRT
<213> ORGANISM: artificial
```

```
<220> FEATURE:
<223> OTHER INFORMATION: peptide fragment present in lectin-bound
      fraction isolated from human breast carcinomas

<400> SEQUENCE: 78

Val Gly Leu Glu His Leu Arg
1               5

<210> SEQ ID NO 79
<211> LENGTH: 11
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 79

Val Asn His Phe Val Pro Glu Ala Gly Ser Arg
1               5                   10

<210> SEQ ID NO 80
<211> LENGTH: 12
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 80

Val Pro Gln Ile Ala Phe Val Ile Thr Gly Gly Lys
1               5                   10

<210> SEQ ID NO 81
<211> LENGTH: 15
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 81

Ser Val Glu Asp Ala Gln Asp Val Ser Leu Ala Leu Thr Gln Arg
1               5                   10                  15

<210> SEQ ID NO 82
<211> LENGTH: 7
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 82

Val Phe Ala Val Gly Val Arg
1               5

<210> SEQ ID NO 83
<211> LENGTH: 9
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 83

Asn Ile Asp Ser Glu Glu Val Gly Lys
1               5
```

```
<210> SEQ ID NO 84
<211> LENGTH: 10
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 84

Ile Ala Ser Asn Ser Ala Thr Ala Phe Arg
1               5                   10

<210> SEQ ID NO 85
<211> LENGTH: 14
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 85

Ala Cys Asn Leu Asp Val Ile Leu Ser Phe Asp Gly Ser Arg
1               5                   10

<210> SEQ ID NO 86
<211> LENGTH: 9
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 86

Asp Gln Asn Val Phe Val Ala Gln Lys
1               5

<210> SEQ ID NO 87
<211> LENGTH: 27
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 87

Val Ser Val Val Ala Asn Thr Pro Ser Gly Pro Val Glu Ala Phe Asp
1               5                   10                  15

Phe Asp Glu Tyr Gln Pro Glu Met Leu Glu Lys
            20                  25

<210> SEQ ID NO 88
<211> LENGTH: 13
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 88

Ser Gln His Pro Tyr Val Leu Thr Glu Asp Thr Leu Lys
1               5                   10

<210> SEQ ID NO 89
<211> LENGTH: 18
<212> TYPE: PRT
<213> ORGANISM: artificial
<220> FEATURE:
<223> OTHER INFORMATION: peptide fragment present in lectin-bound
      fraction isolated from human breast carcinomas
```

```
<400> SEQUENCE: 89

Val Val Ile His Phe Thr Asp Gly Ala Asp Gly Asp Leu Ala Asp Leu
1               5                   10                  15

His Arg

<210> SEQ ID NO 90
<211> LENGTH: 9
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 90

Ala Leu Ile Leu Val Gly Leu Glu Arg
1               5

<210> SEQ ID NO 91
<211> LENGTH: 6
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 91

Val Val Asn Leu Glu Arg
1               5

<210> SEQ ID NO 92
<211> LENGTH: 20
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 92

Leu Asn Leu Leu Asp Leu Asp Tyr Glu Leu Ala Glu Gln Leu Asp Asn
1               5                   10                  15

Ile Ala Glu Lys
            20

<210> SEQ ID NO 93
<211> LENGTH: 16
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 93

Gly Glu Thr Gly Asp Asp Gly Arg Asp Gly Val Gly Ser Glu Gly Arg
1               5                   10                  15

<210> SEQ ID NO 94
<211> LENGTH: 14
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 94

Gly Asp Ser Ile Asp Gln Cys Ala Leu Ile Gln Ser Ile Lys
1               5                   10
```

<210> SEQ ID NO 95
<211> LENGTH: 19
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 95

Asp Val Val Leu Ser Ile Val Asn Asp Leu Thr Ile Ala Glu Ser Asn
1               5                   10                  15

Cys Pro Arg

<210> SEQ ID NO 96
<211> LENGTH: 15
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 96

Val Ala Val Val Thr Tyr Asn Asn Glu Val Thr Glu Ile Arg
1               5                   10                  15

<210> SEQ ID NO 97
<211> LENGTH: 9
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 97

Asn Leu Gln Val Ala Leu Thr Ser Lys
1               5

<210> SEQ ID NO 98
<211> LENGTH: 11
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 98

Val Ala Val Phe Phe Ser Asn Thr Pro Thr Arg
1               5                   10

<210> SEQ ID NO 99
<211> LENGTH: 21
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 99

Ala Leu Gly Ser Ala Ile Glu Tyr Thr Ile Glu Asn Val Phe Glu Ser
1               5                   10                  15

Ala Pro Asn Pro Arg
            20

<210> SEQ ID NO 100
<211> LENGTH: 19
<212> TYPE: PRT

```
<213> ORGANISM: artificial
<220> FEATURE:
<223> OTHER INFORMATION: peptide fragment present in lectin-bound
      fraction isolated from human breast carcinomas

<400> SEQUENCE: 100

Leu Leu Asp Ser Phe Val Ser Ser Glu Asn Ala Phe Tyr Leu Ser Pro
1               5                   10                  15

Asp Ile Arg

<210> SEQ ID NO 101
<211> LENGTH: 14
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 101

Leu Ile Gly Gln Ile Val Ser Ser Ile Thr Ala Ser Leu Arg
1               5                   10

<210> SEQ ID NO 102
<211> LENGTH: 13
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 102

Thr Ile Gln Phe Val Asp Trp Cys Pro Thr Gly Phe Lys
1               5                   10

<210> SEQ ID NO 103
<211> LENGTH: 14
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 103

Leu Ile Ser Gln Ile Val Ser Ser Ile Thr Ala Ser Leu Arg
1               5                   10

<210> SEQ ID NO 104
<211> LENGTH: 20
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 104

Thr Ile Gly Gly Gly Asp Asp Ser Phe Asn Thr Phe Phe Ser Glu Thr
1               5                   10                  15

Gly Ala Gly Lys
            20

<210> SEQ ID NO 105
<211> LENGTH: 15
<212> TYPE: PRT
<213> ORGANISM: artificial
<220> FEATURE:
<223> OTHER INFORMATION: peptide fragment present in lectin-bound
      fraction isolated from human breast carcinomas
```

```
<400> SEQUENCE: 105

Ala Val Phe Val Asp Leu Glu Pro Thr Val Ile Asp Glu Val Arg
1               5                   10                  15

<210> SEQ ID NO 106
<211> LENGTH: 9
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 106

Glu Ile Ile Asp Leu Val Leu Asp Arg
1               5

<210> SEQ ID NO 107
<211> LENGTH: 14
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 107

Asn Leu Asp Ile Glu Arg Pro Thr Tyr Thr Asn Leu Asn Arg
1               5                   10

<210> SEQ ID NO 108
<211> LENGTH: 21
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 108

Phe Asp Gly Ala Leu Asn Val Asp Leu Thr Glu Phe Gln Thr Asn Leu
1               5                   10                  15

Val Pro Tyr Pro Arg
            20

<210> SEQ ID NO 109
<211> LENGTH: 18
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 109

Val Gly Ile Asn Tyr Gln Pro Pro Thr Val Val Pro Gly Gly Asp Leu
1               5                   10                  15

Ala Lys

<210> SEQ ID NO 110
<211> LENGTH: 9
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 110

Asp Phe Ala Asp Ile Pro Asn Leu Arg
1               5
```

```
<210> SEQ ID NO 111
<211> LENGTH: 19
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 111

Arg Leu Asp Phe Thr Gly Asn Leu Ile Glu Asp Ile Glu Asp Gly Thr
1               5                   10                  15

Phe Ser Lys

<210> SEQ ID NO 112
<211> LENGTH: 16
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 112

Leu Ser Leu Leu Glu Glu Leu Ser Leu Ala Glu Asn Gln Leu Leu Lys
1               5                   10                  15

<210> SEQ ID NO 113
<211> LENGTH: 7
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 113

Leu Pro Val Leu Pro Pro Lys
1               5

<210> SEQ ID NO 114
<211> LENGTH: 19
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 114

Leu Ile His Leu Gln Phe Asn Asn Ile Ala Ser Ile Thr Asp Asp Thr
1               5                   10                  15

Phe Cys Lys

<210> SEQ ID NO 115
<211> LENGTH: 7
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 115

Asp Arg Ile Glu Glu Ile Arg
1               5

<210> SEQ ID NO 116
<211> LENGTH: 10
<212> TYPE: PRT
<213> ORGANISM: artificial
<220> FEATURE:
```

```
<223> OTHER INFORMATION: peptide fragment present in lectin-bound
      fraction isolated from human breast carcinomas

<400> SEQUENCE: 116

Leu Glu Gly Asn Pro Ile Val Leu Gly Lys
1               5                   10

<210> SEQ ID NO 117
<211> LENGTH: 12
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 117

Asp Ile Ala Pro Thr Leu Thr Leu Tyr Val Gly Lys
1               5                   10

<210> SEQ ID NO 118
<211> LENGTH: 8
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 118

Asn Pro Ala Asn Pro Val Gln Arg
1               5

<210> SEQ ID NO 119
<211> LENGTH: 10
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 119

Val Thr Ser Ile Gln Asp Trp Val Gln Lys
1               5                   10

<210> SEQ ID NO 120
<211> LENGTH: 11
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 120

Leu Asp Ile Asp Ser Pro Pro Ile Thr Ala Arg
1               5                   10

<210> SEQ ID NO 121
<211> LENGTH: 13
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 121

Asn Thr Gly Ile Ile Cys Thr Ile Gly Pro Ala Ser Arg
1               5                   10

<210> SEQ ID NO 122
```

```
<211> LENGTH: 23
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 122

Thr Ala Thr Glu Ser Phe Ala Ser Asp Pro Ile Leu Tyr Arg Pro Val
1               5                   10                  15

Ala Val Ala Leu Asp Thr Lys
            20

<210> SEQ ID NO 123
<211> LENGTH: 22
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 123

Leu Ala Pro Ile Thr Ser Asp Pro Thr Glu Ala Thr Ala Val Gly Ala
1               5                   10                  15

Val Glu Ala Ser Phe Lys
            20

<210> SEQ ID NO 124
<211> LENGTH: 8
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 124

Ala Pro Ile Ile Ala Val Thr Arg
1               5

<210> SEQ ID NO 125
<211> LENGTH: 22
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 125

Gly Ile Phe Pro Val Leu Cys Lys Asp Pro Val Gln Glu Ala Trp Ala
1               5                   10                  15

Glu Asp Val Asp Leu Arg
            20

<210> SEQ ID NO 126
<211> LENGTH: 18
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 126

Ala Ala Val Pro Ser Gly Ala Ser Thr Gly Ile Tyr Glu Ala Leu Glu
1               5                   10                  15

Leu Arg
```

```
<210> SEQ ID NO 127
<211> LENGTH: 26
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 127

Asp Ala Thr Asn Val Gly Asp Glu Gly Gly Phe Ala Pro Asn Ile Leu
1               5                   10                  15

Glu Asn Lys Glu Gly Leu Glu Leu Leu Lys
            20                  25

<210> SEQ ID NO 128
<211> LENGTH: 12
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 128

Tyr Ile Ser Pro Asp Gln Leu Ala Asp Leu Tyr Lys
1               5                   10

<210> SEQ ID NO 129
<211> LENGTH: 22
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 129

Ser Gly Glu Thr Glu Asp Thr Phe Ile Ala Asp Leu Val Val Gly Leu
1               5                   10                  15

Cys Thr Gly Gln Ile Lys
            20

<210> SEQ ID NO 130
<211> LENGTH: 12
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 130

Thr Ile Tyr Thr Pro Gly Ser Thr Val Leu Tyr Arg
1               5                   10

<210> SEQ ID NO 131
<211> LENGTH: 18
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 131

Ala Tyr Tyr Glu Asn Ser Pro Gln Gln Val Phe Ser Thr Glu Phe Glu
1               5                   10                  15

Val Lys

<210> SEQ ID NO 132
<211> LENGTH: 16
```

```
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 132

Glu Tyr Val Leu Pro Ser Phe Glu Val Ile Val Glu Pro Thr Glu Lys
1               5                   10                  15

<210> SEQ ID NO 133
<211> LENGTH: 14
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 133

Ile Pro Ile Glu Asp Gly Ser Gly Glu Val Val Leu Ser Arg
1               5                   10

<210> SEQ ID NO 134
<211> LENGTH: 10
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 134

Val Leu Leu Asp Gly Val Gln Asn Pro Arg
1               5                   10

<210> SEQ ID NO 135
<211> LENGTH: 22
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 135

Val Pro Val Ala Val Gln Gly Glu Asp Thr Val Gln Ser Leu Thr Gln
1               5                   10                  15

Gly Asp Gly Val Ala Lys
            20

<210> SEQ ID NO 136
<211> LENGTH: 14
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 136

Thr Lys Lys Gln Glu Leu Ser Glu Ala Glu Gln Ala Thr Arg
1               5                   10

<210> SEQ ID NO 137
<211> LENGTH: 16
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 137
```

```
Thr Glu Leu Arg Pro Gly Glu Thr Leu Asn Val Asn Phe Leu Leu Arg
1               5                   10                  15

<210> SEQ ID NO 138
<211> LENGTH: 22
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 138

Glu Pro Gly Gln Asp Leu Val Val Leu Pro Leu Ser Ile Thr Thr Asp
1               5                   10                  15

Phe Ile Pro Ser Phe Arg
            20

<210> SEQ ID NO 139
<211> LENGTH: 14
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 139

Leu Val Ala Tyr Tyr Thr Leu Ile Gly Ala Ser Gly Gln Arg
1               5                   10

<210> SEQ ID NO 140
<211> LENGTH: 7
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 140

Ile Trp Asp Val Val Glu Lys
1               5

<210> SEQ ID NO 141
<211> LENGTH: 8
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 141

Ala Ser His Leu Gly Leu Ala Arg
1               5

<210> SEQ ID NO 142
<211> LENGTH: 16
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 142

Ser Asn Leu Asp Glu Asp Ile Ile Ala Glu Glu Asn Ile Val Ser Arg
1               5                   10                  15

<210> SEQ ID NO 143
<211> LENGTH: 7
```

```
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 143

Leu Pro Tyr Ser Val Val Arg
1               5

<210> SEQ ID NO 144
<211> LENGTH: 7
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 144

Asn Glu Gln Val Glu Ile Arg
1               5

<210> SEQ ID NO 145
<211> LENGTH: 13
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 145

Ser Ser Leu Ser Val Pro Tyr Val Ile Val Pro Leu Lys
1               5                   10

<210> SEQ ID NO 146
<211> LENGTH: 9
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 146

Thr Gly Leu Gln Glu Val Glu Val Lys
1               5

<210> SEQ ID NO 147
<211> LENGTH: 20
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 147

Ile Leu Leu Asp Gly Thr Pro Val Ala Gln Met Thr Glu Asp Ala Val
1               5                   10                  15

Asp Ala Glu Arg
            20

<210> SEQ ID NO 148
<211> LENGTH: 10
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 148
```

```
Asp Phe Asp Phe Val Pro Pro Val Val Arg
1               5                   10

<210> SEQ ID NO 149
<211> LENGTH: 16
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 149

Val His Gln Tyr Phe Asn Val Glu Leu Ile Gln Pro Gly Ala Val Lys
1               5                   10                  15

<210> SEQ ID NO 150
<211> LENGTH: 11
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 150

Ala Cys Glu Pro Gly Val Asp Tyr Val Tyr Lys
1               5                   10

<210> SEQ ID NO 151
<211> LENGTH: 19
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 151

Val Gln Leu Ser Asn Asp Phe Asp Glu Tyr Ile Met Ala Ile Glu Gln
1               5                   10                  15

Thr Ile Lys

<210> SEQ ID NO 152
<211> LENGTH: 12
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 152

Ser Gly Ser Asp Glu Val Gln Val Gly Gln Gln Arg
1               5                   10

<210> SEQ ID NO 153
<211> LENGTH: 20
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 153

Asp Thr Trp Val Glu His Trp Pro Glu Glu Asp Glu Cys Gln Asp Glu
1               5                   10                  15

Glu Asn Gln Lys
            20
```

```
<210> SEQ ID NO 154
<211> LENGTH: 13
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 154

Asp Tyr Val Ser Gln Phe Glu Gly Ser Ala Leu Gly Lys
1               5                   10

<210> SEQ ID NO 155
<211> LENGTH: 14
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 155

Leu Leu Asp Asn Trp Asp Ser Val Thr Ser Thr Phe Ser Lys
1               5                   10

<210> SEQ ID NO 156
<211> LENGTH: 11
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 156

Gln Gly Leu Leu Pro Val Leu Glu Ser Phe Lys
1               5                   10

<210> SEQ ID NO 157
<211> LENGTH: 12
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 157

Val Ser Phe Leu Ser Ala Leu Glu Glu Tyr Thr Lys
1               5                   10

<210> SEQ ID NO 158
<211> LENGTH: 14
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 158

Ser Val Thr Glu Gln Gly Ala Glu Leu Ser Asn Glu Glu Arg
1               5                   10

<210> SEQ ID NO 159
<211> LENGTH: 12
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 159
```

```
Asp Ile Cys Asn Asp Val Leu Ser Leu Leu Glu Lys
1               5                   10
```

```
<210> SEQ ID NO 160
<211> LENGTH: 12
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 160

Tyr Leu Ala Glu Val Ala Ala Gly Asp Asp Lys Lys
1               5                   10
```

```
<210> SEQ ID NO 161
<211> LENGTH: 19
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 161

Thr Ala Phe Asp Glu Ala Ile Ala Glu Leu Asp Thr Leu Ser Glu Glu
1               5                   10                  15

Ser Tyr Lys
```

```
<210> SEQ ID NO 162
<211> LENGTH: 10
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 162

Val Val Gln Cys Ser Asp Leu Gly Leu Lys
1               5                   10
```

```
<210> SEQ ID NO 163
<211> LENGTH: 20
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 163

Glu Ile Ser Pro Asp Thr Thr Leu Leu Asp Leu Gln Asn Asn Asp Ile
1               5                   10                  15

Ser Glu Leu Arg
            20
```

```
<210> SEQ ID NO 164
<211> LENGTH: 18
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 164

Asn His Leu Val Glu Ile Pro Pro Asn Leu Pro Ser Ser Leu Val Glu
1               5                   10                  15

Leu Arg
```

```
<210> SEQ ID NO 165
<211> LENGTH: 7
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 165

Gly Val Phe Ser Gly Leu Arg
1               5

<210> SEQ ID NO 166
<211> LENGTH: 15
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 166

Asp Leu Pro Glu Thr Leu Asn Glu Leu His Leu Asp His Asn Lys
1               5                   10                  15

<210> SEQ ID NO 167
<211> LENGTH: 11
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 167

Ile Gln Ala Ile Glu Leu Glu Asp Leu Leu Arg
1               5                   10

<210> SEQ ID NO 168
<211> LENGTH: 9
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 168

Leu Gly Leu Gly His Asn Gln Ile Arg
1               5

<210> SEQ ID NO 169
<211> LENGTH: 9
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 169

Val Pro Ser Gly Leu Pro Asp Leu Lys
1               5

<210> SEQ ID NO 170
<211> LENGTH: 13
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 170
```

```
Asp Phe Glu Pro Ser Leu Gly Pro Val Cys Pro Phe Arg
1               5                   10
```

<210> SEQ ID NO 171
<211> LENGTH: 14
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 171

```
Val Val Gln Cys Ser Asp Leu Gly Leu Asp Lys Val Pro Lys
1               5                   10
```

<210> SEQ ID NO 172
<211> LENGTH: 14
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 172

```
Asp Leu Pro Pro Thr Thr Leu Leu Asp Leu Gln Asn Asn Lys
1               5                   10
```

<210> SEQ ID NO 173
<211> LENGTH: 10
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 173

```
Ile Thr Glu Ile Lys Asp Gly Asp Phe Lys
1               5                   10
```

<210> SEQ ID NO 174
<211> LENGTH: 11
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 174

```
Asn Leu His Ala Leu Ile Leu Val Asn Asn Lys
1               5                   10
```

<210> SEQ ID NO 175
<211> LENGTH: 11
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 175

```
Val Ser Pro Gly Ala Phe Thr Pro Leu Val Lys
1               5                   10
```

<210> SEQ ID NO 176
<211> LENGTH: 9
<212> TYPE: PRT
<213> ORGANISM: artificial
<220> FEATURE:

```
<223> OTHER INFORMATION: peptide fragment present in lectin-bound
      fraction isolated from human breast carcinomas

<400> SEQUENCE: 176

Val Pro Gly Gly Leu Ala Glu His Lys
1               5

<210> SEQ ID NO 177
<211> LENGTH: 24
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 177

Ala Ser Tyr Ser Gly Val Ser Leu Phe Ser Asn Pro Val Gln Tyr Trp
1               5                   10                  15

Glu Ile Gln Pro Ser Thr Phe Arg
            20

<210> SEQ ID NO 178
<211> LENGTH: 19
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 178

Ala Ala Pro Ser Val Thr Leu Phe Pro Pro Ser Ser Glu Glu Leu Gln
1               5                   10                  15

Ala Asn Lys

<210> SEQ ID NO 179
<211> LENGTH: 10
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 179

Ala Gly Val Glu Thr Thr Thr Pro Ser Lys
1               5                   10

<210> SEQ ID NO 180
<211> LENGTH: 20
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 180

Ala Thr Leu Val Cys Leu Ile Ser Asp Phe Tyr Pro Gly Ala Val Thr
1               5                   10                  15

Val Ala Trp Lys
            20

<210> SEQ ID NO 181
<211> LENGTH: 15
<212> TYPE: PRT
<213> ORGANISM: artificial
<220> FEATURE:
<223> OTHER INFORMATION: peptide fragment present in lectin-bound
      fraction isolated from human breast carcinomas
```

```
<400> SEQUENCE: 181

Tyr Ala Ala Ser Ser Tyr Leu Ser Leu Thr Pro Glu Gln Trp Lys
1               5                   10                  15

<210> SEQ ID NO 182
<211> LENGTH: 15
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 182

Ser Tyr Ser Cys Gln Val Thr His Glu Gly Ser Thr Val Glu Lys
1               5                   10                  15

<210> SEQ ID NO 183
<211> LENGTH: 12
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 183

Leu Asn Met Gly Ile Thr Asp Leu Gln Gly Leu Arg
1               5                   10

<210> SEQ ID NO 184
<211> LENGTH: 10
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 184

Val Gly Asp Thr Leu Asn Leu Asn Leu Arg
1               5                   10

<210> SEQ ID NO 185
<211> LENGTH: 10
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 185

Ser Phe Phe Pro Glu Asn Trp Leu Trp Arg
1               5                   10

<210> SEQ ID NO 186
<211> LENGTH: 26
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 186

Val Thr Ala Ser Asp Pro Leu Asp Thr Leu Gly Ser Glu Gly Ala Leu
1               5                   10                  15

Ser Pro Gly Gly Val Ala Ser Leu Leu Arg
            20                  25
```

```
<210> SEQ ID NO 187
<211> LENGTH: 15
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 187

Val Leu Ser Leu Ala Gln Glu Gln Val Gly Gly Ser Pro Glu Lys
1               5                   10                  15

<210> SEQ ID NO 188
<211> LENGTH: 15
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 188

Asp Ala Ser Gly Val Thr Phe Thr Trp Thr Pro Ser Ser Gly Lys
1               5                   10                  15

<210> SEQ ID NO 189
<211> LENGTH: 9
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 189

Ser Ala Val Gln Gly Pro Pro Glu Arg
1               5

<210> SEQ ID NO 190
<211> LENGTH: 12
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 190

Thr Phe Thr Cys Thr Ala Ala Tyr Pro Glu Ser Lys
1               5                   10

<210> SEQ ID NO 191
<211> LENGTH: 9
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 191

Thr Pro Leu Thr Ala Thr Leu Ser Lys
1               5

<210> SEQ ID NO 192
<211> LENGTH: 10
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 192
```

```
Trp Leu Gln Gly Ser Gln Glu Leu Pro Arg
1               5                  10

<210> SEQ ID NO 193
<211> LENGTH: 7
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 193

Tyr Leu Thr Trp Ala Ser Arg
1               5

<210> SEQ ID NO 194
<211> LENGTH: 17
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 194

Gln Glu Pro Ser Gln Gly Thr Thr Thr Phe Ala Val Thr Ser Ile Leu
1               5                   10                  15

Arg

<210> SEQ ID NO 195
<211> LENGTH: 15
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 195

Val Val Leu Ala Tyr Glu Pro Val Trp Ala Ile Gly Thr Gly Lys
1               5                   10                  15

<210> SEQ ID NO 196
<211> LENGTH: 12
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 196

Ser Asn Val Ser Asp Ala Val Ala Gln Ser Thr Arg
1               5                   10

<210> SEQ ID NO 197
<211> LENGTH: 12
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 197

Gly Pro Ser Val Phe Pro Leu Ala Pro Ser Ser Lys
1               5                   10

<210> SEQ ID NO 198
<211> LENGTH: 12
<212> TYPE: PRT
<213> ORGANISM: artificial
```

```
<220> FEATURE:
<223> OTHER INFORMATION: peptide fragment present in lectin-bound
      fraction isolated from human breast carcinomas

<400> SEQUENCE: 198

Gly Thr Thr Val Thr Val Ser Ser Ala Ser Thr Lys
1               5                   10

<210> SEQ ID NO 199
<211> LENGTH: 26
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 199

Thr His Thr Cys Pro Pro Cys Pro Ala Pro Glu Leu Leu Gly Gly Pro
1               5                   10                  15

Ser Val Phe Leu Phe Pro Pro Lys Pro Lys
            20                  25

<210> SEQ ID NO 200
<211> LENGTH: 19
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 200

Thr Pro Glu Val Thr Cys Val Val Val Asp Val Ser His Glu Asp Pro
1               5                   10                  15

Glu Val Lys

<210> SEQ ID NO 201
<211> LENGTH: 14
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 201

Phe Asn Trp Tyr Val Asp Gly Val Glu Val His Asn Ala Lys
1               5                   10

<210> SEQ ID NO 202
<211> LENGTH: 17
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 202

Thr Thr Pro Pro Val Leu Asp Ser Asp Gly Ser Phe Phe Leu Tyr Ser
1               5                   10                  15

Lys

<210> SEQ ID NO 203
<211> LENGTH: 14
<212> TYPE: PRT
<213> ORGANISM: artificial
<220> FEATURE:
<223> OTHER INFORMATION: peptide fragment present in lectin-bound
      fraction isolated from human breast carcinomas
```

```
<400> SEQUENCE: 203

Ser Thr Ser Glu Ser Thr Ala Ala Leu Gly Cys Leu Val Lys
1               5                   10

<210> SEQ ID NO 204
<211> LENGTH: 22
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 204

Gly Phe Tyr Pro Ser Asp Ile Ala Val Glu Trp Glu Ser Asn Gly Gln
1               5                   10                  15

Pro Glu Asn Asn Tyr Lys
            20

<210> SEQ ID NO 205
<211> LENGTH: 21
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 205

Thr Pro Glu Val Thr Cys Val Val Val Asp Val Ser His Glu Asp Pro
1               5                   10                  15

Glu Val Gln Phe Lys
            20

<210> SEQ ID NO 206
<211> LENGTH: 12
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 206

Trp Tyr Val Asp Gly Val Glu Val His Asn Ala Lys
1               5                   10

<210> SEQ ID NO 207
<211> LENGTH: 16
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 207

Val Val Ser Val Leu Thr Val Leu His Gln Asp Trp Leu Asn Gly Lys
1               5                   10                  15

<210> SEQ ID NO 208
<211> LENGTH: 7
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 208

Asp Thr Leu Met Ile Ser Arg
```

-continued

```
<210> SEQ ID NO 209
<211> LENGTH: 12
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 209

Gly Pro Ser Val Phe Pro Leu Ala Pro Cys Ser Arg
1               5                   10

<210> SEQ ID NO 210
<211> LENGTH: 10
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 210

Asn Gln Cys Ser Leu Thr Cys Leu Val Lys
1               5                   10

<210> SEQ ID NO 211
<211> LENGTH: 14
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 211

Ser Leu Tyr Ala Ser Ser Pro Gly Gly Val Tyr Ala Thr Arg
1               5                   10

<210> SEQ ID NO 212
<211> LENGTH: 19
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 212

Leu Leu Gln Asp Ser Val Asp Phe Ser Leu Ala Asp Ala Ile Asn Thr
1               5                   10                  15

Glu Phe Lys

<210> SEQ ID NO 213
<211> LENGTH: 9
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 213

Val Glu Leu Gln Glu Leu Asn Asp Arg
1               5

<210> SEQ ID NO 214
<211> LENGTH: 10
<212> TYPE: PRT
<213> ORGANISM: artificial
<220> FEATURE:
```

<223> OTHER INFORMATION: peptide fragment present in lectin-bound
      fraction isolated from human breast carcinomas

<400> SEQUENCE: 214

Ile Leu Leu Ala Glu Leu Glu Gln Leu Lys
1               5                   10

<210> SEQ ID NO 215
<211> LENGTH: 11
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 215

Glu Glu Ala Glu Asn Thr Leu Gln Ser Phe Arg
1               5                   10

<210> SEQ ID NO 216
<211> LENGTH: 10
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 216

Gln Asp Val Asp Asn Ala Ser Leu Ala Arg
1               5                   10

<210> SEQ ID NO 217
<211> LENGTH: 10
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 217

Asn Leu Gln Glu Ala Glu Glu Trp Tyr Lys
1               5                   10

<210> SEQ ID NO 218
<211> LENGTH: 10
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 218

Phe Ala Asp Leu Ser Glu Ala Ala Asn Arg
1               5                   10

<210> SEQ ID NO 219
<211> LENGTH: 13
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 219

Gln Val Gln Ser Leu Thr Cys Glu Val Asp Ala Leu Lys
1               5                   10

<210> SEQ ID NO 220

```
<211> LENGTH: 14
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 220

Ile Ser Leu Pro Leu Pro Asn Phe Ser Ser Leu Asn Leu Arg
1               5                   10

<210> SEQ ID NO 221
<211> LENGTH: 11
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 221

Tyr Ser Leu Glu Pro Val Ala Val Glu Leu Lys
1               5                   10

<210> SEQ ID NO 222
<211> LENGTH: 17
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 222

Ala Cys Ala Asn Pro Ala Ala Gly Ser Val Ile Leu Leu Glu Asn Leu
1               5                   10                  15

Arg

<210> SEQ ID NO 223
<211> LENGTH: 18
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 223

Gln Ile Val Trp Asn Gly Pro Val Gly Val Phe Glu Trp Glu Ala Phe
1               5                   10                  15

Ala Arg

<210> SEQ ID NO 224
<211> LENGTH: 12
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 224

Thr Asn Gln Leu Asn Leu Gln Asn Thr Ala Thr Lys
1               5                   10

<210> SEQ ID NO 225
<211> LENGTH: 16
<212> TYPE: PRT
<213> ORGANISM: artificial
<220> FEATURE:
<223> OTHER INFORMATION: peptide fragment present in lectin-bound
      fraction isolated from human breast carcinomas
```

```
<400> SEQUENCE: 225

His Phe Leu Glu Asn Leu Val Thr Ala Phe Asp Val Gly Ser Glu Lys
1               5                   10                  15

<210> SEQ ID NO 226
<211> LENGTH: 8
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 226

Asp Glu Val Ile Glu Ala Val Arg
1               5

<210> SEQ ID NO 227
<211> LENGTH: 9
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 227

Ile Gly Ile Leu Ile Thr Asp Gly Lys
1               5

<210> SEQ ID NO 228
<211> LENGTH: 10
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 228

Ser Gln Asp Asp Ile Ile Pro Pro Ser Arg
1               5                   10

<210> SEQ ID NO 229
<211> LENGTH: 21
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 229

Ala Ser Ala His Ala Ile Thr Gly Pro Pro Thr Glu Leu Ile Thr Ser
1               5                   10                  15

Glu Val Thr Ala Arg
            20

<210> SEQ ID NO 230
<211> LENGTH: 26
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 230

Trp Asp Ala Val Thr Gly Ala Ser Gly Tyr Leu Ile Leu Tyr Ala Pro
1               5                   10                  15

Leu Thr Glu Gly Leu Ala Gly Asp Glu Lys
```

20                  25

<210> SEQ ID NO 231
<211> LENGTH: 10
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 231

Ile Ser Asn Val Gly Ser Asn Ser Ala Arg
1               5                   10

<210> SEQ ID NO 232
<211> LENGTH: 25
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 232

Ile Val Tyr Asn Asn Ala Asp Gly Thr Glu Ile Asn Glu Val Glu Val
1               5                   10                  15

Asp Pro Ile Thr Thr Phe Pro Leu Lys
            20                  25

<210> SEQ ID NO 233
<211> LENGTH: 13
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 233

Asn Leu Val Val Gly Asp Glu Thr Thr Ser Ser Leu Arg
1               5                   10

<210> SEQ ID NO 234
<211> LENGTH: 12
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 234

Trp Asp Ile Ser Asp Ser Asp Val Gln Gln Phe Arg
1               5                   10

<210> SEQ ID NO 235
<211> LENGTH: 20
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 235

Val Thr Val Thr Pro Ile Tyr Thr Asp Gly Glu Gly Val Ser Val Ser
1               5                   10                  15

Ala Pro Gly Lys
            20

<210> SEQ ID NO 236

```
<211> LENGTH: 11
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 236

Thr Leu Pro Ser Ser Gly Pro Gln Asn Leu Arg
1               5                   10

<210> SEQ ID NO 237
<211> LENGTH: 8
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 237

Val Ser Glu Glu Trp Tyr Asn Arg
1               5

<210> SEQ ID NO 238
<211> LENGTH: 11
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 238

Ile Thr Trp Asp Pro Pro Ser Ser Pro Val Lys
1               5                   10

<210> SEQ ID NO 239
<211> LENGTH: 12
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 239

Thr Leu Phe Leu Gly Val Thr Asn Leu Gln Ala Lys
1               5                   10

<210> SEQ ID NO 240
<211> LENGTH: 9
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 240

Val Val Ile Glu Ser Leu Gln Asp Arg
1               5

<210> SEQ ID NO 241
<211> LENGTH: 14
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 241

Ile Ile Ser Phe Leu Tyr Ser Thr Val Gly Ala Leu Asn Lys
```

-continued

```
1               5                   10
```

<210> SEQ ID NO 242
<211> LENGTH: 10
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 242

```
Thr Lys Glu Thr Leu Leu Asp Ala Ile Lys
1               5                   10
```

<210> SEQ ID NO 243
<211> LENGTH: 11
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 243

```
Asp Thr Leu Phe Thr Ala Glu Ser Gly Thr Arg
1               5                   10
```

<210> SEQ ID NO 244
<211> LENGTH: 9
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 244

```
Val Ile Val Val Ile Thr Asp Gly Arg
1               5
```

<210> SEQ ID NO 245
<211> LENGTH: 12
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 245

```
His Val Phe Phe Val Asp Asp Phe Asp Ala Phe Lys
1               5                   10
```

<210> SEQ ID NO 246
<211> LENGTH: 9
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 246

```
Asp Gly Ile Asp Leu Ala Gly Phe Lys
1               5
```

<210> SEQ ID NO 247
<211> LENGTH: 18
<212> TYPE: PRT
<213> ORGANISM: artificial
<220> FEATURE:
<223> OTHER INFORMATION: peptide fragment present in lectin-bound
      fraction isolated from human breast carcinomas -continued

<400> SEQUENCE: 247

Ile Leu Pro Asp Thr Pro Gln Glu Pro Phe Ala Leu Trp Glu Ile Leu
1               5                   10                  15

Asn Lys

<210> SEQ ID NO 248
<211> LENGTH: 15
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 248

Asn Ser Asp Pro Leu Val Gly Val Ile Leu Asp Asn Gly Gly Lys
1               5                   10                  15

<210> SEQ ID NO 249
<211> LENGTH: 15
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 249

Asp Leu Ala Asp Glu Leu Ala Leu Val Asp Val Ile Glu Asp Lys
1               5                   10                  15

<210> SEQ ID NO 250
<211> LENGTH: 12
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 250

Val Ile Gly Ser Gly Cys Asn Leu Asp Ser Ala Arg
1               5                   10

<210> SEQ ID NO 251
<211> LENGTH: 17
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 251

Asp Ala Glu Glu Ala Ile Ser Gln Thr Ile Asp Thr Ile Val Asp Ile
1               5                   10                  15

Lys

<210> SEQ ID NO 252
<211> LENGTH: 7
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 252

Arg Phe Ile Asp Asn Leu Arg
1               5

```
<210> SEQ ID NO 253
<211> LENGTH: 6
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 253

Phe Ile Asp Asn Leu Arg
1               5

<210> SEQ ID NO 254
<211> LENGTH: 29
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 254

Tyr Leu Ile Val Val Thr Asp Gly His Pro Leu Glu Gly Tyr Lys Glu
1               5                  10                  15

Pro Cys Gly Gly Leu Glu Asp Ala Val Asn Glu Ala Lys
            20                  25

<210> SEQ ID NO 255
<211> LENGTH: 14
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 255

Val Phe Ser Val Ala Ile Thr Pro Asp His Leu Glu Pro Arg
1               5                  10

<210> SEQ ID NO 256
<211> LENGTH: 11
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 256

Leu Ser Ile Ile Ala Thr Asp His Thr Tyr Arg
1               5                  10

<210> SEQ ID NO 257
<211> LENGTH: 13
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 257

Ser Gly Asp Glu Gly Pro Pro Gly Ser Glu Gly Ala Arg
1               5                  10

<210> SEQ ID NO 258
<211> LENGTH: 19
<212> TYPE: PRT
<213> ORGANISM: artificial
<220> FEATURE:
<223> OTHER INFORMATION: peptide fragment present in lectin-bound
``` fraction isolated from human breast carcinomas

<400> SEQUENCE: 258

Ser Leu Gln Trp Met Ala Gly Gly Thr Phe Thr Gly Glu Ala Leu Gln
1               5                   10                  15

Tyr Thr Arg

<210> SEQ ID NO 259
<211> LENGTH: 9
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 259

Ile Ala Leu Val Ile Thr Asp Gly Arg
1               5

<210> SEQ ID NO 260
<211> LENGTH: 21
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 260

Asp Thr Thr Pro Leu Asn Val Leu Cys Ser Pro Gly Ile Gln Val Val
1               5                   10                  15

Ser Val Gly Ile Lys
            20

<210> SEQ ID NO 261
<211> LENGTH: 33
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 261

Asp Val Phe Asp Phe Ile Pro Gly Ser Asp Gln Leu Asn Val Ile Ser
1               5                   10                  15

Cys Gln Gly Leu Ala Pro Ser Gln Gly Arg Pro Gly Leu Ser Leu Val
            20                  25                  30

Lys

<210> SEQ ID NO 262
<211> LENGTH: 13
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 262

Glu Asn Tyr Ala Glu Leu Leu Glu Asp Ala Phe Leu Lys
1               5                   10

<210> SEQ ID NO 263
<211> LENGTH: 19
<212> TYPE: PRT
<213> ORGANISM: artificial
<220> FEATURE:
<223> OTHER INFORMATION: peptide fragment present in lectin-bound fraction isolated from human breast carcinomas

<400> SEQUENCE: 263

Leu Leu Leu Phe Ser Asp Gly Asn Ser Gln Gly Ala Thr Pro Ala Ala
1               5                   10                  15

Ile Glu Lys

<210> SEQ ID NO 264
<211> LENGTH: 12
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 264

Ala Gly Ile Glu Ile Phe Val Val Val Val Gly Arg
1               5                   10

<210> SEQ ID NO 265
<211> LENGTH: 15
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 265

Thr Ala Glu Tyr Asp Val Ala Tyr Gly Glu Ser His Leu Phe Arg
1               5                   10                  15

<210> SEQ ID NO 266
<211> LENGTH: 9
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 266

Val Pro Ser Tyr Gln Ala Leu Leu Arg
1               5

<210> SEQ ID NO 267
<211> LENGTH: 9
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 267

Gly Val Phe His Gln Thr Val Ser Arg
1               5

<210> SEQ ID NO 268
<211> LENGTH: 23
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 268

Ile Glu Asp Ala Asn Leu Ile Pro Pro Val Pro Asp Asp Lys Phe Gln
1               5                   10                  15

Asp Leu Val Asp Ala Val Arg

-continued

<210> SEQ ID NO 269
<211> LENGTH: 12
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 269

Phe Val Phe Gly Thr Thr Pro Glu Asp Ile Leu Arg
1               5                   10

<210> SEQ ID NO 270
<211> LENGTH: 11
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 270

Thr Ile Val Thr Thr Leu Gln Asp Ser Ile Arg
1               5                   10

<210> SEQ ID NO 271
<211> LENGTH: 14
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 271

Lys Val Thr Glu Glu Asn Lys Glu Leu Ala Asn Glu Leu Arg
1               5                   10

<210> SEQ ID NO 272
<211> LENGTH: 15
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 272

Asp Val Trp Gly Ile Glu Gly Pro Ile Asp Ala Ala Phe Thr Arg
1               5                   10                  15

<210> SEQ ID NO 273
<211> LENGTH: 12
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 273

Phe Glu Asp Gly Val Leu Asp Pro Asp Tyr Pro Arg
1               5                   10

<210> SEQ ID NO 274
<211> LENGTH: 9
<212> TYPE: PRT
<213> ORGANISM: artificial
<220> FEATURE:
<223> OTHER INFORMATION: peptide fragment present in lectin-bound
      fraction isolated from human breast carcinomas

```
<400> SEQUENCE: 274

Asn Leu Gln Gly Ile Ser Ser Phe Arg
1               5

<210> SEQ ID NO 275
<211> LENGTH: 11
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 275

Leu Phe Ala Val Ala Pro Asn Gln Asn Leu Lys
1               5                  10

<210> SEQ ID NO 276
<211> LENGTH: 11
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 276

Asp Ile Ala Ser Thr Pro His Glu Leu Tyr Arg
1               5                  10

<210> SEQ ID NO 277
<211> LENGTH: 20
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 277

Asn Asp Tyr Ala Thr Met Leu Pro Asp Ser Thr Glu Ile Asp Gln Asp
1               5                  10                  15

Thr Ile Asn Arg
            20

<210> SEQ ID NO 278
<211> LENGTH: 9
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 278

Asn Phe Val Ile Asn Val Val Asn Arg
1               5

<210> SEQ ID NO 279
<211> LENGTH: 16
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 279

Asn Leu Glu Trp Ile Ala Gly Gly Thr Trp Thr Pro Ser Ala Leu Lys
1               5                  10                  15
```

```
<210> SEQ ID NO 280
<211> LENGTH: 10
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 280

Val Phe Ala Val Val Ile Thr Asp Gly Arg
1               5                   10

<210> SEQ ID NO 281
<211> LENGTH: 7
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 281

Asp Asp Asp Leu Asn Leu Arg
1               5

<210> SEQ ID NO 282
<211> LENGTH: 18
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 282

His Glu Ser Glu Asn Leu Tyr Ser Ile Ala Cys Asp Lys Pro Gln Gln
1               5                   10                  15

Val Arg

<210> SEQ ID NO 283
<211> LENGTH: 8
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 283

Leu Gly Glu Gln Asn Phe His Lys
1               5

<210> SEQ ID NO 284
<211> LENGTH: 7
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 284

Phe Val Glu Gln Val Ala Arg
1               5

<210> SEQ ID NO 285
<211> LENGTH: 9
<212> TYPE: PRT
<213> ORGANISM: artificial
<220> FEATURE:
<223> OTHER INFORMATION: peptide fragment present in lectin-bound
      fraction isolated from human breast carcinomas
```

```
<400> SEQUENCE: 285

Arg Asp Asp Asp Pro Leu Asn Ala Arg
1               5

<210> SEQ ID NO 286
<211> LENGTH: 20
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 286

Ala Ala Val Phe His Glu Lys Asp Tyr Asp Ser Leu Ala Gln Pro Gly
1               5                   10                  15

Phe Phe Asp Arg
            20

<210> SEQ ID NO 287
<211> LENGTH: 12
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 287

Asp Ala Gly Val Ile Ala Gly Leu Asn Val Leu Arg
1               5                   10

<210> SEQ ID NO 288
<211> LENGTH: 31
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 288

Glu Leu Glu Gln Val Cys Asn Pro Ile Ile Ser Gly Leu Tyr Gln Gly
1               5                   10                  15

Ala Gly Gly Pro Gly Pro Gly Gly Phe Gly Ala Gln Gly Pro Lys
            20                  25                  30

<210> SEQ ID NO 289
<211> LENGTH: 9
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 289

Val Ser Phe Glu Leu Phe Ala Asp Lys
1               5

<210> SEQ ID NO 290
<211> LENGTH: 9
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 290

Phe Glu Asp Glu Asn Phe Ile Leu Lys
1               5
```

```
<210> SEQ ID NO 291
<211> LENGTH: 10
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 291

Ser Val Leu Gly Gln Leu Gly Ile Thr Lys
1               5                   10

<210> SEQ ID NO 292
<211> LENGTH: 18
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 292

Val Phe Ser Asn Gly Ala Asp Leu Ser Gly Val Thr Glu Glu Ala Pro
1               5                   10                  15

Leu Lys

<210> SEQ ID NO 293
<211> LENGTH: 14
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 293

Ile Thr Pro Asn Leu Ala Glu Phe Ala Phe Ser Leu Tyr Arg
1               5                   10

<210> SEQ ID NO 294
<211> LENGTH: 8
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 294

Ala Val Leu Thr Ile Asp Glu Lys
1               5

<210> SEQ ID NO 295
<211> LENGTH: 7
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 295

Val Val Asn Pro Thr Gln Lys
1               5

<210> SEQ ID NO 296
<211> LENGTH: 24
<212> TYPE: PRT
<213> ORGANISM: artificial
<220> FEATURE:
<223> OTHER INFORMATION: peptide fragment present in lectin-bound
``` fraction isolated from human breast carcinomas

<400> SEQUENCE: 296

Thr Leu Asn Gln Pro Asp Ser Gln Leu Gln Leu Thr Thr Gly Asn Gly
1               5                   10                  15

Leu Phe Leu Ser Glu Gly Leu Lys
            20

<210> SEQ ID NO 297
<211> LENGTH: 15
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 297

Leu Gln His Leu Glu Asn Glu Leu Thr His Asp Ile Ile Thr Lys
1               5                   10                  15

<210> SEQ ID NO 298
<211> LENGTH: 8
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 298

Ser Ala Ser Leu His Leu Pro Lys
1               5

<210> SEQ ID NO 299
<211> LENGTH: 18
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 299

Leu Ala Ala Leu Asn Pro Glu Ser Asn Thr Ala Gly Leu Asp Ile Phe
1               5                   10                  15

Ala Lys

<210> SEQ ID NO 300
<211> LENGTH: 17
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 300

Phe Leu Asp Gly Asn Glu Leu Thr Leu Ala Asp Cys Asn Leu Leu Pro
1               5                   10                  15

Lys

<210> SEQ ID NO 301
<211> LENGTH: 14
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 301

Gly Val Asp Glu Val Thr Ile Val Asn Ile Leu Thr Asn Arg
1               5                   10

<210> SEQ ID NO 302
<211> LENGTH: 11
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 302

Thr Pro Ala Gln Tyr Asp Ala Ser Glu Leu Lys
1               5                   10

<210> SEQ ID NO 303
<211> LENGTH: 16
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 303

Gly Leu Gly Thr Asp Glu Asp Ser Leu Ile Glu Ile Ile Cys Ser Arg
1               5                   10                  15

<210> SEQ ID NO 304
<211> LENGTH: 10
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 304

Thr Asn Gln Glu Leu Gln Glu Ile Asn Arg
1               5                   10

<210> SEQ ID NO 305
<211> LENGTH: 17
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 305

Thr Asp Leu Glu Lys Asp Ile Ile Ser Asp Thr Ser Gly Asp Phe Arg
1               5                   10                  15

Lys

<210> SEQ ID NO 306
<211> LENGTH: 16
<212> TYPE: PRT
<213> ORGANISM: artificial
<220> FEATURE:
<223> OTHER INFORMATION: peptide fragment present in lectin-bound
      fraction isolated from human breast carcinomas

<400> SEQUENCE: 306

Gly Leu Gly Thr Asp Glu Glu Ser Ile Leu Thr Leu Leu Thr Ser Arg
1               5                   10                  15

<210> SEQ ID NO 307
<211> LENGTH: 13
<212> TYPE: PRT

-continued

```
<213> ORGANISM: artificial
<220> FEATURE:
<223> OTHER INFORMATION: peptide fragment present in lectin-bound
      fraction isolated from human breast carcinomas

<400> SEQUENCE: 307

Asp Leu Leu Asp Asp Leu Lys Ser Glu Leu Thr Gly Lys
1               5                   10

<210> SEQ ID NO 308
<211> LENGTH: 21
<212> TYPE: DNA
<213> ORGANISM: artificial
<220> FEATURE:
<223> OTHER INFORMATION: synthetic oligonucleotide primer

<400> SEQUENCE: 308
cccttcaccc agttggacct g                                             21

<210> SEQ ID NO 309
<211> LENGTH: 20
<212> TYPE: DNA
<213> ORGANISM: artificial
<220> FEATURE:
<223> OTHER INFORMATION: synthetic oligonucleotide primer

<400> SEQUENCE: 309
gtgattccca tcctggtcat                                               20

<210> SEQ ID NO 310
<211> LENGTH: 20
<212> TYPE: DNA
<213> ORGANISM: artificial
<220> FEATURE:
<223> OTHER INFORMATION: synthetic oligonucleotide primer

<400> SEQUENCE: 310
tgctggagac tgtggtatgc                                               20

<210> SEQ ID NO 311
<211> LENGTH: 20
<212> TYPE: DNA
<213> ORGANISM: artificial
<220> FEATURE:
<223> OTHER INFORMATION: synthetic oligonucleotide primer

<400> SEQUENCE: 311
agcaagagtg ccctgaatgt                                               20

<210> SEQ ID NO 312
<211> LENGTH: 20
<212> TYPE: DNA
<213> ORGANISM: artificial
<220> FEATURE:
<223> OTHER INFORMATION: synthetic oligonucleotide primer

<400> SEQUENCE: 312
gcgtgatggt gtgctgttcc                                               20

<210> SEQ ID NO 313
<211> LENGTH: 20
<212> TYPE: DNA
<213> ORGANISM: artificial
<220> FEATURE:
<223> OTHER INFORMATION: synthetic oligonucleotide primer

<400> SEQUENCE: 313
```
cgagggcatc tacttcaagc                              20

<210> SEQ ID NO 314
<211> LENGTH: 21
<212> TYPE: DNA
<213> ORGANISM: artificial
<220> FEATURE:
<223> OTHER INFORMATION: synthetic oligonucleotide primer

<400> SEQUENCE: 314
gcgacagaca gaaggcaaac c                            21

<210> SEQ ID NO 315
<211> LENGTH: 21
<212> TYPE: DNA
<213> ORGANISM: artificial
<220> FEATURE:
<223> OTHER INFORMATION: synthetic oligonucleotide primer

<400> SEQUENCE: 315
aaggtctacc aagggcatac g                            21

<210> SEQ ID NO 316
<211> LENGTH: 20
<212> TYPE: DNA
<213> ORGANISM: artificial
<220> FEATURE:
<223> OTHER INFORMATION: synthetic oligonucleotide primer

<400> SEQUENCE: 316
aggtgacgtg gtggacattt                              20

<210> SEQ ID NO 317
<211> LENGTH: 21
<212> TYPE: DNA
<213> ORGANISM: artificial
<220> FEATURE:
<223> OTHER INFORMATION: synthetic oligonucleotide primer

<400> SEQUENCE: 317
tgcactcgta cctgactgac a                            21

<210> SEQ ID NO 318
<211> LENGTH: 20
<212> TYPE: DNA
<213> ORGANISM: artificial
<220> FEATURE:
<223> OTHER INFORMATION: synthetic oligonucleotide primer

<400> SEQUENCE: 318
ccctggaagt tgtcctctca                              20

<210> SEQ ID NO 319
<211> LENGTH: 19
<212> TYPE: DNA
<213> ORGANISM: artificial
<220> FEATURE:
<223> OTHER INFORMATION: synthetic oligonucleotide primer

<400> SEQUENCE: 319
agcctgaaag cagctccat                               19

<210> SEQ ID NO 320
<211> LENGTH: 20
<212> TYPE: DNA
<213> ORGANISM: artificial
<220> FEATURE:

<223> OTHER INFORMATION: synthetic oligonucleotide primer

<400> SEQUENCE: 320
ctctggtgtc cgtgctggtg                                          20

<210> SEQ ID NO 321
<211> LENGTH: 21
<212> TYPE: DNA
<213> ORGANISM: artificial
<220> FEATURE:
<223> OTHER INFORMATION: synthetic oligonucleotide primer

<400> SEQUENCE: 321
gagtgagtct gtggaggatg g                                        21

<210> SEQ ID NO 322
<211> LENGTH: 20
<212> TYPE: DNA
<213> ORGANISM: artificial
<220> FEATURE:
<223> OTHER INFORMATION: synthetic oligonucleotide primer

<400> SEQUENCE: 322
aagcaggtga cggtgtgtgg                                          20

<210> SEQ ID NO 323
<211> LENGTH: 20
<212> TYPE: DNA
<213> ORGANISM: artificial
<220> FEATURE:
<223> OTHER INFORMATION: synthetic oligonucleotide primer

<400> SEQUENCE: 323
gcccagcttc ttctccatct                                          20

<210> SEQ ID NO 324
<211> LENGTH: 21
<212> TYPE: DNA
<213> ORGANISM: artificial
<220> FEATURE:
<223> OTHER INFORMATION: synthetic oligonucleotide primer

<400> SEQUENCE: 324
aacagaagca gccttccacc c                                        21

<210> SEQ ID NO 325
<211> LENGTH: 20
<212> TYPE: DNA
<213> ORGANISM: artificial
<220> FEATURE:
<223> OTHER INFORMATION: synthetic oligonucleotide primer

<400> SEQUENCE: 325
ggtcgagctt cccattgtag                                          20

<210> SEQ ID NO 326
<211> LENGTH: 21
<212> TYPE: DNA
<213> ORGANISM: artificial
<220> FEATURE:
<223> OTHER INFORMATION: synthetic oligonucleotide primer

<400> SEQUENCE: 326
gacagcccta tgccgtcagt g                                        21

<210> SEQ ID NO 327

```
<211> LENGTH: 20
<212> TYPE: DNA
<213> ORGANISM: artificial
<220> FEATURE:
<223> OTHER INFORMATION: synthetic oligonucleotide primer

<400> SEQUENCE: 327
agaaggctgc tgttggtgtt                                                     20

<210> SEQ ID NO 328
<211> LENGTH: 20
<212> TYPE: DNA
<213> ORGANISM: artificial
<220> FEATURE:
<223> OTHER INFORMATION: synthetic oligonucleotide primer

<400> SEQUENCE: 328
gcaccataga cctgggcgag                                                     20

<210> SEQ ID NO 329
<211> LENGTH: 20
<212> TYPE: DNA
<213> ORGANISM: artificial
<220> FEATURE:
<223> OTHER INFORMATION: synthetic oligonucleotide primer

<400> SEQUENCE: 329
taatgcagca gcttgtccag                                                     20

<210> SEQ ID NO 330
<211> LENGTH: 20
<212> TYPE: DNA
<213> ORGANISM: artificial
<220> FEATURE:
<223> OTHER INFORMATION: synthetic oligonucleotide primer

<400> SEQUENCE: 330
actcaatttg ggcactctgg                                                     20

<210> SEQ ID NO 331
<211> LENGTH: 20
<212> TYPE: DNA
<213> ORGANISM: artificial
<220> FEATURE:
<223> OTHER INFORMATION: synthetic oligonucleotide primer

<400> SEQUENCE: 331
tgccatagaa actgcgactg                                                     20

<210> SEQ ID NO 332
<211> LENGTH: 20
<212> TYPE: DNA
<213> ORGANISM: artificial
<220> FEATURE:
<223> OTHER INFORMATION: synthetic oligonucleotide primer

<400> SEQUENCE: 332
acagggactt ccgcatgtgg                                                     20

<210> SEQ ID NO 333
<211> LENGTH: 20
<212> TYPE: DNA
<213> ORGANISM: artificial
<220> FEATURE:
<223> OTHER INFORMATION: synthetic oligonucleotide primer

<400> SEQUENCE: 333
```
cgcttgtcct cgtagtcacc                                              20

<210> SEQ ID NO 334
<211> LENGTH: 21
<212> TYPE: DNA
<213> ORGANISM: artificial
<220> FEATURE:
<223> OTHER INFORMATION: synthetic oligonucleotide primer

<400> SEQUENCE: 334
ccgacagaga cgagtgtagg c                                            21

<210> SEQ ID NO 335
<211> LENGTH: 21
<212> TYPE: DNA
<213> ORGANISM: artificial
<220> FEATURE:
<223> OTHER INFORMATION: synthetic oligonucleotide primer

<400> SEQUENCE: 335
tatcggtgtg atagcccaga a                                            21

<210> SEQ ID NO 336
<211> LENGTH: 20
<212> TYPE: DNA
<213> ORGANISM: artificial
<220> FEATURE:
<223> OTHER INFORMATION: synthetic oligonucleotide primer

<400> SEQUENCE: 336
gcttcaggct ctcttgctca                                              20

<210> SEQ ID NO 337
<211> LENGTH: 20
<212> TYPE: DNA
<213> ORGANISM: artificial
<220> FEATURE:
<223> OTHER INFORMATION: synthetic oligonucleotide primer

<400> SEQUENCE: 337
gaccgagtcc tccttctcct                                              20

<210> SEQ ID NO 338
<211> LENGTH: 20
<212> TYPE: DNA
<213> ORGANISM: artificial
<220> FEATURE:
<223> OTHER INFORMATION: synthetic oligonucleotide primer

<400> SEQUENCE: 338
tcctctgcca gtgccttaat                                              20

<210> SEQ ID NO 339
<211> LENGTH: 20
<212> TYPE: DNA
<213> ORGANISM: artificial
<220> FEATURE:
<223> OTHER INFORMATION: synthetic oligonucleotide primer

<400> SEQUENCE: 339
gccagtgcct tgatgtacct                                              20

<210> SEQ ID NO 340
<211> LENGTH: 21
<212> TYPE: DNA
<213> ORGANISM: artificial
<220> FEATURE:

```
<223> OTHER INFORMATION: synthetic oligonucleotide primer

<400> SEQUENCE: 340
aataggcagg actggcgaac c                                              21

<210> SEQ ID NO 341
<211> LENGTH: 20
<212> TYPE: DNA
<213> ORGANISM: artificial
<220> FEATURE:
<223> OTHER INFORMATION: synthetic oligonucleotide primer

<400> SEQUENCE: 341
gaagatgtga gccagcacct                                                20

<210> SEQ ID NO 342
<211> LENGTH: 21
<212> TYPE: DNA
<213> ORGANISM: artificial
<220> FEATURE:
<223> OTHER INFORMATION: synthetic oligonucleotide primer

<400> SEQUENCE: 342
tgcactcggt ccagcataag g                                              21

<210> SEQ ID NO 343
<211> LENGTH: 19
<212> TYPE: DNA
<213> ORGANISM: artificial
<220> FEATURE:
<223> OTHER INFORMATION: synthetic oligonucleotide primer

<400> SEQUENCE: 343
tgcagctctg gcttctgac                                                 19

<210> SEQ ID NO 344
<211> LENGTH: 21
<212> TYPE: DNA
<213> ORGANISM: artificial
<220> FEATURE:
<223> OTHER INFORMATION: synthetic oligonucleotide primer

<400> SEQUENCE: 344
cattctgcgt gcgagaagct g                                              21

<210> SEQ ID NO 345
<211> LENGTH: 20
<212> TYPE: DNA
<213> ORGANISM: artificial
<220> FEATURE:
<223> OTHER INFORMATION: synthetic oligonucleotide primer

<400> SEQUENCE: 345
gcgaggtctt ctggtacagc                                                20

<210> SEQ ID NO 346
<211> LENGTH: 20
<212> TYPE: DNA
<213> ORGANISM: artificial
<220> FEATURE:
<223> OTHER INFORMATION: synthetic oligonucleotide primer

<400> SEQUENCE: 346
gccacagctc tgccagtacc                                                20

<210> SEQ ID NO 347
```

```
<211> LENGTH: 20
<212> TYPE: DNA
<213> ORGANISM: artificial
<220> FEATURE:
<223> OTHER INFORMATION: synthetic oligonucleotide primer

<400> SEQUENCE: 347
tggtttcttg gtagctgctg                                              20

<210> SEQ ID NO 348
<211> LENGTH: 15
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 348

Asn Gln Leu Thr Ser Asn Pro Glu Asn Thr Val Phe Asp Ala Lys
1               5                   10                  15

<210> SEQ ID NO 349
<211> LENGTH: 12
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 349

Thr Trp Asn Asp Pro Ser Val Gln Gln Asp Ile Lys
1               5                   10

<210> SEQ ID NO 350
<211> LENGTH: 15
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 350

Lys Ser Asp Ile Asp Glu Ile Val Leu Val Gly Gly Ser Thr Arg
1               5                   10                  15

<210> SEQ ID NO 351
<211> LENGTH: 17
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 351

Ser Gln Ile Phe Ser Thr Ala Ser Asp Asn Gln Pro Thr Val Thr Ile
1               5                   10                  15

Lys

<210> SEQ ID NO 352
<211> LENGTH: 9
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 352

Ile Thr Ile Thr Asn Asp Gln Asn Arg
```

<210> SEQ ID NO 353
<211> LENGTH: 11
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 353

Asn Glu Leu Glu Ser Tyr Ala Tyr Ser Leu Lys
1               5                   10

<210> SEQ ID NO 354
<211> LENGTH: 12
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 354

Glu Leu Glu Glu Ile Val Gln Pro Ile Ile Ser Lys
1               5                   10

<210> SEQ ID NO 355
<211> LENGTH: 16
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 355

Ile Ile Asn Glu Pro Thr Ala Ala Ala Ile Ala Tyr Gly Leu Asp Lys
1               5                   10                  15

<210> SEQ ID NO 356
<211> LENGTH: 17
<212> TYPE: PRT
<213> ORGANISM: artificial
<220> FEATURE:
<223> OTHER INFORMATION: peptide fragment present in lectin-bound fraction isolated from
      human ovarian tumors

<400> SEQUENCE: 356

Ile Thr Gly Glu Ala Phe Val Gln Phe Ala Ser Gln Glu Leu Ala Glu
1               5                   10                  15

Lys

<210> SEQ ID NO 357
<211> LENGTH: 17
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 357

Ala Thr Glu Asn Asp Ile Tyr Asn Phe Phe Ser Pro Leu Asn Pro Val
1               5                   10                  15

Arg

<210> SEQ ID NO 358
<211> LENGTH: 9
<212> TYPE: PRT

-continued

```
<213> ORGANISM: artificial
<220> FEATURE:
<223> OTHER INFORMATION: peptide fragment present in lectin-bound
      fraction isolated from human ovarian tumors

<400> SEQUENCE: 358

Thr Val Glu Ser Ile Thr Asp Ile Arg
1               5

<210> SEQ ID NO 359
<211> LENGTH: 16
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 359

Phe Phe Leu Gln Gly Ile Gln Leu Asn Thr Ile Leu Pro Asp Ala Arg
1               5                   10                  15

<210> SEQ ID NO 360
<211> LENGTH: 18
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 360

Asn His Leu Val Glu Ile Pro Pro Asn Leu Pro Ser Ser Leu Val Glu
1               5                   10                  15

Leu Arg

<210> SEQ ID NO 361
<211> LENGTH: 15
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 361

Asp Leu Pro Glu Thr Leu Asn Glu Leu His Leu Asp His Asn Lys
1               5                   10                  15

<210> SEQ ID NO 362
<211> LENGTH: 11
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 362

Ile Gln Ala Ile Glu Leu Glu Asp Leu Leu Arg
1               5                   10

<210> SEQ ID NO 363
<211> LENGTH: 9
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 363

Leu Gly Leu Gly His Asn Gln Ile Arg
```

```
1               5

<210> SEQ ID NO 364
<211> LENGTH: 9
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 364

Val Pro Ser Gly Leu Pro Asp Leu Lys
1               5

<210> SEQ ID NO 365
<211> LENGTH: 24
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 365

Ala Tyr Tyr Asn Gly Ile Ser Leu Phe Asn Asn Pro Val Pro Tyr Trp
1               5                   10                  15

Glu Val Gln Pro Ala Thr Phe Arg
            20

<210> SEQ ID NO 366
<211> LENGTH: 9
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 366

Leu Ala Ile Gln Phe Gly Asn Tyr Lys
1               5

<210> SEQ ID NO 367
<211> LENGTH: 12
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 367

Ala Leu Tyr Leu Gln Tyr Thr Asp Glu Thr Phe Arg
1               5                   10

<210> SEQ ID NO 368
<211> LENGTH: 13
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 368

Gly Ala Tyr Pro Leu Ser Ile Glu Pro Ile Gly Val Arg
1               5                   10

<210> SEQ ID NO 369
<211> LENGTH: 16
<212> TYPE: PRT
<213> ORGANISM: artificial
```

```
<220> FEATURE:
<223> OTHER INFORMATION: peptide fragment present in lectin-bound
      fraction isolated from human ovarian tumors

<400> SEQUENCE: 369

Asn Asn Glu Gly Thr Tyr Tyr Ser Pro Asn Tyr Asn Pro Gln Ser Arg
1               5                   10                  15

<210> SEQ ID NO 370
<211> LENGTH: 26
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 370

Asp Val Asp Lys Glu Phe Tyr Leu Phe Pro Thr Val Phe Asp Glu Asn
1               5                   10                  15

Glu Ser Leu Leu Leu Glu Asp Asn Ile Arg
            20                  25

<210> SEQ ID NO 371
<211> LENGTH: 21
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 371

Lys Ala Glu Glu Glu His Leu Gly Ile Leu Gly Pro Gln Leu His Ala
1               5                   10                  15

Asp Val Gly Asp Lys
            20

<210> SEQ ID NO 372
<211> LENGTH: 13
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 372

Val Asn Lys Asp Asp Glu Glu Phe Ile Glu Ser Asn Lys
1               5                   10

<210> SEQ ID NO 373
<211> LENGTH: 16
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 373

Val Asp Ala Thr Glu Glu Ser Asp Leu Ala Gln Gln Tyr Gly Val Arg
1               5                   10                  15

<210> SEQ ID NO 374
<211> LENGTH: 30
<212> TYPE: PRT
<213> ORGANISM: artificial
<220> FEATURE:
<223> OTHER INFORMATION: peptide fragment present in lectin-bound
      fraction isolated from human ovarian tumors
```

```
<400> SEQUENCE: 374

Thr Gly Pro Ala Ala Thr Thr Leu Pro Asp Gly Ala Ala Ala Glu Ser
1               5                   10                  15

Leu Val Glu Ser Ser Glu Val Ala Val Ile Gly Phe Phe Lys
            20                  25                  30

<210> SEQ ID NO 375
<211> LENGTH: 25
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 375

Gln Phe Leu Gln Ala Ala Glu Ala Ile Asp Asp Ile Pro Phe Gly Ile
1               5                   10                  15

Thr Ser Asn Ser Asp Val Phe Ser Lys
            20                  25

<210> SEQ ID NO 376
<211> LENGTH: 12
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 376

Tyr Gln Leu Asp Lys Asp Gly Val Val Leu Phe Lys
1               5                   10

<210> SEQ ID NO 377
<211> LENGTH: 9
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 377

Thr His Ile Leu Leu Phe Leu Pro Lys
1               5

<210> SEQ ID NO 378
<211> LENGTH: 8
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 378

Ile Leu Glu Phe Phe Gly Leu Lys
1               5

<210> SEQ ID NO 379
<211> LENGTH: 11
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 379

Asn Phe Glu Asp Val Ala Phe Asp Glu Lys Lys
1               5                   10
```

```
<210> SEQ ID NO 380
<211> LENGTH: 23
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 380

Val Ile Ser Thr Ile Thr Asn Asn Ile Gln Gln Ile Glu Ile Glu
1               5                   10                  15

Asp Thr Phe Glu Thr Leu Arg
            20

<210> SEQ ID NO 381
<211> LENGTH: 9
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 381

Ile Leu Gly Asp Pro Glu Ala Leu Arg
1               5

<210> SEQ ID NO 382
<211> LENGTH: 22
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 382

Asp Ile Leu Ala Thr Asn Gly Val Ile His Tyr Ile Asp Glu Leu Leu
1               5                   10                  15

Ile Pro Asp Ser Ala Lys
            20

<210> SEQ ID NO 383
<211> LENGTH: 19
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 383

Thr Leu Phe Glu Leu Ala Ala Glu Ser Asp Val Ser Thr Ala Ile Asp
1               5                   10                  15

Leu Phe Arg

<210> SEQ ID NO 384
<211> LENGTH: 12
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 384

Leu Thr Leu Leu Ala Pro Leu Asn Ser Val Phe Lys
1               5                   10
```

```
<210> SEQ ID NO 385
<211> LENGTH: 15
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 385

Glu Gly Val Tyr Thr Val Phe Ala Pro Thr Asn Glu Ala Phe Arg
1               5                   10                  15

<210> SEQ ID NO 386
<211> LENGTH: 12
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 386

Ser Leu Gln Gly Asp Lys Leu Glu Val Ser Leu Lys
1               5                   10

<210> SEQ ID NO 387
<211> LENGTH: 15
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 387

Asn Phe Ile Asn Asn Pro Leu Ala Gln Ala Asp Trp Ala Ala Lys
1               5                   10                  15

<210> SEQ ID NO 388
<211> LENGTH: 14
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 388

Val Ile Ser Gly Val Leu Gln Leu Gly Asn Ile Val Phe Lys
1               5                   10

<210> SEQ ID NO 389
<211> LENGTH: 7
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 389

Val Val Phe Gln Glu Phe Arg
1               5

<210> SEQ ID NO 390
<211> LENGTH: 10
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 390
```

Ala Leu Glu Leu Asp Ser Asn Leu Tyr Arg
1               5                   10

<210> SEQ ID NO 391
<211> LENGTH: 14
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 391

Ile Ala Glu Phe Thr Thr Asn Leu Thr Glu Glu Glu Glu Lys
1               5                   10

<210> SEQ ID NO 392
<211> LENGTH: 19
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 392

Ile Arg Glu Leu Glu Ser Gln Ile Ser Glu Leu Gln Glu Asp Leu Glu
1               5                   10                  15

Ser Glu Arg

<210> SEQ ID NO 393
<211> LENGTH: 27
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 393

Asp Leu Gly Glu Glu Leu Glu Ala Leu Lys Thr Glu Leu Glu Asp Thr
1               5                   10                  15

Leu Asp Ser Thr Ala Ala Gln Gln Glu Leu Arg
            20                  25

<210> SEQ ID NO 394
<211> LENGTH: 21
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 394

Asp Phe Ser Ala Leu Glu Ser Gln Leu Gln Asp Thr Gln Glu Leu Leu
1               5                   10                  15

Gln Glu Glu Asn Arg
            20

<210> SEQ ID NO 395
<211> LENGTH: 8
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 395

Asp Leu Glu Gly Leu Ser Gln Arg
1               5

-continued

<210> SEQ ID NO 396
<211> LENGTH: 16
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 396

Leu Gln Gln Glu Leu Asp Asp Leu Leu Val Asp Leu Asp His Gln Arg
1               5                   10                  15

<210> SEQ ID NO 397
<211> LENGTH: 19
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 397

Gln Ala Gln Gln Glu Arg Asp Glu Leu Ala Asp Glu Ile Ala Asn Ser
1               5                   10                  15

Ser Gly Lys

<210> SEQ ID NO 398
<211> LENGTH: 21
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 398

Ile Ala Gln Leu Glu Glu Glu Leu Glu Glu Glu Gln Gly Asn Thr Glu
1               5                   10                  15

Leu Ile Asn Asp Arg
            20

<210> SEQ ID NO 399
<211> LENGTH: 16
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 399

Ala Asn Leu Gln Ile Asp Gln Ile Asn Thr Asp Leu Asn Leu Glu Arg
1               5                   10                  15

<210> SEQ ID NO 400
<211> LENGTH: 13
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 400

Ile Ala Gln Leu Glu Glu Gln Leu Asp Asn Glu Thr Lys
1               5                   10

<210> SEQ ID NO 401
<211> LENGTH: 11
<212> TYPE: PRT

```
<213> ORGANISM: artificial
<220> FEATURE:
<223> OTHER INFORMATION: peptide fragment present in lectin-bound
      fraction isolated from human ovarian tumors

<400> SEQUENCE: 401

Gln Leu Glu Glu Ala Glu Glu Ala Gln Arg
1               5                   10

<210> SEQ ID NO 402
<211> LENGTH: 16
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 402

Gln Leu Leu Gln Ala Asn Pro Ile Leu Glu Ala Phe Gly Asn Ala Lys
1               5                   10                  15

<210> SEQ ID NO 403
<211> LENGTH: 11
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 403

Lys Glu Glu Glu Leu Gln Ala Ala Leu Ala Arg
1               5                   10

<210> SEQ ID NO 404
<211> LENGTH: 10
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 404

Lys Phe Asp Gln Leu Leu Ala Glu Glu Lys
1               5                   10

<210> SEQ ID NO 405
<211> LENGTH: 17
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 405

Thr Gln Leu Glu Glu Leu Glu Asp Glu Leu Gln Ala Thr Glu Asp Ala
1               5                   10                  15

Lys

<210> SEQ ID NO 406
<211> LENGTH: 11
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 406

Tyr Gly Leu Val Thr Tyr Ala Thr Tyr Pro Lys
```

-continued

<210> SEQ ID NO 407
<211> LENGTH: 14
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 407

Val Ser Glu Ala Asp Ser Ser Asn Ala Asp Trp Val Thr Lys
1               5                   10

<210> SEQ ID NO 408
<211> LENGTH: 16
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 408

Glu Ala Gly Ile Pro Glu Phe Tyr Asp Tyr Asp Val Ala Leu Ile Lys
1               5                   10                  15

<210> SEQ ID NO 409
<211> LENGTH: 15
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 409

Asn Phe Ile Asn Ser Pro Val Ala Gln Ala Asp Trp Ala Ala Lys
1               5                   10                  15

<210> SEQ ID NO 410
<211> LENGTH: 14
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 410

Val Val Ser Ser Val Leu Gln Leu Gly Asn Ile Val Phe Lys
1               5                   10

<210> SEQ ID NO 411
<211> LENGTH: 11
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 411

Val Asp Tyr Asn Ala Ser Ala Trp Leu Thr Lys
1               5                   10

<210> SEQ ID NO 412
<211> LENGTH: 17
<212> TYPE: PRT
<213> ORGANISM: artificial
<220> FEATURE:
<223> OTHER INFORMATION: peptide fragment present in lectin-bound
      fraction isolated from human ovarian tumors -continued

<400> SEQUENCE: 412

His Ala Gln Ala Val Glu Glu Leu Thr Glu Gln Leu Glu Gln Phe Lys
1               5                   10                  15

Arg

<210> SEQ ID NO 413
<211> LENGTH: 21
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 413

Asp Val Ala Ser Leu Ser Ser Gln Leu Gln Asp Thr Gln Glu Leu Leu
1               5                   10                  15

Gln Glu Glu Thr Arg
            20

<210> SEQ ID NO 414
<211> LENGTH: 15
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 414

Leu Gln Asp Phe Ala Ser Thr Val Glu Ala Leu Glu Glu Gly Lys
1               5                   10                  15

<210> SEQ ID NO 415
<211> LENGTH: 12
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 415

Glu Ile Glu Asn Leu Thr Gln Gln Tyr Glu Glu Lys
1               5                   10

<210> SEQ ID NO 416
<211> LENGTH: 16
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 416

Leu Gln Gln Glu Leu Asp Asp Leu Val Val Asp Leu Asp Asn Gln Arg
1               5                   10                  15

<210> SEQ ID NO 417
<211> LENGTH: 17
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 417

Lys Ala Thr Gln Gln Ala Glu Gln Leu Ser Asn Glu Leu Ala Thr Glu
1               5                   10                  15

Arg

<210> SEQ ID NO 418
<211> LENGTH: 13
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 418

Ile Ala Gln Leu Glu Glu Gln Val Glu Gln Glu Ala Arg
1               5                   10

<210> SEQ ID NO 419
<211> LENGTH: 16
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 419

Gln Leu Leu Gln Ala Asn Pro Ile Leu Glu Ala Phe Gly Asn Ala Lys
1               5                   10                  15

<210> SEQ ID NO 420
<211> LENGTH: 11
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 420

Lys Glu Glu Glu Leu Gln Ala Ala Leu Ala Arg
1               5                   10

<210> SEQ ID NO 421
<211> LENGTH: 10
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 421

Lys Phe Asp Gln Leu Leu Ala Glu Glu Lys
1               5                   10

<210> SEQ ID NO 422
<211> LENGTH: 17
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 422

Thr Gln Leu Glu Glu Leu Glu Asp Glu Leu Gln Ala Thr Glu Asp Ala
1               5                   10                  15
Lys

<210> SEQ ID NO 423
<211> LENGTH: 17
<212> TYPE: PRT
<213> ORGANISM: artificial

```
<220> FEATURE:
<223> OTHER INFORMATION: peptide fragment present in lectin-bound
      fraction isolated from human ovarian tumors

<400> SEQUENCE: 423

Thr Gln Leu Glu Glu Leu Glu Asp Glu Leu Gln Ala Thr Glu Asp Ala
1               5                   10                  15

Lys

<210> SEQ ID NO 424
<211> LENGTH: 9
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 424

Phe Tyr Gly Asp Glu Glu Lys Asp Lys
1               5

<210> SEQ ID NO 425
<211> LENGTH: 9
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 425

Gly Leu Gln Thr Ser Gln Asp Ala Arg
1               5

<210> SEQ ID NO 426
<211> LENGTH: 14
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 426

Phe Tyr Ala Leu Ser Ala Ser Phe Glu Pro Phe Ser Asn Lys
1               5                   10

<210> SEQ ID NO 427
<211> LENGTH: 22
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 427

Ile Asp Asn Ser Gln Val Glu Ser Gly Ser Leu Glu Asp Asp Trp Asp
1               5                   10                  15

Phe Leu Pro Pro Lys Lys
            20

<210> SEQ ID NO 428
<211> LENGTH: 29
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 428
```

Ser Gly Thr Ile Phe Asp Asn Phe Leu Ile Thr Asn Asp Glu Ala Tyr
1               5                   10                  15

Ala Glu Glu Phe Gly Asn Glu Thr Trp Gly Val Thr Lys
            20                  25

<210> SEQ ID NO 429
<211> LENGTH: 23
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 429

Thr Asp Leu Asn Pro Asp Asn Leu Gln Gly Gly Asp Asp Leu Asp Pro
1               5                   10                  15

Asn Tyr Val Leu Ser Ser Arg
            20

<210> SEQ ID NO 430
<211> LENGTH: 16
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 430

Leu Ala Val Glu Ala Leu Ser Ser Leu Asp Gly Asp Leu Ala Gly Arg
1               5                   10                  15

<210> SEQ ID NO 431
<211> LENGTH: 21
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 431

Gly Thr Gly Gly Val Asp Thr Ala Ala Val Gly Gly Val Phe Asp Val
1               5                   10                  15

Ser Asn Ala Asp Arg
            20

<210> SEQ ID NO 432
<211> LENGTH: 17
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 432

Leu Gly Phe Ser Glu Val Glu Leu Val Gln Met Val Val Asp Gly Val
1               5                   10                  15

Lys

<210> SEQ ID NO 433
<211> LENGTH: 11
<212> TYPE: PRT
<213> ORGANISM: artificial
<220> FEATURE:
<223> OTHER INFORMATION: peptide fragment present in lectin-bound
      fraction isolated from human ovarian tumors

```
<400> SEQUENCE: 433

Leu Ala Asp Gly Gly Ala Thr Asn Gln Gly Arg
1               5                   10

<210> SEQ ID NO 434
<211> LENGTH: 14
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 434

Glu Leu Ser Glu Ala Leu Gly Gln Ile Phe Asp Ser Gln Arg
1               5                   10

<210> SEQ ID NO 435
<211> LENGTH: 17
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 435

Thr Leu Gln Ala Leu Glu Phe His Thr Val Pro Phe Gln Leu Leu Ala
1               5                   10                  15

Arg

<210> SEQ ID NO 436
<211> LENGTH: 19
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 436

Ile Tyr Thr Ser Pro Thr Trp Ser Ala Phe Val Thr Asp Ser Ser Trp
1               5                   10                  15

Ser Ala Arg

<210> SEQ ID NO 437
<211> LENGTH: 13
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 437

Ile Pro Gly Asp Gln Val Val Ser Val Val Phe Ile Lys
1               5                   10

<210> SEQ ID NO 438
<211> LENGTH: 20
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 438

Val Ile Ser Ser Gly Ser Val Ala Ser Tyr Val Thr Ser Pro Gln Gly
1               5                   10                  15

Phe Gln Phe Arg
```

20

```
<210> SEQ ID NO 439
<211> LENGTH: 11
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 439

Ala Ser Tyr Ala Gln Gln Pro Ala Glu Ser Arg
1               5                   10

<210> SEQ ID NO 440
<211> LENGTH: 13
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 440

Ile Ala His Val Glu Leu Ala Asp Ala Gly Gln Tyr Arg
1               5                   10

<210> SEQ ID NO 441
<211> LENGTH: 11
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 441

Tyr Glu Leu Gly Ser Gly Leu Ala Val Leu Arg
1               5                   10

<210> SEQ ID NO 442
<211> LENGTH: 15
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 442

Asn Phe Ile Asn Ser Pro Val Ala Gln Ala Asp Trp Ala Ala Lys
1               5                   10                  15

<210> SEQ ID NO 443
<211> LENGTH: 14
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 443

Val Val Ser Ser Val Leu Gln Leu Gly Asn Ile Val Phe Lys
1               5                   10

<210> SEQ ID NO 444
<211> LENGTH: 11
<212> TYPE: PRT
<213> ORGANISM: artificial
<220> FEATURE:
<223> OTHER INFORMATION: peptide fragment present in lectin-bound
      fraction isolated from human ovarian tumors
```

```
<400> SEQUENCE: 444

Val Asp Tyr Asn Ala Ser Ala Trp Leu Thr Lys
1               5                   10

<210> SEQ ID NO 445
<211> LENGTH: 17
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 445

His Ala Gln Ala Val Glu Glu Leu Thr Glu Gln Leu Glu Gln Phe Lys
1               5                   10                  15
Arg

<210> SEQ ID NO 446
<211> LENGTH: 21
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 446

Asp Val Ala Ser Leu Ser Ser Gln Leu Gln Asp Thr Gln Glu Leu Leu
1               5                   10                  15
Gln Glu Glu Thr Arg
            20

<210> SEQ ID NO 447
<211> LENGTH: 15
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 447

Leu Gln Asp Phe Ala Ser Thr Val Glu Ala Leu Glu Glu Gly Lys
1               5                   10                  15

<210> SEQ ID NO 448
<211> LENGTH: 12
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 448

Glu Ile Glu Asn Leu Thr Gln Gln Tyr Glu Glu Lys
1               5                   10

<210> SEQ ID NO 449
<211> LENGTH: 16
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 449

Leu Gln Gln Glu Leu Asp Asp Leu Val Val Asp Leu Asp Asn Gln Arg
1               5                   10                  15
```

```
<210> SEQ ID NO 450
<211> LENGTH: 17
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 450

Lys Ala Thr Gln Gln Ala Glu Gln Leu Ser Asn Glu Leu Ala Thr Glu
1               5                   10                  15

Arg

<210> SEQ ID NO 451
<211> LENGTH: 13
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 451

Ile Ala Gln Leu Glu Glu Gln Val Glu Gln Glu Ala Arg
1               5                   10

<210> SEQ ID NO 452
<211> LENGTH: 16
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 452

Gln Leu Leu Gln Ala Asn Pro Ile Leu Glu Ala Phe Gly Asn Ala Lys
1               5                   10                  15

<210> SEQ ID NO 453
<211> LENGTH: 11
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 453

Lys Glu Glu Glu Leu Gln Ala Ala Leu Ala Arg
1               5                   10

<210> SEQ ID NO 454
<211> LENGTH: 10
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 454

Lys Phe Asp Gln Leu Leu Ala Glu Glu Lys
1               5                   10

<210> SEQ ID NO 455
<211> LENGTH: 17
<212> TYPE: PRT
<213> ORGANISM: artificial
<220> FEATURE:
<223> OTHER INFORMATION: peptide fragment present in lectin-bound
``` fraction isolated from human ovarian tumors

<400> SEQUENCE: 455

Thr Gln Leu Glu Glu Leu Glu Asp Glu Leu Gln Ala Thr Glu Asp Ala
1               5                   10                  15

Lys

<210> SEQ ID NO 456
<211> LENGTH: 11
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 456

Leu Ala Pro Glu Tyr Glu Ala Ala Ala Thr Arg
1               5                   10

<210> SEQ ID NO 457
<211> LENGTH: 10
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 457

Tyr Gly Val Ser Gly Tyr Pro Thr Leu Lys
1               5                   10

<210> SEQ ID NO 458
<211> LENGTH: 12
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 458

Asp Gly Glu Glu Ala Gly Ala Tyr Asp Gly Pro Arg
1               5                   10

<210> SEQ ID NO 459
<211> LENGTH: 26
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 459

Phe Ile Ser Asp Lys Asp Ala Ser Ile Val Gly Phe Phe Asp Asp Ser
1               5                   10                  15

Phe Ser Glu Ala His Ser Glu Phe Leu Lys
            20                  25

<210> SEQ ID NO 460
<211> LENGTH: 24
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 460

Phe Ala His Thr Asn Val Glu Ser Leu Val Asn Glu Tyr Asp Asp Asn

```
                1               5                  10                 15

Gly Glu Gly Ile Ile Leu Phe Arg
            20

<210> SEQ ID NO 461
<211> LENGTH: 13
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 461

Asp Leu Leu Ile Ala Tyr Tyr Asp Val Asp Tyr Glu Lys
1               5                   10

<210> SEQ ID NO 462
<211> LENGTH: 24
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 462

Thr Phe Ser His Glu Leu Ser Asp Phe Gly Leu Glu Ser Thr Ala Gly
1               5                   10                  15

Glu Ile Pro Val Val Ala Ile Arg
            20

<210> SEQ ID NO 463
<211> LENGTH: 11
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 463

Phe Leu Gln Asp Tyr Phe Asp Gly Asn Leu Lys
1               5                   10

<210> SEQ ID NO 464
<211> LENGTH: 12
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 464

Phe Leu Gln Asp Tyr Phe Asp Gly Asn Leu Lys Arg
1               5                   10

<210> SEQ ID NO 465
<211> LENGTH: 13
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 465

Ser Glu Pro Ile Pro Glu Ser Asn Asp Gly Pro Val Lys
1               5                   10

<210> SEQ ID NO 466
```

-continued

```
<211> LENGTH: 11
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 466

Glu Leu Ser Asp Phe Ile Ser Tyr Leu Gln Arg
1               5                  10

<210> SEQ ID NO 467
<211> LENGTH: 9
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 467

Phe Asp Ser Phe Thr Val Gln Tyr Lys
1               5

<210> SEQ ID NO 468
<211> LENGTH: 15
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 468

Leu Gly Glu Leu Trp Val Thr Asp Pro Thr Pro Asp Ser Leu Arg
1               5                  10                  15

<210> SEQ ID NO 469
<211> LENGTH: 15
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 469

Leu Gly Pro Ile Ser Ala Asp Ser Thr Thr Ala Pro Leu Glu Lys
1               5                  10                  15

<210> SEQ ID NO 470
<211> LENGTH: 15
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 470

Leu Ser Gln Leu Ser Val Thr Asp Val Thr Thr Ser Ser Leu Arg
1               5                  10                  15

<210> SEQ ID NO 471
<211> LENGTH: 10
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 471

Leu Phe Asp Gln Ala Phe Gly Leu Pro Arg
```

```
                    1               5                   10
```

<210> SEQ ID NO 472
<211> LENGTH: 38
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 472

```
Leu Pro Glu Glu Trp Ser Gln Trp Leu Gly Gly Ser Ser Trp Pro Gly
1               5                   10                  15

Tyr Val Arg Pro Leu Pro Pro Ala Ala Ile Glu Ser Pro Ala Val Ala
            20                  25                  30

Ala Pro Ala Tyr Ser Arg
        35
```

<210> SEQ ID NO 473
<211> LENGTH: 16
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 473

```
Val Ser Leu Asp Val Asn His Phe Ala Pro Asp Glu Leu Thr Val Lys
1               5                   10                  15
```

<210> SEQ ID NO 474
<211> LENGTH: 11
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 474

```
Thr Lys Asp Gly Val Val Glu Ile Thr Gly Lys
1               5                   10
```

<210> SEQ ID NO 475
<211> LENGTH: 17
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 475

```
Leu Ala Thr Gln Ser Asn Glu Ile Thr Ile Pro Val Thr Phe Glu Ser
1               5                   10                  15

Arg
```

<210> SEQ ID NO 476
<211> LENGTH: 17
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 476

```
Thr Leu Ala Gln Leu Asn Pro Glu Ser Ser Leu Phe Ile Ile Ala Ser
1               5                   10                  15
```

Lys

<210> SEQ ID NO 477
<211> LENGTH: 15
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 477

Thr Phe Thr Thr Gln Glu Thr Ile Thr Asn Ala Glu Thr Ala Lys
1               5                   10                  15

<210> SEQ ID NO 478
<211> LENGTH: 9
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 478

Asn Asn Gln Ile Thr Asn Asn Gln Arg
1               5

<210> SEQ ID NO 479
<211> LENGTH: 11
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 479

Tyr Ser Leu Glu Pro Val Ala Val Glu Leu Lys
1               5                   10

<210> SEQ ID NO 480
<211> LENGTH: 15
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 480

Leu Gly Asp Val Tyr Val Asn Asp Ala Phe Gly Thr Ala His Arg
1               5                   10                  15

<210> SEQ ID NO 481
<211> LENGTH: 17
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 481

Ala Leu Glu Ser Pro Glu Arg Pro Phe Leu Ala Ile Leu Gly Gly Ala
1               5                   10                  15

Lys

<210> SEQ ID NO 482
<211> LENGTH: 18
<212> TYPE: PRT
<213> ORGANISM: artificial
<220> FEATURE:

-continued

<223> OTHER INFORMATION: peptide fragment present in lectin-bound
      fraction isolated from human ovarian tumors

<400> SEQUENCE: 482

Ile Thr Leu Pro Val Asp Phe Val Thr Ala Asp Lys Phe Asp Glu Asn
1               5                   10                  15

Ala Lys

<210> SEQ ID NO 483
<211> LENGTH: 7
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 483

Tyr Ala Glu Ala Val Thr Arg
1               5

<210> SEQ ID NO 484
<211> LENGTH: 18
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 484

Gln Ile Val Trp Asn Gly Pro Val Gly Val Phe Glu Trp Glu Ala Phe
1               5                   10                  15

Ala Arg

<210> SEQ ID NO 485
<211> LENGTH: 24
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 485

Trp Asn Thr Glu Asp Lys Val Ser His Val Ser Thr Gly Gly Gly Ala
1               5                   10                  15

Ser Leu Glu Leu Leu Glu Gly Lys
            20

<210> SEQ ID NO 486
<211> LENGTH: 19
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 486

Ser Thr Ala Ile Ser Leu Phe Tyr Glu Leu Ser Glu Asn Asp Leu Asn
1               5                   10                  15

Phe Ile Lys

<210> SEQ ID NO 487
<211> LENGTH: 18
<212> TYPE: PRT
<213> ORGANISM: artificial
<220> FEATURE:
<223> OTHER INFORMATION: peptide fragment present in lectin-bound -continued fraction isolated from human ovarian tumors

<400> SEQUENCE: 487

Ala Leu Leu Glu Leu Gln Leu Glu Pro Glu Glu Leu Tyr Gln Thr Phe
1               5                   10                  15

Gln Arg

<210> SEQ ID NO 488
<211> LENGTH: 20
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 488

Ala Arg Pro Phe Pro Asp Gly Leu Ala Glu Asp Ile Asp Lys Gly Glu
1               5                   10                  15

Val Ser Ala Arg
            20

<210> SEQ ID NO 489
<211> LENGTH: 9
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 489

Tyr Glu Trp Asp Val Ala Glu Ala Arg
1               5

<210> SEQ ID NO 490
<211> LENGTH: 16
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 490

Ala Tyr Leu Pro Val Asn Glu Ser Phe Gly Phe Thr Ala Asp Leu Arg
1               5                   10                  15

<210> SEQ ID NO 491
<211> LENGTH: 21
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 491

Leu Gly Glu Ile Val Thr Thr Ile Pro Thr Ile Gly Phe Asn Val Glu
1               5                   10                  15

Thr Val Glu Tyr Lys
            20

<210> SEQ ID NO 492
<211> LENGTH: 14
<212> TYPE: PRT
<213> ORGANISM: artificial
<220> FEATURE:
<223> OTHER INFORMATION: peptide fragment present in lectin-bound
      fraction isolated from human ovarian tumors

```
<400> SEQUENCE: 492

Asn Ile Ser Phe Thr Val Trp Asp Val Gly Gly Gln Asp Lys
1               5                   10

<210> SEQ ID NO 493
<211> LENGTH: 21
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 493

Leu Gly Glu Ile Val Thr Thr Ile Pro Thr Ile Gly Phe Asn Val Glu
1               5                   10                  15

Thr Val Glu Tyr Lys
            20

<210> SEQ ID NO 494
<211> LENGTH: 14
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 494

Asn Ile Ser Phe Thr Val Trp Asp Val Gly Gly Gln Asp Lys
1               5                   10

<210> SEQ ID NO 495
<211> LENGTH: 17
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 495

Thr Asp Tyr Asn Ala Ser Val Ser Val Pro Asp Ser Ser Gly Pro Glu
1               5                   10                  15

Arg

<210> SEQ ID NO 496
<211> LENGTH: 16
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 496

Ile Leu Ser Ile Ser Ala Asp Ile Glu Thr Ile Gly Glu Ile Leu Lys
1               5                   10                  15

<210> SEQ ID NO 497
<211> LENGTH: 15
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 497

Leu Leu Ile His Gln Ser Leu Ala Gly Gly Ile Ile Gly Val Lys
1               5                   10                  15
```

```
<210> SEQ ID NO 498
<211> LENGTH: 12
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 498

Ile Ile Leu Asp Leu Ile Ser Glu Ser Pro Ile Lys
1               5                   10

<210> SEQ ID NO 499
<211> LENGTH: 11
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 499

Ile Asp Glu Pro Leu Glu Gly Ser Glu Asp Arg
1               5                   10

<210> SEQ ID NO 500
<211> LENGTH: 23
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 500

Ile Ile Thr Ile Thr Gly Thr Gln Asp Gln Ile Gln Asn Ala Gln Tyr
1               5                   10                  15

Leu Leu Gln Asn Ser Val Lys
            20

<210> SEQ ID NO 501
<211> LENGTH: 17
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 501

Asp Gln Leu Ile Tyr Asn Leu Leu Lys Glu Glu Gln Thr Pro Gln Asn
1               5                   10                  15

Lys

<210> SEQ ID NO 502
<211> LENGTH: 15
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 502

Asp Leu Ala Asp Glu Leu Ala Leu Val Asp Val Ile Glu Asp Lys
1               5                   10                  15

<210> SEQ ID NO 503
<211> LENGTH: 17
<212> TYPE: PRT
<213> ORGANISM: artificial
```

```
<220> FEATURE:
<223> OTHER INFORMATION: peptide fragment present in lectin-bound
      fraction isolated from human ovarian tumors

<400> SEQUENCE: 503

Asp Leu Ala Asp Glu Leu Ala Leu Val Asp Val Ile Glu Asp Lys Leu
1               5                   10                  15

Lys

<210> SEQ ID NO 504
<211> LENGTH: 16
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 504

Thr Leu His Pro Asp Leu Gly Thr Asp Lys Asp Lys Glu Gln Trp Lys
1               5                   10                  15

<210> SEQ ID NO 505
<211> LENGTH: 11
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 505

Gln Val Val Glu Ser Ala Tyr Glu Val Ile Lys
1               5                   10

<210> SEQ ID NO 506
<211> LENGTH: 10
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 506

Val Thr Leu Thr Ser Glu Glu Glu Ala Arg
1               5                   10

<210> SEQ ID NO 507
<211> LENGTH: 10
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 507

Ser Ala Asp Thr Leu Trp Gly Ile Gln Lys
1               5                   10

<210> SEQ ID NO 508
<211> LENGTH: 6
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 508

Leu Asn Leu Val Gln Arg
1               5
```

```
<210> SEQ ID NO 509
<211> LENGTH: 20
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 509

Leu Val Pro Leu Leu Asp Thr Gly Asp Ile Ile Ile Asp Gly Gly Asn
1               5                   10                  15

Ser Glu Tyr Arg
            20

<210> SEQ ID NO 510
<211> LENGTH: 17
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 510

Gly Ile Leu Phe Val Gly Ser Gly Val Ser Gly Gly Glu Glu Gly Ala
1               5                   10                  15

Arg

<210> SEQ ID NO 511
<211> LENGTH: 23
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 511

Trp Thr Ala Ile Ser Ala Leu Glu Tyr Gly Val Pro Val Thr Leu Ile
1               5                   10                  15

Gly Glu Ala Val Phe Ala Arg
20

<210> SEQ ID NO 512
<211> LENGTH: 16
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 512

Phe Gln Asp Gly Asp Leu Thr Leu Tyr Gln Ser Asn Thr Ile Leu Arg
1               5                   10                  15

<210> SEQ ID NO 513
<211> LENGTH: 19
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 513

Asp Gln Gln Glu Ala Ala Leu Val Asp Met Val Asn Asp Gly Val Glu
1               5                   10                  15

Asp Leu Arg
```

```
<210> SEQ ID NO 514
<211> LENGTH: 9
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 514

Leu Pro Phe Pro Ile Ile Asp Asp Arg
1               5

<210> SEQ ID NO 515
<211> LENGTH: 7
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 515

Asn Phe Asp Glu Ile Leu Arg
1               5

<210> SEQ ID NO 516
<211> LENGTH: 14
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 516

Asn Val Thr Glu Leu Asn Glu Pro Leu Ser Asn Glu Glu Arg
1               5                   10

<210> SEQ ID NO 517
<211> LENGTH: 10
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 517

Tyr Leu Ala Glu Val Ala Thr Gly Glu Lys
1               5                   10

<210> SEQ ID NO 518
<211> LENGTH: 10
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 518

Ala Tyr Ser Glu Ala His Glu Ile Ser Lys
1               5                   10

<210> SEQ ID NO 519
<211> LENGTH: 19
<212> TYPE: PRT
<213> ORGANISM: artificial
<220> FEATURE:
<223> OTHER INFORMATION: peptide fragment present in lectin-bound
      fraction isolated from human ovarian tumors
```

```
<400> SEQUENCE: 519

Thr Ala Phe Asp Asp Ala Ile Ala Glu Leu Asp Thr Leu Asn Glu Asp
1               5                   10                  15

Ser Tyr Lys

<210> SEQ ID NO 520
<211> LENGTH: 19
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 520

Val Ala Val Leu Gly Ala Ser Gly Gly Ile Gly Gln Pro Leu Ser Leu
1               5                   10                  15

Leu Leu Lys

<210> SEQ ID NO 521
<211> LENGTH: 11
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 521

Ile Phe Gly Val Thr Thr Leu Asp Ile Val Arg
1               5                   10

<210> SEQ ID NO 522
<211> LENGTH: 14
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 522

Val Asp Phe Pro Gln Asp Gln Leu Thr Ala Leu Thr Gly Arg
1               5                   10

<210> SEQ ID NO 523
<211> LENGTH: 21
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 523

Ile Pro Glu Ser Gly Gly Asp Asn Ser Val Phe Asp Ile Phe Glu Leu
1               5                   10                  15

Thr Gly Ala Ala Arg
                20

<210> SEQ ID NO 524
<211> LENGTH: 23
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 524

Ile Glu Asp Ala Asn Leu Ile Pro Pro Val Pro Asp Asp Lys Phe Gln
1               5                   10                  15
```

Asp Leu Val Asp Ala Val Arg
                20

<210> SEQ ID NO 525
<211> LENGTH: 15
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 525

Gly Gly Val Asn Asp Asn Phe Gln Gly Val Leu Gln Asn Val Arg
1               5                   10                  15

<210> SEQ ID NO 526
<211> LENGTH: 12
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 526

Phe Val Phe Gly Thr Thr Pro Glu Asp Ile Leu Arg
1               5                   10

<210> SEQ ID NO 527
<211> LENGTH: 11
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 527

Thr Ile Val Thr Thr Leu Gln Asp Ser Ile Arg
1               5                   10

<210> SEQ ID NO 528
<211> LENGTH: 13
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 528

Gln Val Thr Gln Ser Tyr Trp Asp Thr Asn Pro Thr Arg
1               5                   10

<210> SEQ ID NO 529
<211> LENGTH: 14
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 529

Asn Ala Leu Trp His Thr Gly Asn Thr Pro Gly Gln Val Arg
1               5                   10

<210> SEQ ID NO 530
<211> LENGTH: 16
<212> TYPE: PRT
<213> ORGANISM: artificial

```
-continued

<220> FEATURE:
<223> OTHER INFORMATION: peptide fragment present in lectin-bound
      fraction isolated from human ovarian tumors

<400> SEQUENCE: 530

Gly Thr Tyr Ile Pro Val Pro Ile Val Ser Glu Leu Gln Ser Gly Lys
1               5                   10                  15

<210> SEQ ID NO 531
<211> LENGTH: 17
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 531

Lys Asp Gly Thr His Val Val Glu Asn Val Asp Ala Thr His Ile Gly
1               5                   10                  15

Lys

<210> SEQ ID NO 532
<211> LENGTH: 16
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 532

Asp Gly Thr His Val Val Glu Asn Val Asp Ala Thr His Ile Gly Lys
1               5                   10                  15

<210> SEQ ID NO 533
<211> LENGTH: 9
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 533

Phe Gln Glu Gly Gln Glu Glu Glu Arg
1               5

<210> SEQ ID NO 534
<211> LENGTH: 12
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 534

Ser Thr Val Leu Thr Ile Pro Glu Ile Ile Ile Lys
1               5                   10

<210> SEQ ID NO 535
<211> LENGTH: 22
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 535

Val Gln Asp Asp Glu Val Gly Asp Gly Thr Thr Ser Val Thr Val Leu
1               5                   10                  15
```

Ala Ala Glu Leu Leu Arg
            20

<210> SEQ ID NO 536
<211> LENGTH: 18
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 536

Leu Gly Gly Ser Leu Ala Asp Ser Tyr Leu Asp Glu Gly Phe Leu Leu
1               5                   10                  15

Asp Lys

<210> SEQ ID NO 537
<211> LENGTH: 12
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 537

Gly Ala Thr Gln Gln Ile Leu Asp Glu Ala Glu Arg
1               5                   10

<210> SEQ ID NO 538
<211> LENGTH: 10
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 538

Asp Gly Ala Gly Asp Val Ala Phe Ile Arg
1               5                   10

<210> SEQ ID NO 539
<211> LENGTH: 19
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 539

Ile Asp Ser Gly Leu Tyr Leu Gly Ser Gly Tyr Phe Thr Ala Ile Gln
1               5                   10                  15

Asn Leu Arg

<210> SEQ ID NO 540
<211> LENGTH: 13
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 540

Asp Pro Val Gln Leu Asn Leu Leu Tyr Val Gln Ala Arg
1               5                   10

<210> SEQ ID NO 541

```
<211> LENGTH: 26
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 541

Ala Val Ser Ser Ala Ile Ala Gln Leu Leu Gly Glu Val Ala Gln Gly
1               5                   10                  15

Asn Glu Asn Tyr Ala Gly Ile Ala Ala Arg
            20                  25

<210> SEQ ID NO 542
<211> LENGTH: 8
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 542

Ala Val Thr Gln Ala Leu Asn Arg
1               5

<210> SEQ ID NO 543
<211> LENGTH: 20
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 543

Leu Asn Glu Ala Ala Ala Gly Leu Asn Gln Ala Ala Thr Glu Leu Val
1               5                   10                  15

Gln Ala Ser Arg
            20

<210> SEQ ID NO 544
<211> LENGTH: 14
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 544

Thr Leu Ala Glu Ser Ala Leu Gln Leu Leu Tyr Thr Ala Lys
1               5                   10

<210> SEQ ID NO 545
<211> LENGTH: 14
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 545

Leu Ala Gln Ala Ala Gln Ser Ser Val Ala Thr Ile Thr Arg
1               5                   10

<210> SEQ ID NO 546
<211> LENGTH: 23
<212> TYPE: PRT
<213> ORGANISM: artificial
<220> FEATURE:
```

<223> OTHER INFORMATION: peptide fragment present in lectin-bound
      fraction isolated from human ovarian tumors

<400> SEQUENCE: 546

Val Gly Ala Ile Pro Ala Asn Ala Leu Asp Asp Gly Gln Trp Ser Gln
1               5                   10                  15

Gly Leu Ile Ser Ala Ala Arg
            20

<210> SEQ ID NO 547
<211> LENGTH: 14
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 547

Thr Gly Glu Ala Ile Val Asp Ala Ala Leu Ser Ala Leu Arg
1               5                   10

<210> SEQ ID NO 548
<211> LENGTH: 15
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 548

Leu Ala Ala Val Asp Ala Thr Val Asn Gln Val Leu Ala Ser Arg
1               5                   10                  15

<210> SEQ ID NO 549
<211> LENGTH: 24
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 549

Ala Leu Asp Leu Phe Ser Asp Asn Ala Pro Pro Pro Glu Leu Leu Glu
1               5                   10                  15

Ile Ile Asn Glu Asp Ile Ala Lys
            20

<210> SEQ ID NO 550
<211> LENGTH: 9
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 550

Asn Ser Tyr Leu Glu Val Leu Leu Lys
1               5

<210> SEQ ID NO 551
<211> LENGTH: 13
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 551

Gly Ser Phe Ser Glu Gln Gly Ile Asn Glu Phe Leu Arg
1               5                   10

<210> SEQ ID NO 552
<211> LENGTH: 17
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 552

Gly Ser Thr Ala Pro Val Gly Gly Gly Ala Phe Pro Thr Ile Val Glu
1               5                   10                  15

Arg

<210> SEQ ID NO 553
<211> LENGTH: 23
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 553

Asn Asp Phe Gln Leu Ile Gly Ile Gln Asp Gly Tyr Leu Ser Leu Leu
1               5                   10                  15

Gln Asp Ser Gly Glu Val Arg
            20

<210> SEQ ID NO 554
<211> LENGTH: 17
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 554

Glu Asp Leu Arg Leu Pro Glu Gly Asp Leu Gly Lys Glu Ile Glu Gln
1               5                   10                  15

Lys

<210> SEQ ID NO 555
<211> LENGTH: 9
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 555

Asp Gln Pro Phe Thr Ile Leu Tyr Arg
1               5

<210> SEQ ID NO 556
<211> LENGTH: 11
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 556

Tyr Pro Gly Ala Tyr Tyr Ile Phe Gln Ile Lys
1               5                   10

```
<210> SEQ ID NO 557
<211> LENGTH: 17
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 557

Thr Thr Pro Pro Met Leu Asp Ser Asp Gly Ser Phe Phe Leu Tyr Ser
1               5                   10                  15

Lys

<210> SEQ ID NO 558
<211> LENGTH: 16
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 558

Val Val Ser Val Leu Thr Val Val His Gln Asp Trp Leu Asn Gly Lys
1               5                   10                  15

<210> SEQ ID NO 559
<211> LENGTH: 22
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 559

Gly Phe Tyr Pro Ser Asp Ile Ala Val Glu Trp Glu Ser Asn Gly Gln
1               5                   10                  15

Pro Glu Asn Asn Tyr Lys
            20

<210> SEQ ID NO 560
<211> LENGTH: 12
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 560

Asn Glu Asp Ser Leu Val Phe Val Gln Thr Asp Lys
1               5                   10

<210> SEQ ID NO 561
<211> LENGTH: 14
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 561

Ile Ala Gln Trp Gln Ser Phe Gln Leu Glu Gly Gly Leu Lys
1               5                   10

<210> SEQ ID NO 562
<211> LENGTH: 16
<212> TYPE: PRT
<213> ORGANISM: artificial
```

```
<220> FEATURE:
<223> OTHER INFORMATION: peptide fragment present in lectin-bound
      fraction isolated from human ovarian tumors

<400> SEQUENCE: 562

Gln Phe Ser Phe Pro Leu Ser Ser Glu Pro Phe Gln Gly Ser Tyr Lys
1               5                   10                  15

<210> SEQ ID NO 563
<211> LENGTH: 14
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 563

Thr Glu His Pro Phe Thr Val Glu Glu Phe Val Leu Pro Lys
1               5                   10

<210> SEQ ID NO 564
<211> LENGTH: 9
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 564

Phe Glu Val Gln Val Thr Val Pro Lys
1               5

<210> SEQ ID NO 565
<211> LENGTH: 10
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 565

Gln Gly Ile Pro Phe Phe Gly Gln Val Arg
1               5                   10

<210> SEQ ID NO 566
<211> LENGTH: 18
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 566

Leu Leu Ile Tyr Ala Val Leu Pro Thr Gly Asp Val Ile Gly Asp Ser
1               5                   10                  15

Ala Lys

<210> SEQ ID NO 567
<211> LENGTH: 18
<212> TYPE: PRT
<213> ORGANISM: artificial
<220> FEATURE:
<223> OTHER INFORMATION: peptide fragment present in lectin-bound
      fraction isolated from human ovarian tumors
```

```
<400> SEQUENCE: 567

Val Ser Val Gln Leu Glu Ala Ser Pro Ala Phe Leu Ala Val Pro Val
1               5                   10                  15

Glu Lys

<210> SEQ ID NO 568
<211> LENGTH: 16
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 568

Asp Thr Val Ile Lys Pro Leu Leu Val Glu Pro Glu Gly Leu Glu Lys
1               5                   10                  15

<210> SEQ ID NO 569
<211> LENGTH: 11
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 569

Leu Pro Pro Asn Val Val Glu Glu Ser Ala Arg
1               5                   10

<210> SEQ ID NO 570
<211> LENGTH: 11
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 570

Ala Ile Gly Tyr Leu Asn Thr Gly Tyr Gln Arg
1               5                   10

<210> SEQ ID NO 571
<211> LENGTH: 14
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 571

Thr Ala Gln Glu Gly Asp His Gly Ser His Val Tyr Thr Lys
1               5                   10

<210> SEQ ID NO 572
<211> LENGTH: 15
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 572

Ala Leu Leu Ala Tyr Ala Phe Ala Leu Ala Gly Asn Gln Asp Lys
1               5                   10                  15
```

```
<210> SEQ ID NO 573
<211> LENGTH: 8
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 573

Phe Gln Val Asp Asn Asn Asn Arg
1               5

<210> SEQ ID NO 574
<211> LENGTH: 19
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 574

Val Ser Asn Gln Thr Leu Ser Leu Phe Phe Thr Val Leu Gln Asp Val
1               5                   10                  15

Pro Val Arg

<210> SEQ ID NO 575
<211> LENGTH: 13
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 575

Asn Gln Gly Asn Thr Trp Leu Thr Ala Phe Val Leu Lys
1               5                   10

<210> SEQ ID NO 576
<211> LENGTH: 11
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 576

Ser Ser Gly Ser Leu Leu Asn Asn Ala Ile Lys
1               5                   10

<210> SEQ ID NO 577
<211> LENGTH: 8
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 577

Tyr Gly Ala Ala Thr Phe Thr Arg
1               5

<210> SEQ ID NO 578
<211> LENGTH: 22
<212> TYPE: PRT
<213> ORGANISM: artificial
<220> FEATURE:
<223> OTHER INFORMATION: peptide fragment present in lectin-bound
      fraction isolated from human ovarian tumors
```

-continued

```
<400> SEQUENCE: 578

Glu Lys Pro Tyr Phe Pro Ile Pro Glu Glu Tyr Thr Phe Ile Gln Asn
1               5                   10                  15

Val Pro Leu Glu Asp Arg
            20

<210> SEQ ID NO 579
<211> LENGTH: 15
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 579

Asn Phe Ile Leu Asp Gln Thr Asn Val Ser Ala Ala Ala Gln Arg
1               5                   10                  15

<210> SEQ ID NO 580
<211> LENGTH: 11
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 580

His Gly Glu Ser Ala Trp Asn Leu Glu Asn Arg
1               5                   10

<210> SEQ ID NO 581
<211> LENGTH: 14
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 581

Ala Leu Pro Phe Trp Asn Glu Glu Ile Val Pro Gln Ile Lys
1               5                   10

<210> SEQ ID NO 582
<211> LENGTH: 14
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 582

Gln Met Glu Gln Ile Ser Gln Phe Leu Gln Ala Ala Glu Arg
1               5                   10

<210> SEQ ID NO 583
<211> LENGTH: 18
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 583

Tyr Gly Ile Asn Thr Thr Asp Ile Phe Gln Thr Val Asp Leu Trp Glu
1               5                   10                  15

Gly Lys
```

```
<210> SEQ ID NO 584
<211> LENGTH: 14
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 584

Asp Asp Gly Leu Phe Ser Gly Asp Pro Asn Trp Phe Pro Lys
1               5                   10

<210> SEQ ID NO 585
<211> LENGTH: 11
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 585

Asn Phe Ser Asp Asn Gln Leu Gln Glu Gly Lys
1               5                   10

<210> SEQ ID NO 586
<211> LENGTH: 8
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 586

Val Thr Val Leu Gly Gln Pro Lys
1               5

<210> SEQ ID NO 587
<211> LENGTH: 19
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 587

Ala Asn Pro Thr Val Thr Leu Phe Pro Pro Ser Ser Glu Glu Leu Gln
1               5                   10                  15

Ala Asn Lys

<210> SEQ ID NO 588
<211> LENGTH: 16
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 588

Phe Ser Gly Ser Asn Ser Gly Asn Thr Ala Thr Leu Thr Ile Ser Arg
1               5                   10                  15

<210> SEQ ID NO 589
<211> LENGTH: 15
<212> TYPE: PRT
<213> ORGANISM: artificial
<220> FEATURE:
<223> OTHER INFORMATION: peptide fragment present in lectin-bound
      fraction isolated from human ovarian tumors
```

```
<400> SEQUENCE: 589

Tyr Ala Ala Ser Ser Tyr Leu Ser Leu Thr Pro Glu Gln Trp Lys
1               5                   10                  15

<210> SEQ ID NO 590
<211> LENGTH: 14
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 590

Leu Val Ile Thr Gly Asn Leu Ile Thr Ile Phe Gln Glu Arg
1               5                   10

<210> SEQ ID NO 591
<211> LENGTH: 14
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 591

Leu Ile Ser Trp Tyr Asp Asn Glu Phe Gly Tyr Ser Asn Arg
1               5                   10

<210> SEQ ID NO 592
<211> LENGTH: 8
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 592

Thr Phe Asp Gly Asp Val Phe Arg
1               5

<210> SEQ ID NO 593
<211> LENGTH: 11
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 593

Ala Ala Tyr Glu Asp Phe Asn Val Gln Leu Arg
1               5                   10

<210> SEQ ID NO 594
<211> LENGTH: 11
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 594

Leu Thr Pro Leu Gln Phe Gly Asn Leu Gln Lys
1               5                   10

<210> SEQ ID NO 595
<211> LENGTH: 10
<212> TYPE: PRT
<213> ORGANISM: artificial
```

```
<220> FEATURE:
<223> OTHER INFORMATION: peptide fragment present in lectin-bound
      fraction isolated from human ovarian tumors

<400> SEQUENCE: 595

Leu Thr Asp Pro Asn Ser Ala Phe Ser Arg
1               5                   10

<210> SEQ ID NO 596
<211> LENGTH: 16
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 596

Leu Phe Val Glu Ser Tyr Glu Leu Ile Leu Gln Glu Gly Thr Phe Lys
1               5                   10                  15

<210> SEQ ID NO 597
<211> LENGTH: 14
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 597

Ser Val Val Gly Asp Ala Leu Glu Phe Gly Asn Ser Trp Lys
1               5                   10

<210> SEQ ID NO 598
<211> LENGTH: 13
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 598

Ser Glu Gln Leu Gly Gly Asp Val Glu Ser Tyr Asp Lys
1               5                   10

<210> SEQ ID NO 599
<211> LENGTH: 18
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 599

Glu Glu Gly Leu Ile Leu Phe Asp Gln Ile Pro Val Ser Ser Gly Phe
1               5                   10                  15

Ser Lys

<210> SEQ ID NO 600
<211> LENGTH: 20
<212> TYPE: PRT
<213> ORGANISM: artificial
<220> FEATURE:
<223> OTHER INFORMATION: peptide fragment present in lectin-bound
      fraction isolated from human ovarian tumors
```

-continued

```
<400> SEQUENCE: 600

Val Asp Ile Pro Ala Leu Gly Val Ser Val Thr Phe Asn Gly Gln Val
1               5                   10                  15

Phe Gln Ala Arg
            20

<210> SEQ ID NO 601
<211> LENGTH: 12
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 601

Trp Tyr Val Asp Gly Val Glu Val His Asn Ala Lys
1               5                   10

<210> SEQ ID NO 602
<211> LENGTH: 16
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 602

Val Val Ser Val Leu Thr Val Leu His Gln Asp Trp Leu Asn Gly Lys
1               5                   10                  15

<210> SEQ ID NO 603
<211> LENGTH: 9
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 603

Gly Leu Glu Trp Val Ala Asn Ile Lys
1               5

<210> SEQ ID NO 604
<211> LENGTH: 11
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 604

Ala Leu Gln Ala Thr Val Gly Asn Ser Tyr Lys
1               5                   10

<210> SEQ ID NO 605
<211> LENGTH: 21
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 605

Gly Ser Phe Thr Tyr Phe Ala Pro Ser Asn Glu Ala Trp Asp Asn Leu
1               5                   10                  15

Asp Ser Asp Ile Arg
            20
```

```
<210> SEQ ID NO 606
<211> LENGTH: 18
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 606

Ile Ile His Gly Asn Gln Ile Ala Thr Asn Gly Val Val His Val Ile
1               5                  10                  15

Asp Arg

<210> SEQ ID NO 607
<211> LENGTH: 23
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 607

Val Leu Thr Gln Ile Gly Thr Ser Ile Gln Asp Phe Ile Glu Ala Glu
1               5                  10                  15

Asp Asp Leu Ser Ser Phe Arg
            20

<210> SEQ ID NO 608
<211> LENGTH: 14
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 608

Ala Ala Ala Ile Thr Ser Asp Ile Leu Glu Ala Leu Gly Arg
1               5                  10

<210> SEQ ID NO 609
<211> LENGTH: 16
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 609

Asp Gly His Phe Thr Leu Phe Ala Pro Thr Asn Glu Ala Phe Glu Lys
1               5                  10                  15

<210> SEQ ID NO 610
<211> LENGTH: 22
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 610

Asp Ile Val Thr Asn Asn Gly Val Ile His Leu Ile Asp Gln Val Leu
1               5                  10                  15

Ile Pro Asp Ser Ala Lys
            20
```

-continued

```
<210> SEQ ID NO 611
<211> LENGTH: 18
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 611

Val Gly Leu Asn Glu Leu Tyr Asn Gly Gln Ile Leu Glu Thr Ile Gly
1               5                   10                  15

Gly Lys

<210> SEQ ID NO 612
<211> LENGTH: 14
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 612

Phe Ser Thr Phe Leu Ser Leu Leu Glu Ala Ala Asp Leu Lys
1               5                   10

<210> SEQ ID NO 613
<211> LENGTH: 20
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 613

Leu Leu Tyr Pro Ala Asp Thr Pro Val Gly Asn Asp Gln Leu Leu Glu
1               5                   10                  15

Ile Leu Asn Lys
            20

<210> SEQ ID NO 614
<211> LENGTH: 23
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 614

Ala Gly Ala Ala Pro Tyr Val Gln Ala Phe Asp Ser Leu Leu Ala Gly
1               5                   10                  15

Pro Val Ala Glu Tyr Leu Lys
            20

<210> SEQ ID NO 615
<211> LENGTH: 18
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 615

Val Glu Asn Gln Glu Asn Val Ser Asn Leu Val Ile Glu Asp Thr Glu
1               5                   10                  15

Leu Lys
```

```
<210> SEQ ID NO 616
<211> LENGTH: 19
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 616

Glu Val Ser Gln Pro Asp Trp Thr Pro Pro Glu Val Thr Leu Val
1               5                  10                  15

Leu Thr Lys

<210> SEQ ID NO 617
<211> LENGTH: 11
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 617

Val Asp Ala Thr Ala Glu Thr Asp Leu Ala Lys
1               5                  10

<210> SEQ ID NO 618
<211> LENGTH: 10
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 618

Ile Ala Asp Gly Tyr Glu Gln Ala Ala Arg
1               5                  10

<210> SEQ ID NO 619
<211> LENGTH: 17
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 619

Trp Val Gly Gly Pro Glu Ile Glu Leu Ile Ala Ile Ala Thr Gly Gly
1               5                  10                  15

Arg

<210> SEQ ID NO 620
<211> LENGTH: 16
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 620

Leu Gly Phe Ala Gly Leu Val Gln Glu Ile Ser Phe Gly Thr Thr Lys
1               5                  10                  15

<210> SEQ ID NO 621
<211> LENGTH: 20
<212> TYPE: PRT
<213> ORGANISM: artificial
```

```
-continued

<220> FEATURE:
<223> OTHER INFORMATION: peptide fragment present in lectin-bound
      fraction isolated from human ovarian tumors

<400> SEQUENCE: 621

Glu Ile Ser Pro Asp Thr Thr Leu Leu Asp Leu Gln Asn Asn Asp Ile
1               5                   10                  15

Ser Glu Leu Arg
            20

<210> SEQ ID NO 622
<211> LENGTH: 21
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 622

Glu Ile Ser Pro Asp Thr Thr Leu Leu Asp Leu Gln Asn Asn Asp Ile
1               5                   10                  15

Ser Glu Leu Arg Lys
            20

<210> SEQ ID NO 623
<211> LENGTH: 14
<212> TYPE: PRT
<213> ORGANISM: artificial
<220> FEATURE:
<223> OTHER INFORMATION: peptide fragment present in lectin-bound
      fraction isolated from human ovarian tumors

<400> SEQUENCE: 623

Gly Leu Gln His Leu Tyr Ala Leu Val Leu Val Asn Asn Lys
1               5                   10
```